US008288371B2

(12) United States Patent
Paradkar et al.

(10) Patent No.: US 8,288,371 B2
(45) Date of Patent: Oct. 16, 2012

(54) ORTHO PYRROLIDINE, BENZYL-SUBSTITUTED HETEROCYCLE CCR1 ANTAGONISTS FOR AUTOIMMUNE DISEASES AND INFLAMMATION

(75) Inventors: Vidyadhar M. Paradkar, Somerville, NJ (US); Marc Brescia, Cranbury, NJ (US); Ray James, Bensalem, NJ (US); Jinqi Liu, Plainsboro, NJ (US); Ruiyan Liu, Yardley, PA (US); James Robert Merritt, Ewing, NJ (US); Michelle Morris, Lawrenceville, NJ (US); Michael J. Ohlmeyer, Plainsboro, NJ (US); Chongwu Zhang, Dayton, NJ (US); Rui Zhang, Plainsboro, NJ (US)

(73) Assignee: Pharmacopeia, LLC, San Diego, CA (US)

( * ) Notice: Subject to any disclaimer, the term of this patent is extended or adjusted under 35 U.S.C. 154(b) by 681 days.

(21) Appl. No.: 12/245,305

(22) Filed: Oct. 3, 2008

(65) Prior Publication Data
US 2009/0093472 A1 Apr. 9, 2009

Related U.S. Application Data

(60) Provisional application No. 60/977,675, filed on Oct. 5, 2007.

(51) Int. Cl.
*A61K 31/4196* (2006.01)
*A61K 31/44* (2006.01)
*A61K 31/433* (2006.01)
*A61K 31/42* (2006.01)
*A61K 31/425* (2006.01)
*A61K 31/445* (2006.01)
*A61K 31/4164* (2006.01)
*A61K 31/40* (2006.01)
*A61K 31/505* (2006.01)
*A61K 31/4245* (2006.01)
*A61K 31/538* (2006.01)
*C07D 249/08* (2006.01)
*C07D 401/14* (2006.01)
*C07D 285/04* (2006.01)
*C07D 261/06* (2006.01)
*C07D 277/20* (2006.01)
*C07D 233/54* (2006.01)
*C07D 209/02* (2006.01)
*C07D 413/14* (2006.01)
*C07D 403/14* (2006.01)
*C07D 271/08* (2006.01)

(52) U.S. Cl. ............... 514/210.2; 514/231.2; 514/269; 514/326; 514/362; 514/364; 514/365; 514/378; 514/340; 514/383; 514/385; 514/414; 544/132; 544/141; 544/333; 548/134; 548/143; 548/202; 548/247; 548/262.2; 548/300.1; 548/465; 548/950; 546/208; 546/210; 546/276.4; 546/268.4

(58) Field of Classification Search ........... 514/210.2, 514/231.2, 269, 326, 362, 364, 365, 378, 514/340, 383, 385, 414; 544/132, 141, 333; 546/208, 210, 276.4, 268.4; 548/134, 143, 548/202, 247, 262.2, 300.1, 465, 950
See application file for complete search history.

(56) References Cited

U.S. PATENT DOCUMENTS 7,084,145 B2 * 8/2006 Armour et al. ............... 514/256
2005/0288319 A1 12/2005 Carson et al.

FOREIGN PATENT DOCUMENTS

| WO | WO 2004/037809 A1 | 5/2004 |
| WO | WO 2005/080371 A1 | 9/2005 |
| WO | WO 2008/128647 A1 | 10/2008 |
| WO | WO2009/082526 | 7/2009 |

OTHER PUBLICATIONS

Anders et al., "Late Onset of Treatment with a Chemokine Receptor CCR1 Antagonist Prevents Progression of Lupus Nephritis in MRLFas(Ipr) Mice," *J. Am. Soc. Nephrol.*, 2004, 15:1504-1513.
Gladue et al., "CCR1 Antagonists for the Treatment of Autoimmune Diseases," *Curr. Opin. Investig. Drugs*, 2004, 5(5):499-504.
Kiyooka et al., "A Short Synthesis of Pyrrole Derivative Having a Chiral Subsituent," *Synthesis*, 1988, 9:745-746.
Palomo et al., "Generation of Threonine—and Azathreonine N-Carboxy Anhydrides from alpha-Hydroxy beta-Lactams Promoted by 2,2,6,6-Tetramethylpiperidinyl-1-oxyl (TEMPO) in Combination with Sodium Hypochlorite," *J. Org. Chem.*, 1996, 61(13):4400-4404. Palomo, et al., "A Concise Route to Pyrrolizidine Alkaloids Bearing the 1, 2-amino Alcohol Functionality," Database Accession No. 1996:521770, Abstract CAS RN 178207-99-3, 181827-77-0, *Database Caplus* [*Online*] Chemical Abstracts Service, Columbus, Ohio (1996).
Zhang et al., "A proinflammatory chemokine, CCL3, sensitizes the heat- and capsaicin-gated ion channel TRPV1," *Proc. Nat. Acad. Sci.*, 2005, 102(12):4536-4541.
International Search Report and Written Opinion dated Jun. 29, 2009 in International Application No. PCT/US2008/078743, Filed Oct. 3, 2008.
Er-Rhaimini et al., "Synthesis and photochemical degradation of N-arylmethyl derivatives of the herbicide 3-amino-1,2,4-triazole", Journal of Heterocyclic Chem. (1992) 29(6):1561-1566.

* cited by examiner

*Primary Examiner* — Joseph K. McKane
*Assistant Examiner* — Samantha Shterengarts
(74) *Attorney, Agent, or Firm* — Knobbe, Martens, Olson & Bear LLP

(57) ABSTRACT

Compounds of the formula

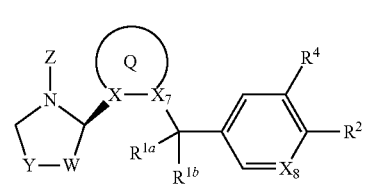

are disclosed. The compounds are CCR1 antagonists which are useful for the treatment and prevention of inflammatory and autoimmune diseases. Other embodiments are also disclosed.

28 Claims, No Drawings

ORTHO PYRROLIDINE, BENZYL-SUBSTITUTED HETEROCYCLE CCR1 ANTAGONISTS FOR AUTOIMMUNE DISEASES AND INFLAMMATION

CROSS-REFERENCE TO RELATED APPLICATIONS

This application claims priority from U.S. Provisional Application Ser. No. 60/977,675, filed Oct. 5, 2007, the entire contents of which are incorporated herein by reference.

FIELD OF THE INVENTION

The present invention relates to substituted heterocycle CCR1 antagonists which are useful for the treatment and prevention of inflammatory and autoimmune diseases.

BACKGROUND

The selective accumulation and activation of leukocytes in inflamed tissues contributes to the pathogenesis of inflammatory and autoimmune diseases. Chemokines and their receptors, which belong to a family of seven transmembrane G-protein coupled receptors are involved in the selective accumulation and activation of leukocytes in inflamed tissues, and in the pathogenesis of inflammatory and autoimmune diseases. One such receptor is CCR1 which is a receptor for CC chemokines, such as CCL5 (RANTES) and CCL3 (MIP-1α).

CCR1 is a therapeutic target for a variety of diseases. In vivo studies on mice indicate that CCR1-mediated leukocyte recruitment is important for interstitial inflammation in the kidney and that CCR1 blockade late in renal disease can halt disease progression and improve renal function (J Am Soc Nephrol 15: 1504-1513, 2004). In vivo studies in mice further indicate that CCR1 may translate inflammatory signals into nociceptor stimuli (Proc. Nat. Acad. Sci. 102: 4536-4541, 2005); CCR1 blockade may therefore obtund inflammatory hyperalgesia. Further, an animal model of neutrophil recruitment in response to MIP-1α demonstrates the positive biological and pharmacodynamic activity of CCR1 antagonists (US 2005/0288319 A1).

SUMMARY OF THE INVENTION

In accordance with embodiments of the present invention there are provided heterocycles which are substituted at adjacent positions by certain pyrrolidine and certain benzyl substituents, which act as CCR1 antagonists. These compounds are useful for the treatment and prevention of inflammatory and autoimmune diseases. In one aspect, the invention relates to compounds of formula I:

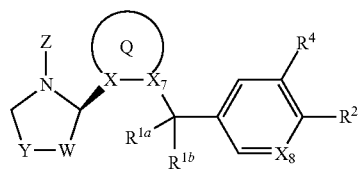

I wherein
X is an $sp^2$-hybridized carbon atom;
$X^7$ is selected from $sp^2$-hybridized C and N;
Q, including X and $X^7$, is a 5- or 6-membered unsaturated, optionally substituted ring and is selected from carbocycle and heterocycle;
$R^{1a}$ and $R^{1b}$ are independently selected from H and $CH_3$ or $R^{1a}$ and $R^{1b}$ taken together with the carbon atom to which they are attached may form a $(C_3\text{-}C_7)$cycloalkyl group, with the proviso that both $R^{1a}$ and $R^{1b}$ cannot be $CH_3$;
$R^2$ is selected from H, methyl, ethyl, methoxy, ethoxy, cyano and halo;
$R^4$ is selected from H, methyl, ethyl, methoxy, ethoxy, cyano and halo;
Y is selected from —C(=O)—, —O—, and —$CR^5R^6$—, wherein $R^5$ is selected from H, methyl, ethyl, methoxy, ethoxy, —OH, F, —OC(=O)$CH_3$ and —OC(=O)$CH_2CH_3$; and $R^6$ is selected from H, methyl and ethyl;
W is —$CHR^8$— or Y—W taken together represents —$CR^5$=$CR^8$—;
$R^8$ is chosen from H, methyl and ethyl, or $R^8$ taken together with $R^5$ forms a carbocycle;
$X^8$ is selected from CH and N;
Z is selected from the group consisting of

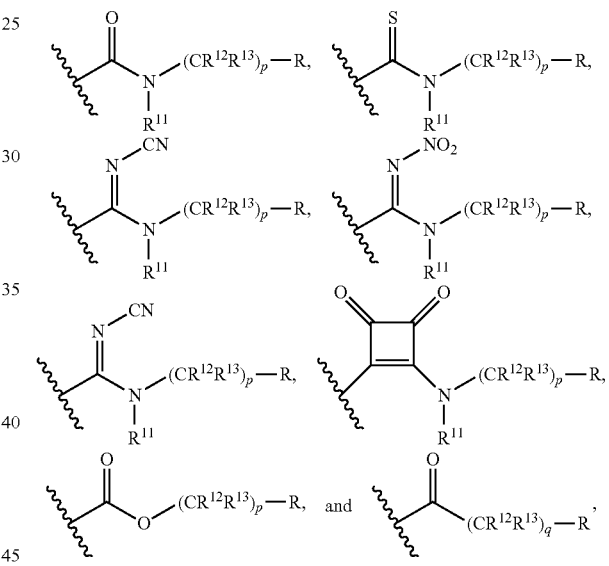

wherein
R is selected from the group consisting of an optionally substituted alkyl group, an optionally substituted carbocycle and an optionally substituted heterocycle, wherein said alkyl group, carbocycle or heterocycle is attached to the remainder of Z through a carbon atom;
$R^{11}$ is selected from H, methyl and ethyl;
$R^{12}$ and $R^{13}$ are independently selected in each occurrence from H, methyl and ethyl or $R^{12}$ and $R^{13}$ taken together with the carbon atom to which they are attached may form a 3 to 7-membered cyclic group;
p is zero, one or two; and
q is one or two.

In another aspect, the invention relates to pharmaceutical formulations comprising one or more compounds of formula I and a pharmaceutically acceptable carrier.

There are also provided, in accordance with embodiments of the invention, methods of treating or preventing inflammatory or autoimmune diseases comprising administering a compound of formula I. In some embodiments the inflammatory disease or autoimmune disease is rheumatoid arthritis; in other embodiments, the inflammatory or autoimmune disease is multiple sclerosis.

There are also provided, in accordance with embodiments of the invention, methods of treating or preventing endometriosis comprising administering a compound of formula I.

There are also provided, in accordance with embodiments of the invention, methods of treating or preventing cancer comprising administering a compound of formula I. In some embodiments, the cancer is multiple myeloma.

There are also provided, in accordance with embodiments of the invention, methods of treating or preventing a disease or condition selected from the group consisting of inflammatory hyperalgesia, hepatocellular carcinoma, respiratory synctial virus (RSV), kidney disease, allergic asthma, Alport disease (which includes glumerulosclerosis and progressive renal fibrosis), prion diseases, sepsis, T-cell mediated liver diseases, severe respiratory viruses, chronic renal injury, and transplant and cardio allograft vascalopathy (chronic rejection) comprising administering a compound of formula I. In some embodiments the Alport disease is renal fibrosis.

DETAILED DESCRIPTION OF THE INVENTION

Definitions

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, which are herein incorporated by reference in their entirety.

Unless otherwise specified, alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself is called "oxo".

Aryl and heteroaryl mean (i) a phenyl group (or benzene) or a monocyclic 5- or 6-membered aromatic or heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein up to three one or more H atoms in each residue are replaced with halogen, haloalkyl, alkyl, acyl, alkoxyalkyl, hydroxyloweralkyl, phenyl, heteroaryl, benzenesulfonyl, hydroxy, loweralkoxy, haloalkoxy, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, mercapto, alkylthio, sulfoxide, sulfone, sulfonylamino, acylamino, amidino, aryl, benzyl, heterocyclyl, phenoxy, benzyloxy, heteroaryloxy, hydroxyimino, alkoxyimino, oxaalkyl, aminosulfonyl, trityl, amidino, guanidino, ureido, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical.

When the substituent group is aryl, cycloalkyl, heterocyclyl, aryloxy, cycloalkyloxy or heterocyclyloxy, e.g. when in a "substituted alkyl" moiety one of the hydrogen atoms is replaced by aryl, cycloalkyl, heterocyclyl, aryloxy, cycloalkyloxy or heterocyclyloxy, the substituent group itself many be further substituted with one to three groups selected from alkyl, halogen, haloalkyl, hydroxy, alkoxy, haloalkoxy, oxaalkyl, thiaalkyl, alkyl-SO$_2$— and —SO$_2$-heterocycle. Furthermore, when reference is made to substituted aryl or substituted heteroaryl, and said aryl or heteroaryl moiety contains a non-aromatic portion (e.g. tetralin or 4,5,6,7-tetrahydrobenzo[c][1,2,5]oxadiazole), the substituent may be attached to either the aromatic or the non-aromatic portion of the aryl or heteroaryl moiety.

Substituted counterparts means the named substituent, but substituted. For instance, if a substituent is chosen from benzene or naphthalene and their substituted counterparts, then the substituted counterpart for benzene is substituted benzene, and the substituted counterpart for naphthalene is substituted napthalene. Thus, for example, where a substituent is pyridinyl, a mono-substituted counterpart is

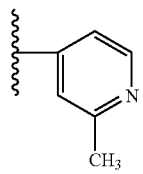

and where a substituent is benzene (i.e. phenyl), a di-substituted counterpart is

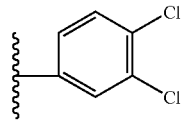

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

Substituents R$^n$ are generally defined when introduced and retain that definition throughout the specification and in all independent claims. Thus, for example, R$^{11}$ is always selected from H and (C$_1$-C$_8$)alkyl; although, in accordance with standard patent practice, in dependent claims it may be restricted to a subset of these values.

Unless otherwise stated, structures depicted herein are also meant to include compounds that differ only in the presence of atoms containing an atomic mass or mass number different from the atomic mass or mass number usually found in nature. Such atoms are often referred to as isotopically enriched. For example, compounds having the present structures except for the replacement of hydrogen by deuterium or tritium, or the replacement of a carbon by a $^{13}$C- or $^{14}$C-enriched carbon are within the scope of this invention. The compounds may also contain one or more radioisotopes of sulfur, phosphorous, fluorine, and chlorine, e.g. $^{35}$S, $^{18}$F, and $^{36}$Cl. Compounds that contain those radioisotopes and/or other radioisotopes of other atoms are within the scope of this invention. Tritiated, i.e. $^3$H, and carbon-14, i.e., $^{14}$C, radioisotopes are particularly known for their ease in preparation and detectability. Radiolabeled compounds of Formulas I and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

The compounds described herein contain at least one asymmetric center and may thus give rise to enantiomers, diastereomers, and other stereoisomeric forms. Each chiral center may be defined, in terms of absolute stereochemistry, as (R)— or (S)—. Unless indicated otherwise (as in the case of the pyrrolidine ring substitution, which is always in the (R)— configuration), embodiments of the present invention are meant to include all such possible isomers, as well as their racemic and optically pure forms. Single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included, unless indicated otherwise.

The graphic representations of chirality in the examples and tables that follow are: Solid and broken wedges are used to denote the absolute configuration of a chiral element; solid and broken bold lines likewise denote absolute configuration and are used interchangeably with solid and broken wedges. Wedge outlines and dotted or broken lines denote enantiomerically pure compounds of indeterminate absolute configuration. Single lines and wavy lines indicate disavowal of any stereochemical implication which the bond they represent could generate.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion, unless noted otherwise.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

As used herein, and as would be understood by the person of skill in the art, the recitation of "a compound"—unless expressly further limited—is intended to include salts, solvates and inclusion complexes of that compound. Thus, for example, the recitation "a compound of formula I" as depicted above, in which R is imidazole would include acid addition salts.

The term n"solvate" refers to a compound of Formulae I or II in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in *Remington: The Science and Practice of Pharmacy* 19$^{th}$ Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, oxalic, napthalenesulfonic and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The abbreviations Me, Et, Bu, Ph, Tf, Ts, Ac, Boc and Ms represent methyl, ethyl, butyl, phenyl, trifluoromethanesulfonyl, toluenesulfonyl, acetyl, butyloxycarbonyl and methanesulfonyl respectively. The abbreviations HPLC, THF, DCM and DMSO represent high performance liquid chromatography, tetrahydrofuran, dichloromethane and dimethylsulfoxide, respectively. The abbreviations Hex, HBTU, MeOH, EtOAc, TFA, r.t. (or rt or RT), conc., eq. and sat. represent hexanes, O-(7-Azabenzotriazol-1-yl)-1,1,3,3-tetramethyluronium hexafluorophosphate, methanol, ethyl acetate, trifluoroacetic acid, room temperature, concentrated, equivalents and saturated, respectively. Additional abbreviations used herein are:

atm=atmospheres
c-=cyclo
cbz=carbobenzyloxy, PhCH$_2$—O—C(=O)—
DIEA=N,N-diisopropylethyl amine
DMF=N,N-dimethylformainide
HOAc=acetic acid
HOBt=hydroxybenzotriazole
LCMS=liquid chromatography-mass spectrometry
mesyl=methanesulfonyl
MS=mass spectrometry
PhOH=phenol
psi=pounds per square inch
sat'd=saturated
s-=secondary
t-=tertiary
TLC=thin-layer chromatography
TMS=trimethylsilyl
TMSI=iodotrimethylsilane A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While in some embodiments of the invention the compounds may be administered as the raw chemical, in other embodiments of the invention they may be presented as a pharmaceutical composition. In accordance with embodiments of the present invention, there are provided a pharmaceutical compositions comprising a compound of formulae I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of general formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations in accordance with embodiments of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions in accordance with embodiments of the present invention may also optionally include other therapeutic ingredients, anti-caking agents, preservatives, sweetening agents, colorants, flavors, desiccants, plasticizers, dyes, and the like. Any such optional ingredient must, of course, be compatible with the active ingredient to insure the stability of the formulation.

The dose range for adult humans is generally from 0.005 mg to 10 g/day orally. Tablets or other forms of presentation provided in discrete units may conveniently contain an amount of compound of formulae I or II, or a combination thereof, which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Compounds of formula I are CCR1 antagonists. As such, they have utility in treating and preventing autoimmune disease and inflammatory diseases. In particular, CCR1 antagonists are therapeutic targets for the treatment and prevention of a variety of diseases, including autoimmune diseases (such as rheumatoid arthritis, Takayasu arthritis, psoriatic arthritis, ankylosing spondylitis, type 1 diabetes (recent onset), lupus, inflammatory bowel disease, Crohn's disease, optic neuritis, psoriasis, multiple sclerosis, polymyalgia rheumatica, uveitis, thyroiditis and vasculitis); fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelial fibrosis, scleroderma (progressive systemic sclerosis), hepatic fibrosis (including that caused by alcoholic or viral hepatitis), primary and secondary biliary cirrhosis); allergic conditions (such as asthma, contact dermatitis and atopic dermatitis); acute and chronic lung inflammation (such as chronic bronchitis, chronic obstructive pulmonary disease, adult Respiratory Distress Syndrome, Respiratory Distress Syndrome of infancy, immune complex alveolitis); atherosclerosis; vascular inflammation resulting from tissue transplant or during restenosis (including, but not limited to restenosis following angioplasty and/or stent insertion); other acute and chronic inflammatory conditions (such as synovial inflammation caused by arthroscopy, hyperuremia, or trauma, osteoarthritis, ischemia reperfusion injury, glomerulonephritis, nasal polyosis, enteritis, Behcet's disease, preeclampsia, oral lichen planus, Guillian-Barre syndrome); acute and/or chronic transplant rejection (including xeno-transplantation); HIV infectivity (co-receptor usage); granulomatous diseases (including sarcoidosis, leprosy and tuberculosis); conditions associated with leptin production (such as obesity, cachexia, anorexia, type II diabetes, hyperlipidemia and hypergonadism); Alzheimer's disease; and sequelae associated with certain cancers such as multiple myeloma. Compounds of formula I may also inhibit the production of metalloproteinases and cytokines at inflammatory sites (including but not limited to MMP9, TNF, IL-1, and IL-6) either directly or indirectly (as a consequence of decreasing cell infiltration) thus providing benefit for diseases or conditions linked to these cytokines (such as joint tissue damage, hyperplasia, pannus formation and bone resorption, hepatic failure, Kawasaki syndrome, myocardial infarction, acute liver failure, septic shock, congestive heart failure, pulmonary emphysema or dyspnea associated therewith). Compounds of formula I may also prevent tissue damage caused by inflammation induced by infectious agents (such as viral induced encephalomyelitis or demyelination, viral inflammation of the lung or liver (e.g. caused by influenza or hepatitis), gastrointestinal inflammation (for example, resulting from H. pylori infection), inflammation resulting from: bacterial meningitis, HIV-1, HIV-2, HIV-3, cytomegalovirus (CMV), adenoviruses, Herpes viruses (Herpes zoster and Herpes simplex) fungal meningitis, lyme disease, malaria).

In one aspect, the invention relates to a compound of formula I as defined above.

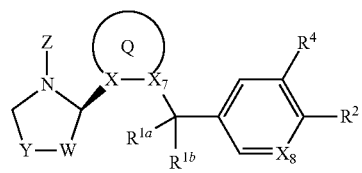

In some embodiments, $X^7$ is an $sp^2$-hybridized carbon.

In some embodiments in which $X^7$ is an $sp^2$-hybridized carbon, Q contains at least one heteroatom. In some such embodiments, Q contains two heteroatoms. In some such embodiments, Q is chosen from pyrimidine, pyrazole, oxazole, pyrrole, thiazole, 1H-1,2,3-triazole, 1,2,3-oxadiazole, 1,2,3-thiadiazole, 1,2,5-thiadiazole, 1,2,5-thiadiazole oxide, 1,2,5-thiadiazole dioxide, 1,2,5-oxadiazole, pyridine, pyrazine, pyridazine and isoxazole. In certain embodiments the compound of formula I has a structure chosen from the following:

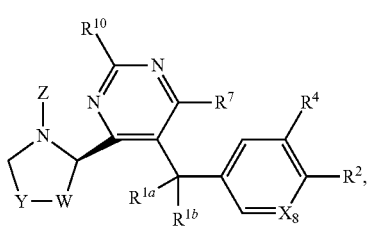

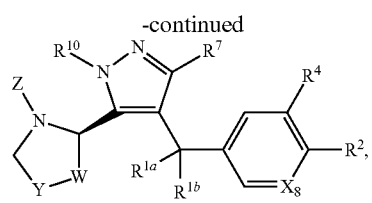

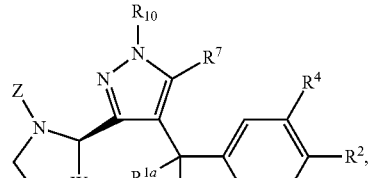

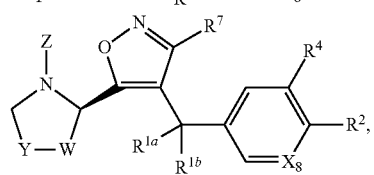

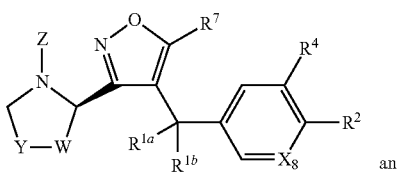

and

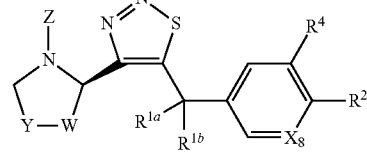

wherein each of the pyrimidine, pyrazole, oxazole, pyrrole, thiazole, 1H-1,2,3-triazole, 1,2,3-oxadiazole, 1,2,3-thiadiazole, 1,2,5-thiadiazole, 1,2,5-thiadiazole oxide, 1,2,5-thiadiazole dioxide, 1,2,5-oxadiazole, pyridine, pyrazine, pyridazine and isoxazole pyrimidine, pyrazole and isoxazole moieties is optionally substituted. In the embodiments shown above $R^7$ is chosen from H, $(C_1-C_4)$alkyl, halo$(C_1-C_4)$alkyl, hydroxy$(C_1-C_4)$alkyl, $(C_1-C_4)$alkoxy$(C_1-C_4)$alkyl, hydroxyl, halo, amino$(C_1-C_4)$alkyl, $(C_1-C_4)$alkylamino$(C_1-C_4)$alkyl, di[$(C_1-C_4)$alkyl]amino$(C_1-C_4)$alkyl, and —C(=O)NH$_2$; and $R^{10}$ is chosen from H and $(C_1-C_4)$alkyl. In some embodiments, $R^7$ is selected from the group consisting of H, $CH_3$, Cl, F, Br, $CF_3$, ethyl, isopropyl, $CH_2OH$, $CH_2OCH_3$, $CH_2NH_2$, C(=O)NH$_2$ and $CH_2NHCH_3$ and $R^{10}$ is hydrogen or methyl. In other embodiments the optional substituents with which Q is optionally substituted are selected from the group consisting of $CH_3$, Cl, F, Br, $CF_3$, ethyl, isopropyl, $CH_2OH$, $CH_2OCH_3$, $CH_2NH_2$ and $CH_2NHCH_3$.

In some embodiments, $X^7$ is N.

In some embodiments in which $X^7$ is N, Q contains at least one heteroatom in addition to $X^7$. In some such embodiments, Q is selected from the group consisting of 1,2,4-triazole, 1,3,4-triazole, imidazole, and tetrazole, and the compound of formula I has a structure chosen from among the following:

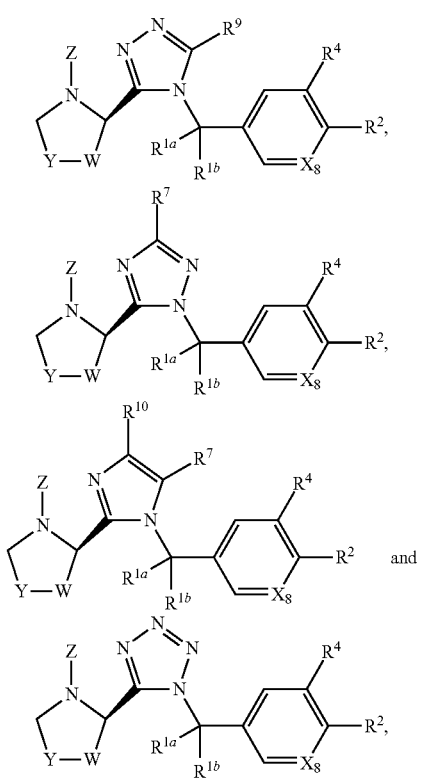

wherein each of the 1,2,4-triazole, 1,3,4-triazole and imidazole moieties is optionally substituted. For example, in the structures above $R^7$ and $R^9$ are chosen from H, $(C_1\text{-}C_4)$alkyl, halo$(C_1\text{-}C_4)$alkyl, hydroxy$(C_1\text{-}C_4)$alkyl, $(C_1\text{-}C_4)$alkoxy$(C_1\text{-}C_4)$alkyl, hydroxyl, halo, amino$(C_1\text{-}C_4)$alkyl, $(C_1\text{-}C_4)$alkylamino$(C_1\text{-}C_4)$alkyl, di[$(C_1\text{-}C_4)$alkyl]amino$(C_1\text{-}C_4)$alkyl, and —C(=O)NH$_2$; and $R^{10}$ is chosen from H and $(C_1\text{-}C_4)$ alkyl. In some such embodiments, the compound has the structure

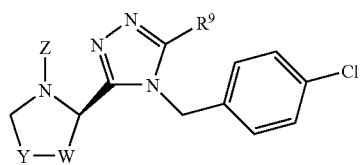

wherein $R^9$ is selected from H, Cl, F, Br, CF$_3$, methyl, ethyl, isopropyl, CH$_2$OH, CH$_2$OCH$_3$, CH$_2$NH$_2$, C(=O)NH$_2$ and CH$_2$NHCH$_3$. Y may be selected from CH$_2$, CHOH, C=O, CHF, C(CH$_3$)OH and CHOC(=O)CH$_3$, in which case W will be —CHR$^8$. Alternatively, Y—W taken together may be —CH=CH—, giving rise to a structure:

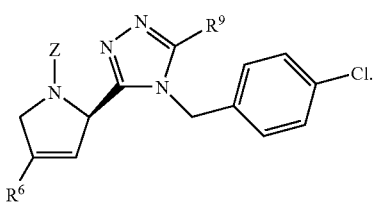

Additionally, Y may be —CR$^5$R$^6$—, W may be —CHR$^8$ and taken together R$^5$ and R$^8$ form a 3-membered carbocycle

giving rise to a structure

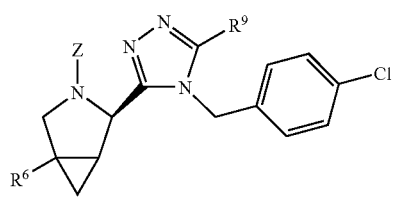

In some embodiments, wherein $R^9$ is selected from the group consisting of H, methyl, ethyl, isopropyl, —CH$_2$OH, —CH$_2$OCH$_3$, —CH$_2$NHCH$_3$, CF$_3$ and Cl, and Y is selected from CH$_2$, CHOH and CHOC(=O)CH$_3$. In some embodiments $R^9$ is selected from H, methyl, ethyl, CH$_2$OH and Cl.

In some embodiments Y is CHR$^5$.

In some embodiments, Z is selected from

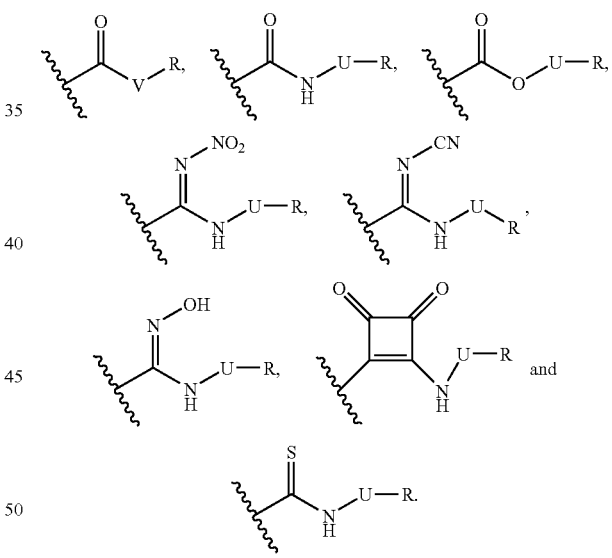

In these compounds U is chosen from a direct bond, —CH$_2$—, —CH(CH$_3$)—, —C(CH$_3$)$_2$—, —CH(CH$_2$CH$_3$)—,

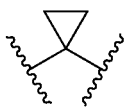

—CH$_2$CH$_2$—, —CH$_2$CH(CH$_3$)—, and —C(CH$_3$)CH$_2$—; and V is chosen from —CH$_2$—, —CH(CH$_3$)—, —C(CH$_3$)$_2$—, —CH(CH$_2$CH$_3$)—,

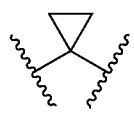

—$CH_2CH_2$—, —$CH_2CH(CH_3)$—, and —$C(CH_3)CH_2$—.

In some embodiments, Z is selected from

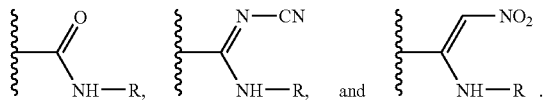

In some such embodiments, Z is

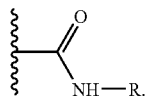

In some embodiments, R is selected from the following, any of which may be optionally substituted: ($C_1$-$C_8$) linear or branched alkyl, ($C_3$-$C_8$)cycloalkyl, phenyl, isoxazolyl, benzoxazinyl, chromanyl, tetrahydronaphthalenyl, furanyl, benzoxepinyl, thiazolyl, pyrazolyl, benzoxadiazolyl, thiochromanyl, benzofuranyl, indanyl, pyridinyl, benzhydryl, naphthalenyl, isochromanyl, pyrimidinyl, piperidinyl, benzothiophenyl, thiadiazolyl, benzoxazolyl, azetidinyl, pyrrolidinyl, tetrahydrofuranyl, tetrahydropyranyl, indolyl and tetrahydroquinolyl. The optional substituents may be selected from ($C_1$-$C_8$)alkyl, phenyl, substituted phenyl, oxo, hydroxy, ($C_1$-$C_8$)fluoroalkyl, halo, ($C_1$-$C_8$)alkoxy, ($C_1$-$C_8$)alkylthio, ($C_1$-$C_8$)fluoroalkylthio, ($C_1$-$C_8$)fluoroalkoxy, cyano, ($C_1$-$C_8$) alkylsulfonyl, di[($C_1$-$C_8$)alkyl]amino, ($C_1$-$C_8$)alkylcarbonyl, amino, aminocarbonyl [$H_2NC(=O)$—], ($C_1$-$C_8$)alkylaminocarbonyl, di[($C_1$-$C_8$)alkyl]aminocarbonyl, aminosulfonyl [$H_2NSO_2$—], ($C_1$-$C_8$)alkylaminosulfonyl [$CH_3NHSO_2$—], di[($C_1$-$C_8$)alkyl]aminosulfonyl, hydroxysulfonyl [$HOSO_2$—], ($C_1$-$C_8$)alkylcarbonyl, carboxy [$HOOC$—], pyridinyl, pyrimidinyl, tetrahydropyranyloxy, pyrazolyl, substituted pyrazolyl, thienyl, and, in the case of nitrogen and sulfur-containing rings, oxide and dioxide. In some such embodiments R may be methyl, ethyl, propyl, butyl, phenyl, oxo, hydroxy, trifluoromethyl, chloro, fluoro, bromo, methoxy, ethoxy, methylthio, trifluoromethylthio, trifluoromethoxy, cyano, methanesulfonyl, dimethylamino, methoxycarbonyl [$CH_3OC(=O)$—], amino, aminocarbonyl [$H_2NC(=O)$—], methylaminocarbonyl [$CH_3NHC(=O)$—], dimethylaminocarbonyl [$(CH_3)_2NC(=O)$—], aminosulfonyl [$H_2NSO_2$—], methylaminosulfonyl [$CH_3NHSO_2$—], dimethylaminosulfonyl [$(CH_3)_2NSO_2$—], hydroxysulfonyl [$HOSO_2$—], acetyl, carboxy [$HOOC$—], halophenyl, methoxyphenyl, pyridinyl, pyrimidinyl, tetrahydropyranyloxy, pyrazolyl, methylpyrazolyl, methyltrifluoromethylpyrazolyl, thienyl, oxide or dioxide. In some such embodiments, R is selected from the group consisting of 4-trifluoromethylphenyl, 2-methyl-4-trifluoromethylphenyl, 2,6-dimethyl-4-trifluoromethylphenyl and 4-chloro-2-fluorophenyl. In other such embodiments, R is selected from the group consisting of 3,5-dimethyl-isoxazol-4-yl, 3-methyl-5-phenyl-isoxazole-4-yl and 5-methyl-3-phenyl-isoxazol-4-yl. In other such embodiments, R is 1-(2-trifluoromethylpyridin-5-yl)-ethyl or 1-(2-trifluoromethylpyridin-5-yl)-prop-1-yl. In other such embodiments, R is 2-methyl-6-trifluoromethylpyridin-3-yl. In other such embodiments, R is (S)-7-trifluoromethylchroman-4-yl.

In some embodiments, at least one of $R^2$ and $R^4$ is selected from F, Cl and Br. In some such embodiments, $R^2$ is Cl and $R^4$ is H.

In some embodiments, Y is selected from —$CHR^5$— wherein $R^5$ is selected from H, $CH_3$, —OH, —$OCH_3$, and —$OCOCH_3$.

In some embodiments, $R^1$ in both instances is H. In some such embodiments, $R^1$ in both instances is H, $X^8$ is CH, $R^4$ is H and $R^2$ is Cl.

In a particular subgenus the compounds may be of formula

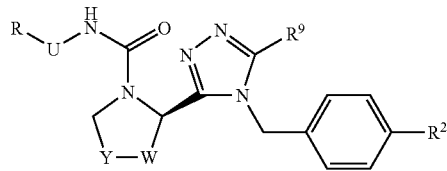

In these compounds R is substituted phenyl or pyridinyl; U is chosen from a direct bond, —$CH_2$—, —$CH(CH_3)$—, —$C(CH_3)_2$—, —$CH(CH_2CH_3)$—,

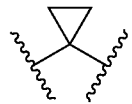

—$CH_2CH_2$—, —$CH_2CH(CH_3)$—, and —$C(CH_3)CH_2$—; Y is selected from —$C(=O)$— and —$CHR^5$—; W is —$CHR^8$— or Y—W taken together represents —$CR^5=CR^8$—; $R^2$ is selected from H, methyl, ethyl, Cl, F and Br; $R^5$ is selected from H, methyl, ethyl, —OH, F, methoxy, ethoxy, —$OC(=O)CH_3$ and —$OC(=O)CH_2CH_3$; $R^8$ is chosen from H and methyl, ethyl, or $R^8$ taken together with $R^5$ forms cyclopropyl; and $R^9$ is selected from H, methyl, ethyl, $CF_3$ and Cl. In a particular embodiment of this subgenus, R is chosen from 2-fluoro-4-chlorophenyl, 2-methyl-6-trifluoromethylpyridin-3-yl and 2,2-dimethyl-4-trifluoromethylphenyl; U is a direct bond or —$CH(CH_2CH_3)$—; Y is —$CH_2$—; W is —$CH_2$—; $R^2$ is Cl; and $R^9$ is H or methyl.

In some embodiments, the compound is a compound which is listed in Table 1.

There are also provided, in accordance with embodiments of the invention, methods of preventing or treating inflammatory diseases and autoimmune diseases, such as rheumatoid arthritis and multiple sclerosis. There are also provided, in accordance with embodiments of the invention, pharmaceutical formulations comprising one or more compounds of formula I and a pharmaceutically acceptable salt, which can be administered to a patient in need of such treatment or prevention. Pharmaceutical formulations comprising the aforementioned genera act to antagonize the CCR1 receptor. The pharmaceutical formulations may be administered alone or in combination with another agent, hormone, or drug, and may be administered by any number of acceptable routes. Pharmaceutical formulations suitable for the use in accordance with embodiments of the invention include formulations wherein the active ingredients are contained in an effective amount to achieve the intended purpose. The determination of an effective dose is well within the capability of those skilled in the art. The pharmaceutical formulations comprise at least one compound formula I and a pharmaceutically acceptable carrier. Such pharmaceutical formulations can be used to treat or prevent inflammatory diseases or autoimmune diseases. In some embodiments, pharmaceutical formulations containing compounds of formula I can be used to treat multiple sclerosis or rheumatoid arthritis.

Processes for obtaining compounds in accordance with embodiments of the invention are presented below.

EXAMPLES

Section A—1,3,4-triazoles

Example 1

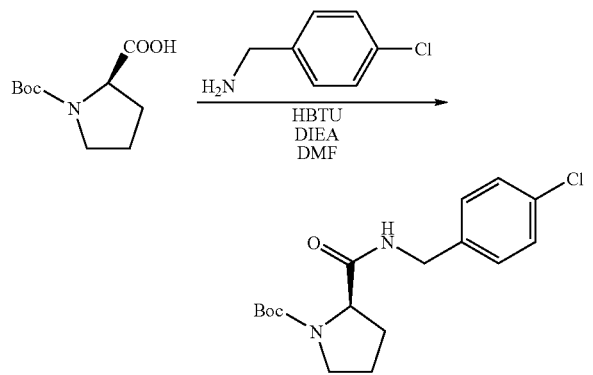

(R)-tert-butyl 2-[4-chlorobenzyl)carbamoyl)pyrrolidine-1-carboxylate. To a stirring mixture of Boc-D-Proline (4.31 g, 20 mmol) and 4-chlorobenzylamine (3.12 g, 1.1 eq.) in DMF (30 ml) cooled to 0° C. was added HBTU (7.58 g, 1 eq.) and N,N-diisopropylethylamine (6.96 mL, 2 eq.) portionwise. The reaction mixture was stirred at 0° C. for 30 minutes, then at room temperature overnight. The reaction mixture was diluted with EtOAc (150 mL), washed with 1N HCl (2×50 mL), sat. aqueous NaHCO$_3$ (2×50 mL) and brine, dried over Na$_2$SO$_4$, and concentrated in vacuo. Flash chromatography purification (Hex/EtOAc) provided the desired product as an oil (5.92 g, 87.4%).

$^1$H NMR (300 MHz, CDCl$_3$) δ 1.42 (s, 9H), 1.67 (m, 1H), 1.90 (m, 2H), 2.20-2.40 (d, 1H), 3.41 (m, 2H), 4.31-4.40 (m, 3H), 7.18-7.21 (d, 2H), 7.28-7.29 (d, 2H).

Example 2

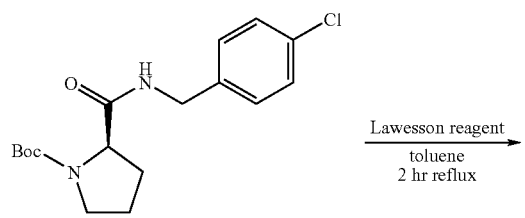

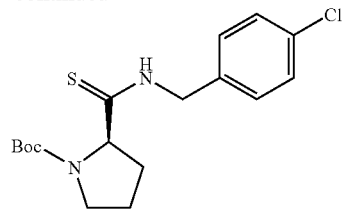

(R)-tert-butyl 2-[4-chlorobenzyl)carbamothioyl)pyrrolidine-1-carboxylate. A mixture of amide from Example 1 (4.01 g, 11.835 mmol) and Lawesson's reagent (2.393 g, 0.5 eq.) in 100 mL of toluene was refluxed for 2 hr under argon. The mixture was cooled to room temperature and then diluted with EtOAc (100 mL), treated with 1N NaOH (2×50 mL), dried over Na$_2$SO$_4$, and concentrated in vacuo. Flash chromatography purification (Hex/EtOAc) provided the desired product as a white powder (3.70 g, 88.1%).

$^1$H NMR (300 MHz, CDCl$_3$) δ 1.39 (s, 9H), 1.87 (m, 2H), 2.30 (m, 2H), 3.41-3.45 (m, 2H), 4.70-4.74 (m, 2H), 5.00 (m, 1H), 7.23-7.32 (dd, 4H). MS: calculated: 354.89, found (MH$^+$): 354.8.

Example 3

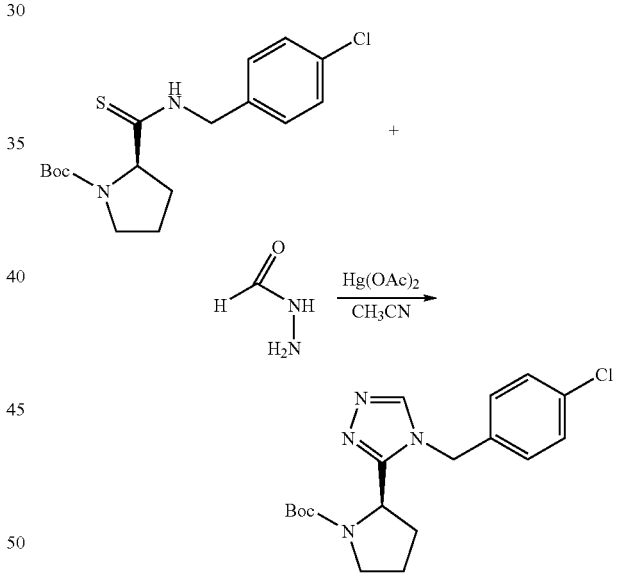

(R)-tert-butyl 2-[4-(4-chlorobenzyl)-4H-1,2,4-triazole-3-yl]pyrrolidine-1-carboxylate. To a mixture of thioamide from Example 2 (1.06 g, 2.987 mmol) and formic hydrazide (0.538 g, 3 eq.) in 20 mL of acetonitrile was added mercury (II) acetate (1.43 g, 1.5 eq.) and the mixture was stirred at room temperature overnight. The mixture was filtered over a Celite-fritted funnel and washed with more acetonitrile. The filtrate was concentrated in vacuo and then diluted with EtOAc (100 mL), treated with H$_2$O (40 mL), dried over Na$_2$SO$_4$, then filtered and concentrated in vacuo. Flash chromatography purification (Hex/EtOAc with 10% of MeOH) provided the desired product as an oil (0.838 g, 77.3%).

$^1$H NMR (300 MHz, CDCl$_3$) δ 1.40 (s, 9H), 1.97-2.09 (m, 3H), 2.50-2.53 (m, 1H), 3.47-3.58 (m, 2H), 4.84-4.88 (m,

1H), 5.40-5.44 (dd, 2H), 7.07-7.09 (d, 2H), 7.33-7.36 (d, 2H), 8.00 (s, 1H). MS: calculated: 362.85, found (MH+): 363.0.

Example 4

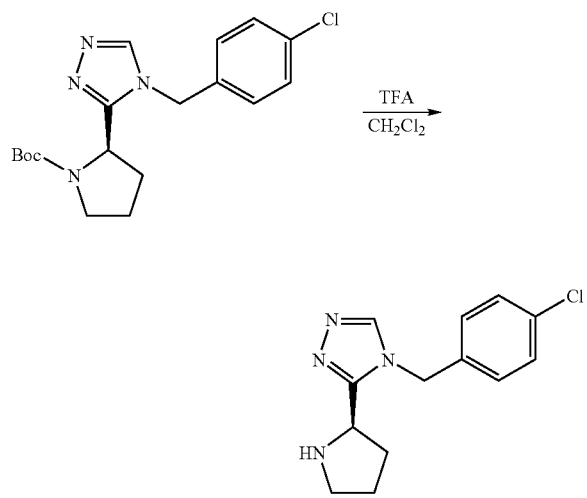

(R)-4-(4-chlorobenzyl)-3-(pyrrolidin-2-yl)-4H-1,2,4-triazole. De-Boc by TFA procedure: A solution of Boc-protected triazole from Example 3 (0.35 g, 0.9645 mmol) in 10 mL of TFA and 10 mL of $CH_2Cl_2$ was stirred at room temperature for 2 h. The mixture was concentrated in vacuo and then treated with saturated aqueous $Na_2CO_3$ (30 mL), extracted with $CH_2Cl_2$ (4×40 mL), dried over $Na_2SO_4$, and concentrated in vacuo. The desired product was obtained as a pale yellow oil (0.13 g, 51.3%).

$^1$H NMR (300 MHz, $CDCl_3$) δ 1.79-2.19 (m, 4H), 2.94-2.99 (m, 1H), 3.04-3.09 (m, 1H), 4.19-4.24 (t, 1H), 5.22-5.36 (quartet, 2H), 7.07-7.10 (d, 2H), 7.34-7.37 (d, 2H), 8.05 (s, 1H).

De-Boc by HCl procedure: A solution of Boc-protected triazole from Example 3 (1.95 g, 5.374 mmol) in 100 mL of 4 N HCl in dioxane was stirred at room temperature for 4 h. The mixture was concentrated in vacuo and then treated with minimum amount of MeOH, diluted with ether, white crystal precipitated out. After filtration, the white crystal was collected and dried in vacuo to yield the HCl salt of desired product (1.67 g, 92.6%, yield calculated based on 2 eq. HCl attached).

Example 5

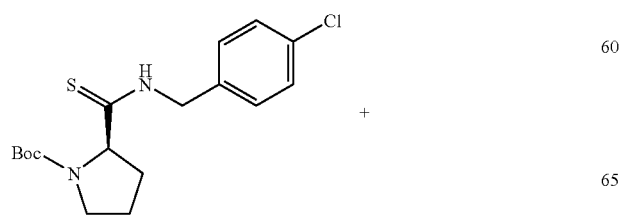

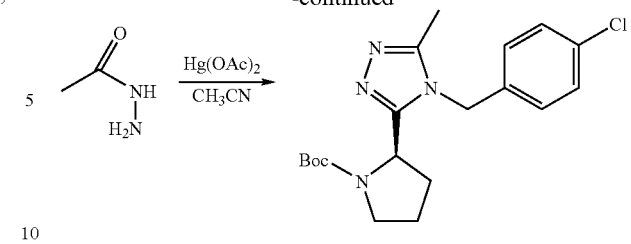

(R)-tert-butyl 2-[4-(4-chlorobenzyl)-5-methyl-4H-1,2,4-triazole-3-yl]pyrrolidine-1-carboxylate. To a mixture of thioamide from Example 2 (0.6743 g, 1.9 mmol) and acetic hydrazide (0.282 g, 2 eq.) in 10 mL of acetonitrile was added mercury (II) acetate (0.908 g, 1.5 eq.) and the mixture was stirred at room temperature overnight. The mixture was filtered over a Celite-fritted funnel and washed with more acetonitrile. The filtrate was concentrated in vacuo and then diluted with EtOAc (100 mL), treated with $H_2O$ (40 mL), dried over $Na_2SO_4$, then filtered and concentrated in vacuo. Flash chromatography purification (Hex/EtOAc with 10% of MeOH) provided the desired product as an oil (0.685 g, 95.6%).

$^1$H NMR (300 MHz, $CDCl_3$) δ 1.38 (s, 9H), 1.90-2.17 (m, 3H), 2.34 (s, 3H), 2.47 (m, 1H), 3.46-3.56 (m, 2H), 4.77-4.81 (dd, 1H), 5.13-5.19 (d, 1H), 5.51-5.57 (d, 1H), 6.90-6.93 (d, 2H), 7.30-7.33 (d, 2H). MS: calculated: 376.88, found (MH+): 377.1.

Example 6

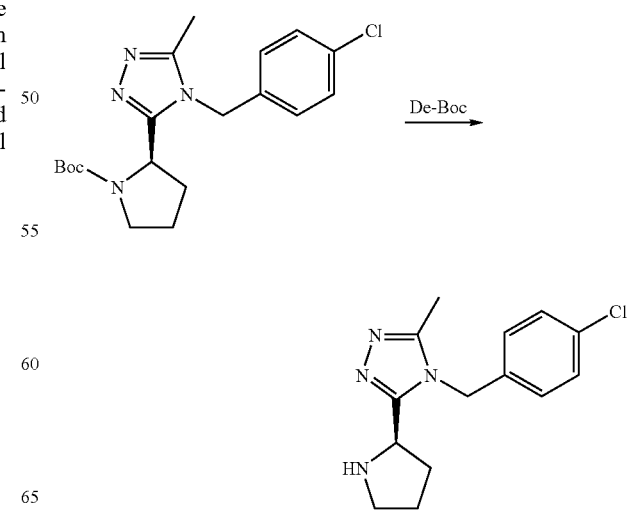

(R)-4-(4-chlorobenzyl)-3-methyl-5-(pyrrolidin-2-yl)-4H-1,2,4-triazole. Exact de-Boc conditions (using TFA or HCl) were followed as for Example 4.

Example 7

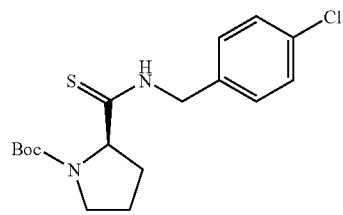
+
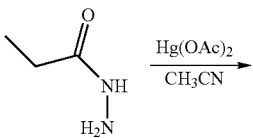
→
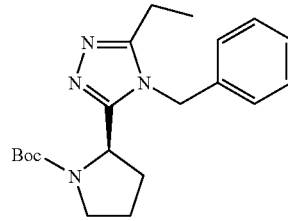

(R)-tert-butyl 2-[4-(4-chlorobenzyl)-5-ethyl-4H-1,2,4-triazole-3-yl]pyrrolidine-1-carboxylate. To a mixture of thioamide from Example 2 (0.71 g, 2 mmol) and propionohydrazide (0.352 g, 2 eq.) in 10 mL of acetonitrile was added mercury (II) acetate (0.96 g, 1.5 eq.) and the mixture was stirred at room temperature overnight. The mixture was filtered over a Celite-fritted funnel and washed with more acetonitrile. The filtrate was concentrated in vacuo and then diluted with EtOAc (100 mL), treated with H$_2$O (40 mL), dried over Na$_2$SO$_4$, then filtered and concentrated in vacuo. Flash chromatography purification (Hex/EtOAc gradient, 10-100% EtOAc with 10% of MeOH) provided the desired product as an oil (0.47 g, 60.1%).

$^1$H NMR (300 MHz, CDCl$_3$) δ 1.26-1.33 (m, 3H), 1.38 (s, 9H), 1.94-2.05 (m, 3H), 2.46-2.56 (m, 1H), 2.60-2.68 (m, 2H), 3.45 (m, 1H), 3.55 (m, 1H), 4.77-4.78 (dd, 1H), 5.14-5.20 (d, 1H), 5.54-5.60 (d, 1H), 6.89-6.92 (d, 2H), 7.30-7.32 (d, 2H). MS: calculated: 390.91, found (MH$^+$): 391.2.

Example 8

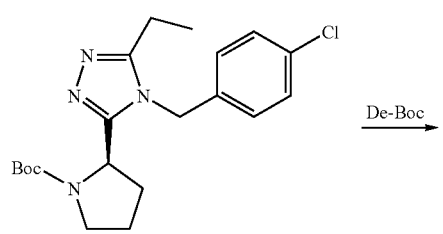
De-Boc →
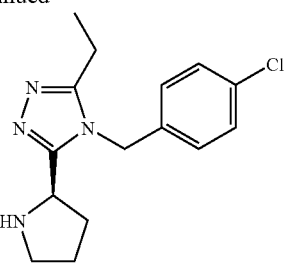

(R)-4-(4-chlorobenzyl)-3-ethyl-5-(pyrrolidin-2-yl)-4H-1,2,4-triazole. Exact de-Boc conditions (using 4N HCl in dioxane) were followed as for Example 4.

Example 9

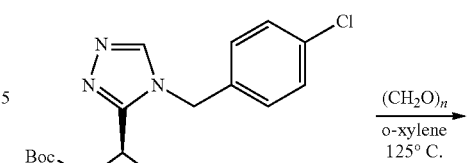
(CH$_2$O)$_n$
o-xylene
125° C. →

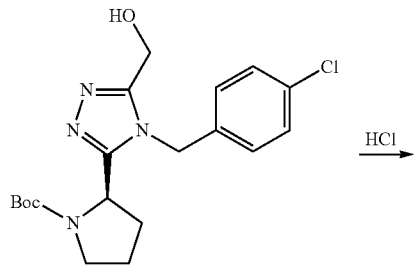
HCl →

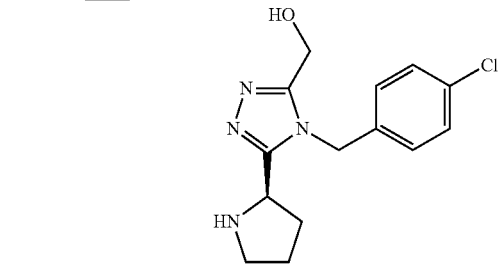

(R)-tert-butyl 2-[4-(4-chlorobenzyl)-5-(hydroxymethyl)-4H-1,2,4-triazol-3-yl]pyrrolidine-1-carboxylate. A mixture of Boc-protected triazole from example 3 (7.7 g, 21.221 mmol) and paraformaldehyde (3.23 g, 5 eq.) in 50 mL of o-xylene was heated at 125° C. for 3 h. After cooling, the mixture was filtered over a Celite-fritted funnel and washed with 10 mL of o-xylene. The filtrate was concentrated in vacuo to provide the desired intermediate as a foam (8.45 g, 100%+)

$^1$H NMR (300 MHz, CDCl$_3$) δ 1.39 (s, 9H), 1.85-1.98 (m, 3H), 2.33 (m, 1H), 3.41-3.47 (m, 1H), 3.54-3.56 (m, 1H), 4.64-4.77 (m, 3H), 5.49 (m, 2H), 7.07-7.09 (d, 2H), 7.30-7.33 (d, 2H). MS: calculated: 392.88, found (MH$^+$): 392.9.

(R)-[4-(4-chlorobenzyl)-5-(pyrrolidin-2-yl)-4H-1,2,4-triazol-3-yl]methanol. De-Boc conditions (using 4N HCl in dioxane) were followed as for Example 4.

Example 10

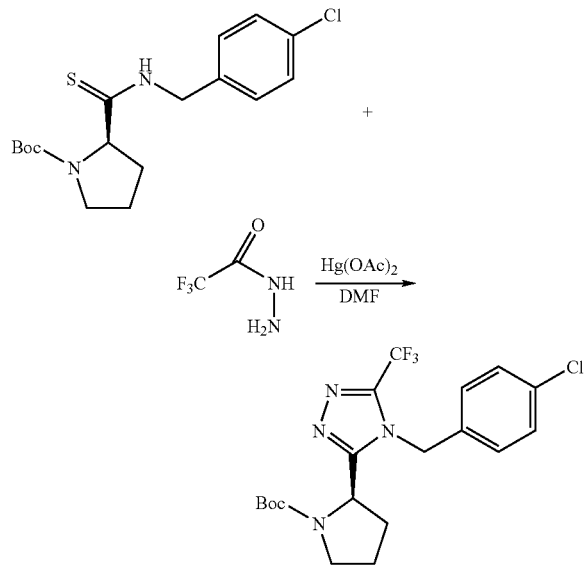

(R)-tert-butyl 2-[4-(4-chlorobenzyl)-5-(trifluoromethyl)-4H-1,2,4-triazole-3-yl]pyrrolidine-1-carboxylate. To a mixture of thioamide from Example 2 (0.9 g, 2.5359 mmol) and 2,2,2-trifluoroacetohydrazide (0.489 g, 3.8038 mmol, 1.5 eq.) in 20 mL of DMF was added mercury (II) acetate (1.212 g, 3.8038 mmol, 1.5 eq.) and the mixture was stirred at 80° C. overnight. The mixture was diluted with 40 mL of acetonitrile, filtered over a Celite-fritted funnel and washed with more acetonitrile. The filtrate was concentrated in vacuo and then diluted with EtOAc (100 mL), treated with H$_2$O (40 mL), dried over Na$_2$SO$_4$, then filtered and concentrated in vacuo. Flash chromatography purification (Hex/EtOAc gradient, 10-100% EtOAc) provided the desired product (0.345 g, 38.3%).

$^1$H NMR (300 MHz, CDCl$_3$) δ 1.40 (s, 9H), 1.93 (m, 3H), 2.47 (m, 1H), 3.45-3.47 (m, 1H), 3.57-3.59 (m, 1H), 4.72 (m, 1H), 5.37-5.42 (d, 1H), 5.73-5.79 (d, 1H), 6.96-6.99 (d, 2H), 7.33-7.35 (d, 2H). MS: calculated: 430.85, found (MH$^+$): 430.8.

Example 11

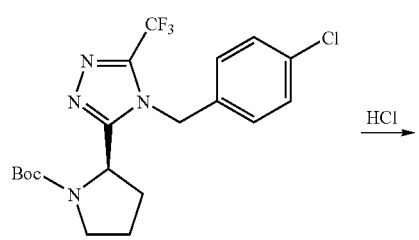

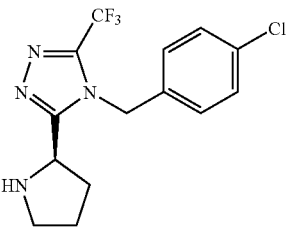

(R)-4-(4-chlorobenzyl)-3-(pyrrolidin-2-yl)-5-(trifluoromethyl)-4H-1,2,4-triazole. De-Boc conditions (using 4N HCl in dioxane) were followed as for Example 4.

Example 12

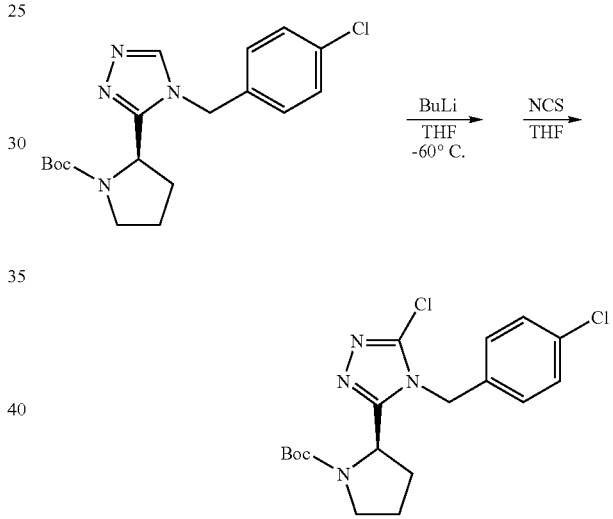

(R)-tert-butyl 2-[4-(4-chlorobenzyl)-5-chloro-4H-1,2,4-triazol-3-yl]pyrrolidine-1-carboxylate. To a solution of Boc-protected triazole from Example 3 (4.344 g, 12 mmol) in 20 mL of THF at −60° C. under argon was slowly added a solution of n-butyl lithium (1.6M) in hexane (7.5 mL, 1.2 eq.) and stirred at −60° C. for 30 minutes. To the mixture was added a suspension of N-chlorosuccinimide (4.67 g, 2.9 eq.) in 20 mL of THF and the mixture was kept at −60° C. for 1 hr before warming up to RT overnight. The reaction mixture was treated with sat. aqueous NaHCO$_3$ (30 mL), then extracted with EtOAc (2×40 mL). The organic phase was dried over Na$_2$SO$_4$ and concentrated in vacuo. Flash chromatography purification ((Hex/EtOAc) provided the desired product (1.011 g, 21.2%).

$^1$H NMR (300 MHz, CDCl$_3$) δ 1.40 (s, 9H), 1.96-2.00 (m, 3H), 2.42 (m, 1H), 3.45 (m, 1H), 3.56 (m, 1H), 4.77 (m, 1H), 5.26-5.32 (d, 1H), 5.53-5.58 (d, 1H), 7.02-7.04 (d, 2H), 7.32-7.35 (d, 2H). MS: calculated: 397.3, found (MH$^+$): 397.4.

Example 13

(R)-4-(4-chlorobenzyl)-3-chloro-5-(pyrrolidin-2-yl)-4H-1,2,4-triazole. De-Boc conditions (by HCl) were followed as for Example 4.

Example 14

Typical Urea Synthesis:

Method A:

$R_2$ = H, Me, Et, Cl, CF$_3$, CH$_2$OH, etc.

Method B:

$R_2$ = H, Me, Et, Cl, CF$_3$, CH$_2$OH, etc.

Method A: To a stirring solution of triphosgene (0.0205 g, 0.691 mmol) in 8 mL of CH$_2$Cl$_2$ at 0° C. was added dropwise a mixed solution of amine R$_1$—NH$_2$ (0.2068 mmol) and N,N-diisopropylethylamine (0.108 mL, 0.620 mmol) in dichloromethane (2 mL). The reaction mixture was stirred at 0° C. for 30 minutes. Then to the mixture at 0° C. was slowly added a solution of the H-134-Triazole salt (0.207 mmol) and N,N-diisopropylethylamine (0.108 mL, 0.620 mmol) in dichloromethane (2 mL). The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification (Hex/EtOAc gradient, 10-100% EtOAc with 10% of MeOH unless specified) provided the desired product urea.

Method B: To a stirring solution of R$_1$-isocyanate (0.2688 mmol) in 8 mL of CH$_2$Cl$_2$ at 0° C. was slowly added dropwise a solution of the H-134-Triazole salt (0.207 mmol) and N,N-diisopropylethylamine (0.108 mL, 0.620 mmol) in dichloromethane (2 mL). The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification (Hex/EtOAc gradient, 10-100% EtOAc with 10% of MeOH unless specified) provided the desired product urea.

Example 15

Step A

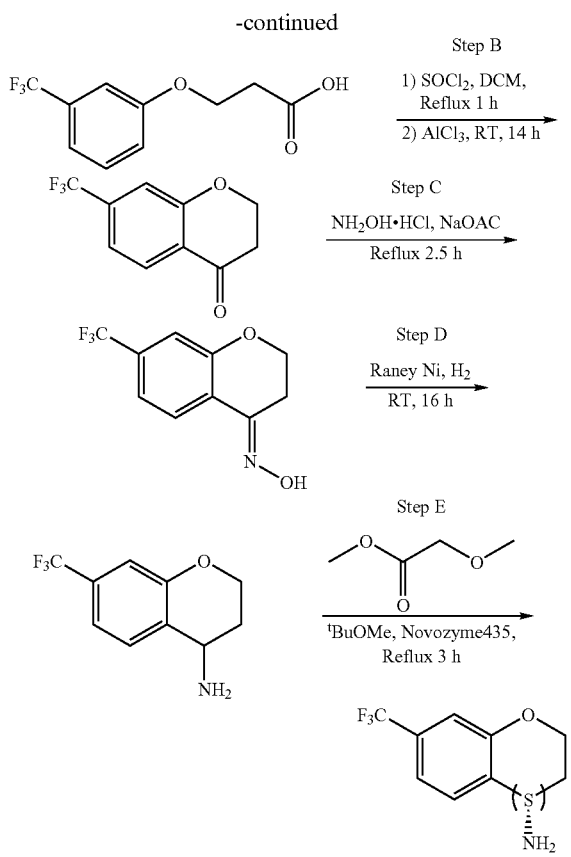

Step A:

Sodium hydroxide (16.28 g, 0.407 mol, 2.2 eq.) was added to 112 mL of water and the resulting solution was cooled to r.t. 3-(trifluoromethyl)phenol (30 g, 0.185 mol) was added drop-wise to the solution at 0° C., followed by portion-wise addition of 3-bromo-propionic acid (34 g, 0.222 mol, 1.2 eq.) at 0° C. The reaction was stirred for about 30 min, and then refluxed for 3 h. Then it was cooled to about 10° C. and acidified in an ice-water bath with conc. HCl to pH=2. DCM (40 mL) was added, and the aqueous layer was extracted with DCM (50 mL×3). The combined organic layers were dried with MgSO$_4$, and concentrated. The residue was purified by column chromatography (petroleum ether:EtOAc=4:1) to give 12 g of compound.

Step B:

To a solution of the product of step A (6 g, 0.0256 mol) in 30 mL of dry DCM was added drop-wise 7.48 mL of SOCl$_2$ (4 eq.). The reaction mixture was heated to reflux, at which time two drops of DMF were added. Refluxing of the reaction was continued for 1 h. The mixture was cooled to room temperature. The solvent and the excess of SOCl$_2$ were removed at reduced pressure to give corresponding crude propionyl chloride, which was used in the next step. The solution of this crude propionyl chloride in 40 mL of dry DCM was firstly cooled in an ice-water bath, followed slowly by addition of solid aluminum chloride (3.75 g, 0.02816 mol, 1.1 eq.). The reaction mixture was stirred overnight at room temperature, and then poured into 100 mL of crushed ice. The organic layer was recovered and the aqueous layer was extracted 3 times with DCM. All of the organic extracts were combined, washed with brine and water, concentrated, and the residue was purified by HPLC to give 4.14 g of product.

Step C:

A solution of the product from Step B (2 g, 9.26 mmol), NH$_2$OH.HCl (960 mg, 13.9 mmol, 1.5 eq) and NaOAc (1.14 g, 13.9 mmol, 1.5 eq.) in 50 mL of EtOH was heated under reflux for 4 h. Then the reaction mixture was concentrated, washed with water and brine, extracted with EtOAc, dried with MgSO$_4$ and concentrated to give 1.8 g of product.

Step D:

To a solution of the product from Step C (2 g, 8.66 mmol) in 60 mL of methanol/ammonia (2:1) was added 0.8 g of Raney Ni. The reaction mixture was stirred overnight under H$_2$ atmosphere at room temperature. Then the mixture was filtrated, concentrated in vacuo to remove methanol and washed with water to give 1.8 g of 98% pure product.

Step E:

The product from Step D (0.5 g, 2.3 mmol) and methyl-2-methoxyacetate (0.284 g, 2.76 mmol, 1.2 eq) were dissolved in tert-butylmethyl ether (15 mL), then Novozyme 435 (lipase acrylic resin from Candida antarctica, 0.142 g) was added, and the resulting mixture was refluxed for 3 h. The reaction mixture was filtered and the filter paper was washed with MeOH-DCM 1/1. The filtrate was concentrated in vacuo. The residue was dissolved in 5% HCl solution (40 mL), and washed with DCM to remove corresponding amide. The aqueous layer was basified with 2N NaOH solution to pH=11, and extracted with DCM to give the product (0.23 g).

Example 16

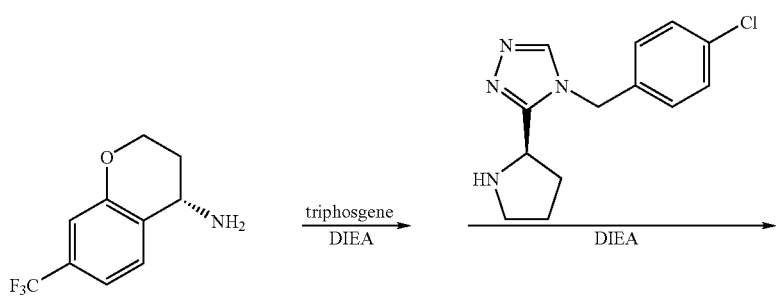

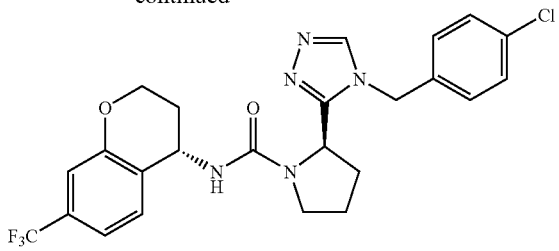

(R)-2-(4-(4-chlorobenzyl)-4H-1,2,4-triazol-3-yl)-N—((S)-7-(trifluoromethyl)chroman-4-yl)pyrrolidine-1-carboxamide. To a stirring solution of triphosgene (0.0205 g, 0.691 mmol) in 8 mL of $CH_2Cl_2$ at 0° C. was added dropwise a mixed solution of (S)-7-(trifluoromethyl)chroman-4-amine (44.91 mg, 0.2068 mmol) and N,N-diisopropylethylamine (0.108 mL, 0.620 mmol) in dichloromethane (2 mL). The reaction mixture was stirred at 0° C. for 30 minutes. Then to the mixture at 0° C. was slowly added a solution of the (R)-4-(4-chlorobenzyl)-3-(pyrrolidin-2-yl)-4H-1,2,4-triazole TFA salt (0.125 g, 0.2068 mmol) and N,N-diisopropylethylamine (0.108 mL, 0.620 mmol) in dichloromethane (2 mL). The resulting mixture was stirred 0° C. for 30 minutes, then at room temperature overnight. The reaction mixture was treated with sat. aqueous $NaHCO_3$ (10 mL) and brine, dried over $Na_2SO_4$, and concentrated in vacuo. Flash chromatography purification (Hex/EtOAc gradient, 10-100% EtOAc with 10% of MeOH) afforded the desired product (55 mg, 52.6%).

$^1$H NMR (300 MHz, $CDCl_3$) δ 2.03-2.18 (m, 5H), 2.70 (m, 1H), 3.31-3.34 (m, 1H), 3.52-3.55 (m, 1H), 4.19-4.28 (m, 2H), 4.53 (m, 1H), 4.95-5.04 (m, 2H), 5.34-5.39 (d, 1H), 5.56-5.62 (d, 1H), 7.06-7.13 (dd, 4H), 7.29 (s, 1H), 7.34-7.40 (d, 2H), 8.04 (s, 1H), MS: calculated: 505.92, found ($MH^+$): 506.0.

Example 17

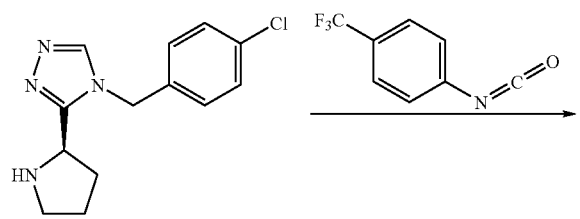

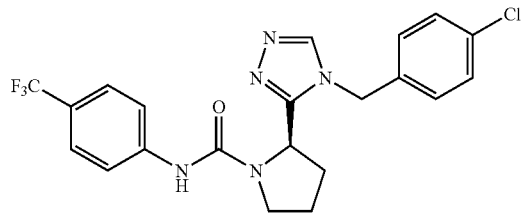

(R)-2-(4-(4-chlorobenzyl)-4H-1,2,4-triazol-3-yl)-N-(4-(trifluoromethyl)phenyl)pyrrolidine-1-carboxamide. To a stirring solution of 1-isocyanato-4-(trifluoromethyl)benzene (46.3 mg, 0.2474 mmol) in 8 mL of $CH_2Cl_2$ at 0° C. was slowly added a solution of (R)-4-(4-chlorobenzyl)-3-(pyrrolidin-2-yl)-4H-1,2,4-triazole (0.050 g, 0.1903 mmol) in dichloromethane (2 mL). The resulting mixture was stirred 0° C. for 30 minutes, then at room temperature overnight. The reaction mixture was concentrated in vacuo. Flash chromatography purification ((Hex/EtOAc with 10% of MeOH) afforded the desired product (68 mg, 79.4%).

$^1$H NMR (300 MHz, $CDCl_3$ with drops of $CD_3OD$) 1.94-2.08 (m, 3H), 2.48-2.51 (m, 1H), 3.52-3.57 (m, 1H), 3.75-3.79 (m, 1H), 5.06-5.10 (m, 1H), 5.30-5.36 (d, 1H), 5.44-5.49 (d, 1H), 7.10-7.13 (d, 2H), 7.28-7.48 (m, 6H), 8.05 (s, 1H). MS: calculated: 449.86, found ($MH^+$): 450.0.

Example 18

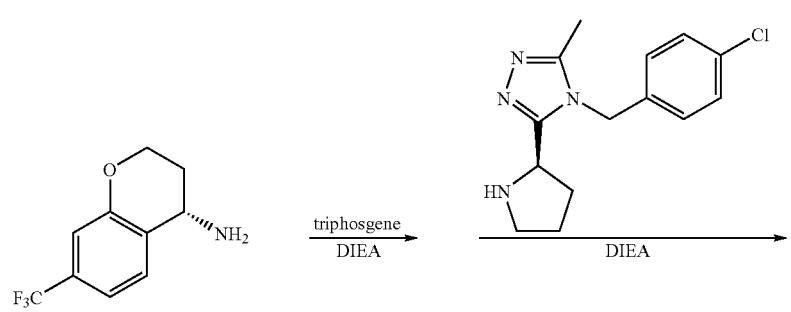

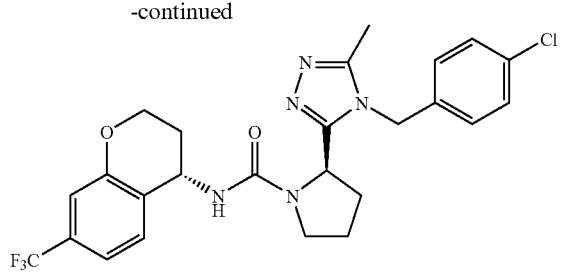

(R)-2-(4-(4-chlorobenzyl)-5-methyl-4H-1,2,4-triazol-3-yl)-N—(S)-7-(trifluoromethyl)chroman-4-yl)pyrrolidine-1-carboxamide. To a stirring solution of triphosgene (20.5 mg, 0.0689 mmol) in 8 mL of CH$_2$Cl$_2$ at 0° C. was added dropwise a mixed solution of (S)-7-(trifluoromethyl)chroman-4-amine (44.91 mg, 0.2068 mmol) and N,N-diisopropylethylamine (0.1081 mL, 0.6204 mmol) in dichloromethane (2 mL). The reaction mixture was stirred at 0° C. for 30 minutes. Then to the mixture at 0° C. was added a solution of the (R)-4-(4-chlorobenzyl)-3-methyl-5-(pyrrolidin-2-yl)-4H-1,2,4-triazole TFA salt (127.97 mg, 0.2068 mmol) and N,N-diisopropylethylamine (0.1081 mL, 0.6204 mmol) in dichloromethane (2 mL) slowly. The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification ((Hex/EtOAc with 10% of MeOH) afforded the desired product as white solid (80.9 mg, 75.2%).

$^1$H NMR (300 MHz, CDCl$_3$) δ 2.04-2.18 (m, 5H), 2.37 (s, 3H), 2.65 (m, 1H), 3.33-3.35 (m, 1H), 3.57 (m, 1H), 4.20-4.28 (m, 2H), 4.63 (m, 1H), 4.93-4.99 (m, 2H), 5.14-5.20 (d, 1H), 5.64-5.69 (d, 1H), 6.93-6.96 (d, 2H), 7.06-7.13 (t, 2H), 7.23-7.26 (d, 1H), 7.33-7.35 (d, 2H). MS: calculated: 519.95, found (MH$^+$): 520.0.

Example 19

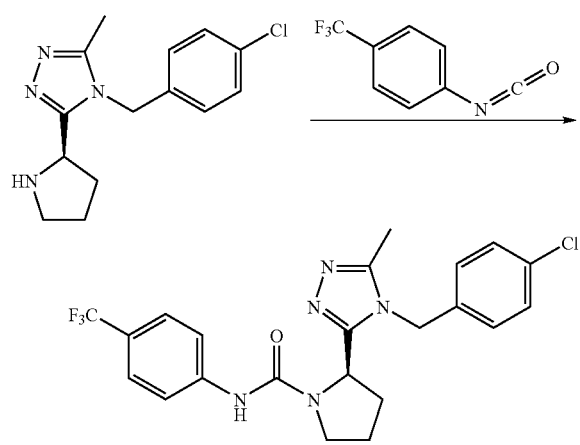

(R)-2-(4-(4-chlorobenzyl)-5-methyl-4H-1,2,4-triazol-3-yl)-N-(4-(trifluoromethyl)phenyl)pyrrolidine-1-carboxamide. To a stirring solution of 1-isocyanato-4-(trifluoromethyl)benzene (48.6 mg, 0.26 mmol) in 8 mL of CH$_2$Cl$_2$ at 0° C. was slowly added a solution of the (R)-4-(4-chlorobenzyl)-3-methyl-5-(pyrrolidin-2-yl)-4H-1,2,4-triazole TFA salt (0.1237 g, 0.2 mmol) and N,N-diisopropylethylamine (0.108 mL, 0.620 mmol) in dichloromethane (2 mL). The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification (Hex/EtOAc gradient, 10-100% EtOAc with 10% of MeOH) afforded the desired product (49.2 mg, 53.0%).

$^1$H NMR (300 MHz, CDCl$_3$) δ 2.04-2.10 (m, 3H), 2.36 (s, 3H), 2.57 (m, 1H), 3.55-3.60 (m, 1H), 3.68-3.72 (m, 1H), 5.00-5.04 (m, 1H), 5.09-5.15 (d, 1H), 5.60-5.63 (d, 1H), 6.92-6.95 (d, 2H), 7.31-7.50 (m, 6H). MS: calculated: 463.88, found (MH$^+$): 464.0.

Example 20

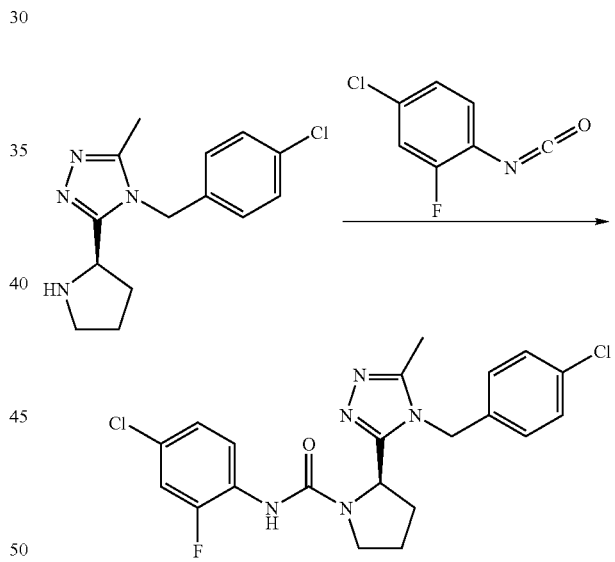

(R)-2-(4-(4-chlorobenzyl)-5-methyl-4H-1,2,4-triazol-3-yl)-N-(4-chloro-2-fluorophenyl)pyrrolidine-1-carboxamide. To a stirring solution of 4-chloro-2-fluoro-1-isocyanatobenzene (102.92 mg, 0.6 mmol) in 20 mL of CH$_2$Cl$_2$ at 0° C. was slowly added a solution of the (R)-4-(4-chlorobenzyl)-3-methyl-5-(pyrrolidin-2-yl)-4H-1,2,4-triazole HCl salt (209.8 mg, 0.6 mmol) and N,N-diisopropylethylamine (0.2091 mL, 1.2 mmol) in dichloromethane (20 mL). The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification (Hex/EtOAc gradient, 10-100% EtOAc with 10% of MeOH) afforded the desired product as white foamy powder (215 mg, 79.9%).

¹H NMR (300 MHz, CDCl₃) δ 2.05-2.18 (m, 3H), 2.37 (s, 3H), 2.70-2.74 (m, 1H), 3.49-3.57 (m, 1H), 3.68-3.74 (m, 1H), 4.99-5.03 (dd, 1H), 5.10-5.16 (d, 1H), 5.58-5.64 (d, 1H), 6.33-6.35 (d, 1H), 6.91-6.94 (d, 2H), 7.05-7.10 (m, 2H), 7.30-7.32 (d, 2H), 7.90-7.96 (t, 1H). MS: calculated: 448.32, found (MH⁺): 448.2.

Example 21

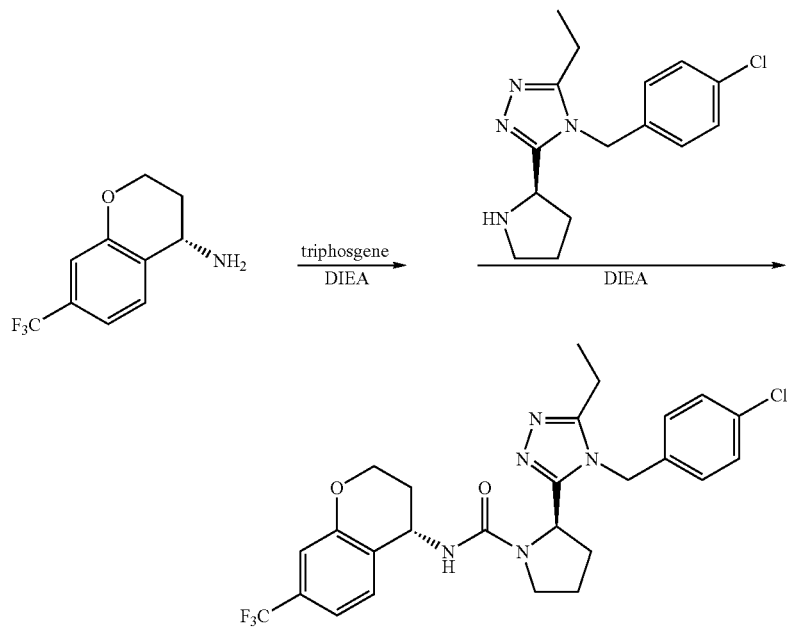

(R)-2-(4-(4-chlorobenzyl)-5-ethyl-4H-1,2,4-triazol-3-yl)-N—((S)-7-(trifluoromethyl)chroman-4-yl)pyrrolidine-1-carboxamide. To a stirring solution of triphosgene (14.87 mg, 0.05 mmol) in 8 mL of CH₂Cl₂ at 0° C. was added dropwise a mixed solution of (S)-7-(trifluoromethyl)chroman-4-amine (32.58 mg, 0.15 mmol) and N,N-diisopropylethylamine (0.07841 mL, 0.45 mmol) in dichloromethane (2 mL). The reaction mixture was stirred at 0° C. for 30 minutes. Then to the mixture at 0° C. was added a solution of the (R)-4-(4-chlorobenzyl)-3-ethyl-5-(pyrrolidin-2-yl)-4H-1,2,4-triazole HCl salt (54.57 mg, 0.15 mmol) and N,N-diisopropylethylamine (0.07841 mL, 0.45 mmol) in dichloromethane (2 mL) slowly. The resulting mixture was stirred 0° C. for 30 minutes, then at room temperature overnight. The reaction mixture was treated with sat. aqueous NaHCO₃ (10 mL) and brine, dried over Na₂SO₄, and concentrated in vacuo. Flash chromatography purification (Hex/EtOAc gradient, 10-100% EtOAc with 10% MeOH) afforded the desired product as a white solid (73.7 mg, 92.0%).

¹H NMR (300 MHz, CDCl₃) δ 1.28-1.34 (t, 3H), 1.98-2.10 (m, 5H), 2.59-2.70 (m, 3H), 3.29-3.32 (m, 1H), 3.49-3.53 (m, 1H), 4.18-4.21 (m, 1H), 4.24-4.27 (m, 1H), 4.49-4.52 (d, 1H), 4.92-4.95 (m, 2H), 5.14-5.20 (d, 1H), 5.65-5.71 (d, 1H), 6.91-6.94 (d, 2H), 7.06 (s, 1H), 7.11-7.13 (d, 1H), 7.25-7.27 (d, 1H), 7.31-7.34 (d, 2H). MS: calculated: 533.97, found (MH⁺): 534.5.

Example 22

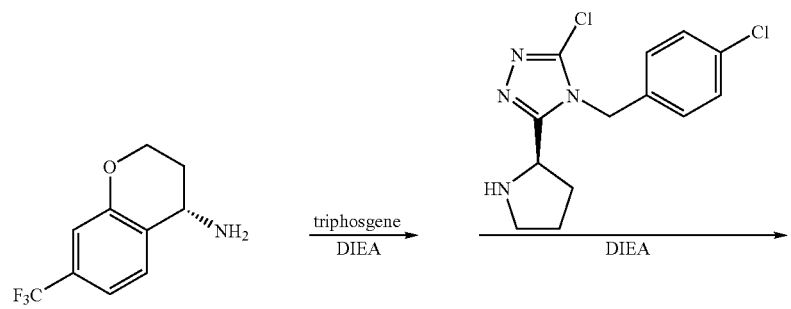

-continued

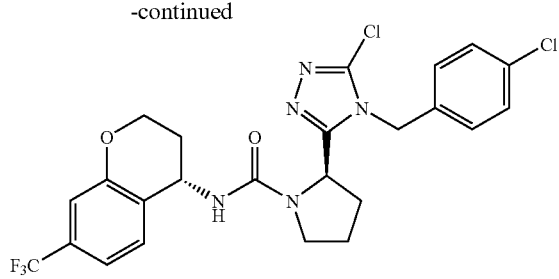

(R)-2-(4-(4-chlorobenzyl)-5-chloro-4H-1,2,4-triazol-3-yl)-N—((S)-7-(trifluoromethyl)chroman-4-yl)pyrrolidine-1-carboxamide. To a stirring solution of triphosgene (14.87 mg, 0.05 mmol) in 8 mL of $CH_2Cl_2$ at 0° C. was added dropwise a mixed solution of (S)-7-(trifluoromethyl)chroman-4-amine (32.58 mg, 0.15 mmol) and N,N-diisopropylethylamine (0.07841 mL, 0.45 mmol) in dichloromethane (2 mL). The reaction mixture was stirred at 0° C. for 30 minutes. Then to the mixture at 0° C. was added a solution of (R)-4-(4-chlorobenzyl)-3-chloro-5-(pyrrolidin-2-yl)-4H-1,2,4-triazole HCl salt (50.05 mg, 0.15 mmol) and N,N-diisopropylethylamine (0.07841 mL, 0.45 mmol) in dichloromethane (2 mL) slowly. The resulting mixture was stirred 0° C. for 30 minutes, then at room temperature overnight. The reaction mixture was treated with sat. aqueous $NaHCO_3$ (10 mL) and brine, dried over $Na_2SO_4$, and concentrated in vacuo. Flash chromatography purification (Hex/EtOAc gradient, 10-100% EtOAc with 10% of MeOH) afforded the desired product as a brown oil (47 mg, 58.0%).

$^1$H NMR (300 MHz, $CDCl_3$) δ 2.04-2.14 (m, 4H), 2.16-2.22 (m, 1H), 2.61-2.63 (m, 1H), 3.27-3.34 (m, 1H), 3.50-3.54 (m, 1H), 4.18-4.23 (m, 1H), 4.25-4.31 (m, 1H), 4.53-4.55 (d, 1H), 4.92-4.97 (m, 2H), 5.29-5.35 (d, 1H), 5.64-5.69 (d, 1H), 7.04-7.07 (d, 3H), 7.11-7.14 (d, 1H), 7.29 (d, 1H), 7.34-7.36 (d, 2H). MS: calculated: 540.36, found ($MH^+$): 540.4.

Example 23

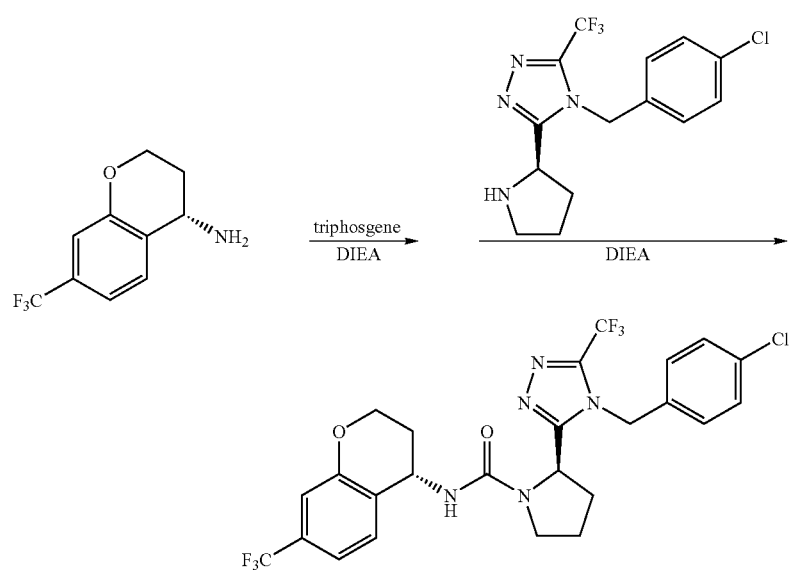

(R)-2-(4-(4-chlorobenzyl)-5-(trifluoromethyl)-4H-1,2,4-triazol-3-yl)-N—((S)-7-(trifluoromethyl)chroman-4-yl)pyrrolidine-1-carboxamide. To a stirring solution of triphosgene (14.87 mg, 0.05 mmol) in 8 mL of $CH_2Cl_2$ at 0° C. was added dropwise a mixed solution of (S)-7-(trifluoromethyl)chroman-4-amine (32.58 mg, 0.15 mmol) and N,N-diisopropylethylamine (0.07841 mL, 0.45 mmol) in dichloromethane (2 mL). The reaction mixture was stirred at 0° C. for 30 minutes. Then to the mixture at 0° C. was added a solution of the (R)-4-(4-chlorobenzyl)-3-(pyrrolidin-2-yl)-5-(trifluoromethyl)-4H-1,2,4-triazole HCl salt (55.09 mg, 0.15 mmol) and N,N-diisopropylethylamine (0.07841 mL, 0.45 mmol) in dichloromethane (2 mL) slowly. The resulting mixture was stirred 0° C. for 30 minutes, then at room temperature overnight. The reaction mixture was treated with sat. aqueous $NaHCO_3$ (10 mL) and brine, dried over $Na_2SO_4$, and concentrated in vacuo. Flash chromatography purification (Hex/EtOAc gradient, 10-100% EtOAc) afforded the desired product as white foam (62 mg, 72.0%).

¹H NMR (300 MHz, CDCl₃) δ 1.93-1.99 (m, 2H), 2.04-2.09 (m, 2H), 2.12-2.19 (m, 1H), 2.64-2.69 (m, 1H), 3.29-3.32 (m, 1H), 3.51-3.55 (m, 1H), 4.19-4.23 (m, 1H), 4.26-4.29 (m, 1H), 4.49-4.51 (d, 1H), 4.89-4.95 (m, 2H), 5.40-5.46 (d, 1H), 5.83-5.89 (d, 1H), 6.99-7.14 (m, 4H), 7.28-7.30 (d, 1H), 7.34-7.37 (d, 2H). MS: calculated: 573.92, found (MH⁺): 574.3.

Example 24

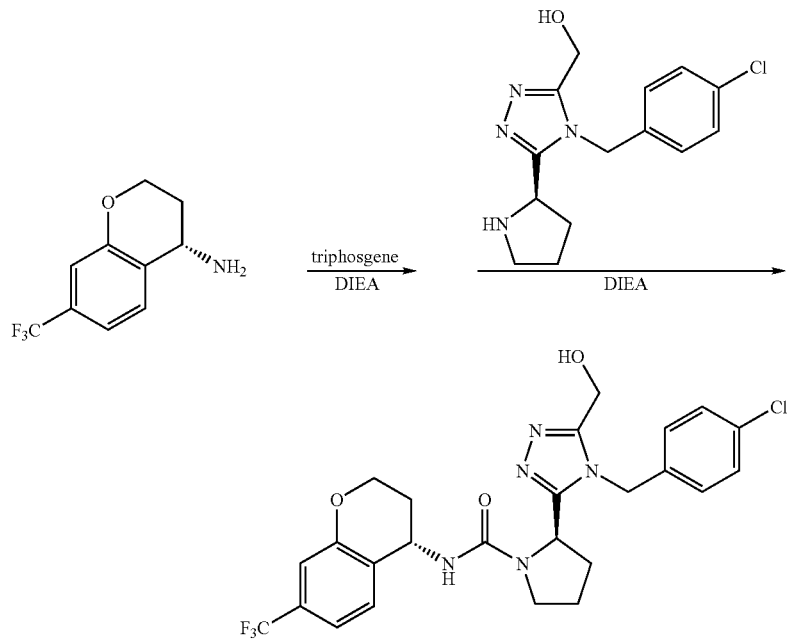

(R)-2-(4-(4-chlorobenzyl)-5-(hydroxymethyl)-4H-1,2,4-triazol-3-yl)-N—((S)-7-(trifluoromethyl)chroman-4-yl)pyrrolidine-1-carboxamide. To a stirring solution of triphosgene (14.87 mg, 0.05 mmol) in 8 mL of CH₂Cl₂ at 0° C. was added dropwise a mixed solution of (S)-7-(trifluoromethyl)chroman-4-amine (32.58 mg, 0.15 mmol) and N,N-diisopropylethylamine (0.07841 mL, 0.45 mmol) in dichloromethane (2 mL). The reaction mixture was stirred at 0° C. for 30 minutes. Then to the mixture at 0° C. was added a solution of the (R)-(4-(4-chlorobenzyl)-5-(pyrrolidin-2-yl)-4H-1,2,4-triazol-3-yl)methanol HCl salt (54.86 mg, 0.15 mmol) and N,N-diisopropylethylamine (0.07841 mL, 0.45 mmol) in dichloromethane (2 mL) slowly. The resulting mixture was stirred 0° C. for 30 minutes, then at room temperature overnight. The reaction mixture was treated with sat. aqueous NaHCO₃ (10 mL) and brine, dried over Na₂SO₄, and concentrated in vacuo. Flash chromatography purification (Hex/EtOAc gradient, 10-100% EtOAc with 10% MeOH) afforded the desired product as white solid (66 mg, 82.1%).

¹H NMR (300 MHz, CDCl₃) δ 1.88-1.94 (m, 2H), 2.00-2.10 (m, 2H), 2.12-2.19 (m, 1H), 2.50-2.57 (m, 1H), 3.26-3.33 (m, 1H), 3.50-3.57 (m, 1H), 4.17-4.29 (m, 2H), 4.54-4.57 (d, 1H), 4.73-4.74 (m, 2H), 4.92-4.96 (m, 2H), 5.47-5.64 (quartet, 2H), 7.05-7.11 (m, 4H), 7.24-7.28 (d, 1H), 7.30-7.33 (d, 2H). MS: calculated: 535.95, found (MH⁺): 536.2.

Example 25

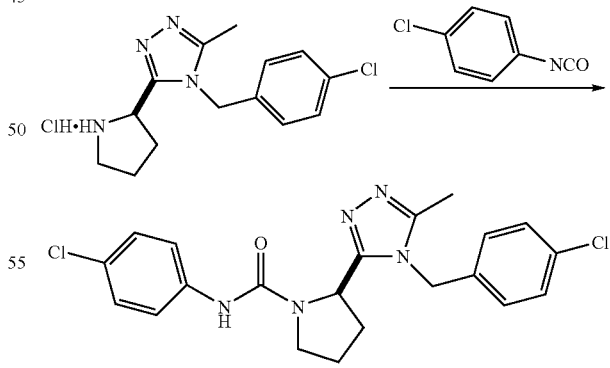

(R)-2-(4-(4-chlorobenzyl)-5-methyl-4H-1,2,4-triazol-3-yl)-N-(4-chlorophenyl)pyrrolidine-1-carboxamide. (R)-4-(4-chlorobenzyl)-3-methyl-5-(pyrrolidin-2-yl)-4H-1,2,4-triazole hydrochloride (58 mg, 0.2 mmol) was dissolved in dichloromethane (2 ml). 4-chlorophenyl isocyanate (0.031 ml, 0.2 mmol) and N,N-diisopropylethylamine-(0.050 ml) were added while stirring. The reaction mixture was stirred for 12 h then evaporated to dryness. Purification by silica gel column chromatography (methanol/dichloromethane gradient, 0-15% methanol) afforded the desired product as a white amorphous solid (75.1 mg, 87%).

¹H NMR (300 MHz, d-DMSO) δ 1.77 (m, 1H), 2.01 (m, 2H), 2.21 (m, 1H), 2.25 (s, 3H), 3.66 (m, 2H), 5.08 (m, 1H), 5.36 (dd, 2H), 7.16 (d, 1H), 7.25 (d, 1H), 7.42 (d, 1H), 7.48 (d, 1H). MS: calculated: 439.13, found (MH⁺): 429.11.

Example 26

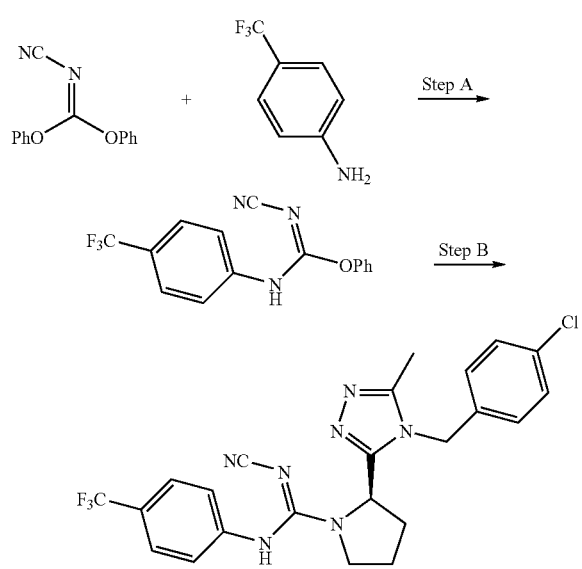

(R,E)-2-(4-(4-chlorobenzyl)-5-methyl-4H-1,2,4-triazol-3-yl)-N'-cyano-N-(4-(trifluoromethyl)phenyl) pyrrolidine-1-carboxamidine

Step A

Diphenyl cyanocarbonimidate (238 mg, 1.0 mmol) was dissolved in acetonitrile (2 ml). 4-(trifluoromethyl)aniline (0.116 ml, 1.0 mmol) was added and the mixture stirred at 85° C. for 16 h. The reaction mixture was evaporated and the residue purified by silica gel column chromatography (ethyl acetate/hexane gradient, 10-100% EtOAc with 10% of MeOH) to afford the desired product as a white amorphous solid (200 mg, 66%).

Step B

The purified product from Step A (61 mg, 0.2 mmol) (R)-4-(4-chlorobenzyl)-3-methyl-5-(pyrrolidin-2-yl)-4H-1,2,4-triazole hydrochloride (58 mg, 0.2 mmol) were dissolved in acetonitrile (1 ml) with N,N-diisopropylethylamine (0.050 ml). The mixture was stirred at 85° C. for 16 h. The reaction mixture was evaporated and the residue purified by silica gel column chromatography (ethyl acetate/hexane gradient, 10-100% EtOAc) to afford the desired product as a white amorphous solid (44.7 mg, 46%).

¹H NMR (300 MHz, d-DMSO) δ 1.67 (m, 1H), 1.92 (m, 1H), 2.10 (m, 2H), 2.22 (s, 3H), 3.61 (m, 2H), 4.11 (m, 2H), 5.31 (m, 1H), 7.15 (d, 1H), 7.25 (d, 1H), 7.39 (d, 1H), 7.65 (d, 1H), 9.08 (s, 1H). MS: calculated: 487.15, found (MH⁺): 488.4.

Example 27

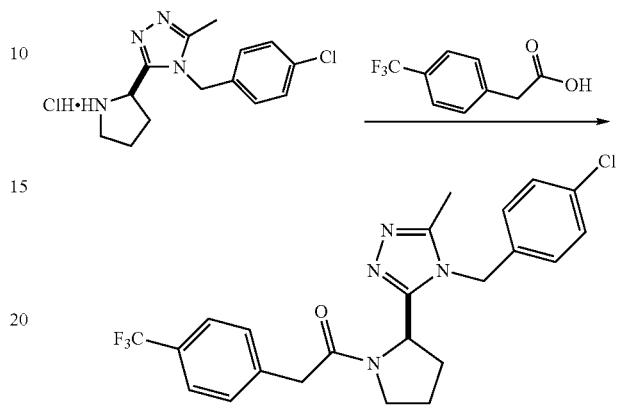

(R)-1-(2-(4-(4-chlorobenzyl)-5-methyl-4H-1,2,4-triazol-3-yl)pyrrolidin-1-yl)-2-(4-(trifluoromethyl)phenyl)ethanone. (R)-4-(4-chlorobenzyl)-3-methyl-5-(pyrrolidin-2-yl)-4H-1,2,4-triazole hydrochloride (50 mg, 0.8 mmol) was dissolved in dichloromethane (2 ml). HATU (75 mg, 0.19 mmol), (α,α,α-trifluoro-p-tolyl)acetic acid (37 mg, 0.18 mmol) and N,N-diisopropylethylamine (0.078 ml, 0.45 mmol) were added while stirring. The reaction mixture was stirred for 12 h then evaporated to dryness. Residue was taken up in EtOAc (20 ml) and washed with saturated solutions of NaHCO₃ and NaCl. Organics were dried (NaSO₄), filtered and concentrated. Purification by HPLC (water/acetonitrile gradient, 20% to 100% acetonitrile with 0.1% TFA) afforded the desired product as a white amorphous solid (76.3 mg, 91%).

¹H NMR (300 MHz, CDCl₃) δ 2.00 (m, 3H), 2.47 (m, 1H), 2.52 (s, 3H), 3.57 (m, 1H), 3.69 (m, 2H), 3.84 (m, 1H), 4.89 (m, 1H), 5.14 (d, 1H), 5.56 (d, 1H), 6.97 (d, 2H), 7.31 (m, 4H), 7.55 (d, 2H). MS: calculated: 462.14, found (MH⁺): 463.3.

Example 28

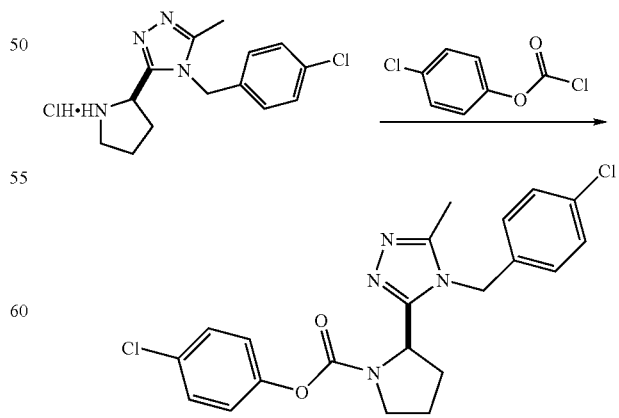

(R)-4-chlorophenyl-2-(4-(4-chlorobenzyl)-5-methyl-4H-1,2,4-triazol-3-yl)pyrrolidine-1-carboxylate. (R)-4-(4-chlorobenzyl)-3-methyl-5-(pyrrolidin-2-yl)-4H-1,2,4-triazole hydrochloride (50 mg, 0.18 mmol) was dissolved in dichloromethane (2 ml). 4-chlorophenyl chlorofornate (0.025 ml, 0.18 mmol) and N,N-diisopropylethylamine (0.078 ml, 0.45 mmol) were added while stirring. The reaction mixture was stirred for 12 h then evaporated to dryness. Purification by HPLC (water/acetonitrile gradient, 20% to 100% acetonitrile with 0.1% TFA) afforded the desired product as a white amorphous solid (43.8 mg, 56%).

$^1$H NMR (300 MHz, CDCl$_3$) δ 2.14 (m, 3H), 2.49 (m, 1H), 2.59 (s, 3H), 3.72 (m, 1H), 3.82 (m, 1H), 4.80 (m, 1H), 5.15 (d, 1H), 5.62 (d, 1H), 6.98 (m, 4H), 7.32 (m, 4H). MS: calculated: 430.10, found (MH$^+$): 431.3.

Example 29

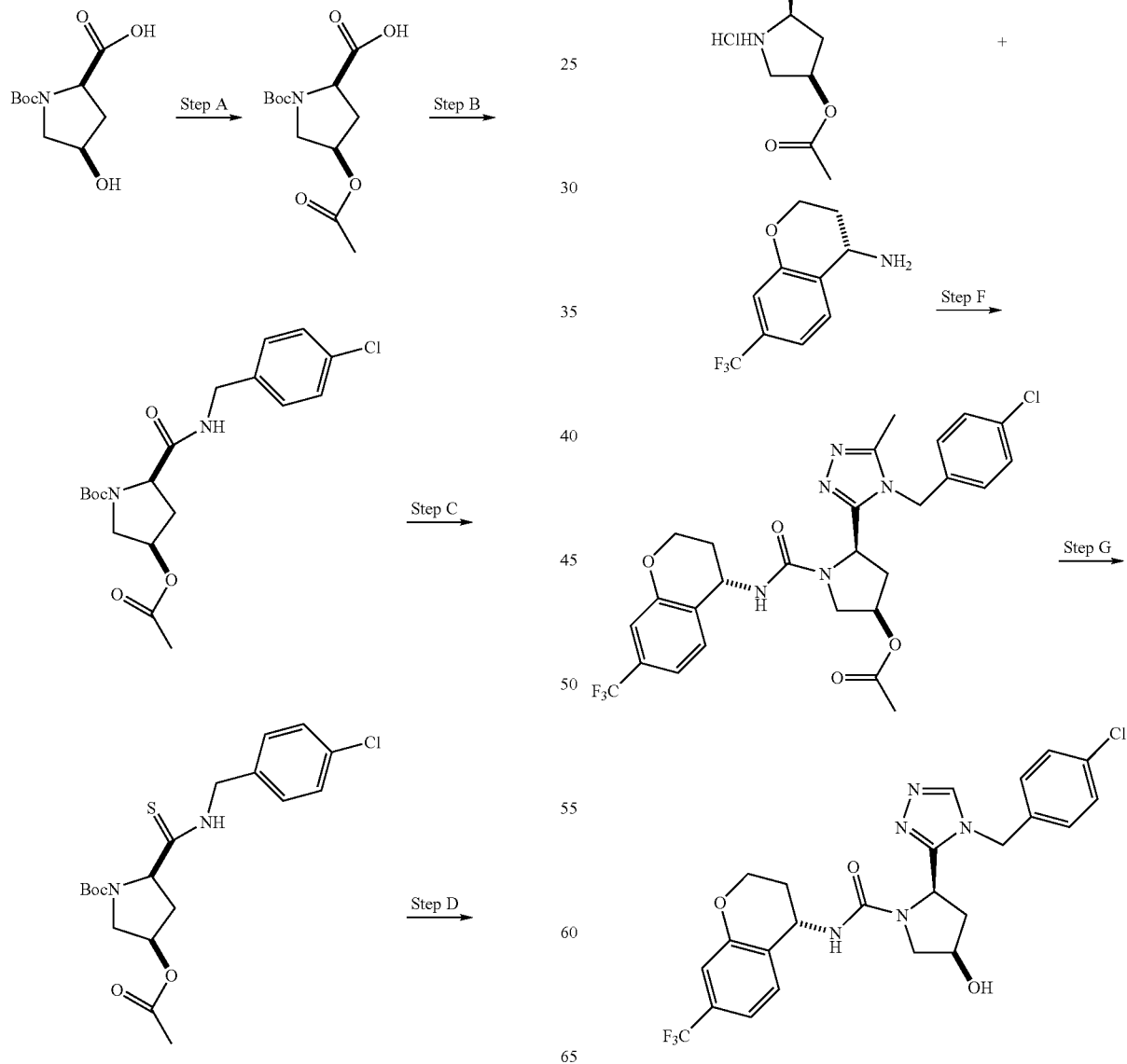

(2R,4R)-2-(4-(4-chlorobenzyl)-5-methyl-4H-1,2,4-triazol-3-yl)-4-hydroxy-N—((S)-7-(trifluoromethyl)chroman-4-yl)pyrrolidine-1-carboxamide Step A (2R,4R)-4-acetoxy-1-(tert-butoxycarbonyl)pyrrolidine-2-carboxylic acid. Acetic anhydride (20 ml, 216 mmol) was added to a stirring solution of N-t-Boc-cis-4-hydroxy-D-proline (5.0 g, 21.6 mmol) in pyridine (80 ml). The resulting mixture was stirred at ambient temperature for 16 h. The reaction mixture was evaporated and the residue azeotroped with pyridine (2×). The white foamy product obtained (5.9 g, 100%) was used without further purification in the next reaction. MS: calculated: 273.12, found (MH$^+$): 274.2, (MH$^+$-Boc), 174.1.

Step B (2R,4R)-tert-butyl-2-((4-chlorobenzyl)carbamoyl)-4-acetoxypyrrolidine-1-carboxylate. The crude product (2R,4R)-4-acetoxy-1-(tert-butoxycarbonyl)pyrrolidine-2-carboxylic acid from Step A (5.9 g, 21.6 mmol) was dissolved in methylene chloride (22 ml) and treated with EDC (4.5 g, 23.8 mmol) and HOBt (3.2 g, 23.8 mmmol). The mixture was stirred at r.t. for an hour before the addition of 4-chlorobenzylamine (2.9 ml, 23.8 mmol). The reaction mixture was stirred at ambient temperature for 16 h. The mixture was diluted with DCM (25 ml) and washed with NaHCO$_3$ (sat'd) and brine, dried (Na$_2$SO$_4$), filtered, evaporated and the residue purified by silica gel column chromatography (ethyl acetate/hexane gradient, 10-100% EtOAc) to afford the desired product as a white amorphous solid (6.5 g, 76% over two steps).

$^1$H NMR (300 MHz, CDCl$_3$) δ 1.45 (br s, 9H), 1.84 (br s, 3H), 2.02 (m, 2H), 3.49 (m, 1H), 3.63 (m, 1H), 4.43 (m, 3H), 5.21 (m, 1H), 6.90 (br s, 1H), 7.21 (d, 2H), 7.26 (d, 2H). MS: calculated: 396.15, found (MH$^+$): 397.2, (MH$^+$-Boc), 297.3.

Step C (2R,4R)-tert-butyl-2-((4-chlorobenzyl)carbamothioyl)-4-acetoxypyrrolidine-1-carboxylate. A mixture of purified (2R,4R)-tert-butyl-2-((4-chlorobenzyl)carbamoyl)-4-acetoxypyrrolidine-1-carboxylate from Step B (4.1 g, 10.3 mmol) and Lawesson's reagent (2.1 g, 5.15 mmol) in toluene (80 ml) was refluxed for 2 h under argon. The mixture was cooled to room temperature and then diluted with EtOAc (80 ml), treated with 1N NaOH (2×40 ml), dried over Na$_2$SO$_4$ and concentrated in vacuo. Flash chromatography purification (Hex/EtOAc gradient, 10-100% EtOAc) provided the desired product as a foamy white solid (1.8 g, 43%).

$^1$H NMR (300 MHz, CDCl$_3$) δ 1.39 (s, 9H), 1.83 (s, 3H), 2.59 (m, 2H), 3.53 (m, 1H), 3.67 (m, 1H), 4.70 (m, 1H), 4.83 (m, 1H), 5.02 (m, 1H), 5.23 (br s, 1H), 7.25 (d, 2H), 7.28 (d, 2H), 8.2 (br s, 1H). MS: calculated: 412.12, found (MH$^+$): 413.2, (MH$^+$-Boc), 313.1.

Step D (2R,4R)-tert-butyl-2-(4-(4-chlorobenzyl)-5-methyl-4H-1,2,4-triazol-3-yl)-4-acetoxypyrrolidine-1-carboxylate. To a mixture of (2R,4R)-tert-butyl-2-((4-chlorobenzyl)carbamothioyl)-4-acetoxypyrrolidine-1-carboxylate from Step C (1.6 g, 3.88 mmol) and acetic hydrazide (575 mg, 7.76 mmol) in acetonitrile (18 ml) was added mercury (II) acetate (1.85 g, 5.82 mmol). The reaction mixture was stirred at room temperature for 16 h. The mixture was filtered through a plug of celite and washed with acetonitrile. The combined filtrates were concentrated, the resulting residue taken up in EtOAc (200 ml), then washed with H$_2$O (75 ml), dried (Na$_2$SO$_4$), filtered and concentrated. Flash chromatography purification (Hex/EtOAc gradient, 10-100% EtOAc) provided the desired product MS: calculated: 434.17, found (MH$^+$): 435.3. .

Step E (3R,5R)-5-(4-(4-chlorobenzyl)-5-methyl-4H-1,2,4-triazol-3-yl)pyrrolin-3-yl acetate hydrochloride. (2R,4R)-tert-butyl-2-(4-(4-chlorobenzyl)-5-methyl-4H-1,2,4-triazol-3-yl)-4-acetoxypyrrolidine-1-carboxylate from Step D (1.15 g, 2.64 mmol) was treated with an ethanolic solution of hydrochloric acid (15 ml, 14 wt. % HCl in ethanol). The resultant mixture was stirred at room temperature for 2 h. The mixture was concentrated in vacuo, azeotroped with DCM (2×25 mL) and thoroughly dried under vacuum to afford the desired hydrochloride salt as a yellowish foamy solid (900 mg, 100%) which was used without further purification in the next reaction.

$^1$H NMR (300 MHz, CD$_3$OD) δ 2.19 (s, 3H), 2.41 (m, 1H), 2.75 (m, 1H), 2.82 (s, 3H), 3.74 (m, 2H), 4.72 (m, 1H), 5.34 (m, 1H), 5.72 (m, 2H), 7.43 (m, 2H), 7.63 (m, 2H). MS: calculated: 334.12, found (MH$^+$): 335.3.

Step F (3R,5R)-1-(((S)-7-(trifluoromethyl)chroman-4-yl)carbamoyl)-5-(4-(4-chlorobenzyl)-5-methyl-4H-1,2,4-triazol-3-yl)pyrrolidin-3-yl acetate. To a stirring solution of triphosgene (23 mg, 0.078 mmol) in dichloromethane (0.5 ml) was slowly added dropwise via syringe a premixed solution of (S)-7-(trifluoromethyl)chroman-4-amine (45 mg, 0.21 mmol) and N,N-diisopropylethylamine (0.073 ml, 0.42 mmol) dissolved in dichloromethane (0.8 ml). The reaction mixture was stirred at room temperature for 15 minutes. The isocyanate thereby generated was then treated dropwise with a solution of (3R,5R)-5-(4-(4-chlorobenzyl)-5-methyl-4H-1,2,4-triazol-3-yl)pyrrolidin-3-yl acetate hydrochloride from Step E (70 mg, 0.21 mmol) and N,N-diisopropylethylamine (0.073 ml, 0.42 mmol) dissolved in dichloromethane (0.8 ml). The reaction mixture was stirred at room temperature for 16 h. The reaction mixture was evaporated to dryness, diluted with EtOAc, washed with 10% aqueous KHSO$_4$, 5% aqueous NaHCO$_3$, and brine, dried (Na$_2$SO$_4$), filtered and concentrated to yield an oil (120 mg, 100%) which was used without further purification in the next reaction.

MS: calculated: 577.17, found (MH$^+$): 578.3.

Step G (2R,4R)-2-(4-(4-chlorobenzyl)-5-methyl-4H-1,2,4-triazol-3-yl)-4-hydroxy-N—((S)-7-(trifluoromethyl)chroman-4-yl)pyrrolidine-1-carboxamide. To a solution of crude (3R,5R)-1-(((S)-7-(trifluoromethyl)chroman-4-yl)carbamoyl)-5-(4-(4-chlorobenzyl)-5-methyl-4H-1,2,4-triazol-3-yl)pyrrolidin-3-yl acetate from Step F (120 mg, 0.21 mmol) in aqueous MeOH (2.0 ml, 1:1 water:MeOH) was added potassium carbonated (116 mg, 0.84 mmol). The reaction mixture was stirred at room temperature for 1 h. The reaction mixture was concentrated and the residue dissolved in EtOAc, washed with 1N HCl and then concentrated. Preparative HPLC purification provided the desired compound as a white fluffy solid (47 mg, 72% over 3 steps).

$^1$H NMR (300 MHz, CDCl$_3$) δ 1.99 (s, 1H), 2.09 (m, 3H), 2.23 (m, 1H), 2.47 (s, 3H), 3.30 (m, 1H), 3.75 (m, 1H), 4.20 (m, 2H), 4.69 (m, 1H), 4.87 (m, 1H), 5.10 (m, 1H), 5.24 (m, 1H), 5.26 (d, 1H), 5.64 (d, 1H), 7.03 (m, 4H), 7.17 (m, 1H), 7.37 (d, 2H). MS: calculated: 535.16, found (MH$^+$): 536.3.

Example 30

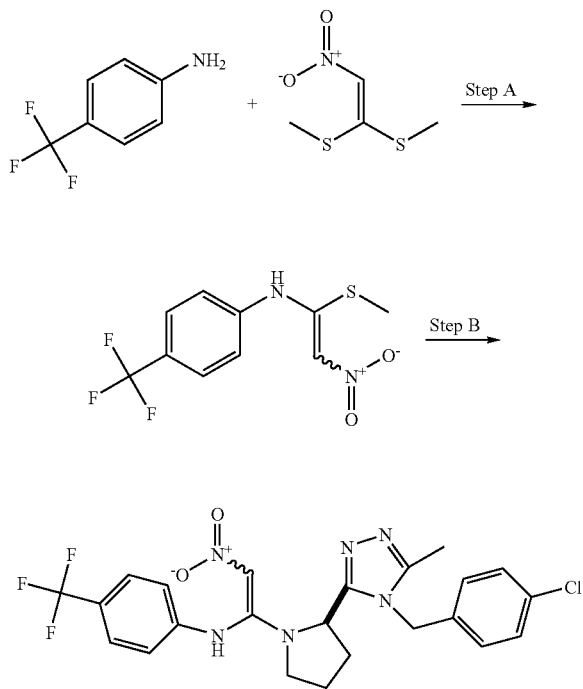

(R)—N-(1-(2-(4-(4-chlorobenzyl)-5-methyl-4H-1,2,4-triazol-3-yl)pyrrolidin-1-yl)-2-nitrovinyl)-4-(trifluoromethyl)benzenamine Step A To a stirred yellow suspension of 1,1-bis(methylthio)-2-nitroethylene (1.0 g, 6.05 mmol) in 10 mL of anhydrous EtOH was added 4-aminobenzotrifluoride (965 µL, 7.56 mmol). The resulting mixture was refluxed for 20 h. After the mixture was cooled to room temperature, the suspension was filtered, and the pale yellow precipitate was rinsed with 2.5 mL of MeOH to give 0.871 g (52%) of pale crystals of N-(1-(methylthio)-2-nitrovinyl)-4-(trifluoromethyl)benzenamide.

$^1$H NMR (300 MHz, CDCl$_3$) δ 2.40 (s, 3H), 6.69 (s, 1H), 7.43 (m, 2H), 7.68 (m, 2H). MS: calculated: 278.03, found (MH$^+$): 279.2.

Step B

The product from Step A (38 mg, 0.136 mmol), (R)-4-(4-chlorobenzyl)-3-methyl-5-(pyrrolidin-2-yl)-4H-1,2,4-triazole hydrochloride (39 mg, 0.124 mmol), and N,N-diisopropylethylamine (25 µL, 0.143 mmol) were dissolved in anhydrous EtOH (0.2 mL). The reaction mixture was heated at 90° C. overnight. The residue was purified with a Gilson preparative HPLC system to afford the desired product as the TFA salt (7.9 mg, 10.3%, brown oil).

$^1$H NMR (300 MHz, CDCl$_3$) δ 2.08 (m, 1H), 2.17-2.40 (m, 2H), 2.52 (m, 1H), 2.61 (s, 3H), 3.64 (m, 1H), 4.05 (m, 1H), 5.32-5.42 (m, 3H), 6.73-6.82 (m, 2H), 7.17 (d, 2H), 7.34 (d, 1H), 7.48-7.57 (m, 1H), 7.62 (d, 1H), 7.72-7.82 (m, 1H). MS: calculated: 506.14, found (MH$^+$): 507.4.

Example 31

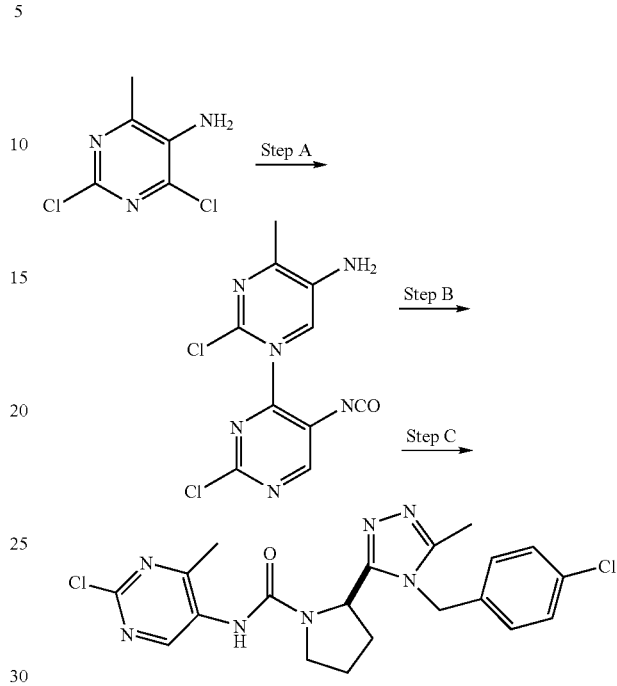

2-[4-(4-chloro-benzyl)-5-methyl-4H-[1,2,4]triazol-3-yl]-pyrrolidine-1-carboxylic acid (2-chloro-4-methyl-pyrimidin-5-yl)-amide Step A 2,4-Dichloro-6-methylpyrimidin-5-amine (1.0 g, 5.62 mmol) was dissolved in anhydrous EtOH (3.5 mL) and H$_2$O (7.0 mL). MgO (1.40 g, 34.74 mmol) and 10% Pd/C (35 mg) were added to the reaction mixture which was hydrogenated at 1 atm, at room temperature, overnight. The reaction mixture was filtered and concentrated. The residue was purified by silica gel column chromatography (MeOH/CH$_2$Cl$_2$ gradient, 0-15% MeOH) to afford 2-chloro-4-methylpyrimidin-5-amine as light pink solid (0.16 g, 20%).

$^1$H NMR (300 MHz, CD$_3$OD) 2.36 (s, 3H), 7.95 (s, 1H). MS: calculated: 143.03, found (MH$^+$): 144.0.

Step B

The purified product from Step A (20.6 mg, 0.143 mmol) was dissolved in anhydrous THF (0.59 mL), N,N-diisopropylethylamine (34 µL, 0.194 mmol) was added to the reaction mixture, followed by triphosgene (14.4 mg, 0.0485 mmol). The reaction mixture was stirred for 10 min to afford the desired product, which was used without further purification.

Step C (R)-4-(4-chlorobenzyl)-3-methyl-5-(pyrrolidin-2-yl)-4H-1,2,4-triazole hydrochloride (50 mg, 0.16 mmol) was dissolved in CH$_2$Cl$_2$ (0.86 ml) with N,N-diisopropylethylamine (76 µL, 0.434 mmol). The solution was added to the material from Step B, then stirred for 10 min. The reaction mixture was evaporated and the residue purified by silica gel column chromatography (MeOH/CH$_2$Cl$_2$ gradient, 0-15% MeOH) to afford the desired product as a white amorphous solid (37.5 mg, 59%).

$^1$H NMR (300 MHz, CDCl$_3$) δ 2.19 (m, 3H), 2.42 (s, 3H), 2.52 (s, 3H), 2.70 (m, 1H), 3.72 (q, 1H), 3.90 (m, 1H), 5.10 (t,

1H), 5.41 (dd, 2H), 6.74 (s, 1H), 7.03 (d, 2H), 7.43 (d, 2H), 8.80 (s, 1H). MS: calculated: 445.12, found (MH⁺): 446.1.

Example 32

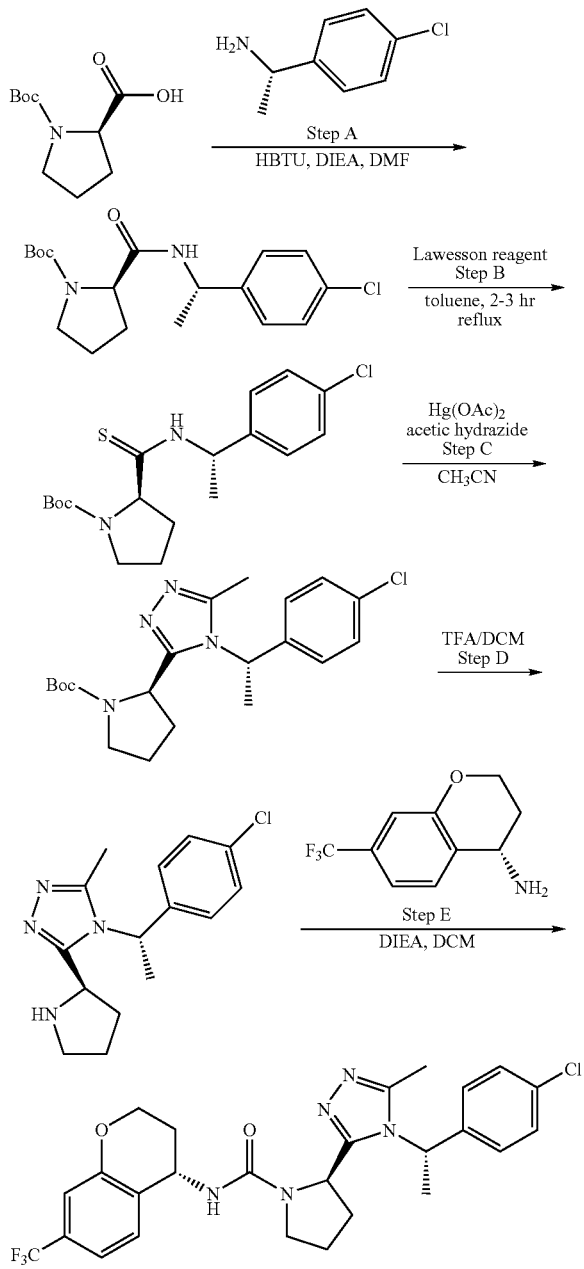

Step A (R)-tert-butyl 2-(((S)-1-(4-chlorophenyl)ethyl)carbamoyl)pyrrolidine-1-carboxylate. Boc-D-Proline (4.3 g, 20 mmol) was dissolved in DMF (100 ml). Then (S)-4-Chloro-α-methybenzylamine (3 ml, 22 mmol) and HBTU (7.58 g, 20 mmol), DIEA (6.96 ml, 40 mmol) were added while stirring. The reaction mixture was stirred overnight. The reaction mixture was diluted with EtOAc (100 ml), washed with 1N HCl (2×50 ml), sat. aq. NaHCO₃ (2×50 ml) and brine, dried over Na₂SO₄, and concentrated in vacuo. The crude desired product as a white solid (6 g, 85.7%) directly used for next step.

$^1$H NMR (300 MHz, CDCl₃) δ 1.40 (s, 9H), 1.55 (m, 2H), 1.80 (m, 3H), 2.20 (m, 1H), 2.25 (m, 1H), 3.20-3.42 (m, 2H), 4.22 (m, 1H), 5.01 (m, 1H), 7.07 (d, 2H), 7.25 (d, 2H).

Step B (R)-tert-butyl 2-(((S)-1-(4-chlorophenyl)ethyl)carbamothioyl)pyrrolidine-1-carboxylate. A mixture the product of Step A (3 g, 8.5 mmol) and Lawesson's reagent (1.7 g, 4.25 mmol) in toluene (100 ml) was refluxed for 2 h. The mixture was cooled to room temperature and then was diluted with EtOAc (100 ml), washed with 1N NaOH (2×50 ml), dried over Na₂SO₄, and concentrated in vacuo. Flash chromatography purification (DCM/MeOH gradient, 0-15% MeOH) provided the desired product as a white solid (2.2 g, 71%)

$^1$H NMR (300 MHz, CDCl₃): δ 1.45 (m, 2H), 1.49 (s, 9H), 1.65 (m, 3H), 2.0 (m, 2H), 3.45 (m, 2H), 4.80 (m, 1H), 5.81 (m, 1H), 7.35 (d, 2H), 7.45 (d, 2H). MS: calculated: 368.13 found (MH⁺): 269.0 (M+−100)

Step C (R)-tert-butyl 2-(4-((S)-1-(4-chlorophenyl)ethyl)-5-methyl-4H-1,2,4-triazol-3-yl)pyrrolidine-1-carboxylate. To a mixture of the product of Step B (1.7 g, 4.6 mmol) and acetic hydrazide (0.76 g, 9.2 mmol) in 30 ml acetonitile was added mercury (II) acetate (2.2 g, 6.9 mmol) and the mixture was stirred at room temperature for overnight. The mixture was filtered over a Celite-fritted funnel and washed with more acetonitrile. The filtrate was concentrated in vacuo. Run wash column yield the desired product containing minor impurities (1.3 g, 72%), was used in the next step without further purification.

(300 MHz, CDCl₃): δ 1.45 (s, 9H), 1.51-1.65 (m, 2H), 1.95 (d, 2H), 2.10 (m, 2H) 2.39 (s, 3H), 3.40 (m, 2H), 4.82 (m, 1H), 5.61 (m, 1H), 7.15 (d, 2H), 7.30 (d, 2H). MS: calculated: 390.18. Found (MH⁺): 291.2

Step D 4-((S)-1-(4-chlorophenyl)ethyl)-3-methyl-5-((R)-pyrrolidin-2-yl)-4H-1,2,4-triazole. A solution of the Boc-protected triazole product of Step C (1 g) in 40 ml of 40% TFA/DCM was stirred at room temperature for 4 h. The mixture was concentrated in vacuo and used directly as the TFA salt in the next step. MS: calculated: 290.13. Found (MH⁺): 291.3

Step E (R)-2-(4-((S)-1-(4-chlorophenyl)ethyl)-5-methyl-4H-1,2,4-triazol-3-yl)-N-((S)—7-(trifluoromethyl)-3,4-dihydro-2H-chromen-4-yl)pyrrolidine-1-carboxamide To a stirring solution of triphosgene (18 mg, 0.06 mmol) in dichloromethane (3 ml) was slowly added dropwise via syringe a premixed solution of (S)-7-(trifluoromethyl)chroman-4-amine (39 mg, 0.18 mmol) and N,N-diisopropylethylamine (0.069 ml) dissolved in dichloromethane (3 ml). The reaction mixture was stirred at room temperature for 30 minutes. The isocyanate thereby generated was then treated dropwise with a solution of 4-((S)-1-(4-chloropheny)ethyl)-3-methyl-5-((R)-pyrrolidine-2-yl)-4H-1,2,4-triazole from Step D (52 mg, 0.18 mmol) and N,N-diisopropylethylamine (0.067 ml, 0.4 mmol) dissolved in dichloromethane (5 ml). The reaction mixture was stirred at room temperature for 16 h. The reaction mixture was evaporated to dryness, diluted with EtOAc, washed with 5% aqueous NaHCO₃ and brine, dried (Na₂SO₄), filtered and concentrated. Purification by preparative HPLC yielded the desired product as a clear oil (21 mg, 22%).

$^1$H NMR (300 MHz, d-CDCl₃) δ 1.51-1.62 (m, 2H), 2.14 (d, 2H), 2.21 (m, 2H), 2.29 (s, 3H), 2.32-2.43 (m, 2H), 3.42 (m, 2H), 3.61 (m, 1H), 3.80 (m, 1H), 4.40 (m, 2H), 5.19 (m,

1H), 5.42 (m, 1H), 7.12 (s, 1H), 7.22 (d, 2H), 7.40 (d, 2H), 7.48 (d, 2H), 7.59 (d, 2H). MS: calculated: 533.18. Found (MH+): 534.3.

Section B—1,2,4-Triazoles

Example 33

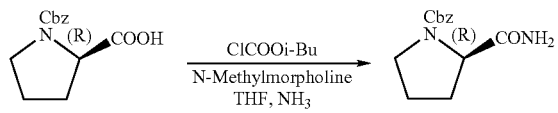

(R)-Benzyl 2-carbamoylpyrrolidine-1-carboxylate. A solution of the carboxylic acid (3.00 g, 12.03 mmol) and N-methylmorpholine (1.21 g, 12.03 mmol) in 40 mL of dry THF was cooled to 0° C. and isobutyl chloroformate (1.643 g, 12.03 mmol) was added dropwise. After 5 min, ammonia gas was passed through the reaction mixture for 15 min and the reaction mixture was stirred overnight at RT. After filtration, the solvent was evaporated and the residue was partitioned between water and EtOAc. The EtOAc layer was successively washed with 1 N HCl, water, sat. NaHCO$_3$, water and brine. After evaporation of the organic layer, the residue was purified by chromatography (silica/hexane:EtOAc (1:4)→EtOAc→EtOAc:methanol (95:5)) to provide 1.56 g of the desired amide.

$^1$H NMR (300 MHz, CDCl$_3$): δ 7.40-7.20 (m, 5H), 6.7 (bs) and 5.8-6.2 (bm) combined 2H, 5.15 (dod, 2H), 4.30 (bs, 1H), 3.60-3.35 (bm, 2H), 2.40-1.80 (m, 4H).

Example 34

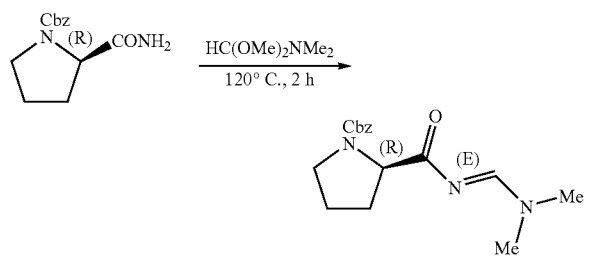

(R)-Benzyl 2-(((dimethylamino)methylene)carbamoyl) pyrrolidine-1-carboxylate. A solution of the amide from Example 33 (1.56 g, 6.28 mmol) in 10 mL of dimethylformamide dimethyl acetal was heated to 120° C. for 2 h. After cooling, the solvent was evaporated under high vacuum and the residue was taken to the next step without further purification.

$^1$H NMR (300 MHz, CDCl$_3$): δ 8.40 (s) and 8.15 (s) combined 1H, 7.35-7.15 (m, 5H), 5.15-4.95 (m, 2H), 4.45-4.30 (m, 1H), 3.65-3.35 (m, 2H), 3.05-2.85 (m, 6H), 2.30-2.10 (m, 1H), 2.10-1.70 (m, 3H).

Example 35

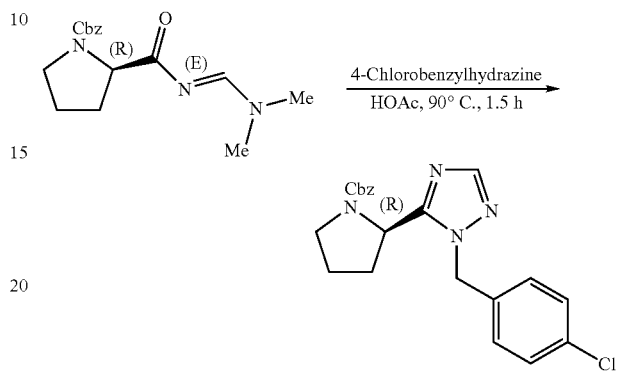

(R)-Benzyl 2-(2-(4-chlorobenzyl)-2H-1,2,4-triazol-3-yl) pyrrolidine-1-carboxylate. A solution of the compound from Example 34 and 4-chlorobenzyl-hydrazine acetate (1.9 g, 8.82 mmol) in 15 mL of HOAc was heated to 90° C. for 1.5 h. After cooling, the reaction mixture was diluted with water and extracted with EtOAc. The EtOAc layer was washed with sat. NaHCO$_3$ followed by water and brine. Evaporation of the solvent and chromatography (silica/hexane:EtOAc (1:1→40:60→20:80)) gave 2.1 g of the desired triazole. $^1$H NMR (300 MHz, CDCl$_3$): δ 7.90 (s, 1H), 7.40-6.80 (m, 9H), 5.50 (dod, 1H), 5.20-4.75 (m, 4H), 3.80-3.45 (m, 2H), 2.45-2.10 (m, 1H), 2.10-1.80 (m, 3H).

Example 36

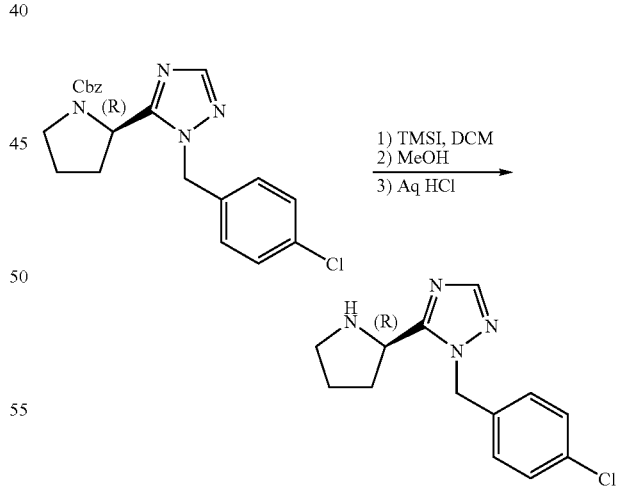

(R)-1-(4-Chlorobenzyl)-5-(pyrrolidin-2-yl)-1H-1,2,4-triazole. A solution of the cbz-derivative product of Example 35 (2.1 g, 5.29 mmol) in dry DCM (30 mL) was cooled on an ice bath and Me$_3$SiI (1.48 g, 7.4 mmol) was added dropwise. The reaction mixture was stirred at RT for 1 h and 5 mL of methanol was added. After 15 min at RT, the solvent was removed in vacuo. The residue was taken in 1 N HCl and washed 3 times with ether. The aqueous layer was basified to pH 9 with K$_2$CO$_3$ and after saturation with solid NaCl, the aqueous layer was repeatedly extracted with DCM. Evaporation of the DCM layer after drying (K$_2$CO$_3$) gave 1.05 g of the desired amine.

$^1$H NMR (300 MHz, CDCl$_3$): δ 7.76 (s, 1H), 7.22 (d, J=8.7 Hz, 2H), 7.07 (d, J=8.7 Hz, 2H), 5.36 (s, 2H), 4.18 (dod, J1=6 Hz, J2=6 Hz, 1H), 3.15-3.00 (m, 1H), 2.95-2.80 (m, 1H), 2.15 (bs, 1H), 2.05-1.65 (m, 4H).

Example 37

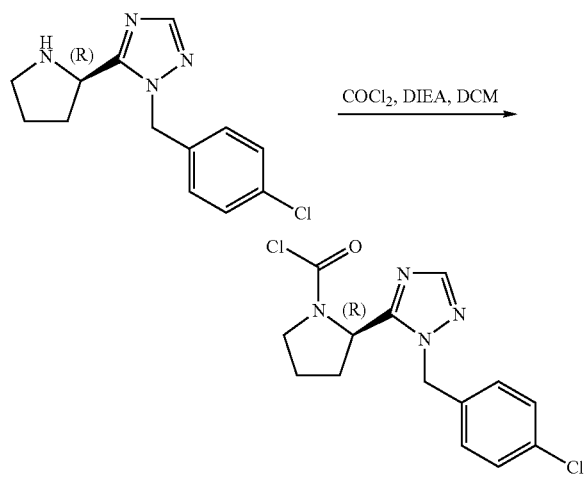

(R)-2-(2-(4-Chlorobenzyl)-2H-1,2,4-triazol-3-yl)pyrrolidine-1-carbonyl chloride. A solution of (R)-1-(4-chlorobenzyl)-5-(pyrrolidin-2-yl)-1H-1,2,4-triazole (216 mg, 0.82 mmol) and DIEA (233 mg, 1.90 mmol) in 5 mL of dry DCM was cooled to −20° C. under Ar, and a solution of phosgene (0.89 mL of 20% solution in toluene, 0.89 mmol) was added. The reaction mixture was stirred at RT for 2.5 days and the solvent was evaporated in vacuo. The residue was purified by chromatography (silica gel, hexane:EtOAc (1:1)) to give 202 mg of the desired product.

$^1$H NMR (300 MHz, CDCl$_3$): δ 7.86 (s) and 7.84 (s) combined 1H, 7.29 (d, J=8.4 Hz, 2H), 7.10 (d, J=8.4 Hz, 2H), 5.44 (s) and 5.34 (q) combined 2H, 5.11-5.07 (m) and 4.99-4.96 (m) combined 1H, 3.95-3.55 (m, 2H), 2.60-1.90 (m, 4H).

Example 38

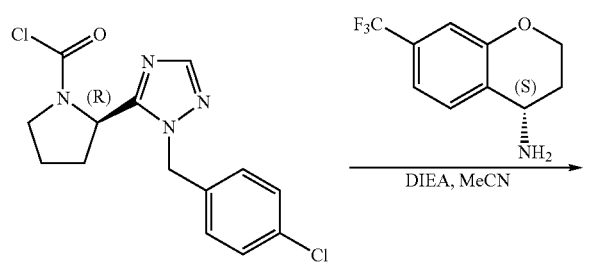

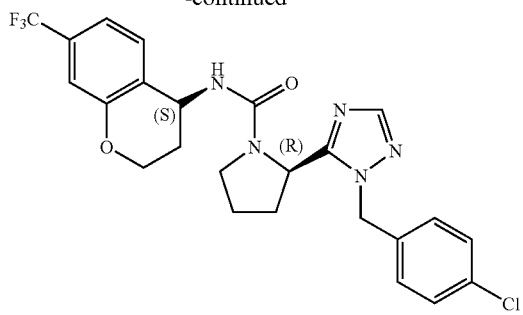

(R)-2-(2-(4-Chlorobenzyl)-2H-1,2,4-triazol-3-yl)-N—((S)-7-(trifluoromethyl)chroman-4-yl)pyrrolidine-1-carboxamide. A solution of (R)-1-(4-chlorobenzyl)-5-(1-chlorocarbonylpyrrolidin-2-yl)-1H-1,2,4-triazole (60 mg), (S)-4-amino-7-trifluoromethylchroman and DIEA in dry MeCN was stirred overnight at RT. The solvent was removed and the residue was partitioned between water and EtOAc. The EtOAc layer was washed with water and evaporated after drying over Na$_2$SO$_4$. The residue was purified by chromatography (silica gel, hexane:EtOAc (1:1)→EtOAc) to give 40 mg of the desired product.

$^1$H NMR (300 MHz, CDCl$_3$): δ 7.87 (s, 1H), 7.34-7.06 (m, 7H), 5.71 (d, J=15.6 Hz, 1H), 5.52 (d, J=15.6 Hz, 1H), 5.15-5.11 (m, 1H), 4.99 (q, J=6 Hz, 1H), 4.50 (d, 1H), 4.35-4.15 (m, 2H), 3.60-3.45 (m, 1H), 3.40-3.25 (m, 1H), 2.65-2.45 (m, 1H), 2.25-1.80 (m, 5H). MS (ESI$^+$) m/z 506 (M+H$^+$).

Example 39

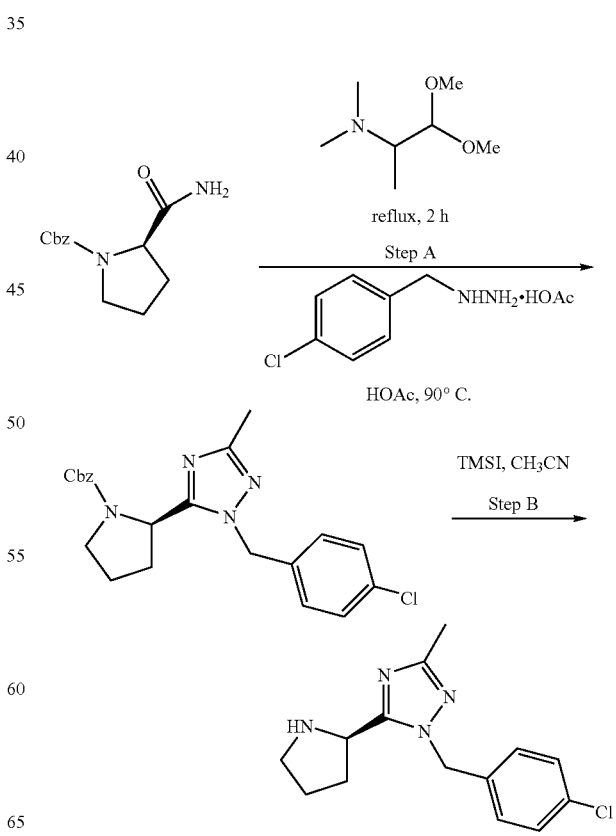

Step A

Preparation of R-benzyl 2-(2-(4-chlorobenzyl)-5-methyl-2H-1,2,4-triazol-3-yl)pyrrolidine-1-carboxylate (R)-Benzyl 2-carbamoylpyrrolidine-1-carboxylate (2.08 g, 8.4 mmol) and N,N-dimethylacetamide dimethylacetal (15 ml) were combined in a round bottom flask and then heated at 120° C. for 2 h. The reaction mixture was concentrated on a rotary evaporator and the residue obtained was dissolved in glacial HOAc (5 ml) and treated with 4-chlorobenzyl hydrazine salt (749 mg, 3.5 mmol), prepared as outlined in the procedure by R. Mornet et al., J Heterocyclic Chem. 29, 1992, 1561. The reaction mixture was heated at 90° C. for 1.5 h, cooled to rt, diluted with $H_2O$ and extracted with EtOAc. The ethyl acetate layer was washed with saturated aqueous $NaHCO_3$ solution, $H_2O$ and brine, then dried over $MgSO_4$. After evaporation of the solvent, the resulting residue was purified by flash column chromatography over silica gel using a gradient of 50% EtOAc-80% EtOAc in hexanes as eluent to give the desired product (2.72 g, 79% yield) as a white solid. Exact mass [MH]$^+$ (Found: 411).

Step B (R)-1-(4-chlorobenzyl)-3-methyl-5-(pyrrolidin-2-yl)-1H-1,2,4-triazole: TMSI (1.3 ml, 9.0 mmol) was added to a solution of the product from Step A (2.65 g, 6.4 mmol) in dry $CH_2Cl_2$ (35 ml) at 0° C. The reaction mixture was stirred at rt for 1 h and then MeOH (6 ml) was added to the reaction mixture. After 15 min at rt, the mixture was concentrated on a rotary evaporator. The resulting light orange residue was diluted with 1 N HCl (15 ml) and washed with $Et_2O$ (3×10 ml). The aqueous layer was cooled to 0° C. and the pH was adjusted to 10-12 using 50% NaOH solution. The aqueous layer was saturated with solid $K_2CO_3$ and NaCl and then extracted with $CHCl_3$ (3×40 ml). The organic layers were combined, dried over anhydrous $K_2CO_3$, and concentrated in vacuo to afford the desired amine as a light yellow oil (132 mg, 31% yield) which was used without further purification.

$^1$H NMR (300 MHz, CDCl$_3$) δ 7.25 7.23 (d, 2H), 7.07-7.03 (d, 2H), 5.36 (s, 2H), 4.09-4.05 (t, 3H), 3.09-3.04 (m, 1H), 2.87-2.81 (m, 1H), 2.28-2.25 (s, 3H), 2.01-1.75 (br m, 4H); Exact mass [MH]$^+$ (Found: 277).

Example 40

(R)-2-(2-(4-chlorobenzyl)-5-methyl-2H-1,2,4-triazol-3-yl)-N—((S)-7-(trifluoromethyl)-3,4-dihydro-2H-chromen-4-yl)pyrrolidine-1-carboxamide. To a stirring solution of triphosgene (18 mg, 0.06 mmol) in dichloromethane (3 ml) was slowly added dropwise via syringe a premixed solution of (S)-7-(trifluoromethyl)chroman-4-amine (39 mg, 0.18 mmol) and N,N-diisopropylethylamine (0.069 ml) dissolved in dichloromethane (3 ml). The reaction mixture was stirred at room temperature for 30 minutes. The isocyanate thereby generated was then treated dropwise with a solution of (R)-1-(4-chlorobenzyl)-3-methyl-5-(pyrrolidin-2-yl)-1H-1,2,4-triazole (52 mg, 0.18 mmol) and N,N-diisopropylethylamine (0.067 ml, 0.4 mmol) dissolved in dichloromethane (5 ml). The reaction mixture was stirred at room temperature for 16 h. The reaction mixture was evaporated to dryness, diluted with EtOAc, washed with 5% aqueous $NaHCO_3$ and brine, dried ($Na_2SO_4$), filtered and concentrated. Purification by preparative HPLC yielded a clear oil (14 mg, 15%)

$^1$H NMR (300 MHz, d-CDCl$_3$) δ 1.50 (m, 2H), 1.80-2.20 (m, 4H), 2.42 (s, 3H), 3.30-3.42 (m, 2H), 3.88 (m, 2H), 4.25 (m, 1H), 4.95 (m, 1H), 5.40 (s, 2H), 7.01 (s, 1H), 7.10 (m, 1H), 7.15 (m, 1H), 7.26 (d, 2H). 7.35 (d, 2H). MS: calculated: 519.16, found (MH$^+$): 520.0

Section C—Tetrazole Synthesis

Example 41

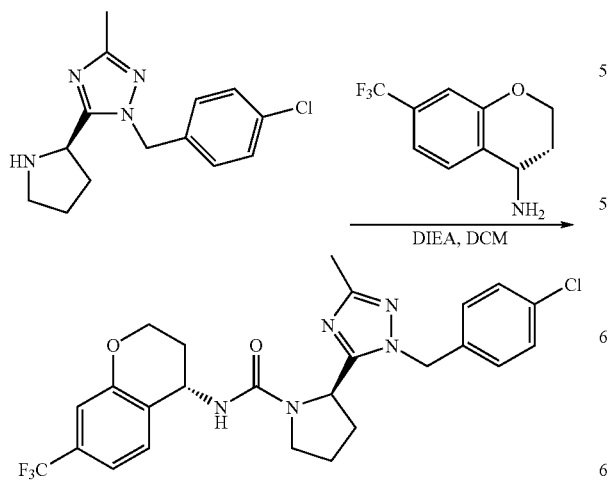

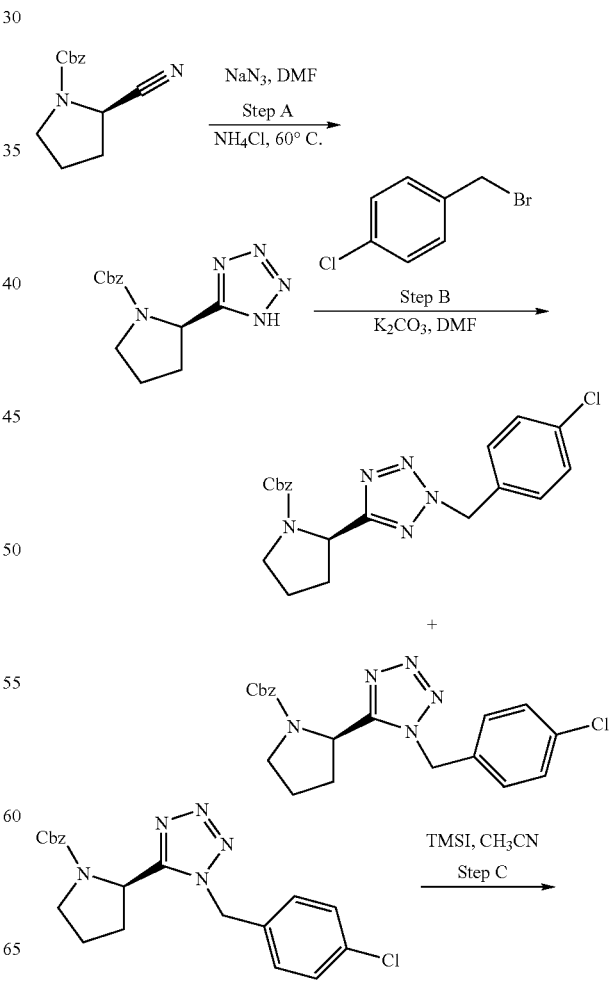

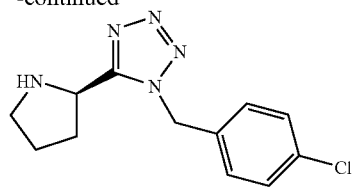

Step A:

(R)-benzyl 2-(1H-tetrazol-5-yl)pyrrolidine-1-carboxylate: A solution of the product from Example 43, Step B (1.60 g, 6.9 mmol) in dry DMF (50 ml) was treated with NH$_4$Cl (410 mg, 7.6 mmol) followed by NaN$_3$ (474 mg, 7.3 mmol) and the resulting suspension was heated at 90° C. for 16 h and then poured into a solution of 10% citric acid and crushed ice. The resulting aqueous solution was extracted with EtOAc (2×50 ml). The combined organic layers were washed with brine, dried over MgSO$_4$, and concentrated on a rotary evaporator to afford the desired tetrazole (1.90 g, 100% yield) as a light yellow oil. This compound was used in the next step without further purification. [MH]$^+$=274.

Step B:

(R)-benzyl 2-(1-(4-chlorobenzyl)-1H-tetrazol-5-yl)pyrrolidine-1-carboxylate and (R)-benzyl 2-(1-(4-chlorobenzyl)-2H-tetrazol-5-yl)pyrrolidine-1-carboxylate: The crude oil from step A was dissolved in dry DMF (13 ml) and treated with K$_2$CO$_3$ (3.15 g, 22.8 mmol) followed by the addition of 4-chlorobenzyl bromide (3.13 g, 15.2 mmol). The reaction mixture was stirred at rt for 1 h and then diluted with 50 ml of H$_2$O. The resulting aqueous mixture was extracted with EtOAc (2×50 ml). The organic layers were combined, dried over MgSO$_4$, and concentrated on a rotary evaporator to give crude residue. The crude residue was purified by flash column chromatography over silica gel using a gradient of 0%-60% EtOAc in hexanes as eluent, affording the two regioisomers ([MH]$^+$=268) and ([MH]$^+$=268) as white solids in 64% overall yield.

Step C:

(R)-1-(4-chlorobenzyl)-5-(pyrrolidin-2-yl)-1H-tetrazole: TMSI (900 µl, 6.36 mmol) was added to a solution of the product from step B (633 mg, 1.59 mmol) in dry CH$_3$CN (5 ml) at rt. The reaction mixture was stirred at rt for 30 min. and then concentrated on a rotary evaporator. The resulting dark orange residue was diluted with 2 N HCl (10 ml) and washed with Et$_2$O (3×10 ml). A solid that separated was collected by filtration to afford (314 mg, 66% yield, white solid) as the hydrochloride salt. The aqueous layer was cooled to 0° C. and the pH was adjusted to 10-12 using 50% NaOH solution. The aqueous layer was saturated with solid K$_2$CO$_3$ and NaCl and then extracted with CHCl$_3$ (3×40 ml). The organic layers were combined, dried over anhydrous K$_2$CO$_3$, and concentrated in vacuo to afford the desired amine as a light yellow oil (132 mg, 31% yield). [MH]$^+$=264.

Example 42

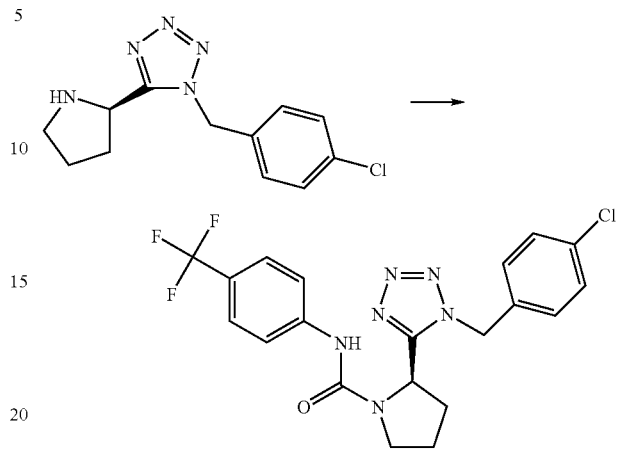

(R)-2-(1-(4-chlorobenzyl)-1H-tetrazol-5-yl)-N-(4-(trifluoromethyl)phenyl)pyrrolidine-1-carboxylate: The amine from Example 40 (77.5 mg, 0.26 mmol) was treated with DIEA (100 µl, 0.57 mmol) and 1-isocyanato-4-(trifluoromethyl)benzene (104 mg, 0.52 mmol) to give after purification the desired urea (109 mg, 91% yield) as a white powder.

$^1$H NMR (300 MHz, CDCl$_3$) δ 7.60-7.40 (m, 4H), 7.29-7.26 (d, 2H), 7.22-7.08 (d, 2H), 6.44 (br s, 1H), 5.82 (s, 2H), 5.20 (dd, 1H), 3.75 (m, 1H), 3.55 (m, 1H), 2.70 (m, 1H), 2.25-1.80 (br m, 3H); Exact mass [M+H]$^+$ (found: 451).

Example 43

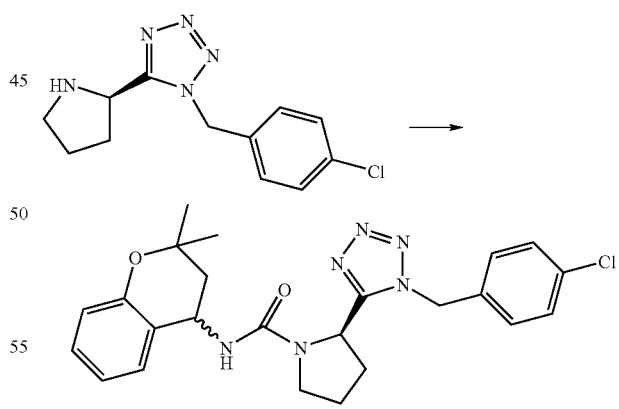

(2R)-2-(1-(4-chlorobenzyl)-1H-tetrazol-5-yl)-N-(2,2-dimethylchroman-4-yl)pyrrolidine-1-carboxylate: The amine from Example 40 (84 mg, 0.28 mmol) was treated with DIEA (146 µl, 0.84 mmol) and 4-isocyanato-2,2-dimethylchroman (100 mg, 0.56 mmol) to give after purification the desired urea (115 mg, 88% yield) as a white powder. $^1$H NMR (300 MHz, CDCl$_3$) δ 7.36-7.14 (m, 6H), 6.85 (dd, 1H), 6.75 (dd, 1H), 5.85 (s, 2H), 5.23-5.14 (m, 1H), 5.1-4.8 (m, 1H), 4.50-4.40 (dd, 1H), 3.50 (m, 1H), 3.35 (m, 1H), 2.25-1.90 (m, 4H), 1.80-1.50 (m, 1H), 1.40 (d, 3H), 1.29 (d, 3H); Exact mass [M+H]$^+$ (found: 467).

Section D—Imidazole Synthesis

Example 44

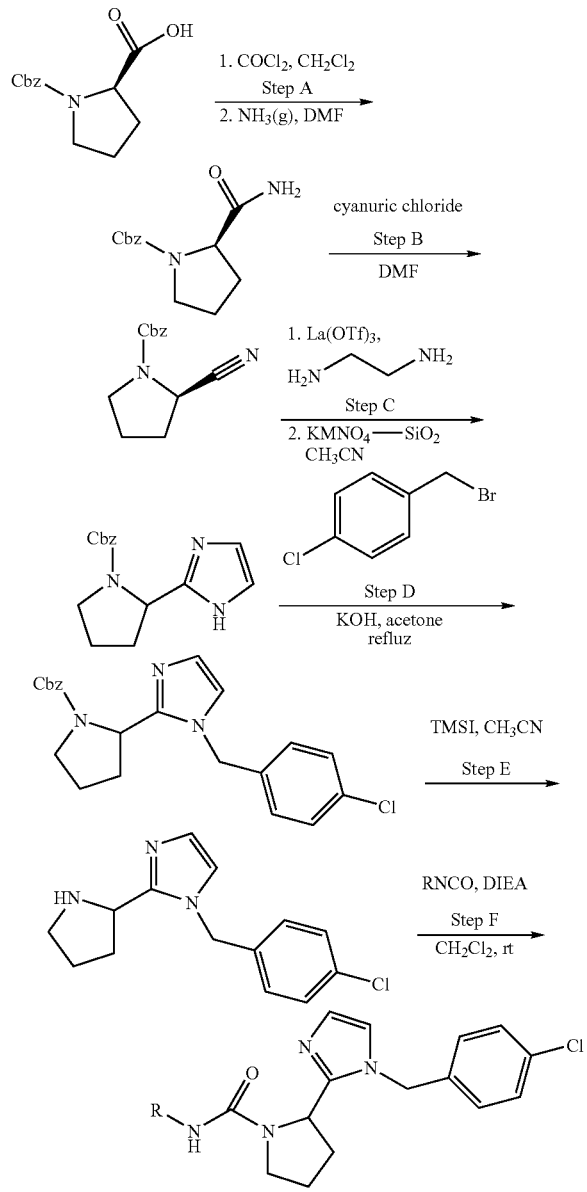

Step A (R)-Benzyl 2-carbamoylpyrrolidine-1-carboxylate: A solution of the Cbz protected D-proline (19.59 g, 78.6 mmol) in CH$_2$Cl$_2$ (200 ml) was treated with oxalyl chloride (9.5 ml, 110 mmol) at ambient temperature followed by addition of a catalytic amount of DMF (60 µl). The reaction mixture was stirred at ambient temperature for 1 h and the volatiles were evaporated in vacuo. The resulting oily residue was dissolved in DMF (200 ml) and cooled to 0° C. Ammonia was bubbled into the solution for 10 min at which time a white precipitate began to form. The reaction mixture was stirred at ambient temperature for 16 h and then concentrated to remove excess DMF. The residue was diluted with ethyl acetate (100 ml) and washed with saturated aqueous Na$_2$CO$_3$ solution (2×30 ml), H$_2$O (30 ml), brine (30 ml), dried (MgSO$_4$), filtered and concentrated in vacuo to afford the desired amide as a white powder in quantitative yield. The amide was used in the next step without further purification.

Step B:

A solution of the amide from Step A (7.88.0 g, 31.7 mmol) in dry DMF (100 ml) under an argon atmosphere was cooled in an ice bath and cyanuric chloride (3.80 g, 20.6 mmol) was added in one portion. The reaction mixture was stirred while slowly warming to ambient temperature over 16 h. The reaction was quenched with the addition of 200 ml of water and the resulting solution was extracted with ethyl acetate (240 ml). The organic layer was washed with water (5×80 ml), dried with MgSO$_4$, and evaporated on a rotary evaporator. The residue was dissolved in 40 ml of ethyl acetate and 80 ml of hexanes and then filtered through a short plug of silica gel, followed by an equal amount of the same solvent composition. The combined filtrates were evaporated on a rotary evaporator to give a yellow oil.

Step C:

The crude residue of from Step B was transferred to a flame dried sealed tube and ethylenediamine (2.1 ml, 31.7 mmol) was added followed by La(OTf)$_3$ (190 mg, 0.3 mmol). The resulting mixture was heated at 80° C. for 24 h and then cooled to room temperature. The reaction mixture was diluted with aqueous 2 N HCl (80 ml) and washed with EtOAc (2×10 mL). The aqueous layer was cooled to 0° C., basified with the careful addition of 50% NaOH solution, and extracted with CH$_2$Cl$_2$ (3×50 ml). The organic layers were combined and dried over anhydrous potassium carbonate and concentrated in vacuo to afford the desired imidazoline (4.15 g, 48% yield) as a yellow oil (MH$^+$=274). The crude imidazoline was dissolved in CH$_3$CN (250 ml) and oxidized to the imidazole with KMnO$_4$/alumina (prepared by mixing 2.6 g of KMnO$_4$ and 8.8 g of Al$_2$O$_3$ in a mortar) at r.t. for 2 h. The reaction mixture was filtered through Celite to give a clear liquid which was concentrated in vacuo to give a low melting solid which was used in the next step without further purification. (MH$^+$=272).

Step D:

The Imidazole from Step C (1.63 g, 6.0 mmol) was dissolved in acetone (20 ml) and treated with powdered KOH (404 mg, 7.2 mmol) followed by 4-chlorobenzyl bromide (1.36 g, 6.6 mmol). The resulting suspension was stirred at ambient temperature for 16 h and then concentrated on a rotary evaporator. The residue was diluted with ethyl acetate (40 ml) and washed with water (2×20 ml), brine (20 ml), dried (K$_2$CO$_3$), and concentrated on a rotary evaporator to give the crude product as a viscous oil. The residue was purified by flash column chromatography over silica gel eluting with 40% EtOAc in hexanes to afford the desired product (800 mg, 42% yield) as a tanned foam.

$^1$H NMR (300 MHz, CDCl$_3$) data for the mixture of rotomers: δ 7.35 (m, 4H), 7.297.05 (m, 3H), 6.91-6.60 (m, 3H), 5.61-5.10 (m, 2H), 5.0-4.4 (m, 3H), 3.90-3.45 (m, 2H), 2.72-1.60 (br m, 4H); Exact mass [MH]+ (Found: 396).

Step E:

TMSI (1.2 ml, 8.01 mmol) was added to a solution of the product from Step D (800 mg, 2.02 mmol) in dry CH$_3$CN (15 ml) at rt. The reaction mixture was stirred at rt for 30 min. and then concentrated on a rotary evaporator. The resulting dark orange residue was diluted with 2 N HCl (10 ml) and washed with Et$_2$O (3×10 ml). The aqueous layer was cooled to 0° C. and the pH was adjusted to 10-12 with 50% NaOH solution. The aqueous layer was saturated with solid K$_2$CO$_3$ and NaCl and then extracted with CHCl$_3$ (3×40 ml). The organic layers were combined, dried over anhydrous K$_2$CO$_3$, and concentrated in vacuo to afford the desired amine as a light yellow oil (409 mg, 77% yield). Exact Mass [MH]+: Found=262.

Step F:

General procedure for the reaction of Step E amine with commercially available isocyanates: A solution of the Step E amine (101.7 mg, 0.39 mmol) in dry CH$_2$Cl$_2$ (2 ml) was treated with DIEA (140 μl, 0.82 mmol, 2.1 equiv.) followed by the addition of appropriate isocyanate (2 equiv). The reaction mixture was stirred at rt for 16 h and then added directly to 1000μ silica gel preparatory TLC plates for purification using 5-10% MeOH in dichloromethane as mobile phase. In cases where a voluminous precipitate formed the reaction mixture was filtered and the solids were washed with cold CH$_2$Cl$_2$ to afford the pure product.

Example 45

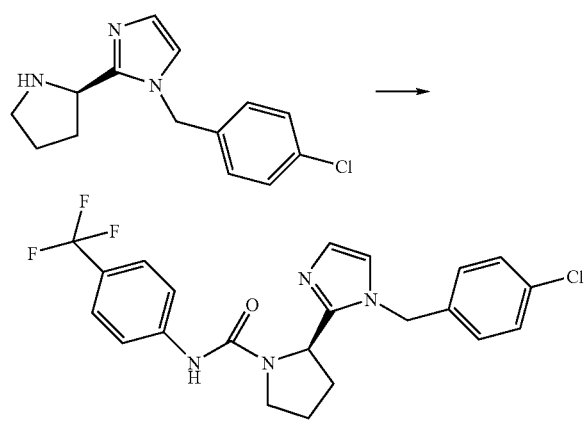

2-(1-(4-chlorobenzyl)-1H-imidazol-2-yl)-N-(4-(trifluoromethyl)phenyl)pyrrolidine-1-carboxylate: Following the general procedure of Example 43, Step F, reaction of 1-(4-chlorobenzyl)-2-(pyrrolidin-2-yl)-1H-imidazole (101.7 mg, 0.39 mmol) with 1-isocyanato-4-(trifluoromethyl)benzene (145.4 mg, 0.68 mmol) afforded the desired urea (37.1 mg, 59% yield) as a white powder after filtration of the reaction mixture.

$^1$H NMR (300 MHz, CDCl$_3$) δ 7.45 (s, 5H), 7.30 (d, 2H), 7.05 (d, 2H), 6.95 (s, 1H), 6.80 (s, 1H), 5.41 (d, 1H), 5.15 (d, 1H), 5.01 (t, 1H), 4.80 (m, 1H), 3.50 (m, 1H), 2.60 (s, 1H), 2.20 (m, 1H), 2.00-1.65 (m, 3H); Exact mass [M+H]$^+$ (Found: 449).

Example 46

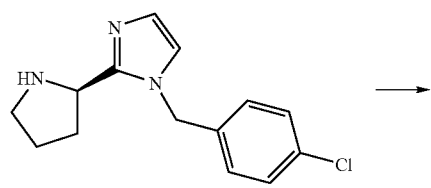

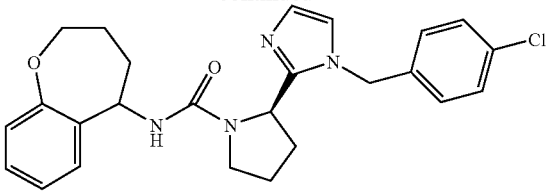

2-(1-(4-chlorobenzyl)-1H-imidazol-2-yl)-N-(2,3,4,5-tetrahydrobenzo[b]oxepin-5-yl)pyrrolidine-1-carboxylate: Following the general procedure of Example 43, Step F, reaction of 1-(4-chlorobenzyl)-2-(pyrrolidin-2-yl)-1H-imidazole (82.9 mg, 0.32 mmol) with 5-isocyanato-2,3,4,5-tetrahydrobenzo[b]oxepine (120 mg, 0.63 mmol) afforded the desired urea (68 mg, 64% yield) as a white powder after purification by flash chromatography over silica gel.

$^1$H NMR (300 MHz, CDCl$_3$) δ 7.46-7.23 (m, 4H), 7.20-7.00 (m, 5H), 6.00 (dd, 1H), 5.70-5.54 (q, 1H), 5.36-5.05 (m, 4H), 4.38 (br d, 1H), 3.90-3.40 (m, 3H), 2.67-2.46 (m, 1H), 2.36-1.95 (m, 7H), 1.94-1.70 (m, 1H); Exact mass [M+H]$^+$ (Found: 451).

Example 47

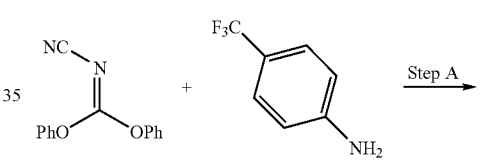

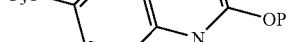

((E)-2-(1-(4-chlorobenzyl)-1H-imidazol-2-yl)-N-cyano-N-(4-(trifluoromethyl)phenyl)pyrrolidine-1-carboxamidine (D21): Following the procedure outlined for Example 26 using 1-(4-chlorobenzyl)-2-(pyrrolidin-2-yl)-1H-imidazole (36.5 mg, 0.14 mmol) from Example 43, Step E, the desired compound was isolated as off-white solids (39.1 mg, 59% yield).

$^1$H NMR (CDCl$_3$) δ 7.62 (d, 2H), 7.40 (d, 2H), 7.23 (d, 2H) 7.18-7.02 (m, 3H), 6.90 (s, 1H), 5.46 (d, 1H), 5.33-5.13 (m,

2H), 3.80-3.68 (m, 1H), 3.55-3.30 (m, 1H), 2.25-2.10 (m, 1H), 2.05-1.80 (m, 3H); Exact mass [M+H]+ (found 473).

Section E—Other Heterocycles

Preparation of Pyrimidines:

Example 48

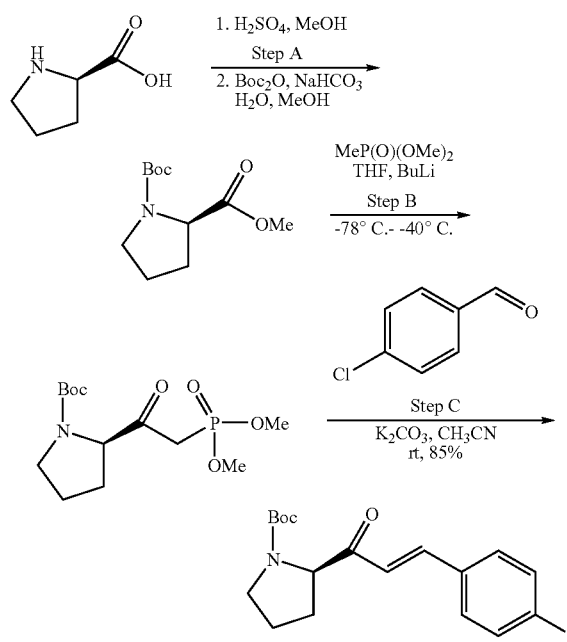

Step A (R)-1-tert-Butyl 2-methyl pyrrolidine-1,2-dicarboxylate: To a solution of D-proline (10 g, 46.4 mmol) in MeOH (80 ml) was added 20 ml of concentrated $H_2SO_4$ over 10 min at rt. An exothermic reaction resulted. The resulting solution was stirred at rt for 16 h and then poured into 200 g of crushed ice and made basic with the careful addition of solid $K_2CO_3$. The mixture was extracted with $CH_2Cl_2$ (2×50 ml). The combined organic layers were dried over $K_2CO_3$ and concentrated on a rotary evaporator to give the crude amino ester. The proline ester was dissolved in MeOH (140 ml) and $H_2O$ (140 ml) and treated with 12.0 g of $NaHCO_3$ followed by the addition of 17.4 g of Boc anhydride. The resulting mixture was stirred at rt for 16 h and the methanol was removed on a rotary evaporator. The aqueous layer was cooled to 0° C. and acidified with careful addition of 0.5 N HCl (360 ml) and extracted with EtOAc (3×140 ml). The combined organic layers were washed with 20% $NaHCO_3$ (160 ml) and brine (180 ml), dried over $MgSO_4$ and concentrated on a rotary evaporator to give the product (10.4 g, 96% yield) as a clear syrup.

Step B (R)-1-tert-butyl 2-(2-(dimethoxyphosphoryl)acetyl)pyrrolidine-1-carboxylate: To a solution of dimethyl methylphosphonate (19.8 g, 160 mmol) in dry THF (330 ml) at −78° C. was added a solution of 2.5 M n-BuLi in hexanes (70.2 ml, 176 mmol), dropwise. After the addition was complete, the reaction mixture was stirred for an additional 30 min. A solution of the product from Step A (6.1 g, 27 mmol) in dry THF (330 ml) was then added dropwise to the n-BuLi solution. After the addition was complete, the mixture was stirred for an additional 3 h at −78° C. The reaction mixture was quenched with a solution of saturated aqueous $NH_4Cl$ and extracted with EtOAc (3×200 ml). The organic extracts were combined, dried over $MgSO_4$ and concentrated on a rotary evaporator to give a crude oil. The crude residue was purified by flash column chromatography over silica gel using 50% EtOAc in hexanes as eluent, affording the desired phosphonate (9.5 g, 100% yield) as a clear syrup.

$R_f$=2.1 (5% MeOH in $CH_2Cl_2$); $^1$H NMR (CDCl$_3$) δ 4.41-4.40 (m, 1H), 3.90-3.60 (m, 6H), 3.59-3.32 (m, 2H), 3.30-2.95 (m, 2H), 2.22-2.00 (m, 2H), 1.95-1.65 (m, 2H), 1.40 (s, 9H).

Step C:

(R,E)-tert-butyl 2-(3-(4-chlorophenyl)acryloyl) pyrrolidine-1-carboxylate: A solution of the b-ketophosphonate from Step B (9.5 g, 27 mmol) in dry $CH_3CN$ (140 ml) was treated with powdered $K_2CO_3$ (11 g, 80 mmol) and the resulting mixture was stirred at rt. for 15 min. 4-Chlorobenzaldehyde (4.5 g, 32 mmol) was added to the above solution as a solution in dry $CH_3CN$ (40 ml). The mixture was stirred at rt for 72 h after which aqueous 10% citric acid solution was added until pH 5 was reached. The mixture was extracted with $CH_2Cl_2$ (3×140 ml) and the organic layers were combined and successively washed with $H_2O$ and brine, then dried over $MgSO_4$. After filtration and evaporation of the solvents, a crude product was obtained as tan solids. Purification of the crude solids by flash column chromatography over silica gel and eluting with 0%-50% EtOAc in hexanes, afforded the desired alkene (8.1 g, 91% yield) as an off-white solid.

$^1$H NMR (300 MHz, CDCl$_3$ δ 7.67-7.56 (m, 1H), 7.50-7.41 (br m, 3H), 7.39-7.30 (m, 3H), 6.80 (d, 1H), 4.39 (m, 1H), 3.68-3.40 (m, 3H), 3.32-2.10 (m, 1H), 2.00-1.80 (m, 4H), 1.70 (br s, 1H), 1.50-1.29 (d, 9H).

Example 49

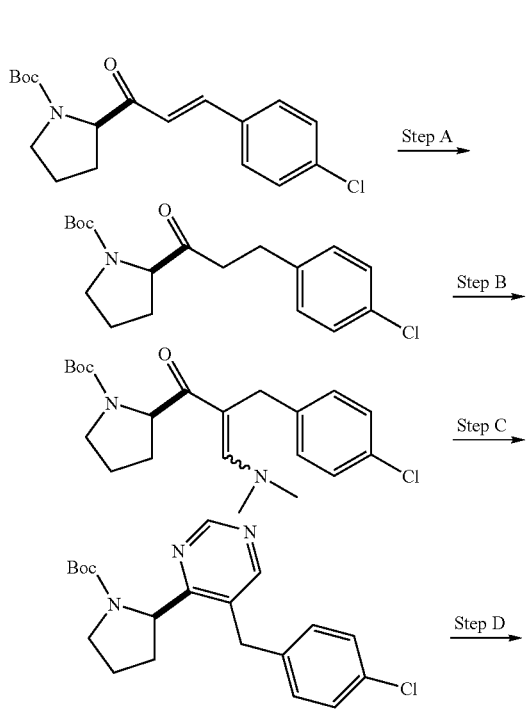

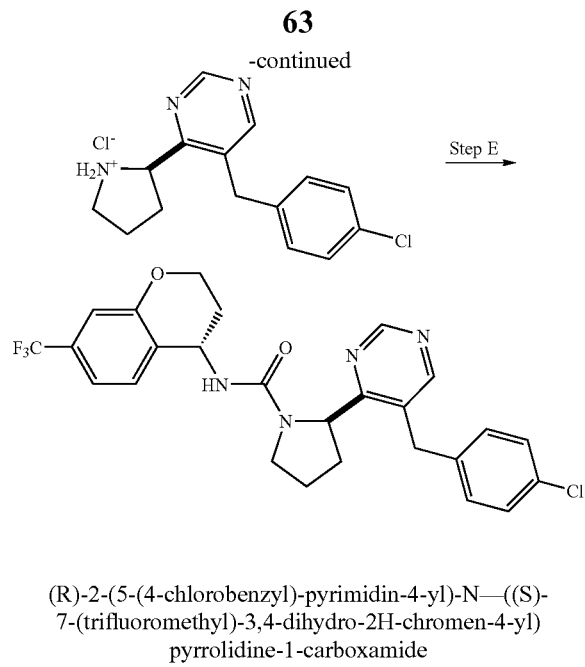

(R)-2-(5-(4-chlorobenzyl)-pyrimidin-4-yl)-N—((S)-7-(trifluoromethyl)-3,4-dihydro-2H-chromen-4-yl) pyrrolidine-1-carboxamide Step A (R)-tert-butyl 2-(3-(4-chlorobenzyl)propanoyl)pyrrolidine-1-carboxylate. To a solution of (R)-tert-butyl 2-(3-(4-chlorobenzyl)acyloyl)pyrrolidine-1-carboxylate (2 g, 5.97 mmol) in ethanol (50 mL) was added a half spatula Raney Ni in water. The mixture was pressurized with hydrogen to 30 psi on a Parr hydrogenator and shaken for 3 h. The reaction mixture was filtered and the filtrate was concentrated in vacuo to provide the desired product in quantitative yield as colorless oil. MS: calculated: 337.14 found (MH+): 338.4.

Step B (R)-tert-butyl 2-(2-(4-chlorobenzyl)-3-dimethylamino)acryloyl)pyrrolidine-1-carboxylate. A mixture of (R)-tert-butyl 2-(3-(4-chlorobenzyl)propanoyl)pyrrolidine-1-carboxylate (500 mg, 1.5 mmol) and tert-butoxy-N,N,N',N'-tetramethylmethane diamine (5 mL, 15 mmol) was heated at 90° C. for 16 h. The product was obtained after evaporation of excess tert-butoxy-N,N,N',N'-tetramethylmethane diamine and was used in the next step without purification. MS: calculated: 392.19 found (MH+): 393.3.

Step C (R)-tert-butyl 2-(5-(4-chlorobenzyl)pyrimidine-4-yl)pyrrolidine-1-carboxylate. To a solution of (R)-tert-butyl 2-(2-(4-chlorobenzyl)-3-(dimethylamino)acryloyl)pyrrolidine-1-carboxylate (1.5 mmol) in n-butanol (10 mL) was added sodium ethoxide in ethanol (5.6 mL, 21 wt. %, 15 mmol) and formamidine acetate (1.56 g, 15 mmol). The reaction mixture was heated at 90° C. for 12 h. After removal of the solvents in vacuo, the residue was dissolved in ethyl acetate. The organic layer was washed with brine three times, dried over sodium sulfate and the solvent was removed in vacuo. Purification by silica gel column chromatography (ethyl acetate/hexane gradient, 10-100% EtOAc) afforded the desired product (320 mg, combined yield for step B and step C was 57%). MS: calculated: 373.16 found (MH+): 374.4.

Step D (R)-5-(4-chlorobenzyl)-4-(pyrrolidine-2-yl)pyrimidine hydrochloride. (R)-tert-butyl 2-(5-(4-chlorobenzyl)pyrimidine-4-yl)pyrrolidine-1-carboxylate from step C was treated with 4M HCl in dioxane (10 mL) for 2 h. Removal of the solvent in vacuo gave the product in quantitative yield as an oil, which was used in the next step without purification. MS: calculated: 273.1 found (MH+): 274.3.

Step E (R)-2-(5-(4-chlorobenzyl)-pyrimidin-4-yl)-N—((S)-7-(trifluoromethyl)-3,4-dihydro-2H-chromen-4-yl) pyrrolidine-1-carboxamide. (R)-4-(4-chlorobenzyl)-4-(pyrrolidin-2-yl)pyrimidine hydrochloride (50 mg, 0.16 mmol) and N,N-diisopropyl-ethylamine (0.080 mL) were dissolved in dichloromethane (2 mL). (S)-4-isocyanato-7-(trifluoromethyl)-3,4-dihydro-2H-chromen (0.177 mmol) was added while stirring. The reaction mixture was stirred for 16 h and then concentrated in vacuo. Purification of the resulting residue by semi-preparative HPLC afforded the desired product (49.7 mg, 61%).

¹H NMR (300 MHz, d-Chloroform) δ 1.61 (m, 1H), 1.93 (m, 2H), 2.02-2.36 (m, 2H), 3.42 (t, 1H), 3.64 (m, 1H), 4.00-4.35 (m, 4H), 4.67 (s, 2H), 4.98 (t, 1H), 5.14 (m, 1H), 7.05 (m, 4H), 7.27 (m, 4H), 8.47 (s, 1H), 9.08 (d, 1H). MS: calculated: 516.15 found (MH+): 517.4.

Example 50

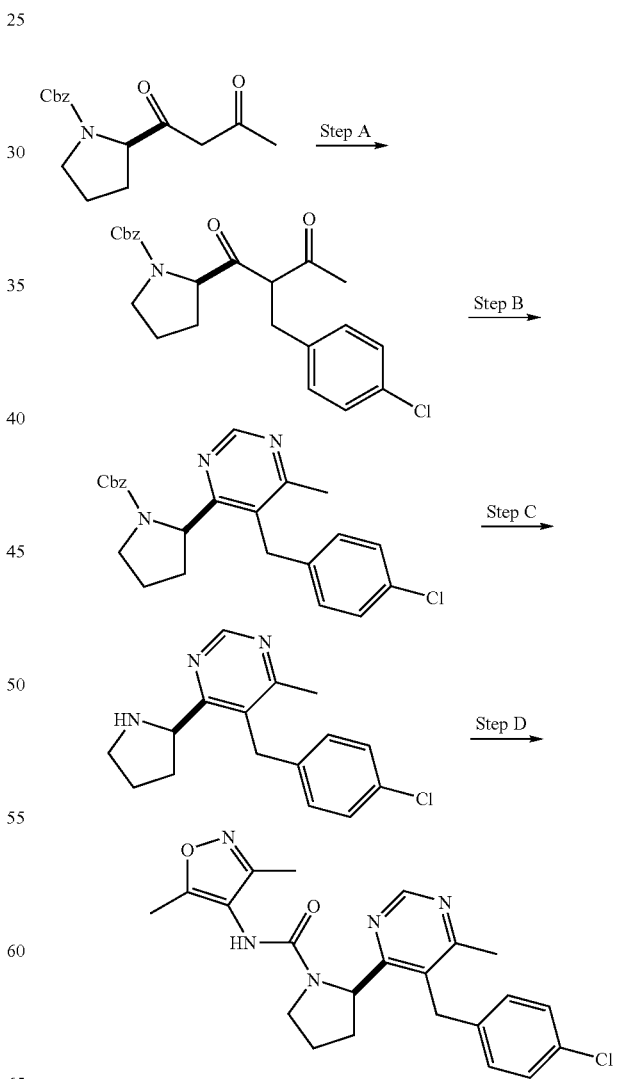

(R)-2-(5-(4-chlorobenzyl) 6-methylpyrimidin-4-yl)-N-(3,5-dimethylisoxazol-4-yl)pyrrolidine-1-carboxamide Step A (2R)-benzyl 2-(2-(4-chlorobenzyl)-3-oxobutanoyl)pyrrolidine-1-caboxylate. To a solution of (R)-benzyl 2-(3-oxobutanoyl)pyrrolidine-1-caboxylate (670 mg, 2.32 mmol) in anhydrous THF (20 mL) was added sodium hydride (111 mg, 60 wt. % in mineral oil, 2.78 mmol). The mixture was stirred at room temperature for 30 min and added to a solution of 4-chlorobenzyl bromide (715 mg, 3.48 mmol) in THF (10 mL). The reaction mixture was stirred at 60° C. for 18 h and then the solvents were removed in vacuo. Purification of the resulting residue by silica gel column chromatography (ethyl acetate/hexane gradient, 10-100% EtOAc) afforded the desired product (812 mg, 86%). MS: calculated: 413.14, found (MH+): 414.3.

Step B (R)-benzyl 2-(5-(4-chlorobenzyl)-6-methylpyrimidin-4-yl)pyrrolidine-1-carboxylate. To a solution of (2R)-benzyl 2-(2-(4-chlorobenzyl)-3-oxobutanoyl)pyrrolidine-1-carboxylate (50 mg, 0.12 mmol) in DMSO (3 mL) was added formamide acetate (125 mg, 1.2 mmol), molecular sieves (4A, 5 pieces). The reaction mixture was heated at 110° C. for 18 h, cooled to room temperature and filtered. The solvent was removed in vacuo and the residue was purified by silica gel column (ethyl acetate/hexane gradient, 10-100% EtOAc) to give desired product (20 mg, 39%). MS: calculated: 421.16, found (MH+): 422.4.

Step C (R)-5-(4-chlorobebzyl)-4-methyl-(pyrrolidine-2-yl)pyrimidine hydrochloride. (R)-benzyl-2-(5-(4-chlorobenzyl)-6-methylpyrimidin-4-yl)pyrrolidine-1-carboxylate (55 mg, 0.133 mmol) was dissolved in dichloromethane and cooled to 0° C. Iodotrimethylsilane (28 µl, 0.19 mmol) was added. The reaction mixture was warmed to room temperature and stirred for 3 h. The solvent was removed in vacuo and residue was dissolved in 10% HCl. The aqueous layer was washed twice with ethyl acetate and the water was removed in vacuo to afford the desired product. The product was used for the next step without further purification. MS: calculated: 287.12, found (MH+): 288.4.

Step D (R)-2-(5-(4-chlorobenzyl) 6-methylpyrimidin-4-yl)-N-(3,5-dimethylisoxazol-4-yl) pyrrolidine-1-carboxamide. (R)-5-(4-chlorobenzyl)-4-methyl-6-(pyrrolidin-2-yl)pyrimidine hydrochloride (30 mg, 0.066 mmol) and N,N-diisopropylethylamine (0.041 mL) were dissolved in dichloromethane (2 mL). 4-isocyanato-3,5-dimethylisoxazole (15 mg, 0.11 mmol) was added while stirring. The reaction mixture was stirred for 16 h then evaporated to dryness. Purification by semi-preparative HPLC afforded the desired product (7.9 mg, 27.8%).

¹H NMR (300 MHz, d-Chloroform) 1.71 (m, 1H), 1.99 (m, 2H), 2.12 (s, 3H), 2.26 (s, 3H), 2.63 (s, 3H), 3.61 (m, 1H), 3.85 (m, 1H), 4.18 (s, 2H), 5.22 (t, 1H), 5.69 (s, 1H), 7.01 (d, 2H), 7.34 (d, 2H), 9.18 (s, 1H). MS: calculated: 425.16, found (MH+): 425.9.

Example 51

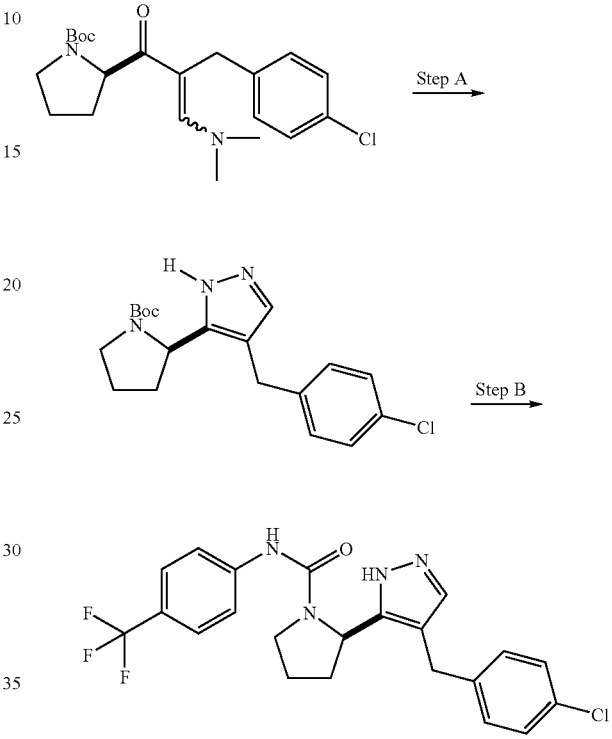

(R)-2-(4-(4-chlorobenzyl)-1H-pyrazol-5-yl)-N-(4-(trifluoromethyl)phenyl)pyrrolidine-1-carboxamide Step A To a solution of (R)-tert-butyl 2-(2-(4-chlorobenzyl)-3-(dimethylamino)acryloyl)pyrrolidine-1-carboxylate (580 mg, 1.5 mmol) in ethanol (10 mL) was added hydrazine (480 mg, 15 mmol). The resulting solution was heated at 70° C. for 2 h and concentrated in vacuo. Purification of the resulting residue by silica gel column chromatography (hexanes/ethyl acetate gradient, 10-100% EtOAc) afforded (R)-tert-butyl 2-(4-(4-chlorobenzyl)-1H-pyrazol-5-yl)pyrrolidine-1-carboxylate (360 mg, 67%). LCMS: calculated: 365, found (MH+): 366.

Step B

A solution of (R)-tert-butyl 2-(4-(4-chlorobenzyl)-1H-pyrazol-5-yl)pyrrolidine-1-carboxylate (30 mg, 0.8 mmol) was dissolved in 4M HCl in 1,4-dioxane (1 mL), stirred for 2 h and then concentrated in vacuo. The resulting residue was suspended in dicloromethane (2 mL) and DIEA (56 µL, 0.32 mmol) before 1-isocyanato-4-(trifluoromethyl)benzene (8.5 µL, 0.08 mmol) was added. After 10 min of stirring the reaction mixture was concentrated in vacuo. Purification of the resulting residue by semi-preparative HPLC afforded (R)-2-(4-(4-chlorobenzyl)-1H-pyrazol-5-yl)-N-(4-(trifluoromethyl)phenyl)pyrrolidine-1-carboxamide (10 mg, 28%). LCMS: calculated: 448, found (MH+): 449.

Example 52

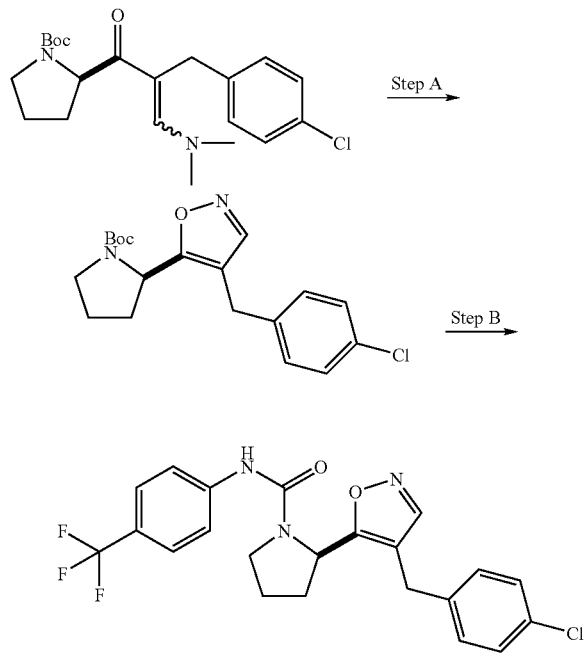

(R)-2-(4-(4-chlorobenzyl)isoxazol-5-yl)-N-(4-(trifluoromethyl)phenyl)pyrrolidine-1-carboxamide Step A To a solution of (R)-tert-butyl 2-(2-(4-chlorobenzyl)-3-(dimethylamino)acryloyl)pyrrolidine-1-carboxylate (580 mg, 1.5 mmol) in ethanol (10 mL) was added hydroxylamine hydrochloride (210 mg, 3 mmol). The resulting solution was heated at 70° C. for 2 h and then concentrated in vacuo. Purification of the resulting residue by silica gel column chromatography (hexanes/ethyl acetate gradient, 10-100% EtOAc) afforded (R)-tert-butyl 2-(4-(4-chlorobenzyl)isoxazol-5-yl)pyrrolidine-1-carboxylate (410 mg, 75%). LCMS: calculated: 365, found (M-tBuH+): 307

Step B

A solution of (R)-tert-butyl 2-(4-(4-chlorobenzyl)isoxazol-5-yl)pyrrolidine-1-carboxylate (32 mg, 0.9 mmol) was dissolved in 4M HCl in 1,4-dioxane (2 mL), stirred for 2 h and then concentrated in vacuo. The resulting reaction residue was suspended in dicloromethane (2 mL) and DIEA (31 μL, 0.18 mmol) before 1-isocyanato-4-(trifluoromethyl)benzene (25 mg, 0.13 mmol) was added. After 16 h of stirring, the reaction mixture was concentrated in vacuo. Purification of the resulting residue by silica gel column chromatography (hexanes/ethyl acetate gradient, 10-100% EtOAc) afforded (R)-2-(4-(4-chlorobenzyl)isoxazol-5-yl)-N-(4-(trifluoromethyl)phenyl)pyrrolidine-1-carboxamide (19 mg, 47%).

$^1$H NMR (300 MHz, d-Chloroform) δ 2.09 (m, 3H), 2.42 (m, 1H), 3.53 (m, 1H), 3.62 (m, 1H), 3.87 (s, 2H), 5.26 (m, 1H), 6.40 (s, 1H), 7.11 (d, 2H), 7.22 (d, 2H), 7.42 (d, 2H), 7.49 (d, 2H), 7.93 (s, 1H). LCMS: calculated: 449, found (MH+): 450.

Example 53

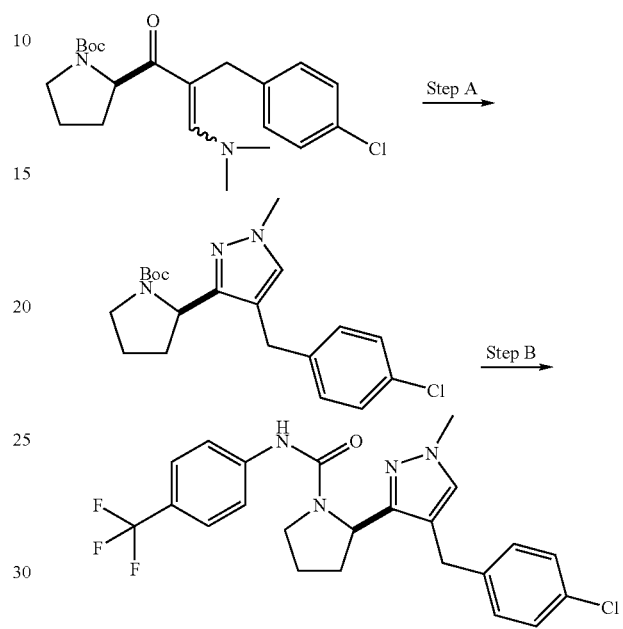

(R)-2-(4-(4-chlorobenzyl)-1-methyl-1H-pyrazol-3-yl)-N-(4-(trifluoromethyl)phenyl)pyrrolidine-1-carboxamide Step A To a solution of (R)-tert-butyl 2-(2-(4-chlorobenzyl)-3-(dimethylamino)acryloyl)pyrrolidine-1-carboxylate (120 mg, 0.3 mmol) in ethanol (4 mL) was added 1-methylhydrazine (60 μL, 2.4 mmol). The resulting solution was heated at 70° C. for 3 h and concentrated in vacuo. Purification of the resulting residue by silica gel column chromatography (hexanes/ethyl acetate gradient, 10-100% ethyl acetate) afforded (R)-tert-butyl 2-(4-(4-chlorobenzyl)-1-methyl-1H-pyrazol-3-yl)pyrrolidine-1-carboxylate (78 mg, 75%). LCMS: calculated: 375, found (MH+): 376.

Step B

A solution of (R)-tert-butyl 2-(4-(4-chlorobenzyl)-1-methyl-1H-pyrazol-3-yl)pyrrolidine-1-carboxylate (39 mg, 0.1 mmol) was dissolved in 4M HCl in 1,4-dioxane (2 mL), stirred for 2 hr and then concentrated in vacuo. The resulting residue was then suspended in dichloromethane (2 mL) and DIEA (34 μL, 0.2 mmol) before 1-isocyanato-4-(trifluoromethyl)benzene (28 μL, 0.15 mmol) was added. After 16 h of stirring, the reaction mixture was concentrated in vacuo. Purification of the resulting residue by silica gel column chromatography (hexanes/ethyl acetate gradient, 10-100% EtOAc) afforded (R)-2-(4-(4-chlorobenzyl)-1-methyl-1H-pyrazol-3-yl)-N-(4-(trifluoromethyl)phenyl)pyrrolidine-1-carboxamide (12 mg, 26%).

$^1$H NMR (300 MHz, d-Chloroform) δ 2.11 (m, 3H), 2.38 (m, 1H), 3.51 (m, 1H), 3.89 (m, 3H), 4.02 (s, 3H), 5.13 (m, 1H), 6.06 (s, 1H), 7.14 (d, 2H), 7.28 (m, 4H), 7.41 (s, 1H), 7.57 (d, 2H). LCMS: calculated: 462, found (MH+): 463.

Example 54

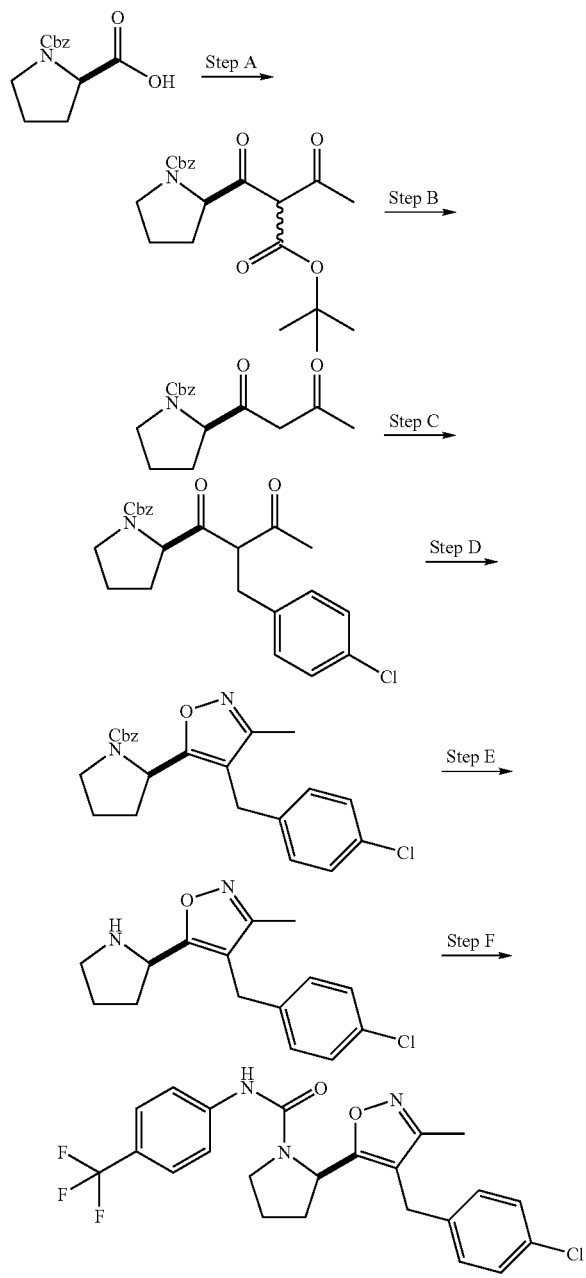

(R)-2-(4-(4-chlorobenzyl)-3-methylisoxazol-5-yl)-N-(4-(trifluoromethyl)phenyl)pyrrolidine-1-carboxamide Step A To a suspension of (+)-carbobenzyloxy-D-proline (10 g, 40 mmol) in dichloromethane (250 mL) was added oxalyl chloride (6.9 mL, 80 mmol) followed by dimethyl formamide (15 μL, 0.2 mmol). The reaction mixture was then stirred for 2 h and concentrated in vacuo. The resulting acid chloride in dichloromethane (50 mL) was added to a mixture of magnesium chloride (4 g, 40 mmol) and tert-butyl acetoacetate (6.5 mL, 4 mmol) in pyridine (6.5 mL, 80 mmol) and dichloromethane (50 mL) at 0° C. and stirred for 30 min. The reaction mixture was then stirred at room temperature for 16 h and then diluted with EtOAc (25 mL). The organic layer was washed with 10% HCl solution (1×250 mL), saturated NaHCO$_3$ solution (1×250 mL) and then brine (1×250 mL). The separated organic layer was then dried over Na$_2$SO$_4$ and concentrated in vacuo to afford (2R)-benzyl 2-(2-(carbonyl)-3-oxobutanoyl)pyrrolidine-1-carboxylate. LCMS: 6.51 min, calculated: 389, found (MH+): 390.

Step B

A solution of (2R)-benzyl 2-(2-(carbonyl)-3-oxobutanoyl)pyrrolidine-1-carboxylate in TFA (50 mL) and dichloromethane (50 mL) was stirred at room temperature for 1 hr and then concentrated in vacuo. The resulting residue was purified by silica gel column chromatography (hexanes/ethyl acetate gradient, 10-100% EtOAc) to afford (R)-benzyl 2-(3-oxobutanoyl)pyrrolidine-1-carboxylate (2.1 g, 18% over two steps). LCMS: 6.9 min calculated: 289, found (MH+): 290.

Step C

A solution of (R)-benzyl 2-(3-oxobutanoyl)pyrrolidine-1-carboxylate (1 g, 3.5 mmol) in THF (50 mL) was added sodium hydride (130 mg, 5.3 mmol) followed by 4-chlorobenzyl bromide (710 mg, 3.5 mmol). The reaction mixture was then heated at 60° C. for 6 h. After concentrating the reaction mixture in vacuo, the resulting residue was purified by silica gel column chromatography (hexanes ethyl acetate) to afford (2R)-benzyl 2-(2-(4-chlorobenzyl)-3-oxobutanoyl)pyrrolidine-1-carboxylate (300 mg, 21%). LCMS: 8.04 and 8.14 min, calculated: 413, found (MH+): 414.

Step D

To a solution of (2R)-benzyl 2-(2-(4-chlorobenzyl)-3-oxobutanoyl)pyrrolidine-1-carboxylate (300 mg, 0.71 mmol) in ethanol (10 mL) was added hydroxylamine hydrochloride (490 mg, 7.1 mmol). The resulting solution was heated at 70° C. for 3 h and then diluted with EtOAc (30 mL). The organic layer was washed with saturated NaHCO$_3$ solution (1×40 mL) and then brine (1×40 mL). The separated organic layer was then dried over Na$_2$SO$_4$ and concentrated in vacuo. Purification of the resulting residue by silica gel column chromatography (hexanes/ethyl acetate gradient, 10-100% EtOAc) afforded (R)-benzyl 2-(4-(4-chlorobenzyl)-3-methylisoxazol-5-yl)pyrrolidine-1-carboxylate (220 mg, 76%). LCMS: calculated: 410, found (MH+): 411.

Step E

To a solution of (R)-benzyl 2-(4-(4-chlorobenzyl)-3-methylisoxazol-5-yl)pyrrolidine-1-carboxylate (220 mg, 0.54 mmol) in dichloromethane (20 mL) at 0° C. was added iodotrimethylsilane (110 μL, 0.8 mmol). The reaction mixture was allowed to warm to room temperature, stirred for 3 h, concentrated in vacuo and diluted with ether (30 mL). The organic layer was extracted with 1M HCl (2×50 mL). The aqueous layer was basified with 6 M NaOH and extracted with dichloromethane (3×50 mL). The combined organic layers were dried over Na$_2$SO$_4$ and concentrated in vacuo to afford (R)-4-(4-chlorobenzyl)-3-methyl-5-(pyrrolidin-2-yl)isoxazole (110 mg, 74%). LCMS: calculated: 276, found (MH+): 277.

Step F

To a solution of (R)-4-(4-chlorobenzyl)-3-methyl-5-(pyrrolidin-2-yl)isoxazole (20 mg, 0.07 mmol) in dichloromethane (2 mL) was added 1-isocyanato-4-(trifluoromethyl)benzene (13 mg, 0.07 mmol). The reaction mixture was stirred at room temperature for 10 min and concentrated in vacuo. Purification of the resulting residue by semi-preparative HPLC afforded (R)-2-(4-(4-chlorobenzyl)-3-methyl-isoxazol-5-yl)-N-(4-(trifluoromethyl)phenyl)pyrrolidine-1-carboxamide (20 mg, 62%).

$^1$H NMR (300 MHz, CD$_3$OD) δ 2.00 (m, 1H), 2.04 (s, 3H), 364 (m, 1H), 3.72 (m, 1H), 3.86 (dd, 2H), 5.31 (m, 1H), 7.16 (d, 2H), 7.27 (d, 2H), 7.52 (m, 4H). LCMS: calculated: 463, found (MH$^+$): 464.

Example 55

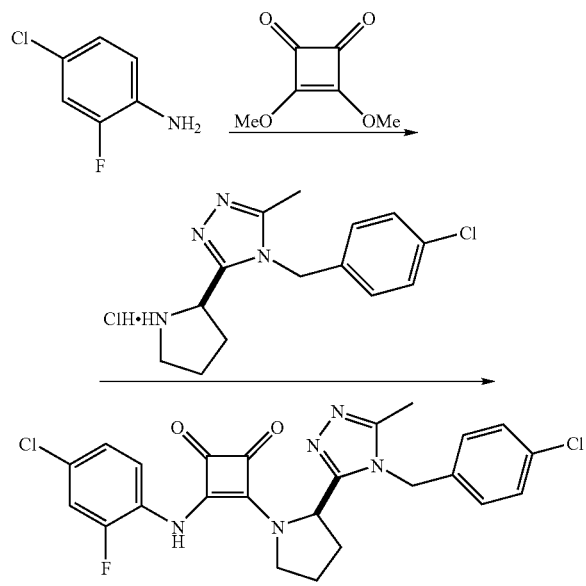

(R)-3-(2-(4-(4-chlorobenzyl)-5-methyl-4H-1,2,4-triazol-3-yl)pyrrolidin-1-yl)-4-(4-chloro-2-fluorophenylamino)cyclobut-3-ene-1,2-dione. Dimethoxycyclobutenedione (28 mg) and the 4-chloro-2-fluoroaniline (30 mg) were dissolved in methanol (1 ml) and DIEA (0.035 ml). The reaction was stirred at 75° C. overnight. (R)-4-(4-chlorobenzyl)-3-methyl-5-(pyrrolidin-2-yl)-4H-1,2,4-triazole hydrochloride (58 mg) was added and stirring and heating was continued overnight. Flash chromatography purification (0-10% methanol/DCM) afforded the desired product as residue (11 mg, 11%).

$^1$H NMR (300 MHz, CDCl$_3$) 1.51-1.78 (m, 2H), 2.03-2.12 (m, 2H), 2.51 (s, 3H), 3.18-3.20 (m, 1H), 3.60-3.78 (m, 1H), 4.26-4.29 (m, 1H), 5.29-5.35 (d, 1H), 5.60-5.70 (m, 2H), 7.08-7.11 (m, 2H), 7.20-7.27 (m, 3H), 7.43-7.45 (m, 2H), 8.21-8.35 (m, 1H), 11.30-11.50 (m, 1H). MS: calculated: 500.35, found (MH$^+$): 500.1

Example 56

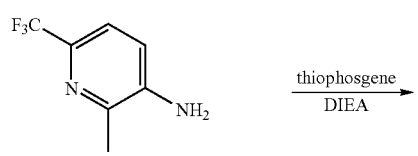

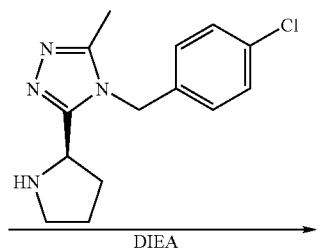

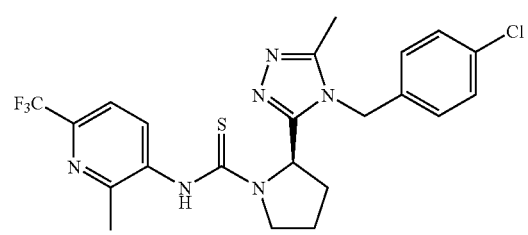

(R)-2-(4-(4-chlorobenzyl)-5-methyl-4H-1,2,4-triazol-3-yl)-N-(2-methyl-6-(trifluoromethyl)pyridin-3-yl)pyrrolidine-1-carbothioamide. To a stirring solution of thiophosgene (0.23 mL, 3 mmol) in 50 mL of CH$_2$Cl$_2$ at 0° C. was added dropwise a mixed solution of 2-methyl-6-(trifluoromethyl)pyridin-3-amine (0.528 g, 3 mmol) and N,N-diisopropylethylamine (0.522 mL, 3 mmol) in dichloromethane (10 mL). The reaction mixture was stirred at 0° C., warming up to room temperature within an hour. Then the mixture was cooled at 0° C. and to it was added a solution of the (R)-4-(4-chlorobenzyl)-3-ethyl-5-(pyrrolidin-2-yl)-4H-1,2,4-triazole HCl salt (1.05 g, 3 mmol) and N,N-diisopropylethylamine (1.044 mL, 6 mmol) in dichloromethane (10 mL) slowly. The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Flash chromatography purification (Hex/EtOAc with 10% of MeOH) afforded the desired product as yellow solid (0.4 g, 26.9%).

$^1$H NMR (300 MHz, CDCl$_3$) 1.96-2.19 (m, 3H), 2.30 (s, 3H), 2.56 (s, 3H), 2.69-2.72 (m, 1H), 3.74-3.77 (m, 1H), 4.21-4.25 (m, 1H), 5.02-5.08 (d, 1H), 5.51-5.57 (d, 1H), 5.59-5.60 (d, 1H), 7.00-7.03 (d, 2H), 7.31-7.35 (dd, 2H), 7.44-7.46 (d, 1H), 7.66 (s, 1H), 7.77-7.80 (d, 1H). MS: calculated: 494.96, found (MH$^+$): 495.0.

Example 57

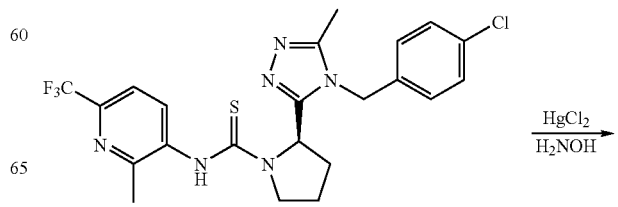

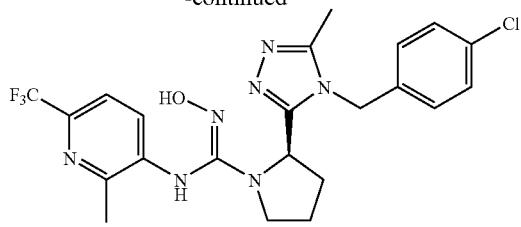

(R,E)-2-(4-(4-chlorobenzyl)-5-methyl-4H-1,2,4-triazol-3-yl)-N'-hydroxy-N-(2-methyl-6-(trifluorometbyl)pyridin-3-yl)pyrrolidine-1-carboxamidine. To a stirring solution of (R)-2-(4-(4-chlorobenzyl)-5-methyl-4H-1,2,4-triazol-3-yl)-N-(2-methyl-6-(trifluoromethyl)pyridin-3-yl)pyrrolidine-1-carbothioamide (74.24 mg, 0.15 mmol) and hydroxylamine hydrochloride (10.43 mg, 1 eq.) in 4 mL of DMF was added HgCl2 (40.8 mg, 1 eq.). The reaction mixture was stirred at room temperature overnight. The reaction mixture was diluted with $CH_2Cl_2$ (20 mL), treated with sat. aqueous $NaHCO_3$ (10 mL) and brine, dried over $Na_2SO_4$, and concentrated in vacuo. Flash chromatography purification (Hex/EtOAc with 10% of MeOH) afforded the desired product (3 mg, 4%).

$^1$H NMR (300 MHz, $CDCl_3$) 1.92-2.11 (m, 4H), 2.35 (s, 3H), 2.53 (s, 3H), 3.07-3.14 (m, 1H), 3.24-3.26 (m, 1H), 4.28 (m, 1H), 5.03-5.09 (d, 1H), 5.33-5.38 (d, 1H), 6.92-6.95 (d, 2H), 7.31-7.33 (d, 2H), 7.52-7.55 (d, 1H), 7.94 (d, 1H). MS: calculated: 493.97, found (MH$^+$): 494.2.

Example 58

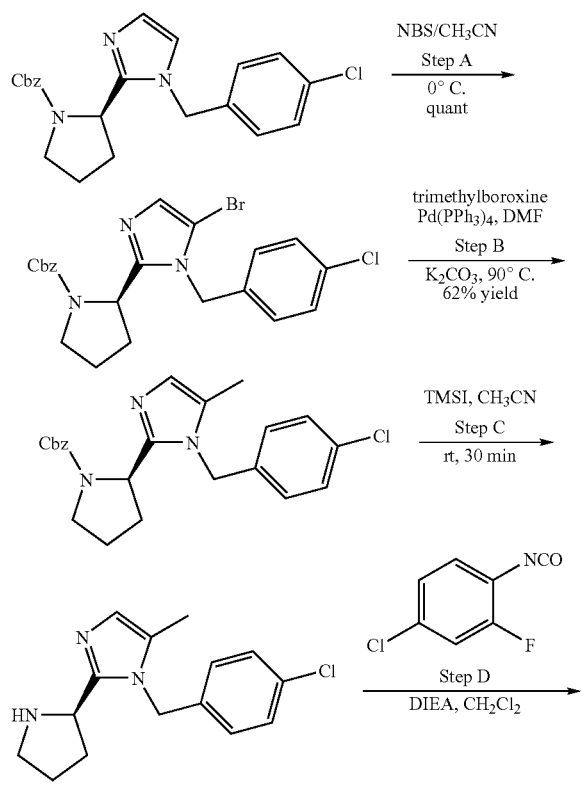

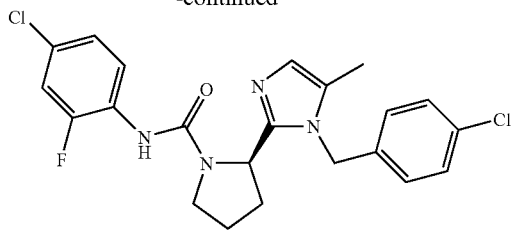

(R)-2-(1-(4-chlorobenzyl)-5-methyl-1H-imidazol-2-yl)-N-(4-chloro-2-fluorophenyl)pyrrolidine-1-carboxamide Step A N-Bromosuccinamide (473 mg, 2.66 mmol) was added in portions to a suspension of the imidazole (See Example 43) (1.0 g, 2.5 mmol) in dry acetonitrile (100 ml) cooled to 0° C. and under vigorous stirring. After 15 min the reaction mixture was diluted with saturated aqueous $NaHCO_3$. The resulting suspension was extracted with EtOAc (3×). The combined organic layer was washed with brine, dried ($MgSO_4$), filtered and concentrated in vacuo to give a clear oil. Purification of the residue on the ISCO MPLC system (40 g Silicycle silica gel column) using 0-100% EtOAc—$CH_2Cl_2$ gradient as eluent afforded the desired bromoimidazole (1.13 g, 95% yield) as white solids. LCMS: Calc'd 473 found [M+H]$^+$=474.

Step B

In a sealed tube, a solution of bromoimidazole (1.05 g, 2.21 mmol) in dry DMF (15 ml) was deoxygenated by bubbling argon through the solution for 10 min. The resulting solution was treated with $K_2CO_3$ (1.22 g, 8.8 mmol), trimethylboroxine (1.2 ml, 8.8 mmol) and Pd(PPh$_3$)$_4$ (255 mg, 0.22 mmol) and heated at 90° C. for 16 h. The resulting dark orange mixture was cooled to RT, diluted with water, and extracted with EtOAc (3×20 ml). The combined organic layer was washed with 1:1:1:1 (water, saturated aqueous NaHCO3, brine, saturated aqueous $NH_4Cl$) twice, brine, dried ($Na_2SO_4$), filtered and concentrated in vacuo to give a yellow residue. The residue was passed through a small silica gel plug eluting with $CH_2Cl_2$ and then EtOAc to give the crude methyl imidazole (560 mg, 62% yield) as white solids, which was used in the next step without further purification. LCMS calc'd 409 found [M+H]$^+$=410.

Step C

A solution of the methyl imidazole (550 mg, 1.34 mmol) in dry $CH_3CN$ (7 ml) was treated with TMSI (760 μl, 5.36 mmol). After stirring at RT for 30 min, the volatiles were removed on a rotary evaporator and the resulting orange foam was treated with 1 N HCl (7 ml) and diluted with diethyl ether (7 ml). The aqueous layer was collected and washed with $Et_2O$ (3×7 ml), cooled to 0° C., and the pH was adjusted to 10 with slow addition of 6 N NaOH. The resulting solution Was saturated with and NaCl and extracted with $CHCl_3$ (5×10 ml). The combined organic layer was dried ($K_2CO_3$), filtered and concentrated to give the amine (300 mg, 81% yield) as a light-yellow oil. LCMS calc'd 275 found [M+H]$^+$=276.

Step D

The reaction was carried out according to the general procedure outlined for Example 43 using the amine from Step C (104.1 mg, 0.38 mmol) to afford the urea (130 mg, 77% yield) as a white foam. $^1$H 400 MHz NMR ($CDCl_3$) δ 8.03-7.93 (t, 1H), 7.32-7.26 (d, 2H), 7.10-7.01 (m, 1H), 6.94-6.87 (d, 1H), 6.86-6.81 (s, 1H), 6.50-6.44 (s, 1H), 5.57-5.46 (d, 1H), 5.15-5.07 (d, 1H), 5.03-4.97 (t, 1H), 3.80-3.72 (br m, 1H), 3.61-

3.51 (br m, 1H), 2.59-2.43 (m, 1H), 2.14-2.08 (s, 3H), 2.07-1.98 (m, 3H); LCMS calc'd 446, found [M+H]+=447.

Example 59

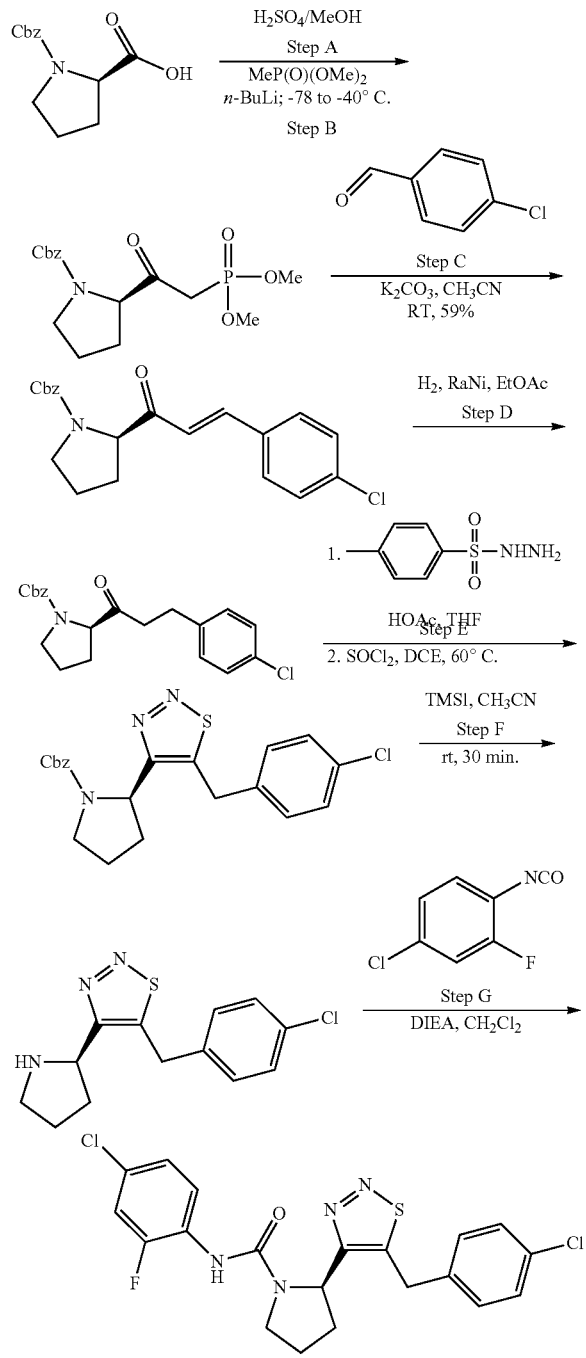

(R)-2-(5-(4-chlorobenzyl)-1,2,3-thiadiazol-4-yl)-N-(4-chloro-2-fluorophenyl)pyrrolidine-1-carboxamide Step A To a solution of (D)-Cbz-Pro (30 g, 120 mmol) in MeOH (240 ml) was added 60 ml of concentrated $H_2SO_4$ over 10 min at RT. An exothermic reaction resulted. The resulting solution was stirred at RT for 16 h and then poured unto 300 g of crushed ice. The mixture was extracted with $Et_2O$ (2×200 ml). The combined organic layers were dried over $K_2CO_3$ and concentrated on a rotary evaporator to give the crude amino ester (31 g, 99% yield) as clear syrup.

Step B

To a solution of dimethyl methylphosphonate (20.9 g, 169 mmol) in dry THF (400 ml) at −78° C. was added a solution of 1.6 M n-BuLi in hexanes (116 ml, 186 mmol), dropwise. After the addition was complete, the reaction mixture was stirred for an additional 30 min. A solution of the product from Step A (7.40 g, 28.1 mmol) in dry THF (400 ml) was then added dropwise to the n-BuLi solution. After the addition was complete, the mixture was stirred for an additional 3 h at −78° C., warmed to −40° C. and quenched with a solution of saturated aqueous $NH_4Cl$. The resulting two phased mixture was extracted with EtOAc (3×200 ml). The organic extracts were combined, dried over $MgSO_4$ and concentrated on a rotary evaporator to give a crude oil. The crude residue was purified by flash column chromatography over silica gel using 50% EtOAc in hexanes as eluent, affording the desired phosphonate (5.96 g, 60% yield) as a clear syrup. $R_f$=2.2 (5% MeOH in $CH_2Cl_2$); $^1$H NMR ($CDCl_3$) δ 7.42-7.29 (m, 5H),), 5.21-5.00 (m, 2H) 4.56-4.39 (m, 1H), 3.87-3.62 (m, 8H), 3.62-3.44 (m, 2H), 3.33-3.14 (m, 1H), 3.10-2.82 (m, 1H), 2.24-1.81 (br m, 6H); LCMS calc'd 355, found [M+H]+=356.

Step C:

A solution of the β-ketophosphonate from Step B (5.95 g, 16.7 mmol) in dry $CH_3CN$ (90 ml) was treated with powdered $K_2CO_3$ (11.7 g, 84.4 mmol) and the resulting mixture was stirred at rt. for 15 min. 4-Chlorobenzaldehyde (2.82 g, 20.1 mmol) was added to the above solution as a solution in dry $CH_3CN$ (40 ml). The mixture was stirred at RT for 72 h after which aqueous 10% citric acid solution was added until pH 5 was reached. The mixture was extracted with $CH_2Cl_2$ (3×90 ml) and the organic layers were combined and successively washed with $H_2O$ and brine, then dried over $MgSO_4$. After filtration and evaporation of the solvents, a crude product was obtained as tanned solids. Purification of the crude solids by flash column chromatography over silica gel and eluting with 0%-50% EtOAc in hexanes, afforded the desired alkene (3.66 g, 59% yield) as white solids. LCMS APCI calc'd 368, found [M+H]+=370.

Step D

To a solution of the olefin (3.66 g, 9.91 mmol) in EtOAc (50 mL) was added a half spatula Raney Nickel in EtOH. The mixture was pressurized with hydrogen to 50 psi on a Parr hydrogenator and shaken for 24 h. The reaction mixture was filtered through a pad of Celite and the filtrate was concentrated in vacuo to provide the desired product in quantitative yield as colorless oil. $^1$H NMR (400 MHz, D-Chloroform) δ 7.48-7.03 (m, 9H), 5.25-4.92 (m, 2H), 4.49-4.24 (dd, 1H), 3.81-3.44 (m, 2H), 3.03-2.49 (m, 4H), 2.28-1.66 (m, 4H); LCMS calc'd: 371 found [M+H]+: 372.

Step E

A solution of the ketone (1.59 g, 4.28 mmol) in dry THF was treated with HOAc (1.3 ml) and p-toluenesulfonyl hydrazide (960 mg, 5.14 mmol). The resulting mixture was heated at 50° C. for 4 h and cooled to RT. The resulting residue was diluted with 1,2-dichloroethane (20 ml) and treated with $SOCl_2$ (6.3 ml, 85.9 mmol) and heated at 60° C. for 5 h. The reaction mixture concentrated in vacuo. The residue was diluted with saturated aqueous $NaHCO_3$ solution (40 ml) and extracted with $CH_2Cl_2$ (3×40 ml). The combined organic layers were washed with brine, dried ($MgSO_4$), filtered and concentrated. Purification of the crude residue by flash column chromatography over silica gel and eluting with 0%-100% EtOAc in CH$_2$Cl$_2$, afforded the desired thiadiazole (1.17 g, 66% yield) as clear syrup. LCMS: calc'd: 413 found [M+H]$^+$: 414.

Step F

The thiadiazole (1.17 g, 2.83 mmol) was dissolved in dichloromethane (20 ml) and cooled to 0° C. Iodotrimethylsilane (1.5 ml, 11.3 mmol) was added dropwise. The reaction mixture was warmed up to room temperature and stirred for 1 hr. The solvent was removed in vacuo and residue was, suspended in 10% HCl. The aqueous layer was washed with ethyl acetate two times and the water was removed in vacuo to afford the desired product as dark brown solids. The product was used for the next step without further purification. MS: calculated: 287.12, found [M+H]$^+$: 288.4.

Step G

The crude amine (116.9 mg, 0.42 mmol) and N,N-diisopropylethylamine (150 μL, 0.84 mmmol) were dissolved in dichloromethane (2 ml). The isocyanate (108 mg, 0.63 mmol) was added with stirring. The reaction mixture was stirred for 1 h then evaporated to dryness. Purification by semi-preparative TLC (5% MeOH—CH$_2$Cl$_2$) afforded the desired product (146.4 mg, 77% yield) as an off-white solid.

$^1$H NMR (400 MHz, D-Chloroform) δ 8.11-7.95 (d, 1H), 7.33-7.28 (d, 2H), 7.20 (d, 7.15), 7.09-7.02 (m, 2H), 6.44-6.36 (s, 1H), 5.38-5.33 (q, 1H), 4.58-4.50 (d, 1H), 4.39-4.32 (d, 1H), 3.87-3.78 (m, 1H), 3.70-3.61 (q, 1H), 2.81-2.65 (m, 1H), 2.39-2.56 (m, 2.06 (m, 2H); LCMS calc'd 451 found [M+H]$^+$: 452.

Example 60

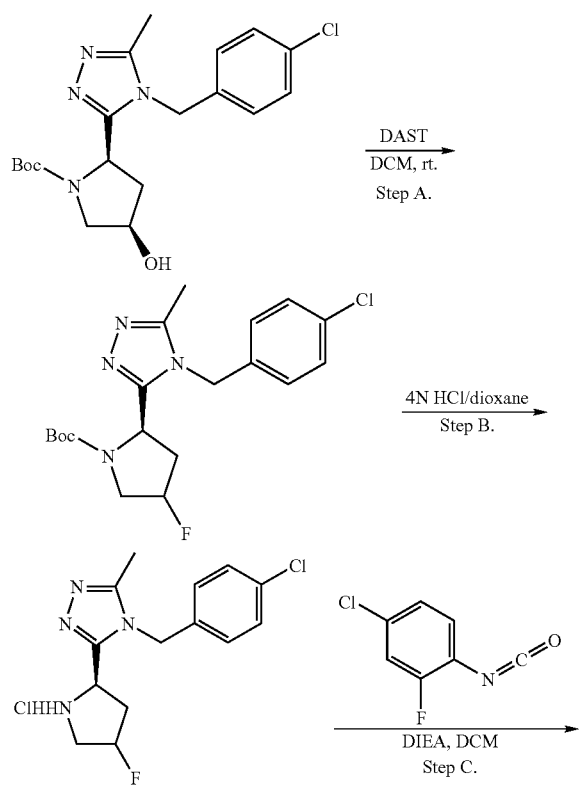

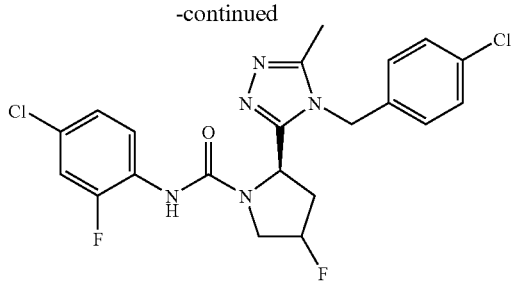

(2R)-tert-butyl 2-(4-(4-chlorobenzyl)-5-methly-4H-1,2,4-triazol-3-yl)-4-fluoropyrrolidine-1-carboxylate Step A:

To the 4-hydroxypyrrolidine (0.4 g, 1 mmol) in dry DCM (20 mL) was added (diethylamino)sulfurtrifluoride (DAST) (0.2 mL) slowly. The resulting reaction mixture was stirred at room temperature for overnight. The reaction was treated with ice water, extracted with DCM (3×), washed with brine, dried over Na$_2$SO$_4$, and concentrated in vacuo. Purification of the resulting residue by semi-preparative HPLC afforded the desired product (0.24 g, 60%). MS: calculated: 394.16 found (MH$^+$): 395.2 $^1$H NMR (300 MHz, d-Chloroform) δ 1.49 (s, 9H), 2.47 (s, 3H), 2.80-3.05 (m, 2H), 3.75-4.01 (m, 2H), 5.04 (m, 1H), 5.23-5.80 (m, 3H), 6.95 (d, 2H), 7.72 (d, 2H).

Step B:

A solution of Boc-protected triazole (0.2 g, 0.5 mmol) in 15 mL of 4 N HCl in dioxane was stirred at room temperature for 4 h. The mixture was concentrated in vacuo. MeOH (10 ml) was added (2×), conc. dried in vacuo to yield the HCl salt of desired product (0.16 g, 94%, yield calculated based on 1 eq. HCl), which was used directly for the next step.

Step C:

To a stirring solution of 4-chloro-2-fluoro-1-isocyanatobenzene (0.255 mmol) in 8 mL of CH$_2$Cl$_2$ at 0° C. was slowly added dropwise a solution of the triazole salt (0.17 mmol) and N,N-diisopropylethylamine (0.06 mL, 0.34 mmol) in dichloromethane (2 mL). The resulting mixture was stirred 0° C. for 30 minutes, then at room temperature overnight. The reaction mixture was treated with sat. aqueous NaHCO$_3$ (10 mL) and brine, dried over Na$_2$SO$_4$, and concentrated in vacuo. Purification of the resulting residue by semi-preparative HPLC afforded the desired product (42 mg, 53%). MS: calculated: 465.09 found (MH$^+$): 466.0. $^1$H NMR (300 MHz, d-Chloroform) δ 2.30 (m, 1H), 2.55 (s, 3H), 2.63 (m, 1H), 3.79-4.10 (m, 3H), 5.15 (t, 1H), 5.34-5.62 (m, 2H), 6.65 (s, 1H), 7.00 (m, 4H), 7.40 (d, 2H), 7.70 (m, 1H).

CCR1 Binding Protocol

The following protocol was used to test compounds for CCR1 binding. A mixture, including scintillation proximity assay (SPA) beads and cell membrane expressing human CCR1, was prepared in assay buffer (130 mM NaCl+5 mM KCl+1 mM MnCl+50 mM Tris HCl at pH 7.4+0.1% bovine serum albumin (BSA)) at the ratio of 50 μg/ml membrane to 10 mg/ml SPA beads. 10 μl of the mixture was transferred to each well of a 384-well assay plate yielding a final concentration for the membrane and SPA beads of 0.5 μg/well and 100 μg/well, respectively To generate different concentrations of the test compound, compound stocks were prepared using 10 step ½ log dilutions with a high concentration of 10 mM in DMSO and the lowest concentration being DMSO only without compound. An intermediate 40× dilution was then prepared in the assay buffer. The compound was then transferred at 10 μl/well to the assay plate. 0.5 nM [$^{125}$I]-labeled macrophage inflammatory protein-1α (MIP-1α, an endogenous CCR1 ligand) in the assay buffer was transferred to the assay plate at 5 μl/well, for a final ligand concentration of 0.1 nM. The assay plate was then centrifuged at 2500 rpm for 2 minutes and incubated for 4 hours at ambient temperature, at which time the raw data was recorded using microbeta. The IC$_{50}$ was then calculated using Graphpad Prism.

Chemotaxis Protocol

Human monocyte cell line THP1 and a 5 mM chemotaxis plate from Chemicon were used. Cells were resuspended at 2×10$^6$ cells/ml in assay buffer (RPMI with 0.1% BSA). Compounds were initially diluted in DMSO and then with the assay buffer. Compounds were preincubated with the cells at 37° C. for 15 minutes. A solution of 1 nM MIP-1α in the assay buffer was prepared. 150 μl of 1 nM MIP-1α solution was then added to the bottom chamber of the assay plate, the insert re-placed into the assay plate and the plate allowed to equilibrate for 15 minutes at 37° C. 100 μL cells +/− compound were added to the appropriate wells. The plate was then incubated at 37° C. for three hours. The insert was removed from the plate and 25 μL/well was transferred to the 96 well white bottom plate. The cells were quantified by adding 25 μL/well of cell titre followed by measurement of luminescence.

Using synthetic methods analogous to those described above and the CCR1 assay described above, the compounds listed in Table 1 were synthesized and found to be CCR1 antagonists in vitro having an IC$_{50}$ of 5 μM or less.

While embodiments of the invention have been described in conjunction with the detailed description thereof, the foregoing description is intended to illustrate and not limit the scope of the invention, which is defined by the scope of the appended claims.

TABLE 1

| Compound # | Structure | Relative potency (IC$_{50}$)<br>* = 0.5-5.0 μM<br>** = 0.05-0.5 μM<br>*** < 0.05 μM |
|---|---|---|
| 1 | 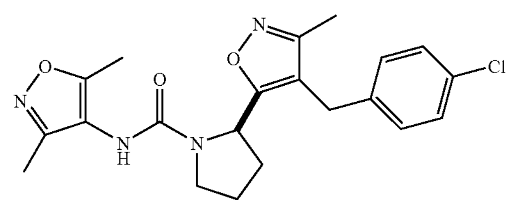 | *** |
| 2 | 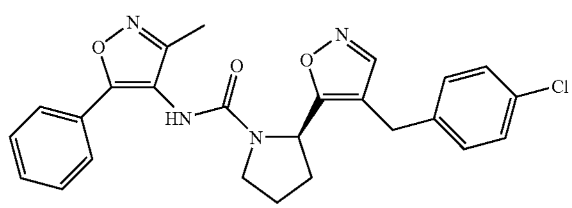 | ** |
| 3 | 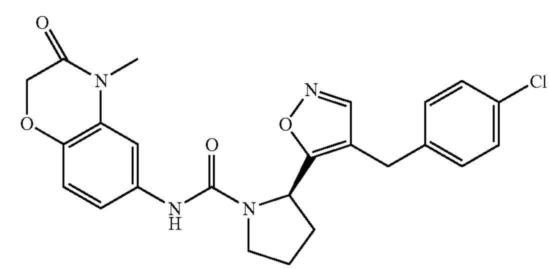 | ** |
| 4 | 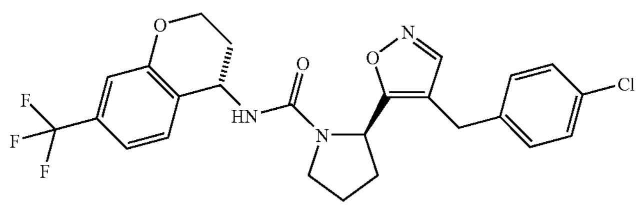 | ** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 5 | 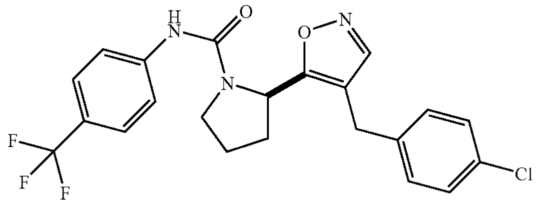 | ** |
| 6 | 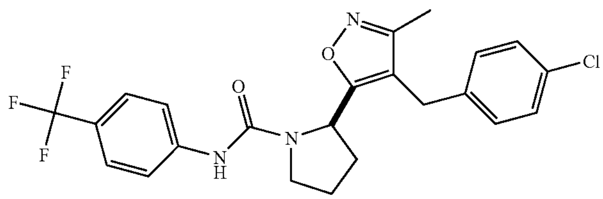 | * |
| 7 | 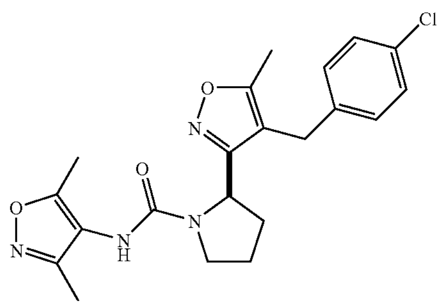 | ** |
| 8 | 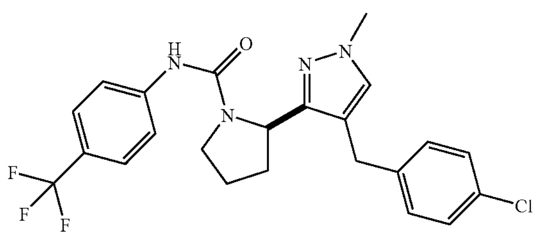 | ** |
| 9 | 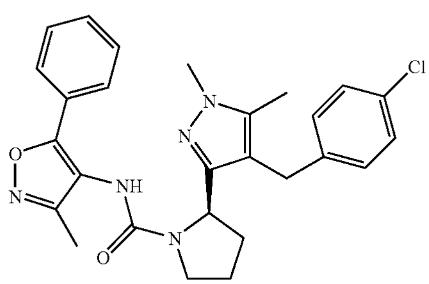 | * |
| 10 | 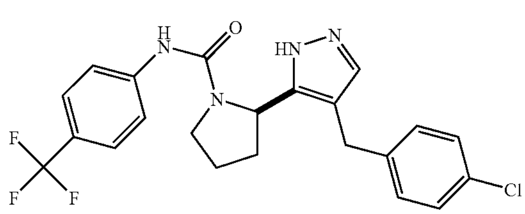 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 11 | 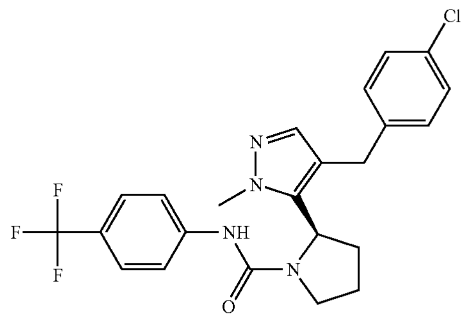 | * |
| 12 | 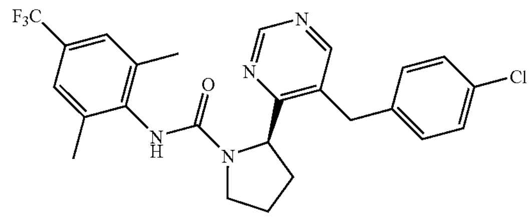 | *** |
| 13 | 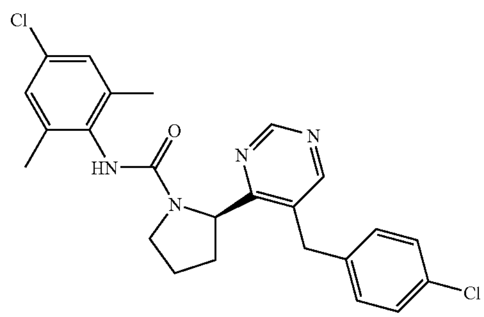 | *** |
| 14 | 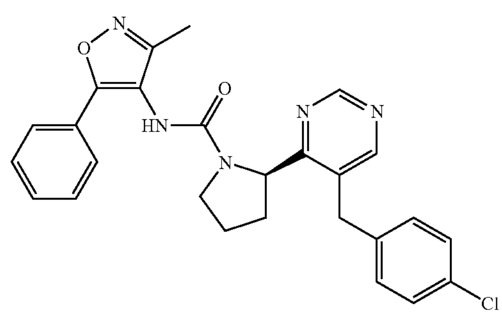 | *** |
| 15 | 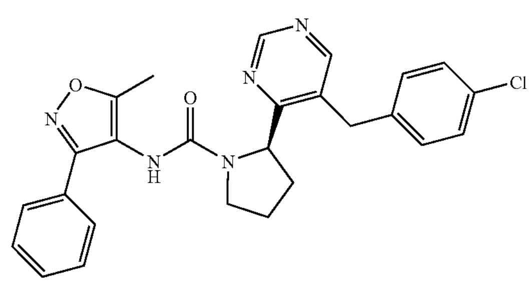 | *** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 16 | 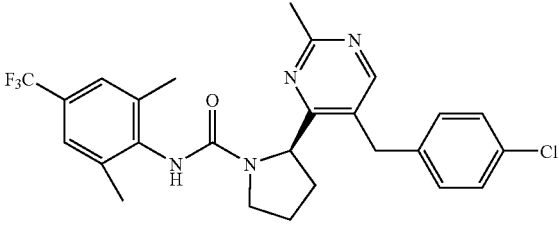 | ** |
| 17 | 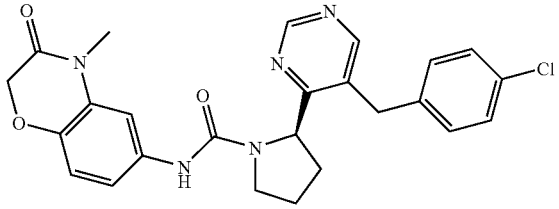 | ** |
| 18 | 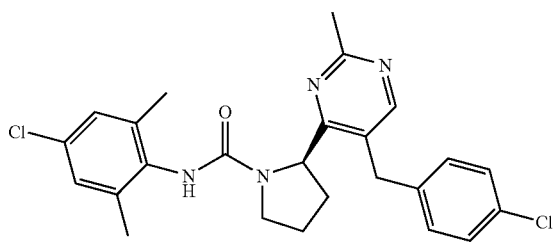 | ** |
| 19 | 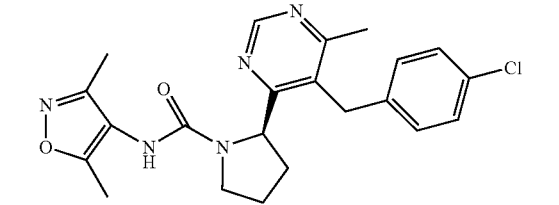 | ** |
| 20 | 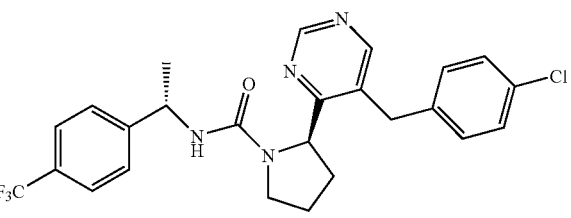 | ** |
| 21 | 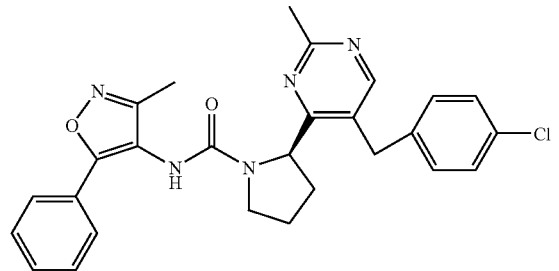 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 22 | 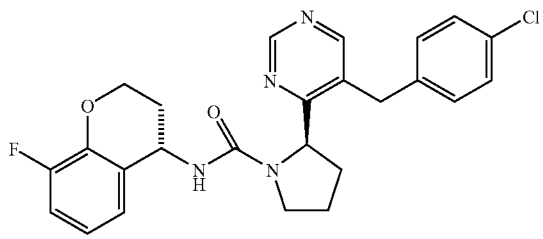 | ** |
| 23 | 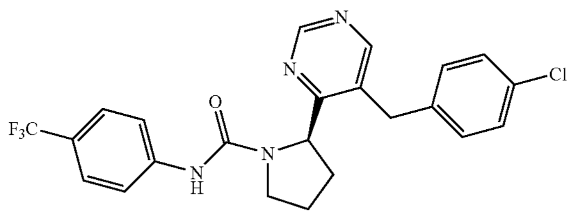 | ** |
| 24 | 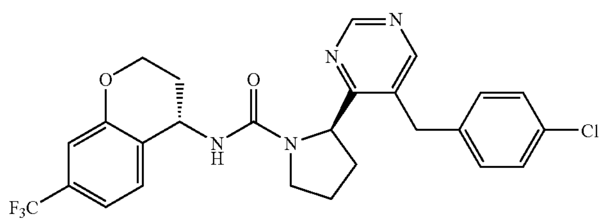 | ** |
| 25 | 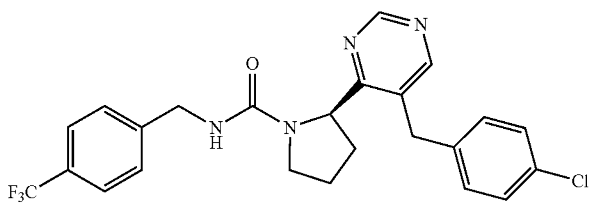 | ** |
| 26 | 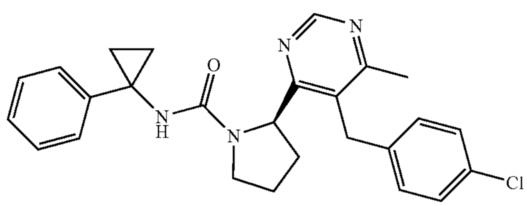 | ** |
| 27 | 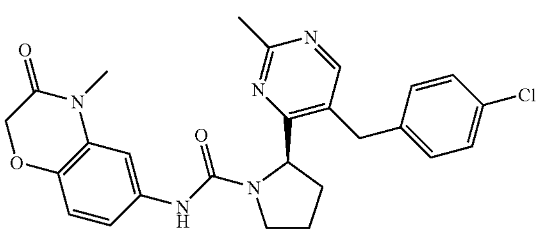 | * |
| 28 | 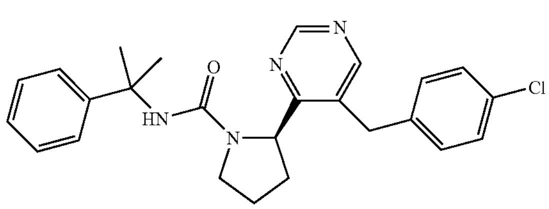 | * |

TABLE 1-continued

| Compound # | Structure | Relative potency (IC$_{50}$) <br> * = 0.5-5.0 μM <br> ** = 0.05-0.5 μM <br> *** < 0.05 μM |
|---|---|---|
| 29 | 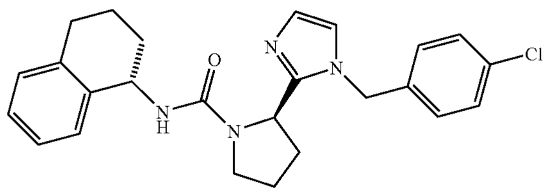 | *** |
| 30 | 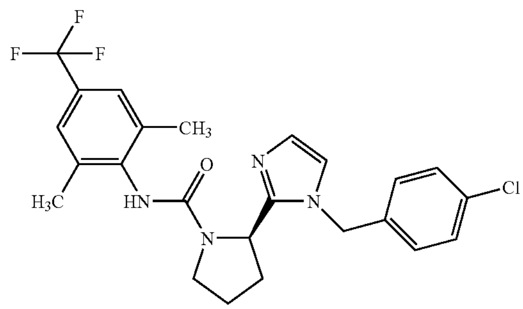 | *** |
| 31 | 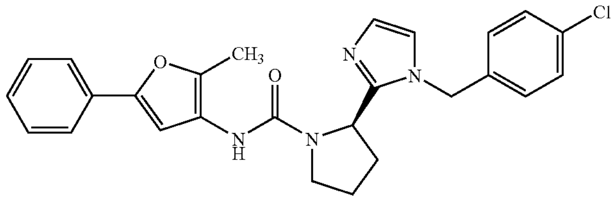 | *** |
| 32 | 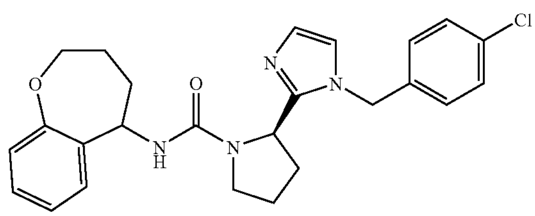 | *** |
| 33 | 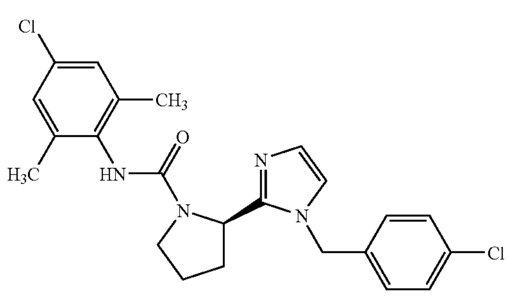 | *** |
| 34 | 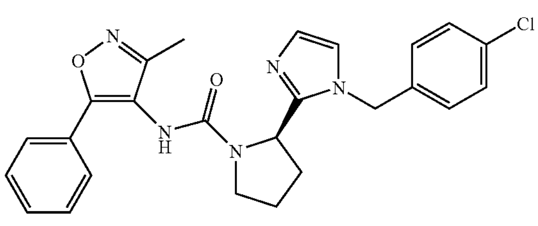 | *** |

TABLE 1-continued
| Compound # | Structure | Relative potency (IC$_{50}$) * = 0.5-5.0 μM ** = 0.05-0.5 μM *** < 0.05 μM |
|---|---|---|
| 35 | 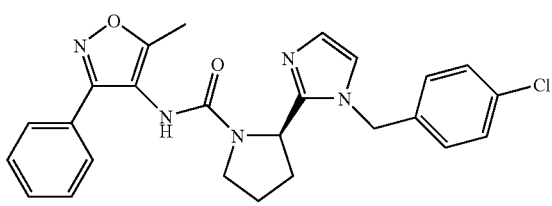 | *** |
| 36 | 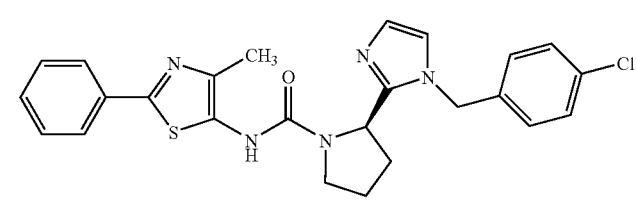 | *** |
| 37 | 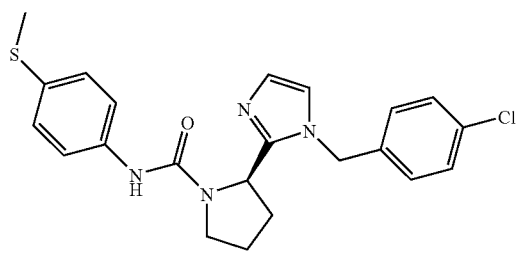 | *** |
| 38 | 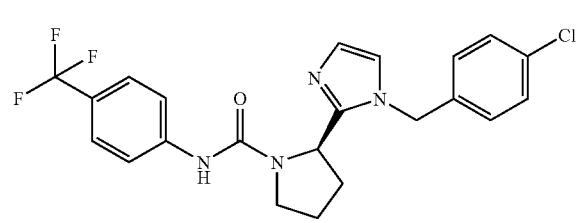 | ** |
| 39 | 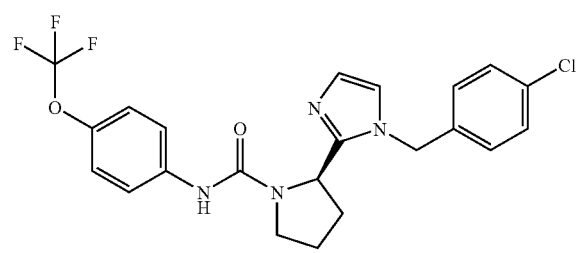 | ** |
| 40 | 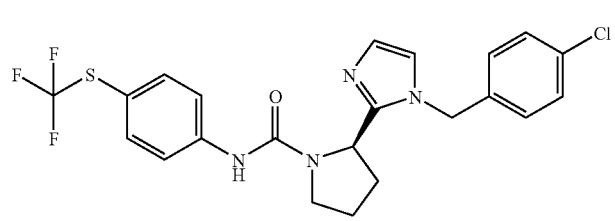 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 41 | 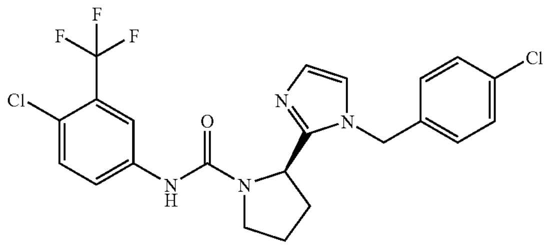 | ** |
| 42 | 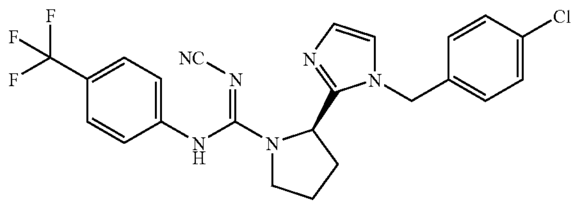 | ** |
| 43 | 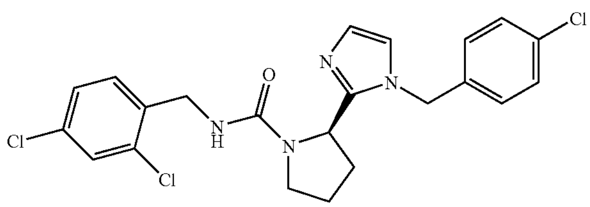 | ** |
| 44 | 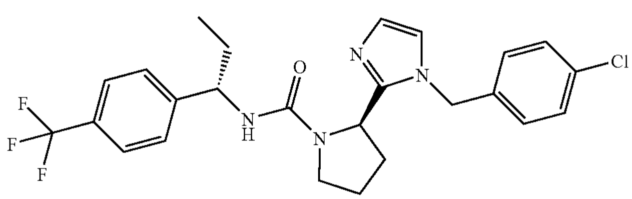 | ** |
| 45 | 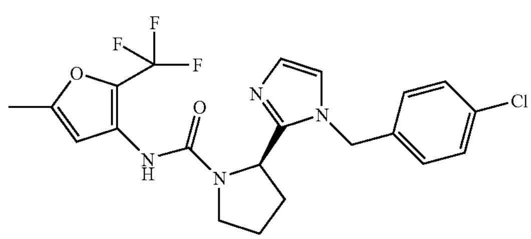 | * |
| 46 | 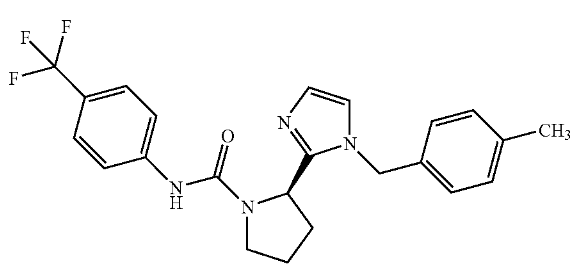 | * |

TABLE 1-continued

| Compound # | Structure | Relative potency (IC$_{50}$) * = 0.5-5.0 μM ** = 0.05-0.5 μM *** < 0.05 μM |
|---|---|---|
| 47 | 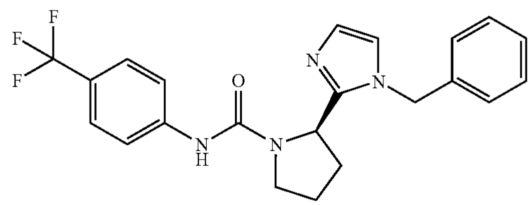 | * |
| 48 | 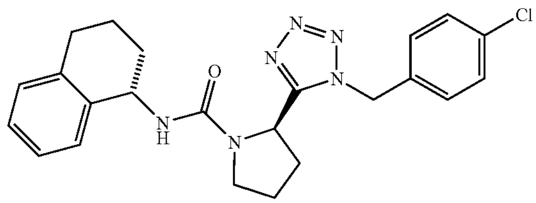 | *** |
| 49 | 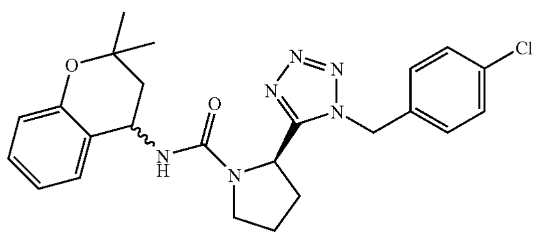 | ** |
| 50 | 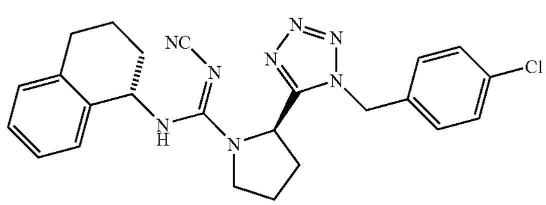 | * |
| 51 | 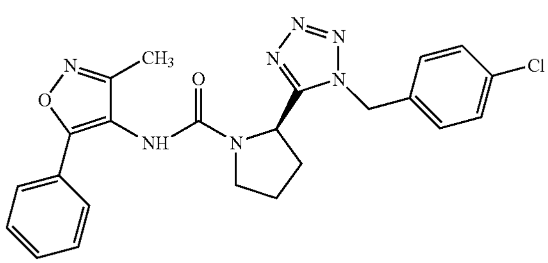 | *** |
| 52 | 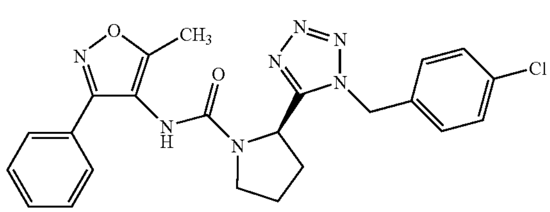 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 53 | 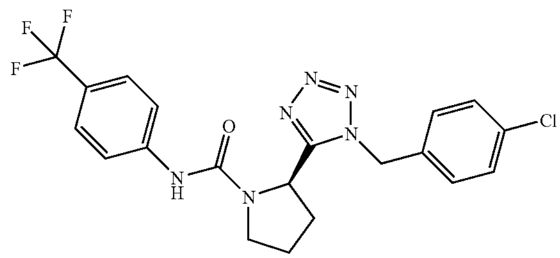 | *** |
| 54 | 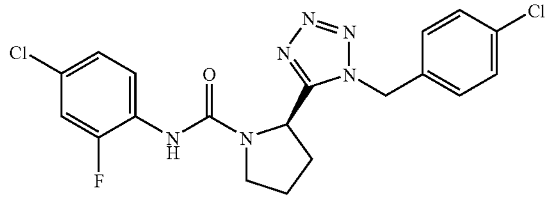 | ** |
| 55 | 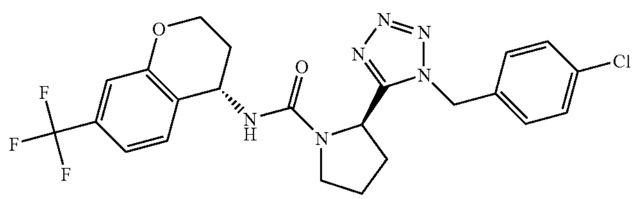 | *** |
| 56 | 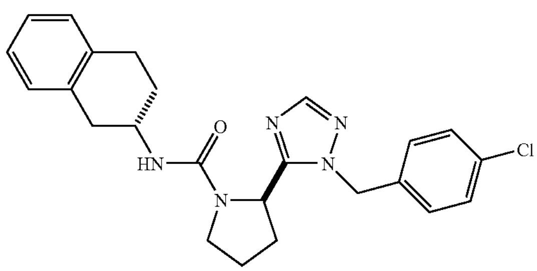 | *** |
| 57 | 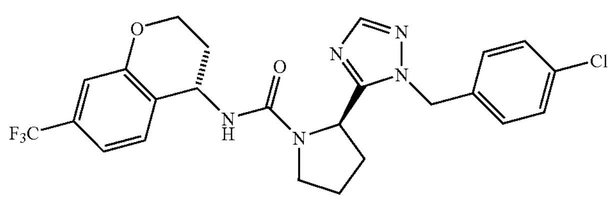 | *** |
| 58 | 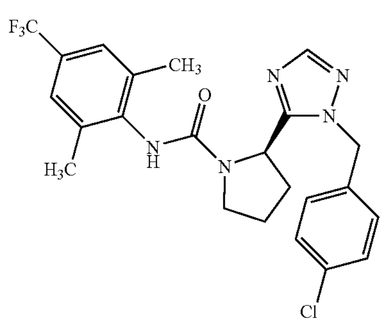 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 59 | 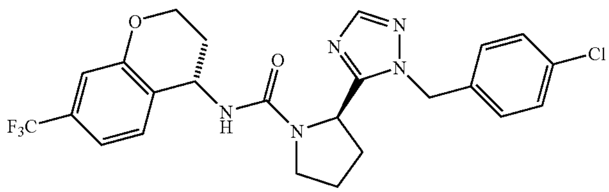 | *** |
| 60 | 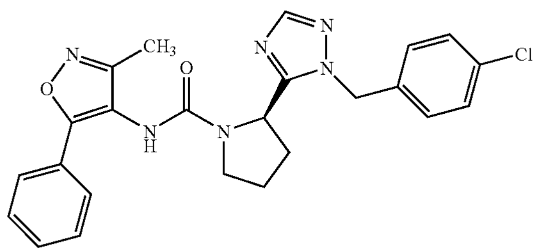 | *** |
| 61 | 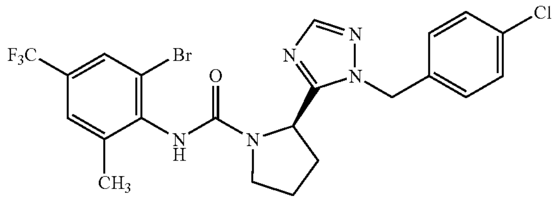 | *** |
| 62 | 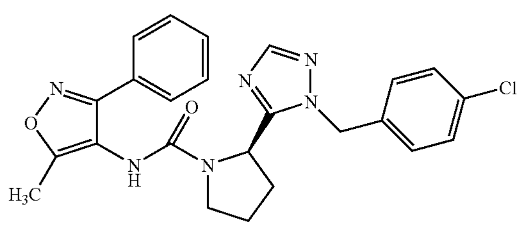 | *** |
| 63 | 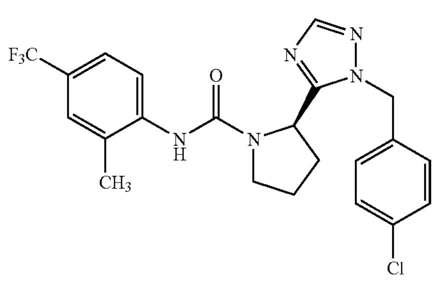 | *** |
| 64 | 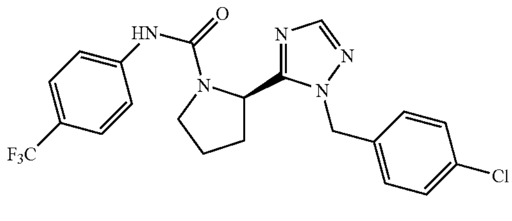 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 65 | 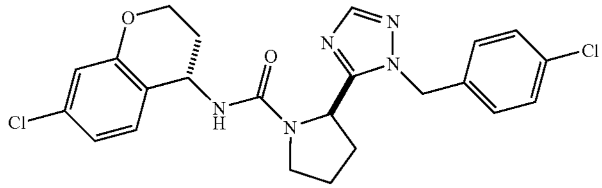 | ** |
| 66 | 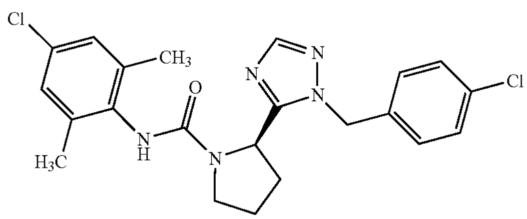 | ** |
| 67 | 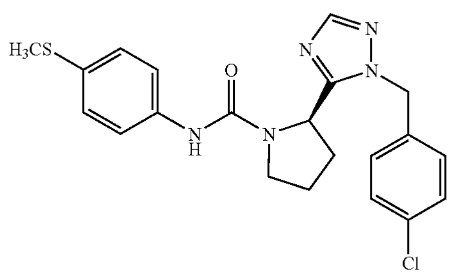 | ** |
| 68 | 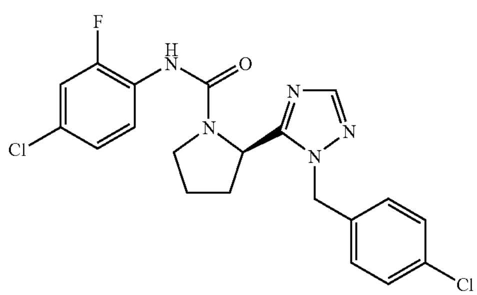 | ** |
| 69 | 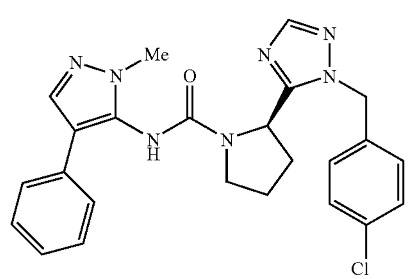 | ** |
| 70 | 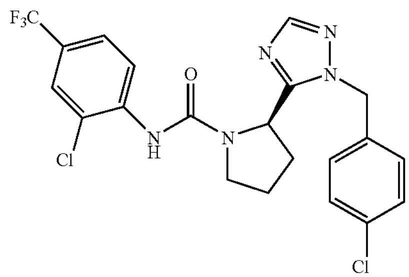 | ** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 71 | 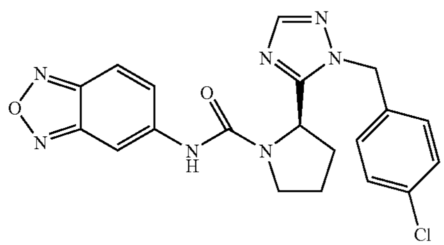 | \*\* |
| 72 | 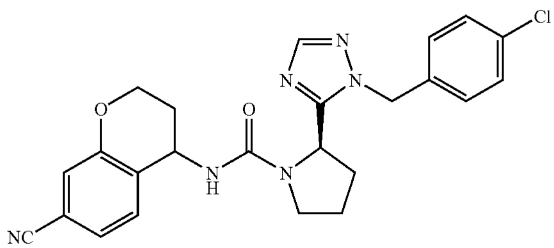 | \*\* |
| 74 | 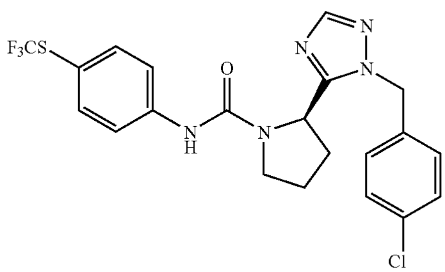 | \*\* |
| 75 | 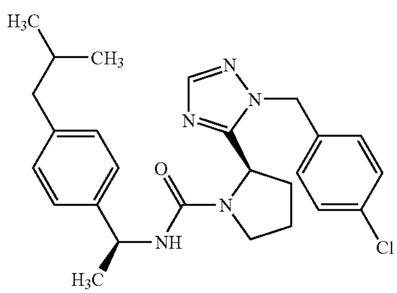 | \*\* |
| 76 | 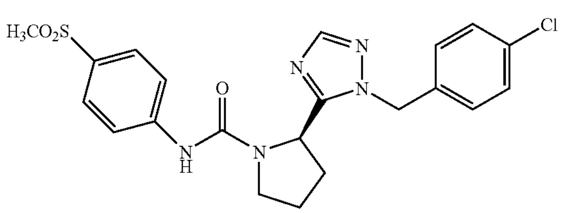 | \*\* |
| 77 | 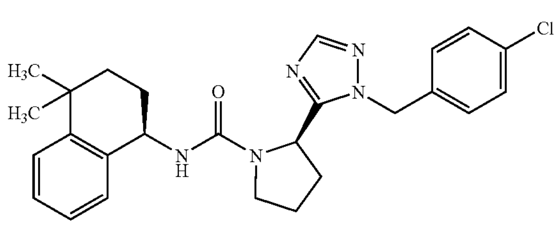 | \*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 78 | 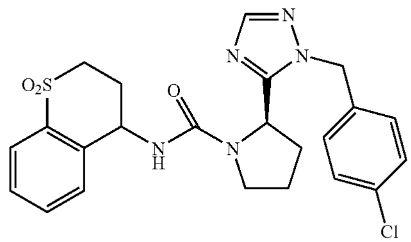 | * |
| 79 | 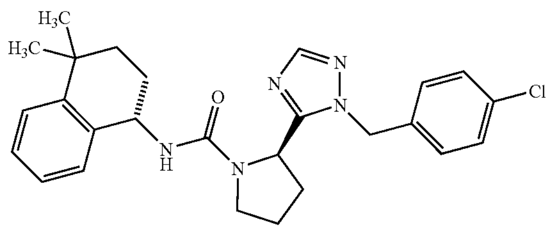 | * |
| 80 | 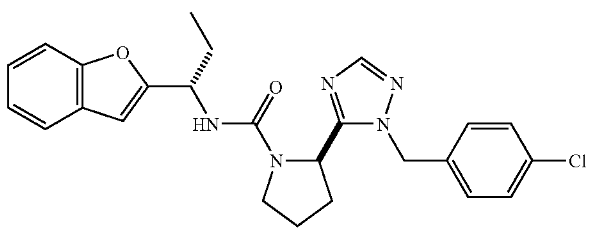 | *** |
| 81 | 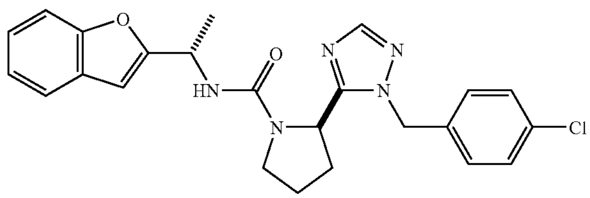 | *** |
| 82 | 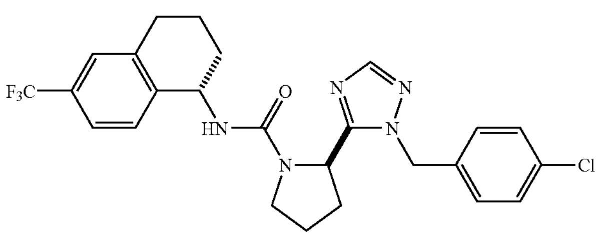 | *** |
| 83 | 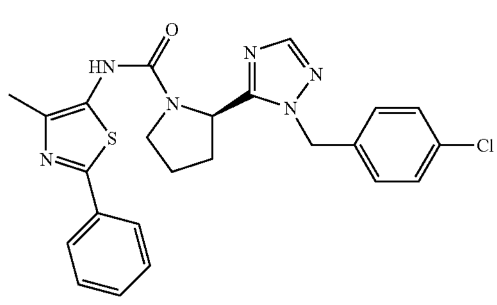 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 84 | 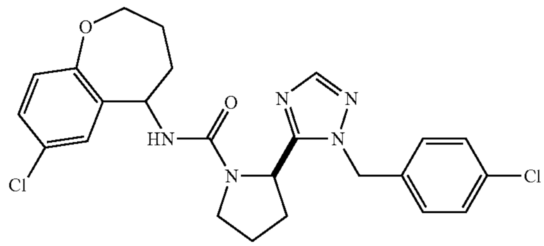 | ** |
| 85 | 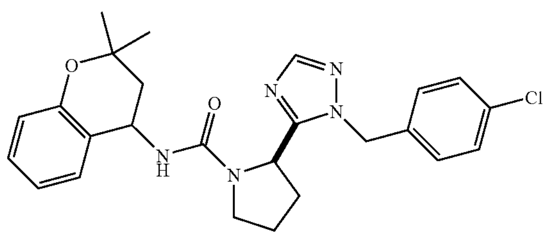 | ** |
| 86 | 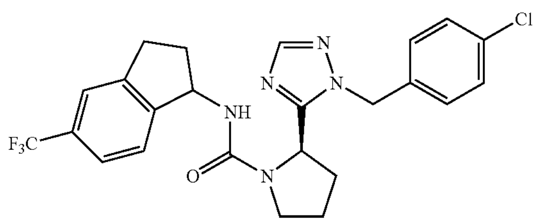 | ** |
| 87 | 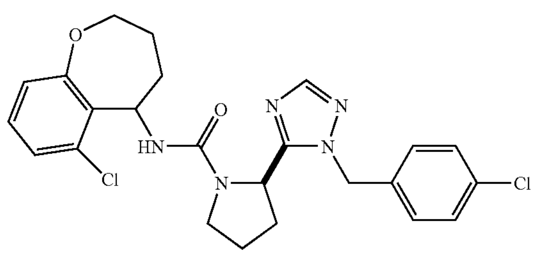 | ** |
| 88 | 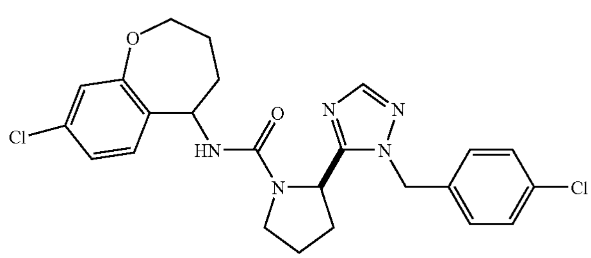 | * |
| 89 | 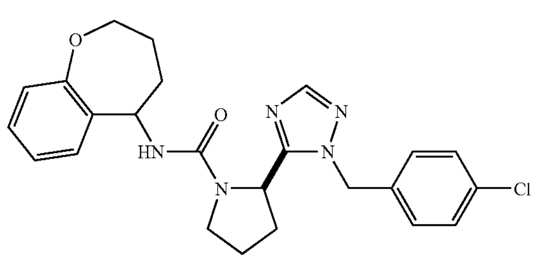 | *** |

TABLE 1-continued

| Compound # | Structure | Relative potency (IC$_{50}$) * = 0.5-5.0 μM ** = 0.05-0.5 μM *** < 0.05 μM |
|---|---|---|
| 90 | 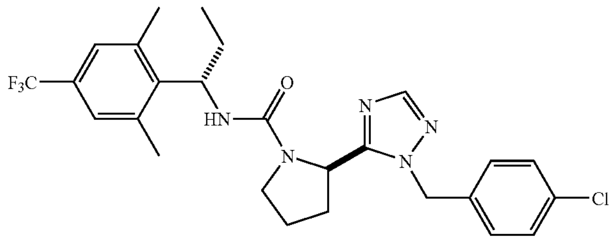 | ** |
| 91 | 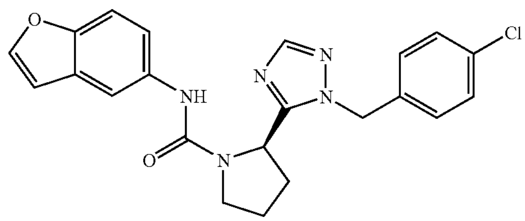 | ** |
| 92 | 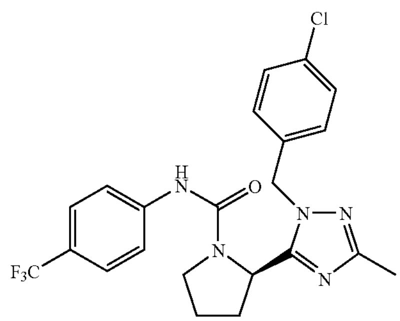 | * |
| 93 | 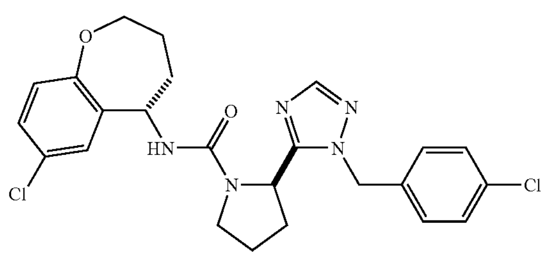 | ** |
| 94 | 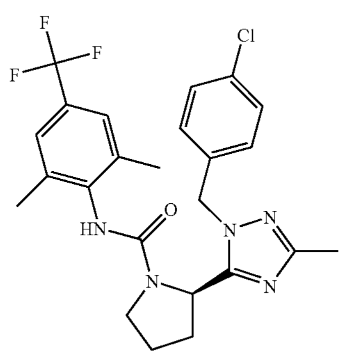 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 95 | 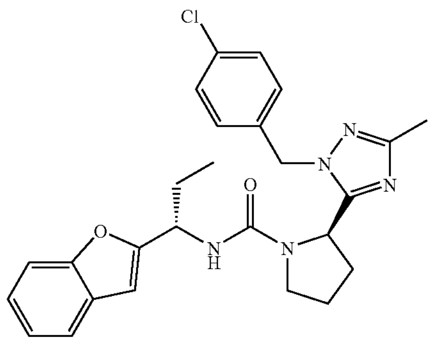 | ** |
| 96 | 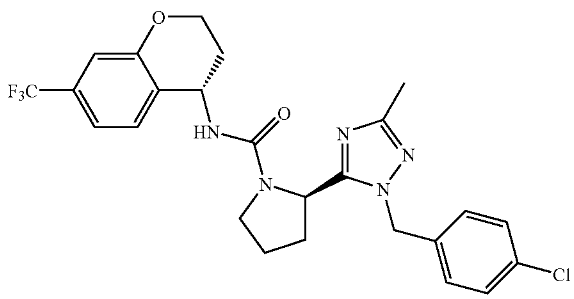 | * |
| 97 | 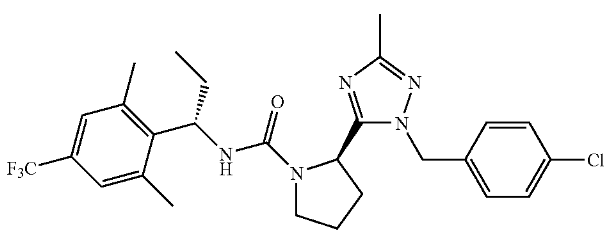 | * |
| 98 | 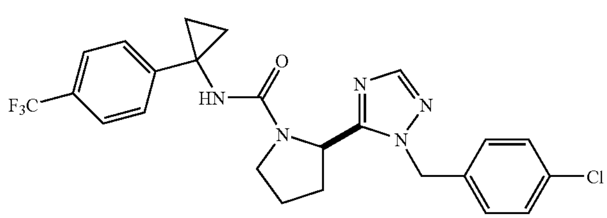 | ** |
| 99 | 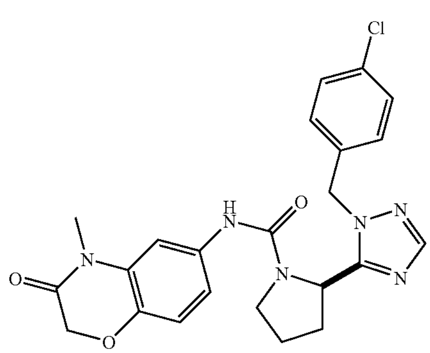 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 100 | 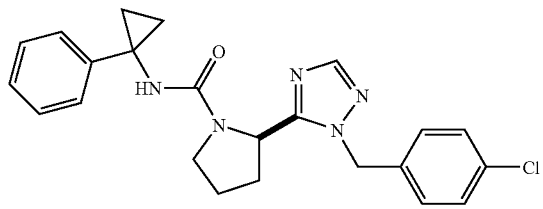 | * |
| 101 | 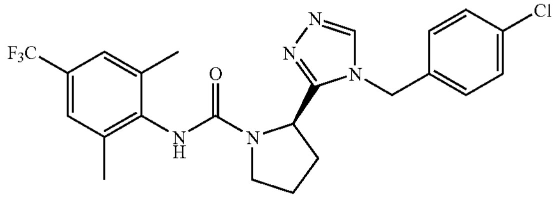 | *** |
| 102 | 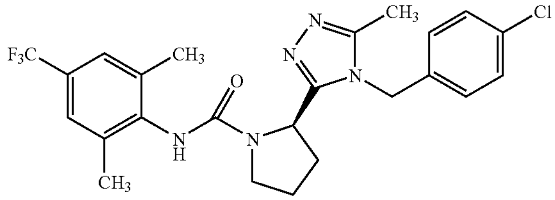 | *** |
| 103 | 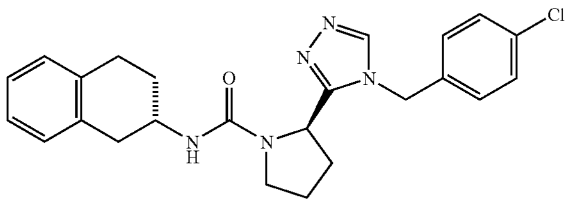 | *** |
| 104 | 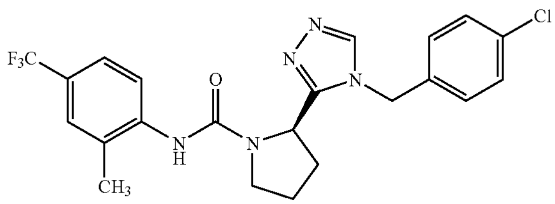 | *** |
| 105 | 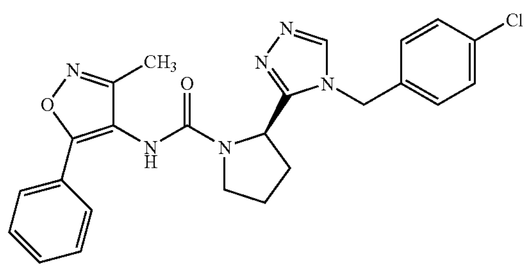 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 106 | 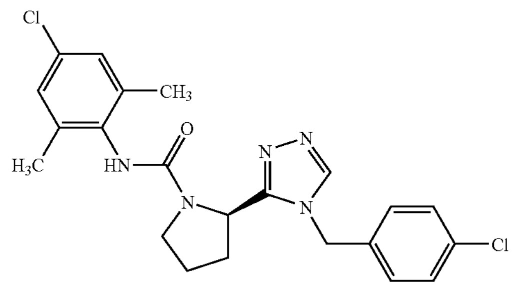 | *** |
| 107 | 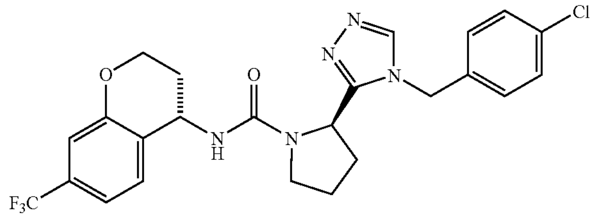 | *** |
| 108 | 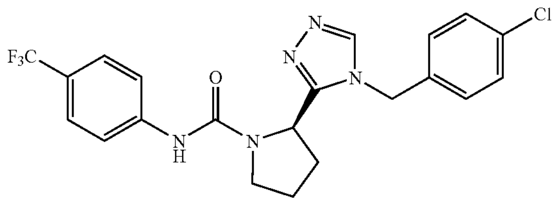 | *** |
| 109 | 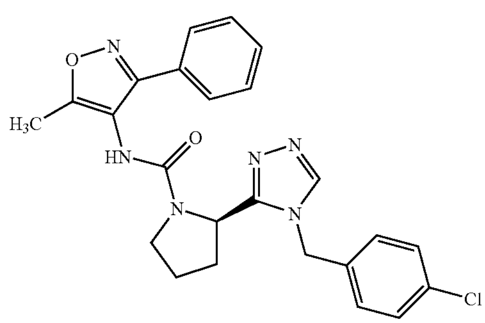 | *** |
| 110 | 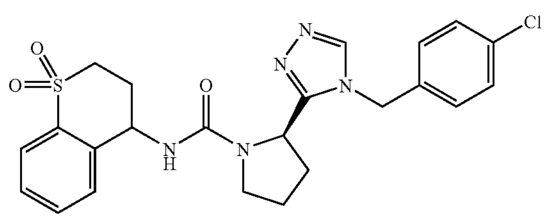 | *** |
| 111 | 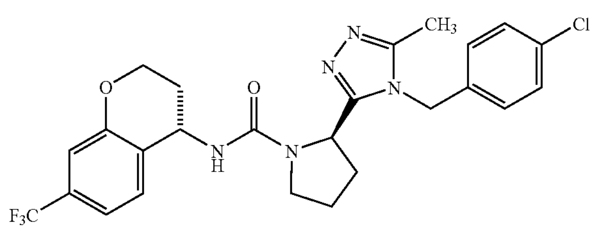 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 112 | 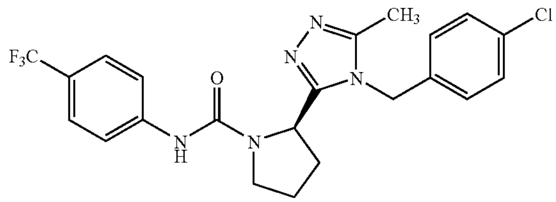 | ** |
| 113 | 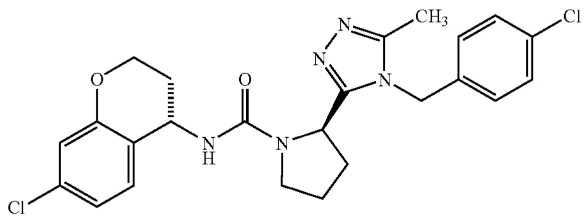 | *** |
| 114 | 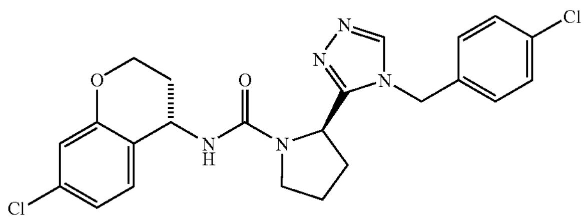 | *** |
| 115 | 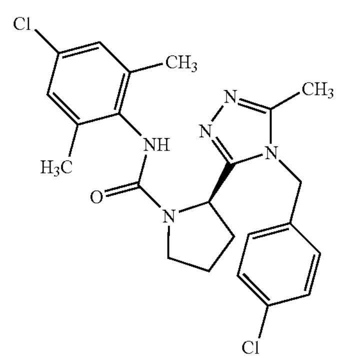 | *** |
| 116 | 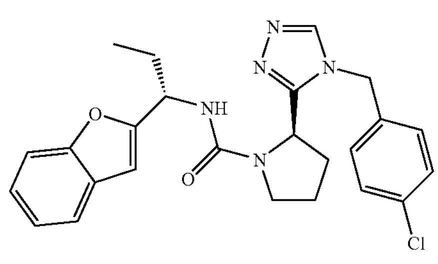 | *** |
| 117 | 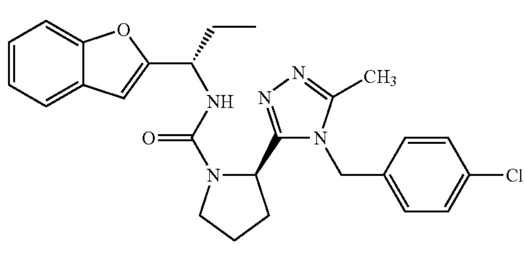 | *** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 118 | 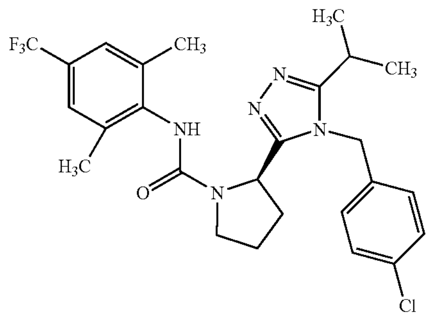 | \*\* |
| 119 | 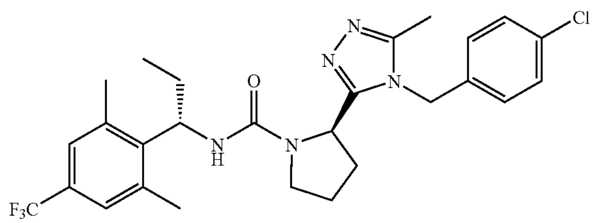 | \*\*\* |
| 120 | 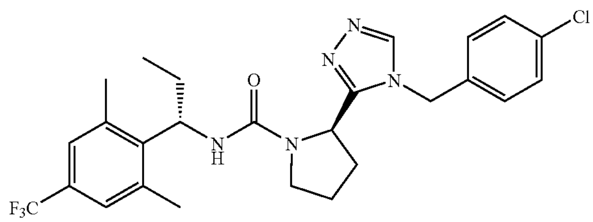 | \*\*\* |
| 121 | 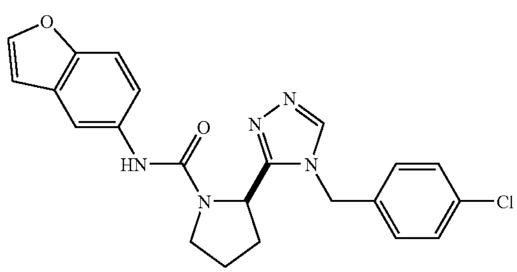 | \*\* |
| 122 | 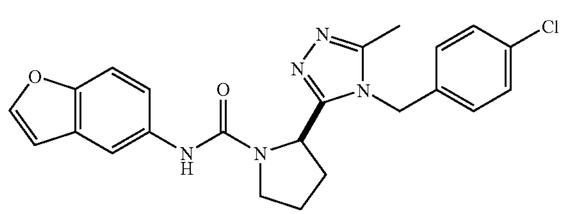 | \*\* |
| 123 | 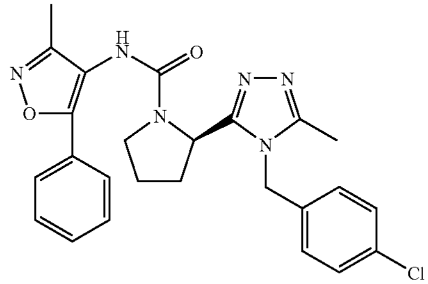 | \*\*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 124 | 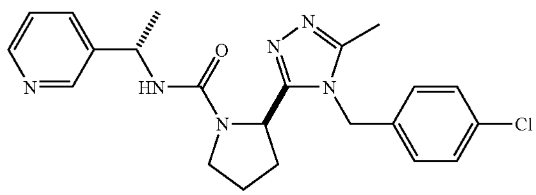 | *** |
| 125 | 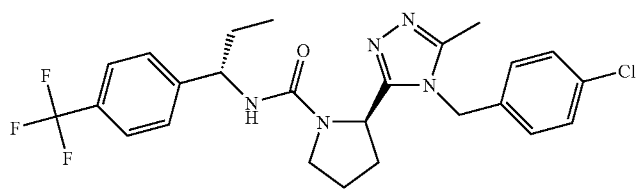 | *** |
| 126 | 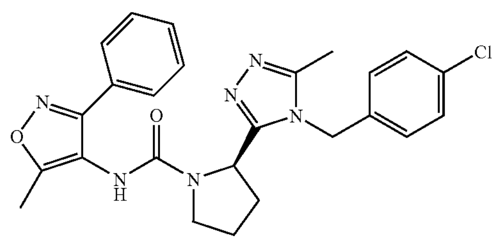 | *** |
| 127 | 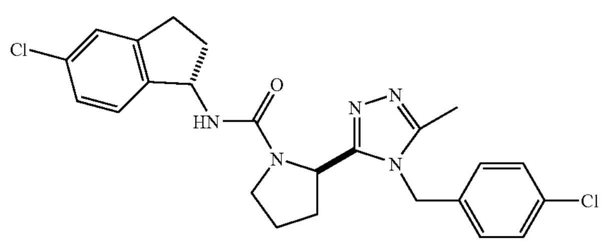 | *** |
| 128 | 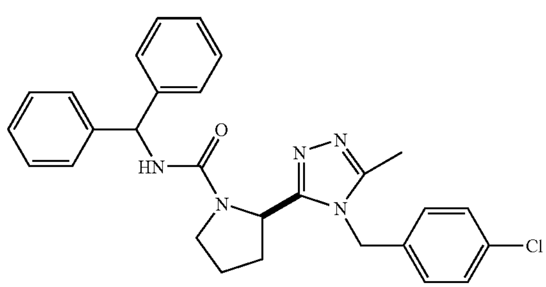 | *** |
| 129 | 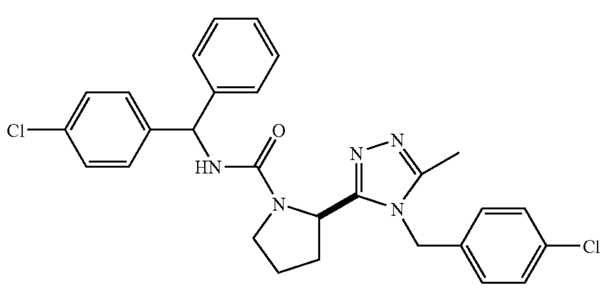 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 130 | 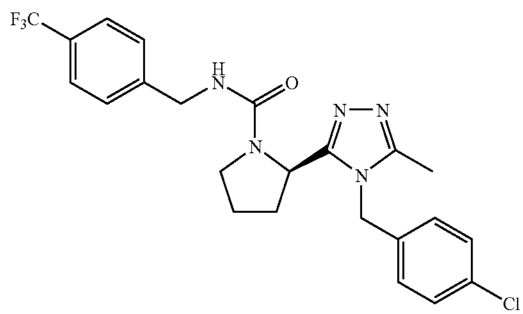 | *** |
| 131 | 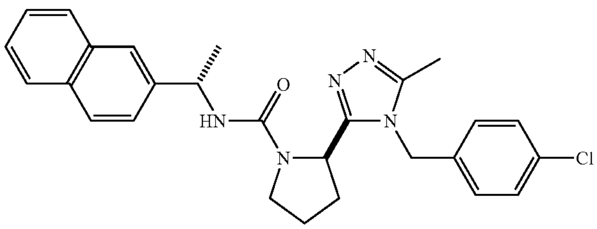 | *** |
| 132 | 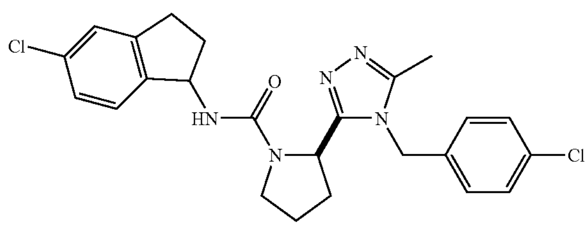 | *** |
| 133 | 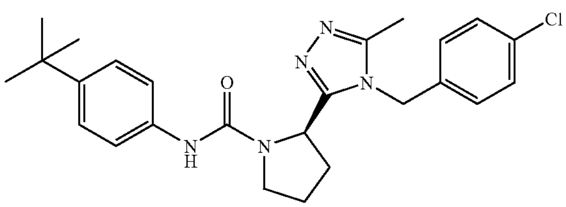 | *** |
| 134 | 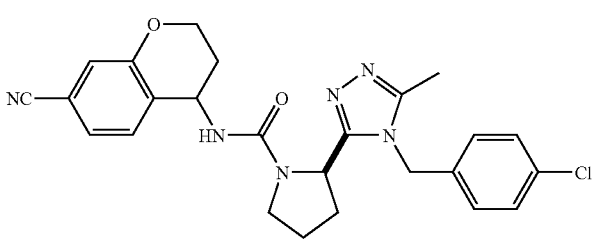 | *** |
| 135 | 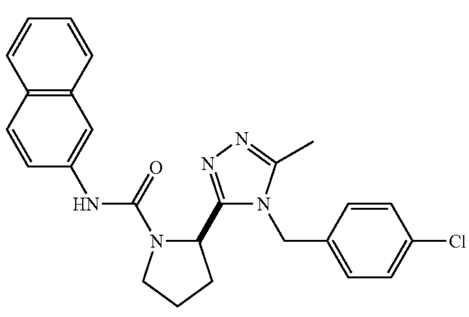 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 136 | 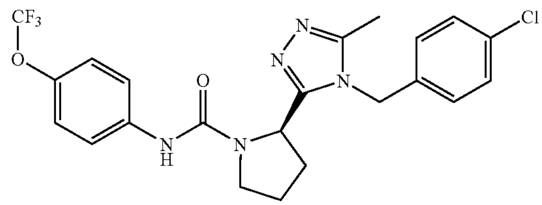 | *** |
| 137 | 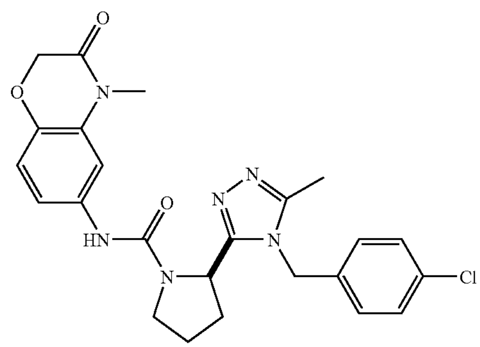 | ** |
| 138 | 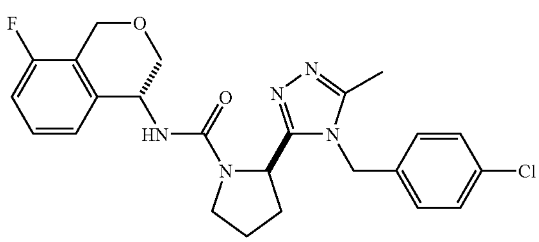 | ** |
| 139 | 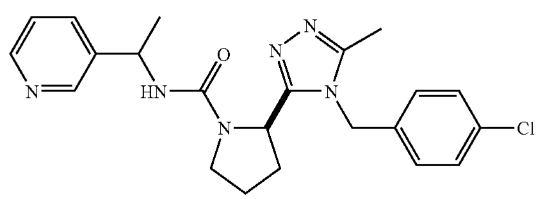 | ** |
| 140 | 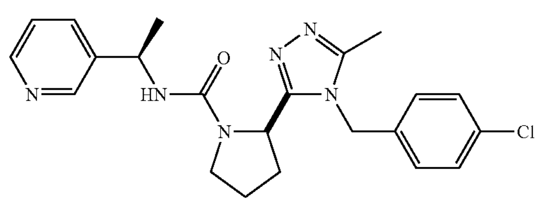 | ** |
| 141 | 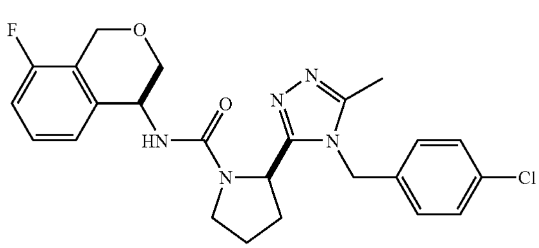 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 142 | 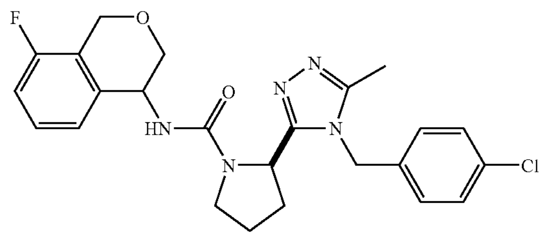 | ** |
| 143 | 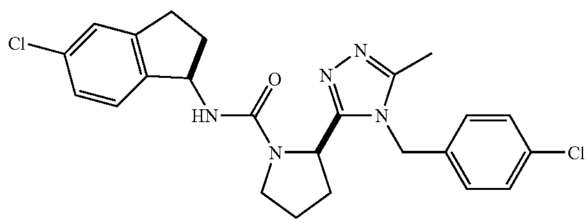 | ** |
| 144 | 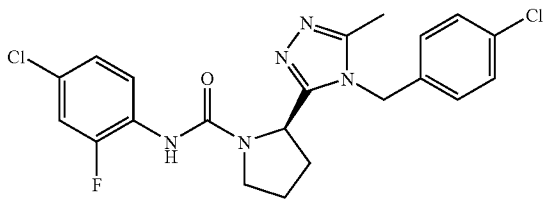 | *** |
| 145 | 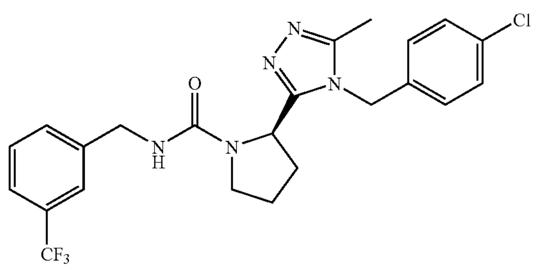 | ** |
| 146 | 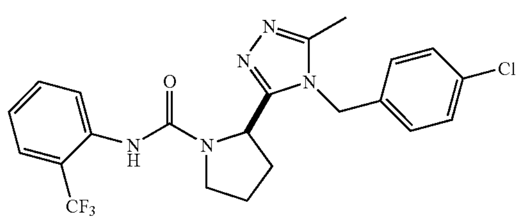 | ** |
| 147 | 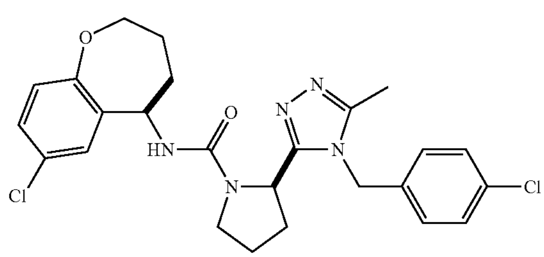 | *** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 148 | 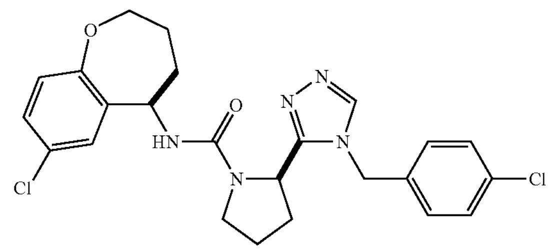 | \*\* |
| 149 | 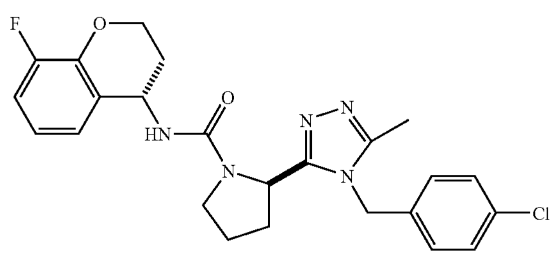 | \*\*\* |
| 150 | 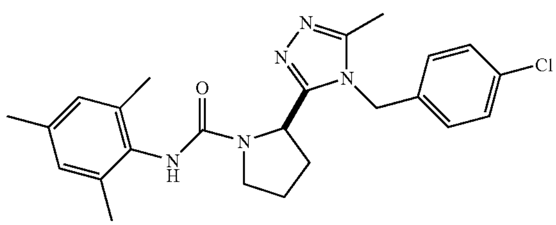 | \*\*\* |
| 151 | 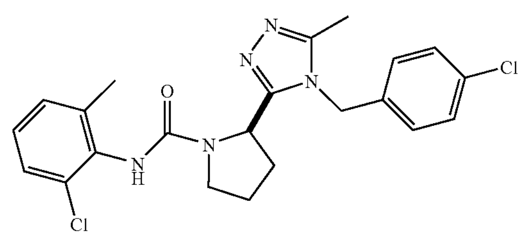 | \*\*\* |
| 152 | 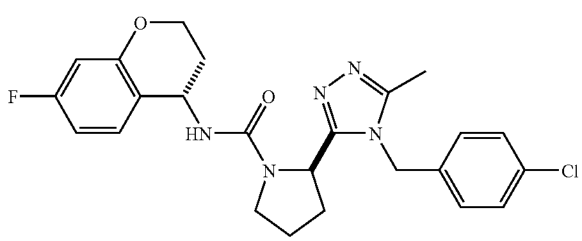 | \*\*\* |
| 153 | 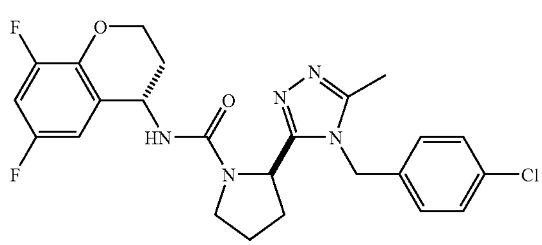 | \*\*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 154 | 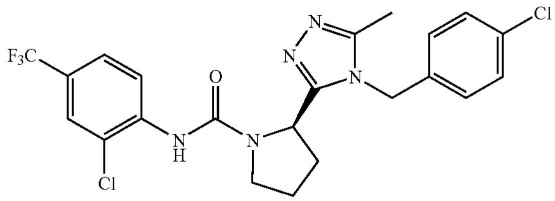 | ** |
| 155 | 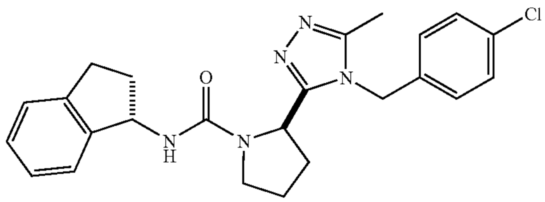 | ** |
| 156 | 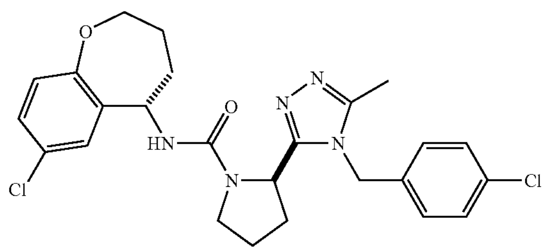 | ** |
| 157 | 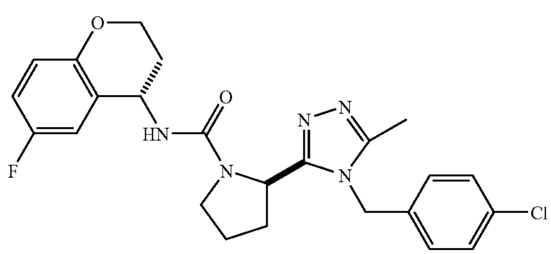 | ** |
| 158 | 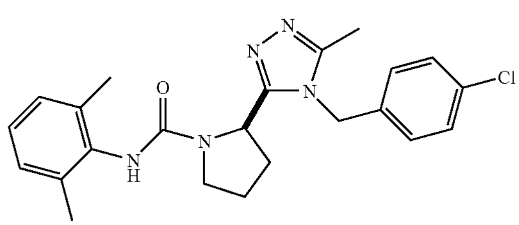 | ** |
| 159 | 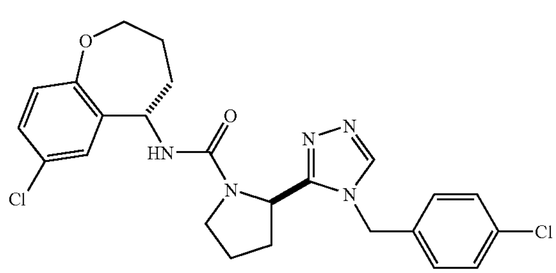 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 160 | 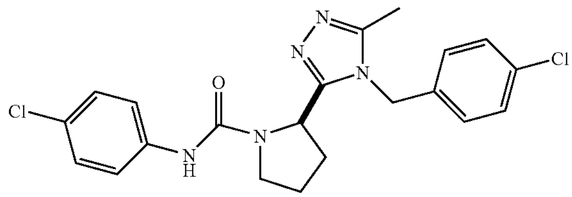 | ** |
| 161 | 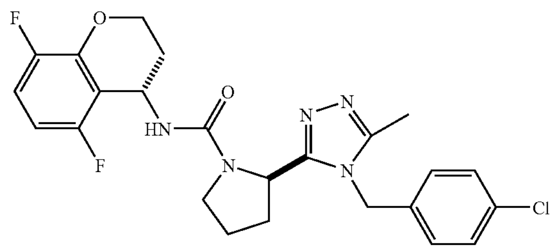 | ** |
| 162 | 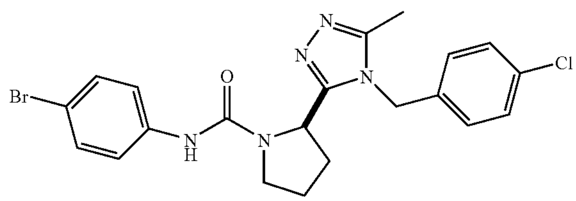 | ** |
| 163 | 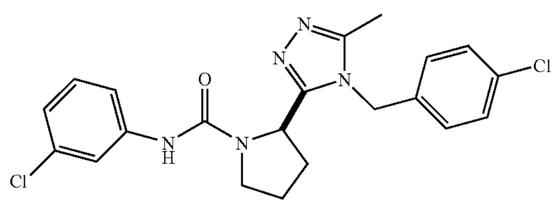 | ** |
| 164 | 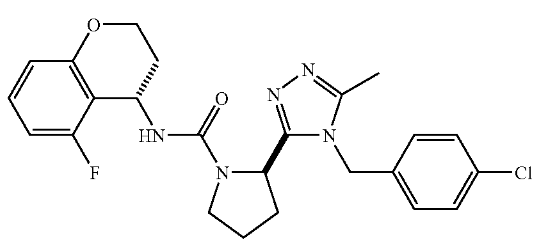 | ** |
| 165 | 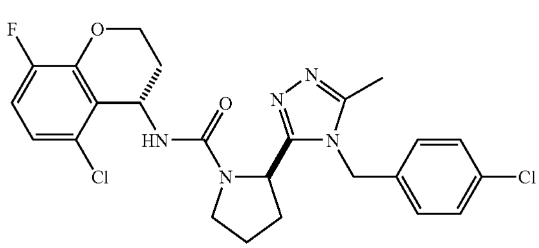 | ** |
| 166 | 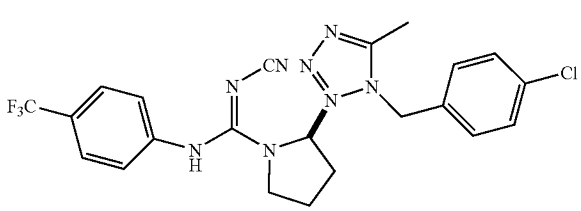 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 167 | 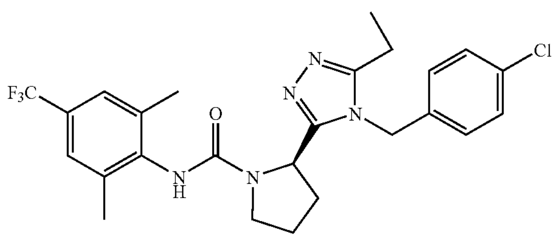 | *** |
| 168 | 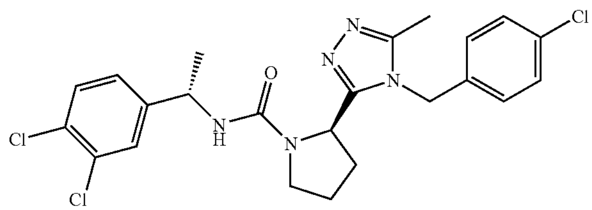 | *** |
| 169 | 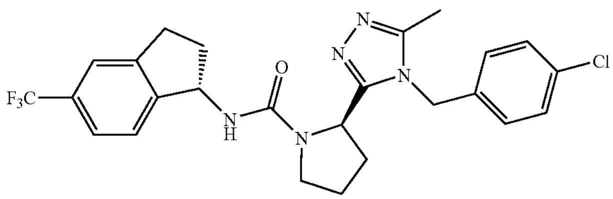 | *** |
| 170 | 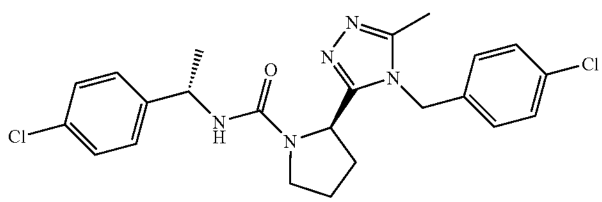 | *** |
| 171 | 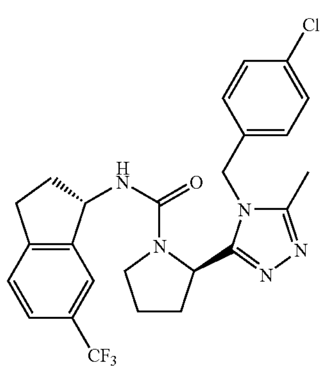 | ** |
| 172 | 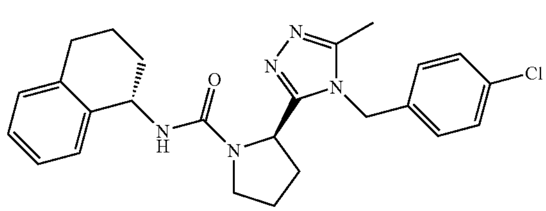 | ** |

TABLE 1-continued

| Compound # | Structure | Relative potency (IC$_{50}$) <br> * = 0.5-5.0 μM <br> ** = 0.05-0.5 μM <br> *** < 0.05 μM |
|---|---|---|
| 173 | 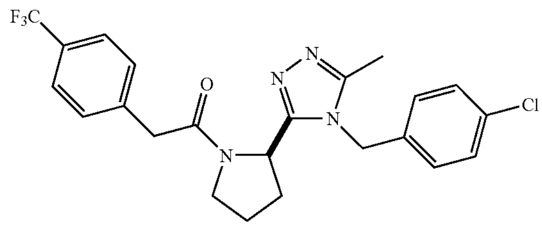 | ** |
| 174 | 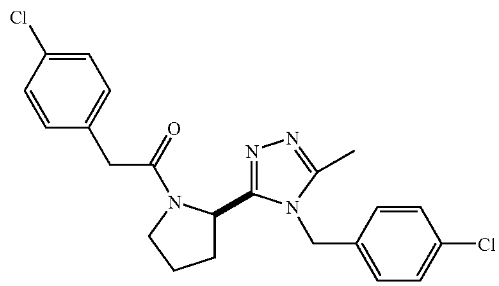 | ** |
| 175 | 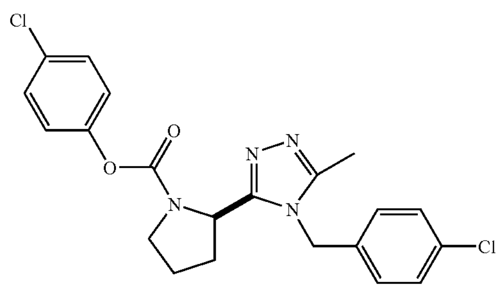 | * |
| 176 | 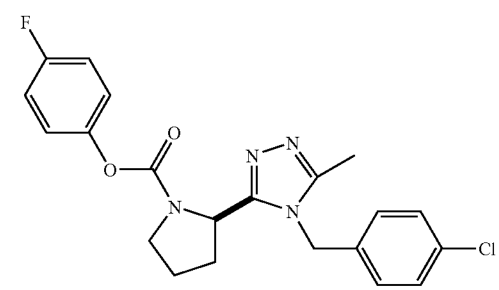 | * |
| 177 | 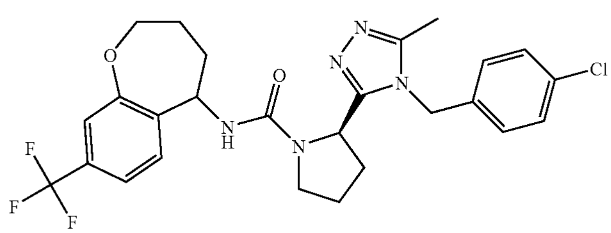 | *** |
| 178 | 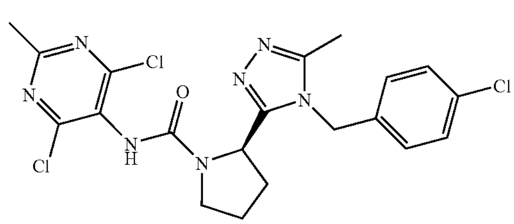 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 179 | 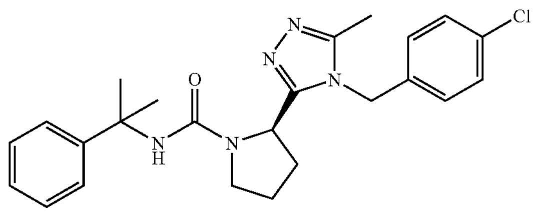 | *** |
| 180 | 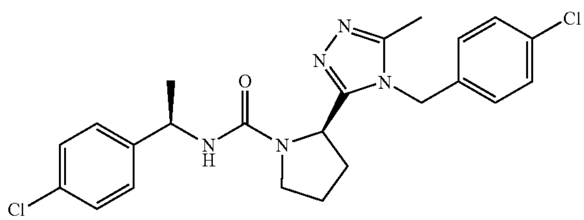 | *** |
| 181 | 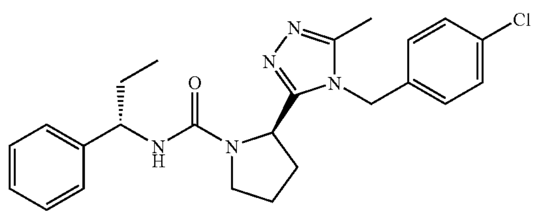 | *** |
| 182 | 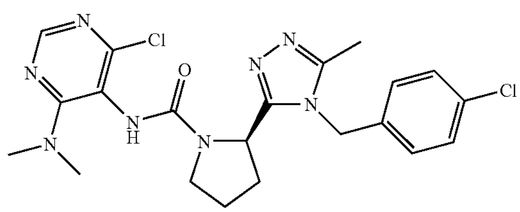 | *** |
| 183 | 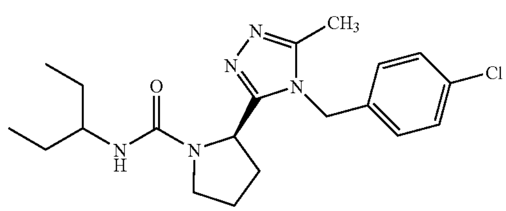 | ** |
| 184 | 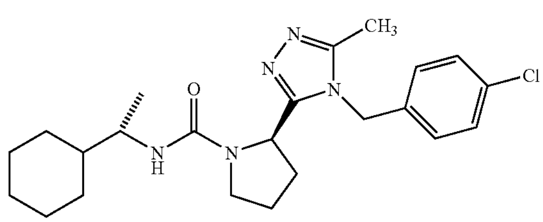 | ** |
| 185 | 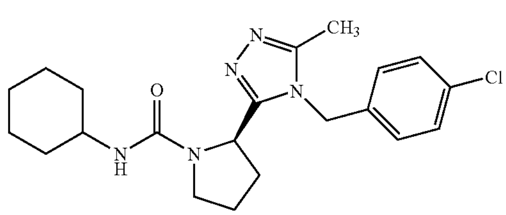 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 186 | 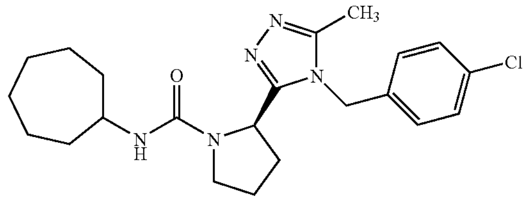 | ** |
| 187 | 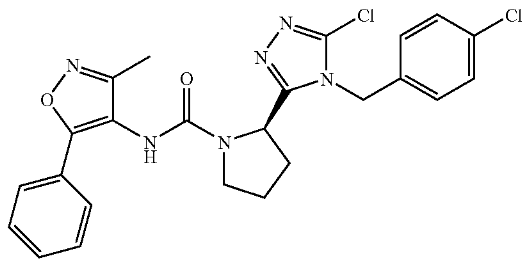 | *** |
| 188 | 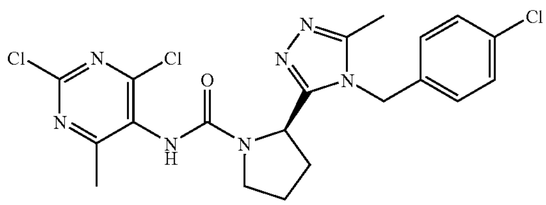 | *** |
| 189 | 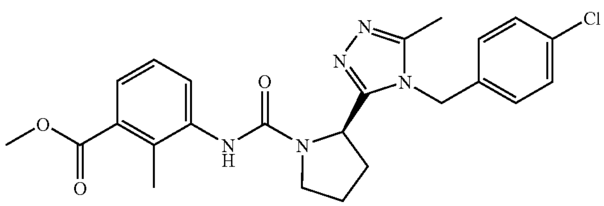 | *** |
| 190 | 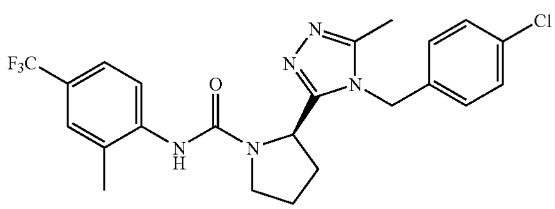 | *** |
| 191 | 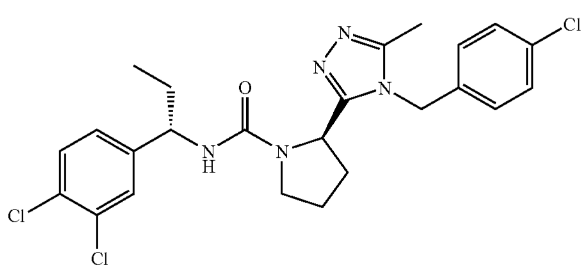 | *** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 192 | 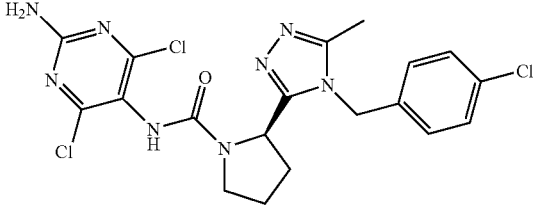 | *** |
| 193 | 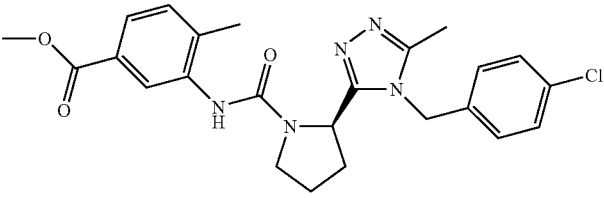 | *** |
| 194 | 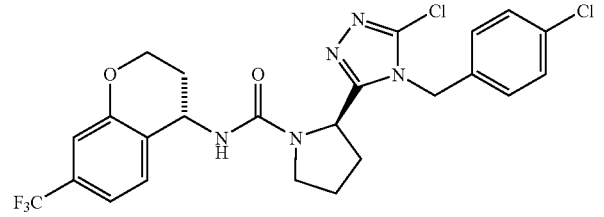 | *** |
| 195 | 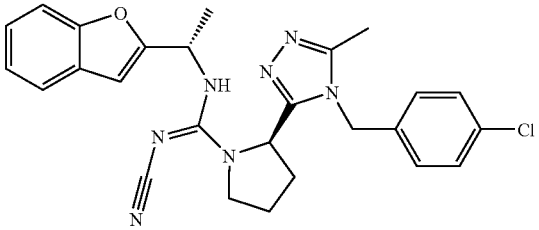 | *** |
| 196 | 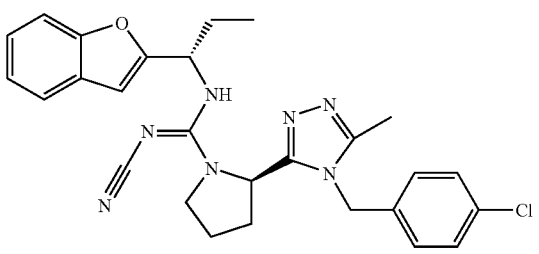 | *** |
| 197 | 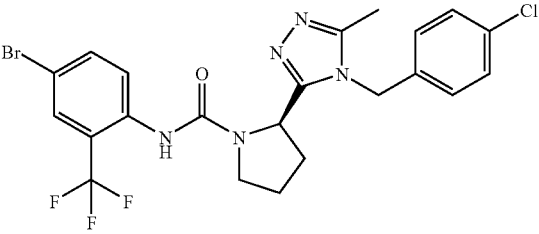 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 198 | 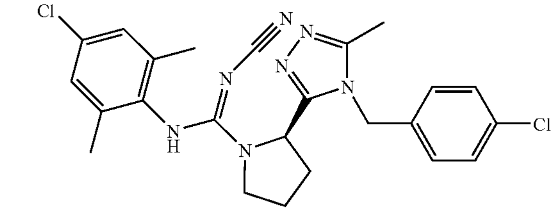 | *** |
| 199 | 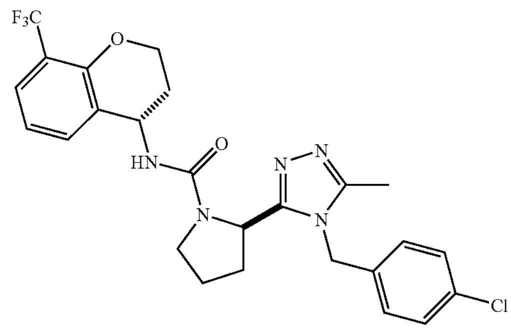 | *** |
| 200 | 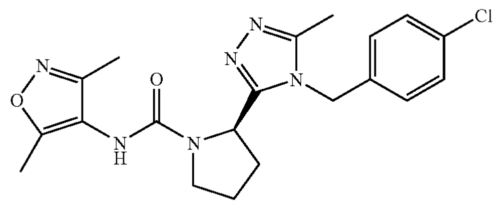 | *** |
| 201 | 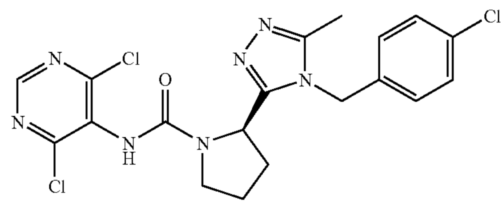 | *** |
| 202 | 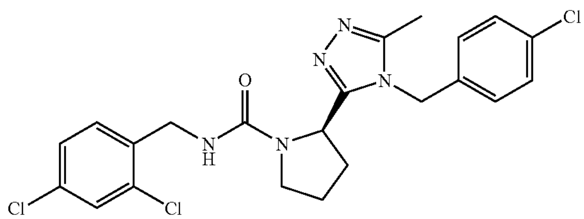 | *** |
| 203 | 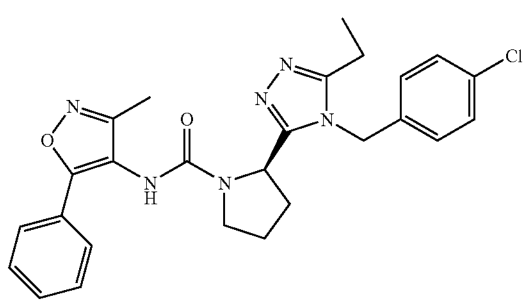 | *** |

TABLE 1-continued
| Compound # | Structure | Relative potency (IC$_{50}$)<br>* = 0.5-5.0 µM<br>** = 0.05-0.5 µM<br>*** < 0.05 µM |
|---|---|---|
| 204 | 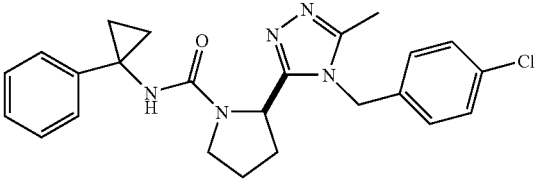 | *** |
| 205 | 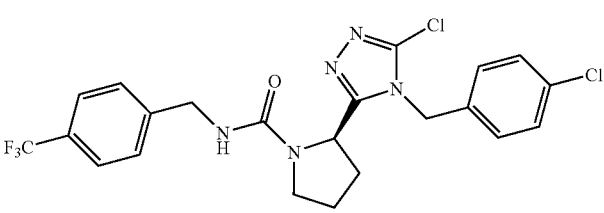 | *** |
| 206 | 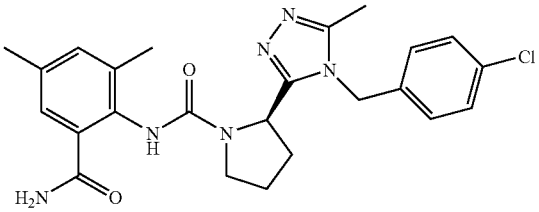 | *** |
| 207 | 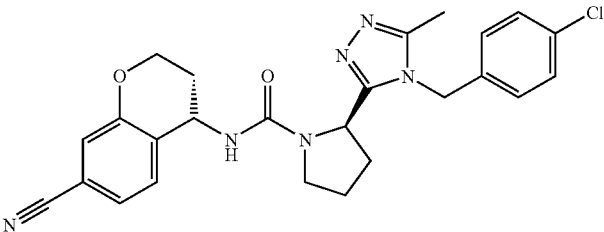 | *** |
| 208 | 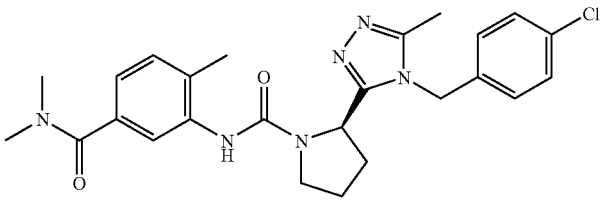 | *** |
| 209 | 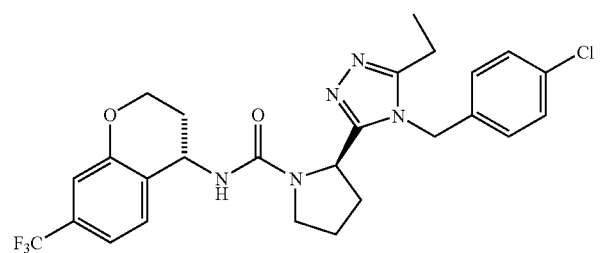 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 210 | 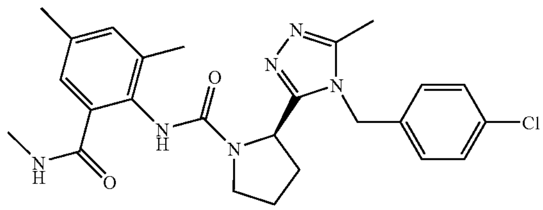 | *** |
| 211 | 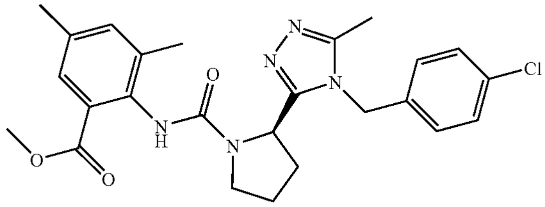 | *** |
| 212 | 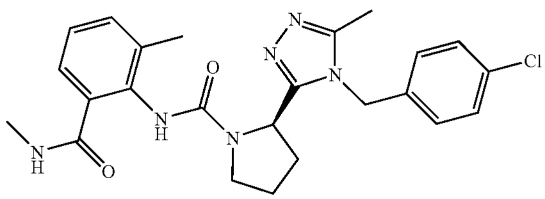 | *** |
| 213 | 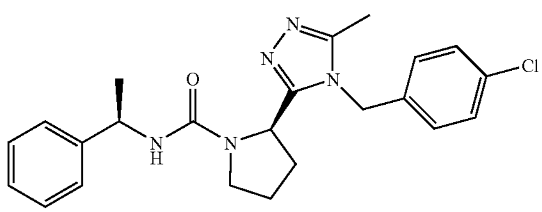 | *** |
| 214 | 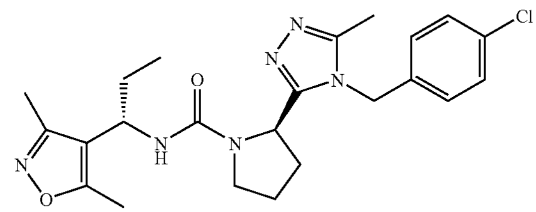 | *** |
| 215 | 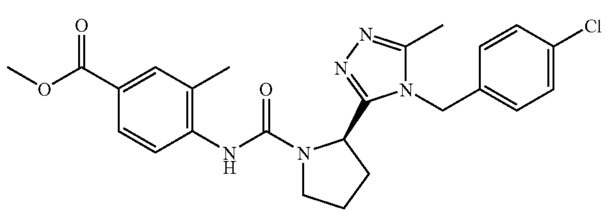 | *** |
| 216 | 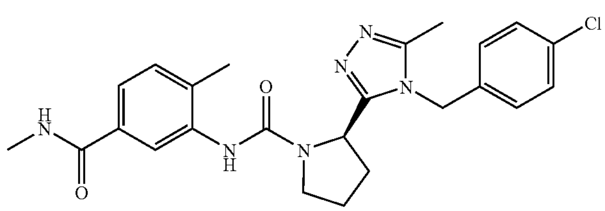 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 217 | 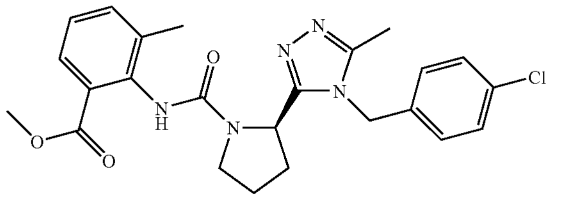 | *** |
| 218 | 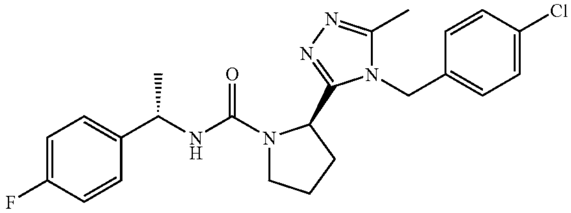 | *** |
| 219 | 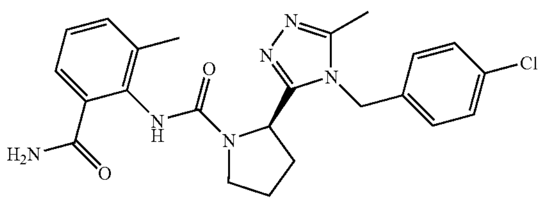 | *** |
| 220 | 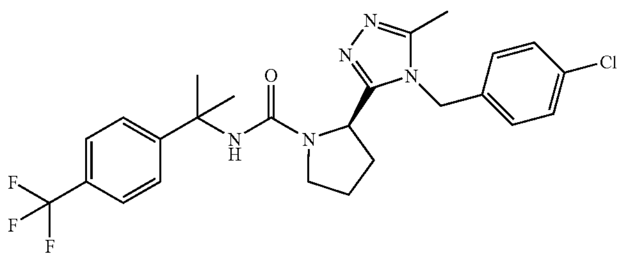 | *** |
| 221 | 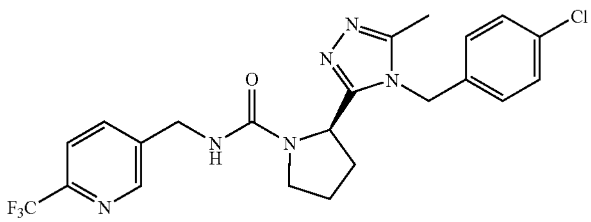 | ** |
| 222 | 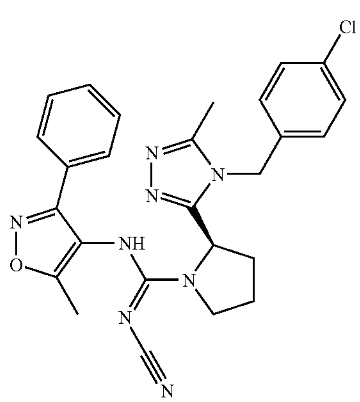 | ** |

TABLE 1-continued

| Compound # | Structure | Relative potency (IC$_{50}$)<br>\* = 0.5-5.0 µM<br>\*\* = 0.05-0.5 µM<br>\*\*\* < 0.05 µM |
|---|---|---|
| 223 | 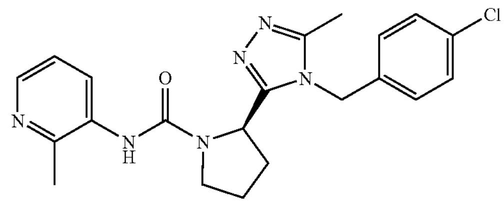 | \*\* |
| 224 | 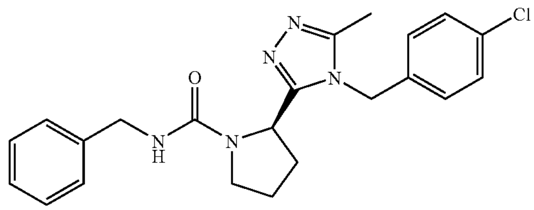 | \*\* |
| 225 | 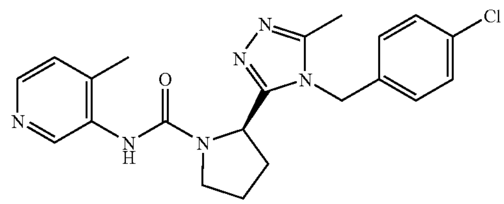 | \*\* |
| 226 | 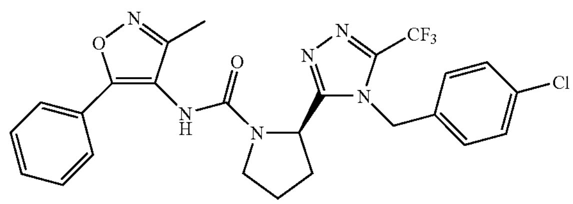 | \*\* |
| 227 | 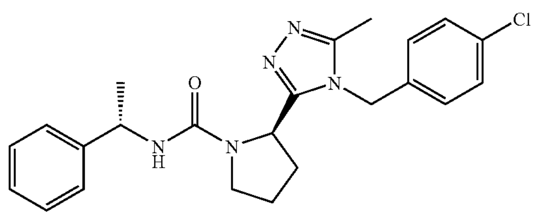 | \*\* |
| 228 | 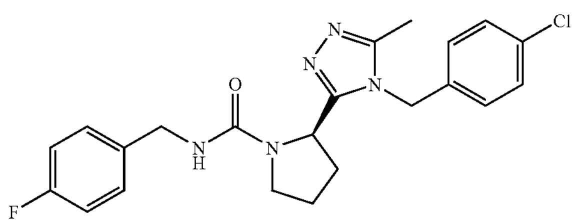 | \*\* |
| 229 | 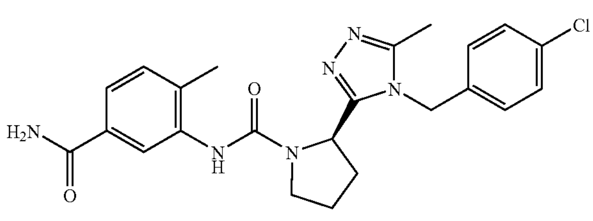 | \*\* |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 230 | 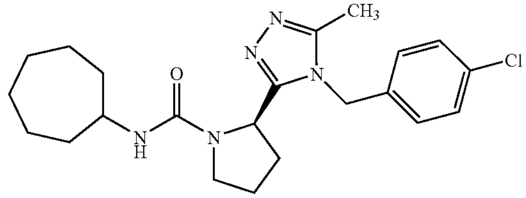 | ** |
| 231 | 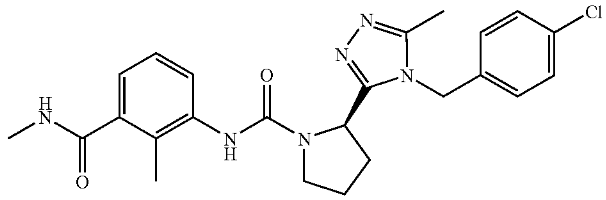 | ** |
| 232 | 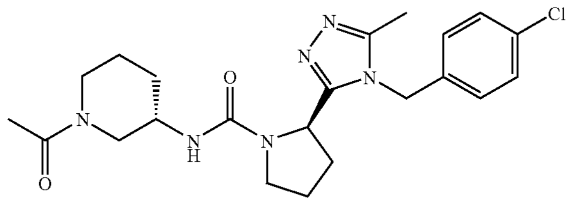 | ** |
| 233 | 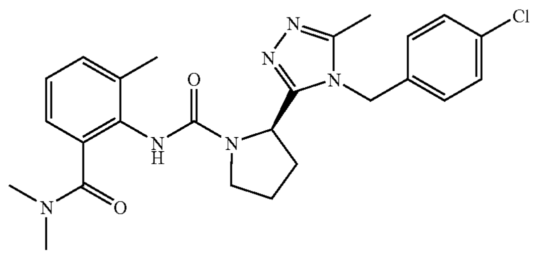 | ** |
| 234 | 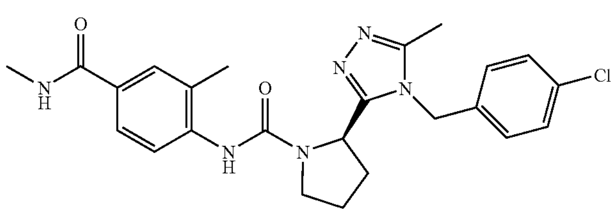 | ** |
| 235 | 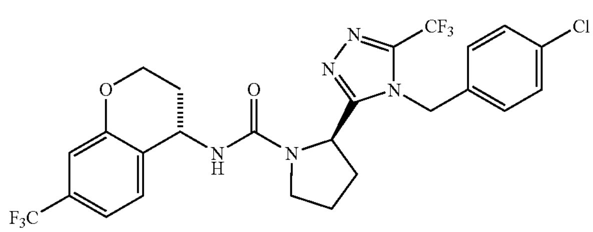 | ** |
| 236 | 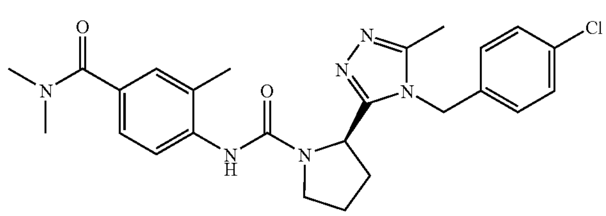 | ** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 237 | 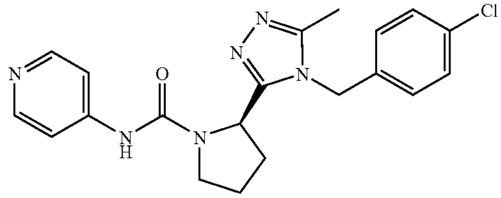 | \*\* |
| 238 | 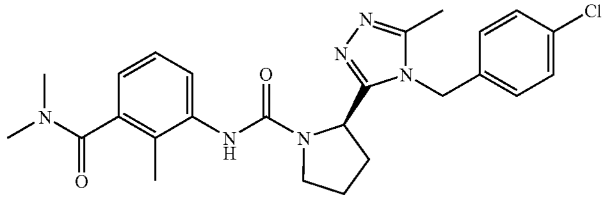 | \*\* |
| 239 | 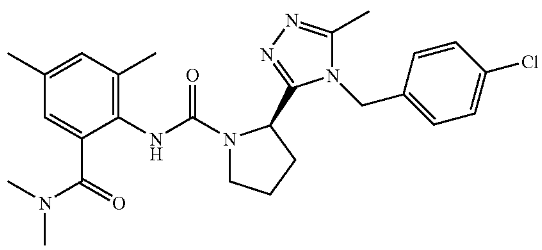 | \*\* |
| 240 | 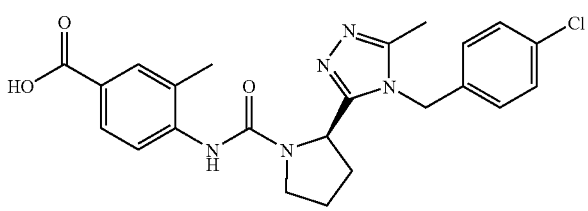 | \*\* |
| 241 | 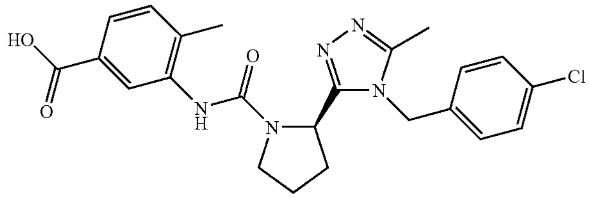 | \*\* |
| 242 | 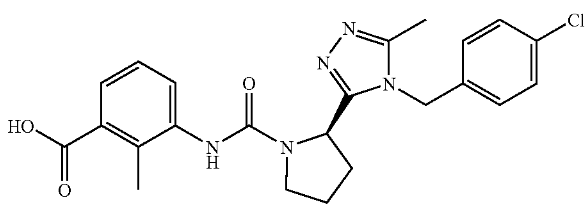 | \*\* |
| 243 | 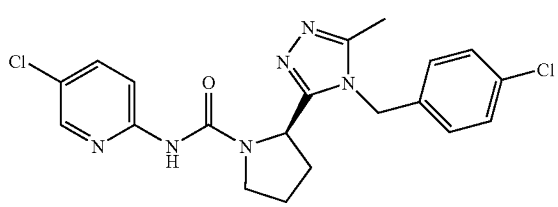 | \*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 244 | 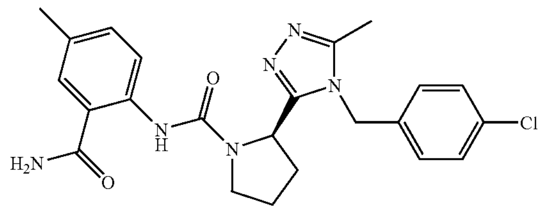 | ** |
| 245 | 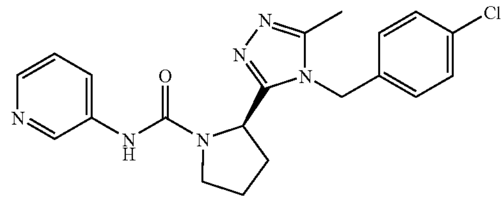 | * |
| 246 | 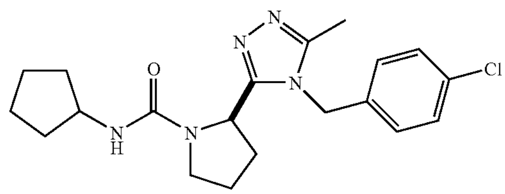 | * |
| 247 | 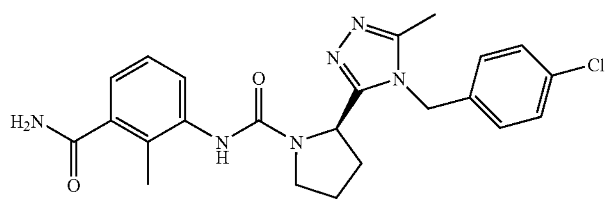 | * |
| 248 | 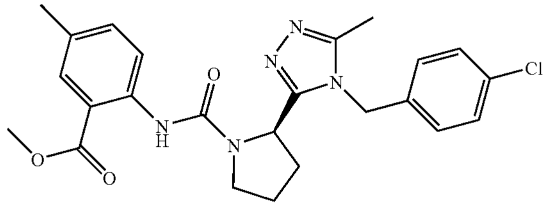 | * |
| 249 | 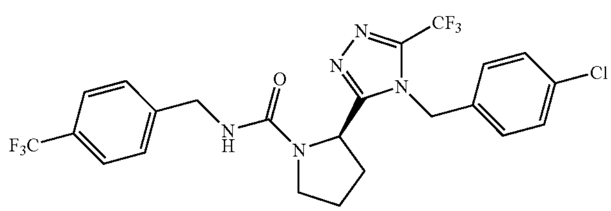 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 250 | 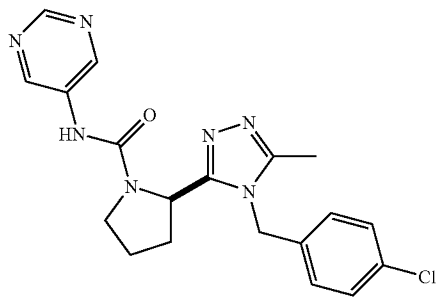 | * |
| 251 | 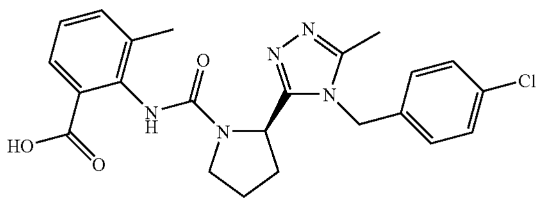 | * |
| 252 | 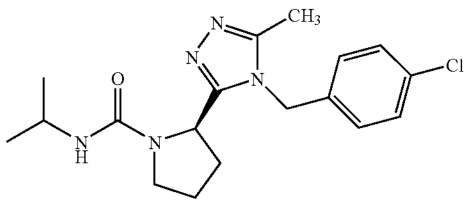 | * |
| 253 | 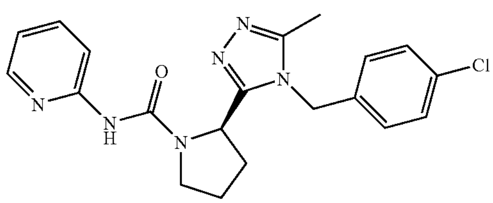 | * |
| 254 | 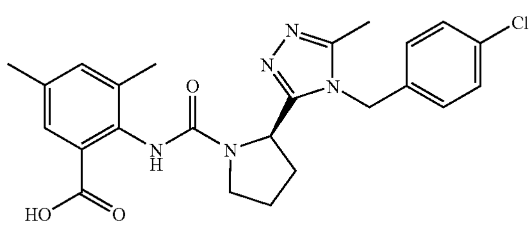 | * |
| 255 | 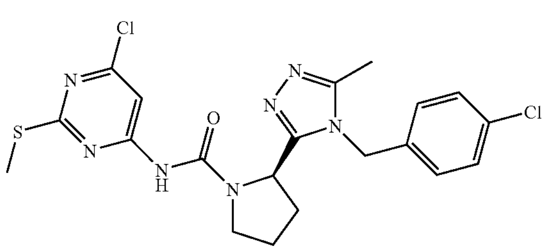 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 256 | 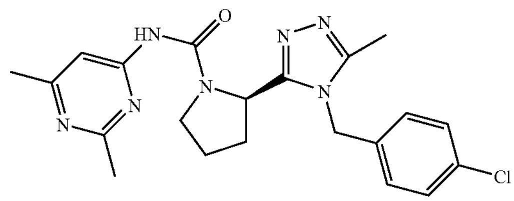 | * |
| 257 | 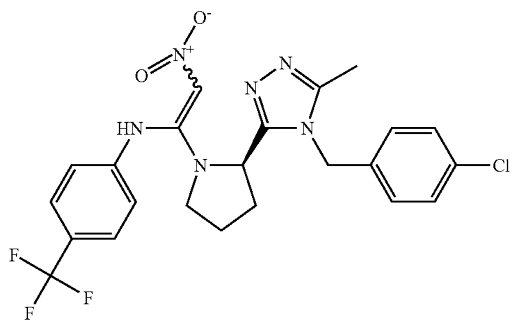 | * |
| 258 | 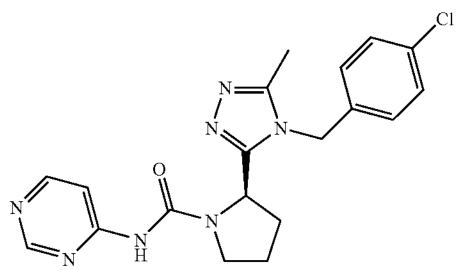 | * |
| 259 | 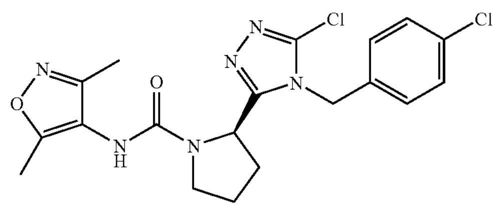 | *** |
| 260 | 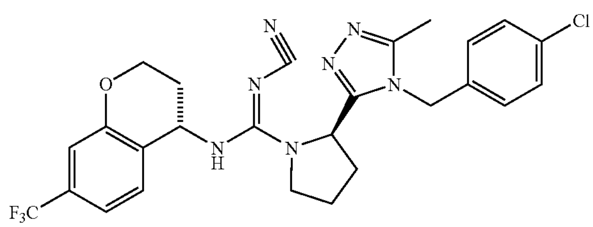 | ** |
| 261 | 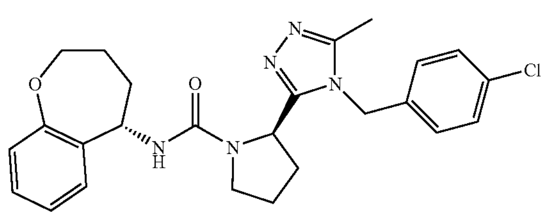 | ** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 262 | 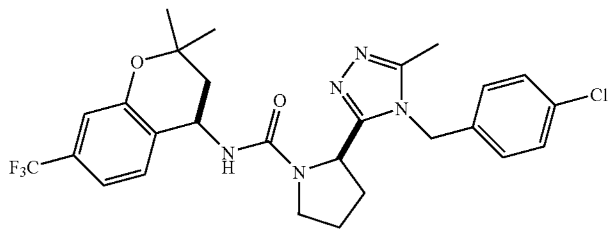 | * |
| 263 | 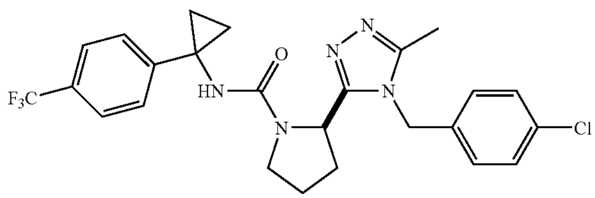 | *** |
| 264 | 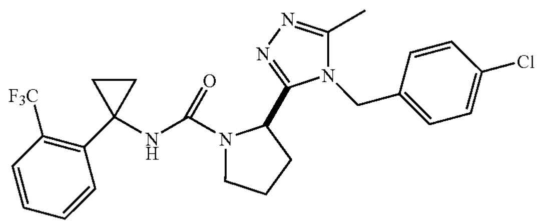 | * |
| 265 | 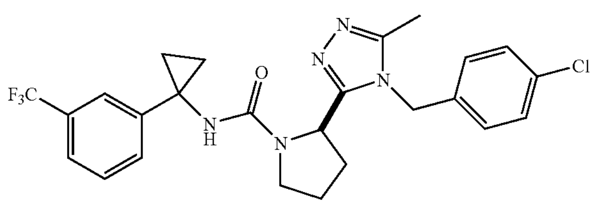 | *** |
| 266 | 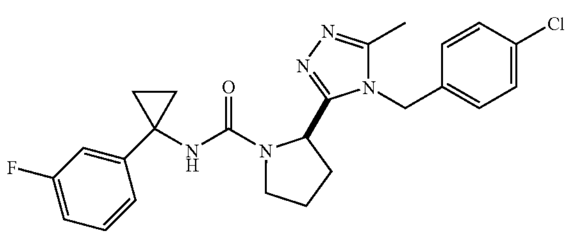 | *** |
| 267 | 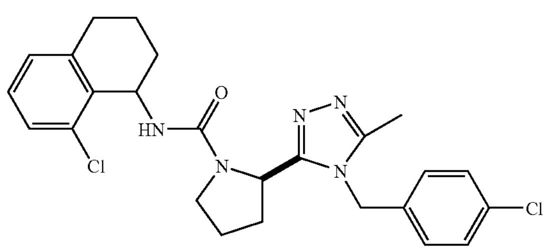 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 268 | 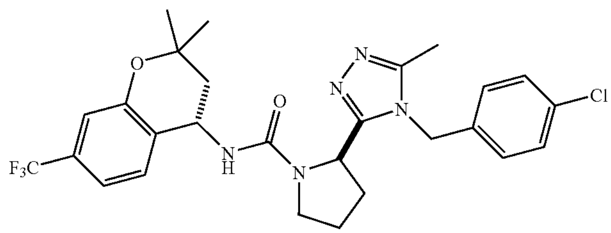 | *** |
| 269 | 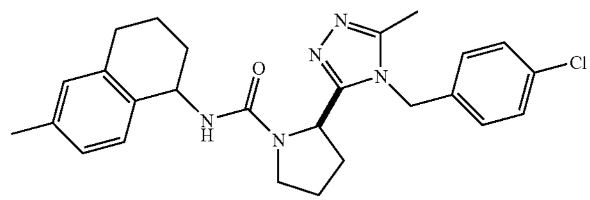 | ** |
| 270 | 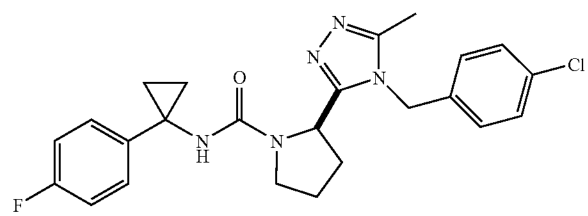 | *** |
| 271 | 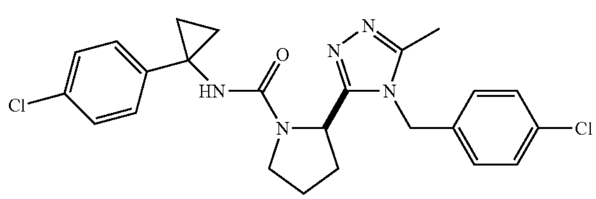 | *** |
| 272 | 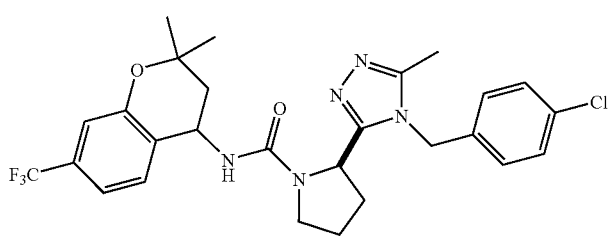 | ** |
| 273 | 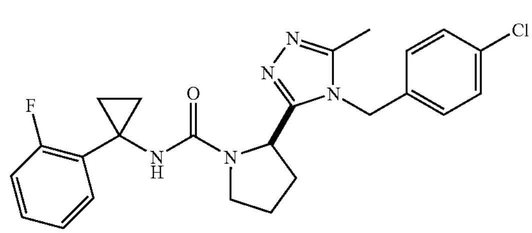 | *** |

TABLE 1-continued

| Compound # | Structure | Relative potency (IC$_{50}$) * = 0.5-5.0 μM ** = 0.05-0.5 μM *** < 0.05 μM |
|---|---|---|
| 274 | 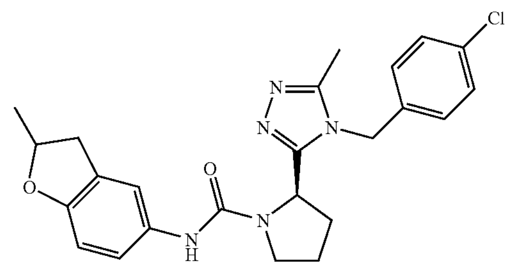 | ** |
| 275 | 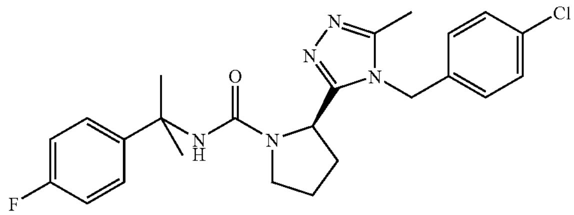 | *** |
| 276 | 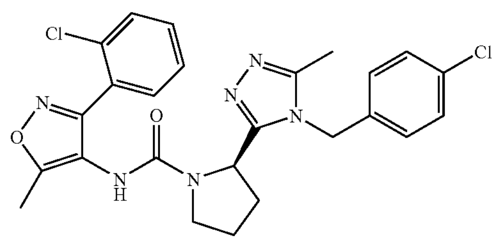 | *** |
| 277 | 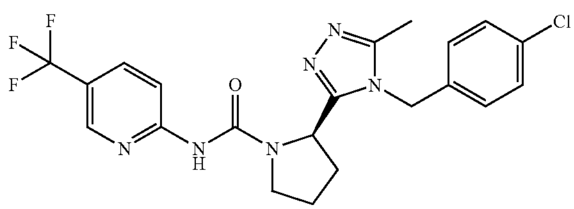 | ** |
| 278 | 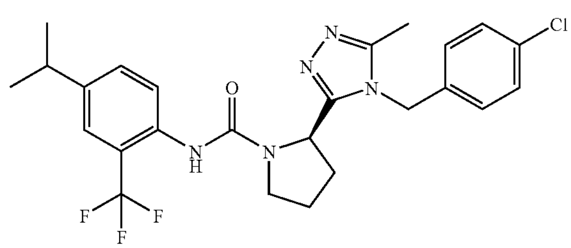 | *** |
| 279 | 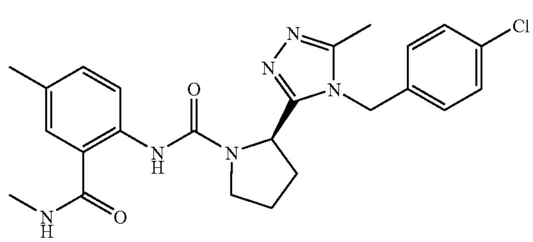 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 280 | 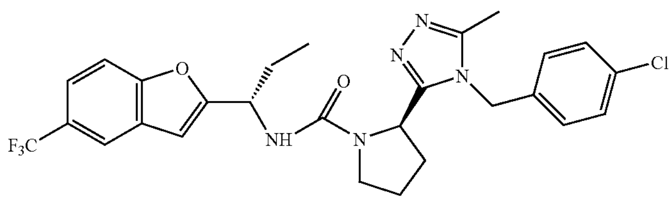 | *** |
| 281 | 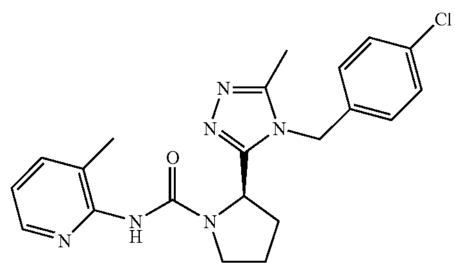 | *** |
| 282 | 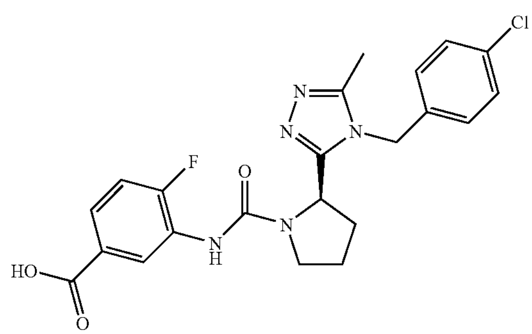 | * |
| 283 | 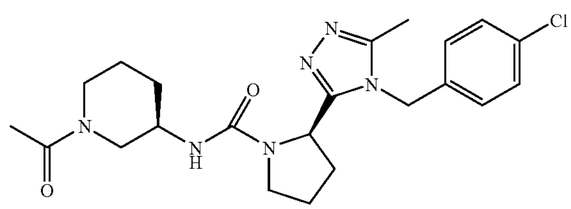 | ** |
| 284 | 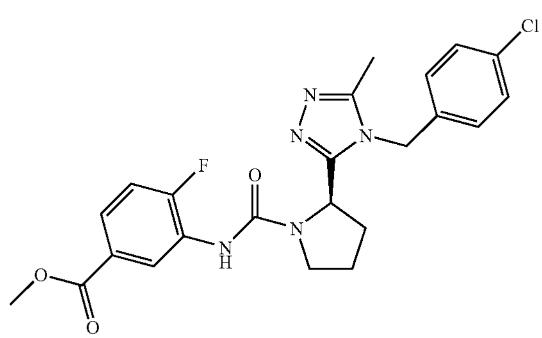 | *** |

TABLE 1-continued
| Compound # | Structure | Relative potency (IC$_{50}$)<br>* = 0.5-5.0 µM<br>** = 0.05-0.5 µM<br>*** < 0.05 µM |
|---|---|---|
| 285 | 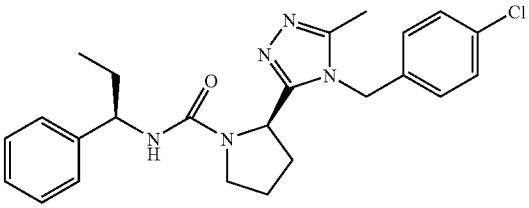 | *** |
| 286 | 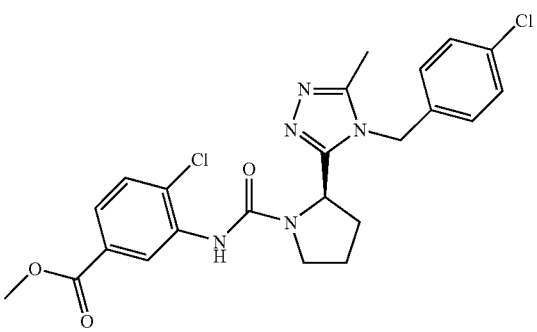 | *** |
| 287 | 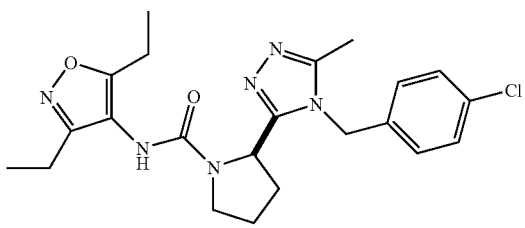 | *** |
| 288 | 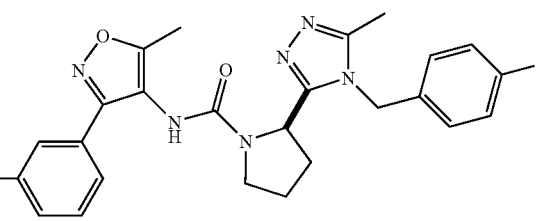 | *** |
| 289 | 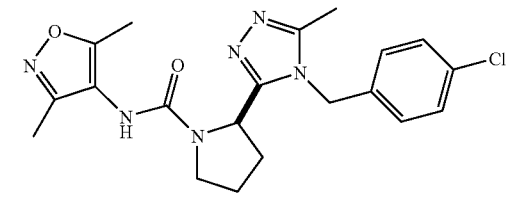 | *** |
| 290 | 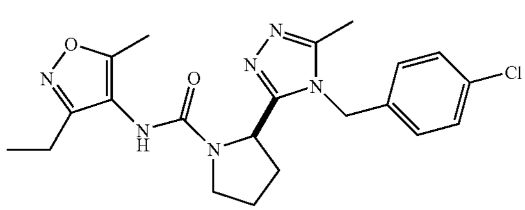 | *** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 291 | 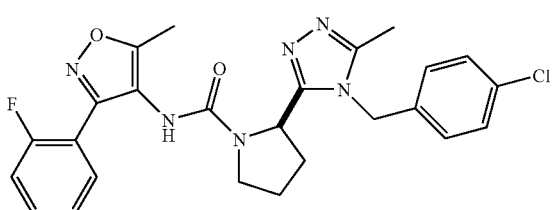 | *** |
| 292 | 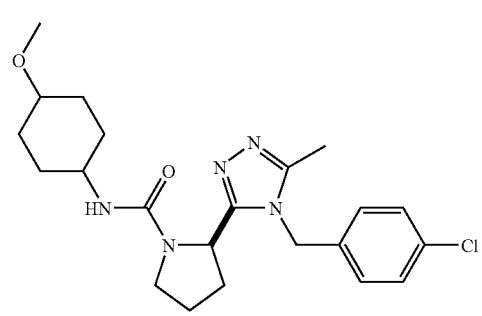 | ** |
| 293 | 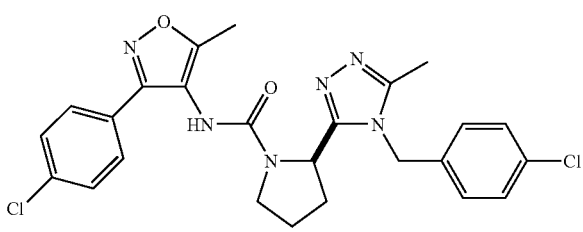 | *** |
| 294 | 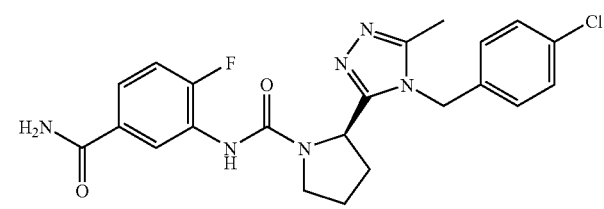 | ** |
| 295 | 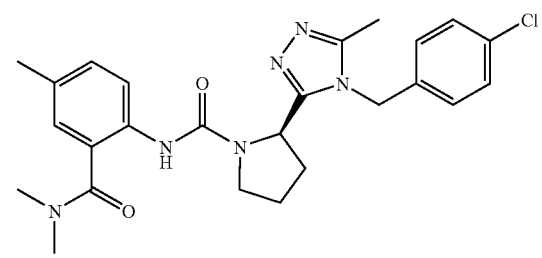 | ** |
| 296 | 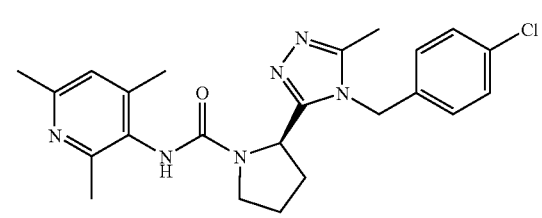 | *** |

TABLE 1-continued

| Compound # | Structure | Relative potency (IC$_{50}$) * = 0.5-5.0 µM ** = 0.05-0.5 µM *** < 0.05 µM |
|---|---|---|
| 297 | 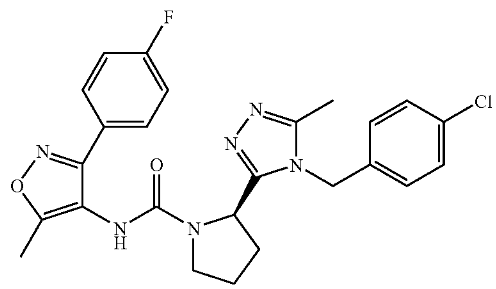 | *** |
| 298 | 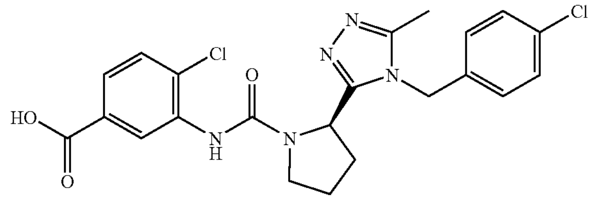 | * |
| 299 | 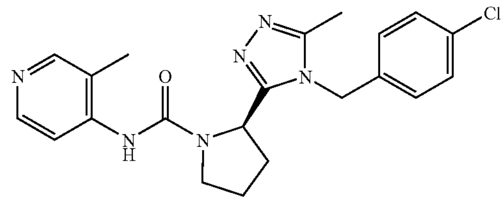 | ** |
| 300 | 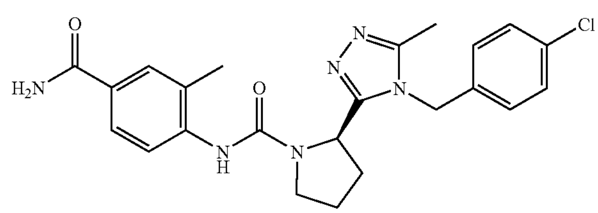 | ** |
| 301 | 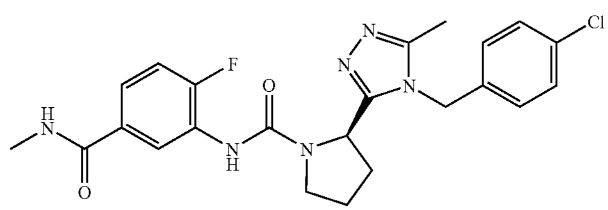 | ** |
| 302 | 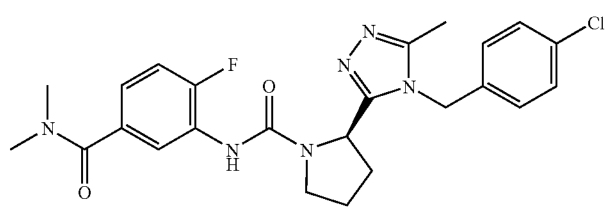 | ** |

TABLE 1-continued

| Compound # | Structure | Relative potency (IC$_{50}$) * = 0.5-5.0 μM ** = 0.05-0.5 μM *** < 0.05 μM |
|---|---|---|
| 303 | 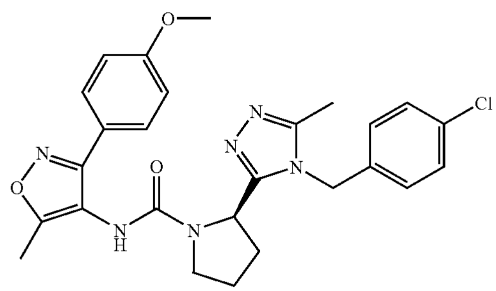 | *** |
| 304 | 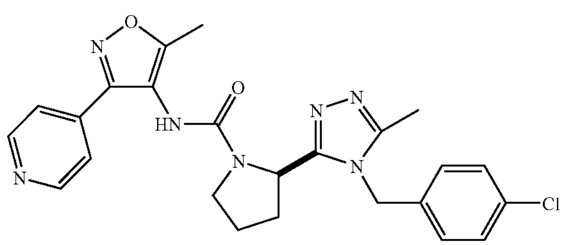 | *** |
| 305 | 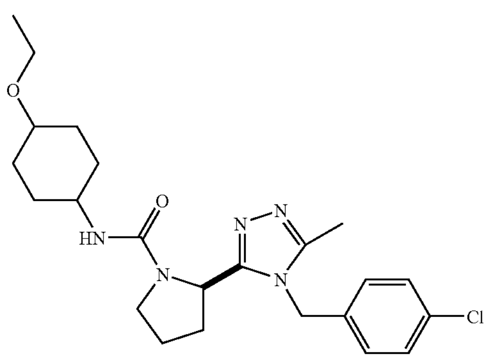 | * |
| 306 | 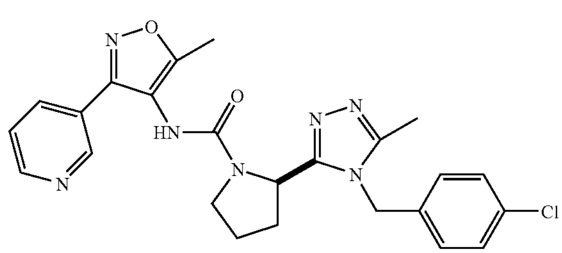 | *** |
| 307 | 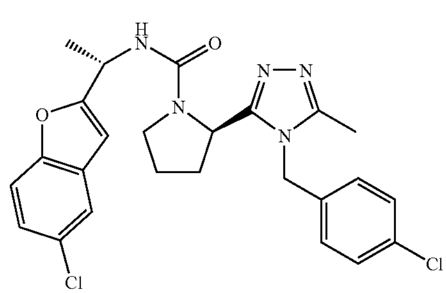 | *** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 308 | 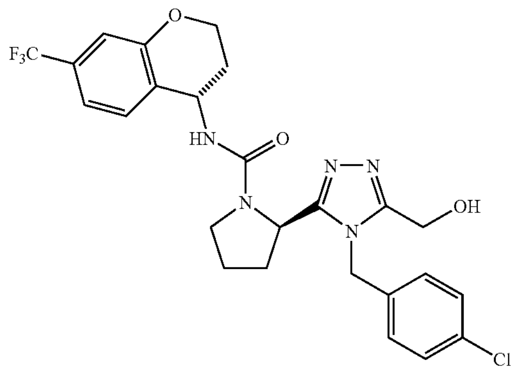 | \*\*\* |
| 309 | 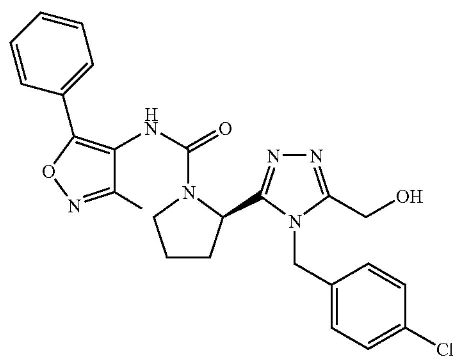 | \*\*\* |
| 310 | 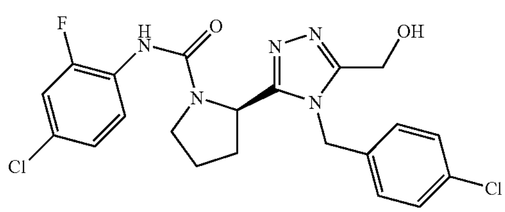 | \*\* |
| 311 | 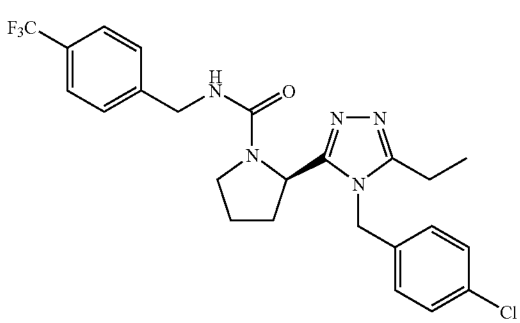 | \*\* |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 312 | 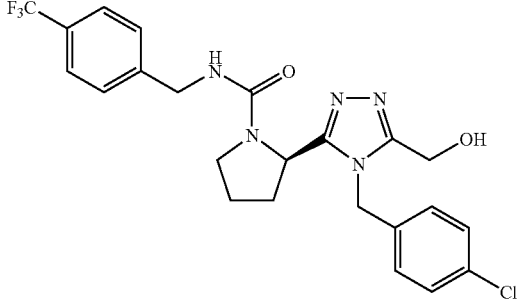 | *** |
| 313 | 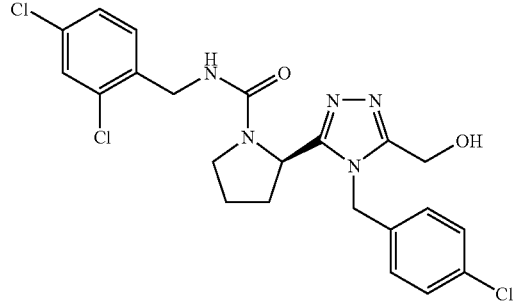 | *** |
| 314 | 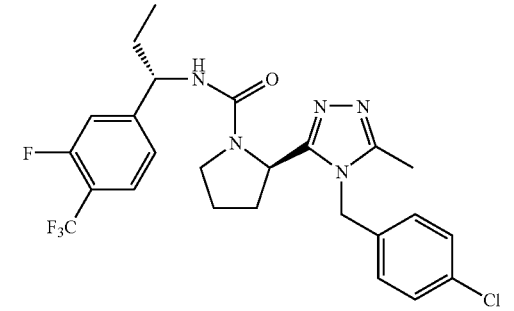 | ** |
| 315 | 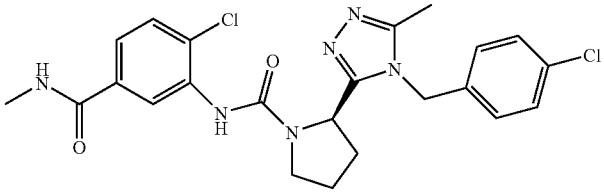 | ** |
| 316 | 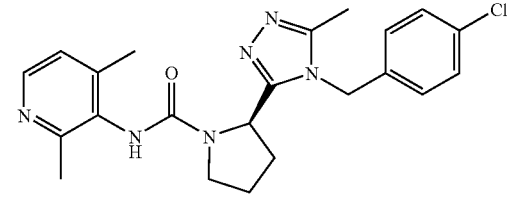 | *** |

TABLE 1-continued
| Compound # | Structure | Relative potency (IC$_{50}$) * = 0.5-5.0 μM ** = 0.05-0.5 μM *** < 0.05 μM |
|---|---|---|
| 317 | 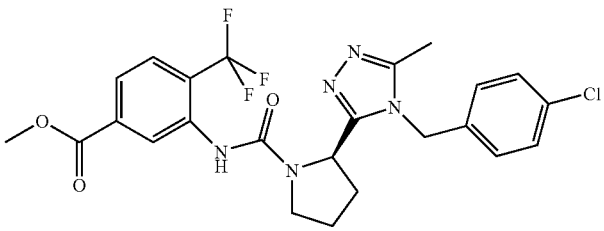 | ** |
| 318 | 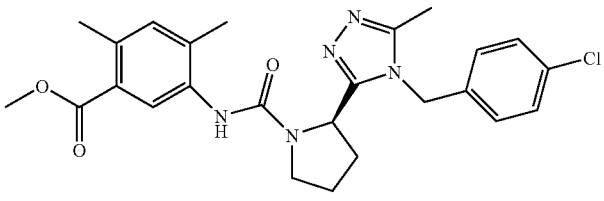 | *** |
| 319 | 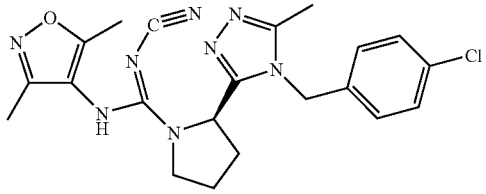 | ** |
| 320 | 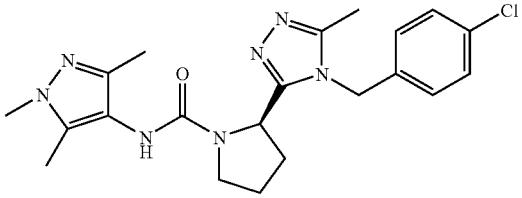 | *** |
| 321 | 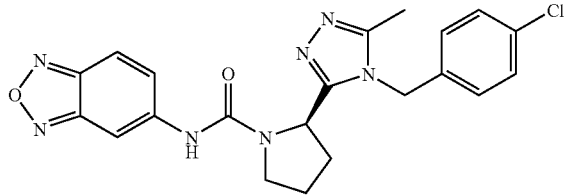 | ** |
| 322 | 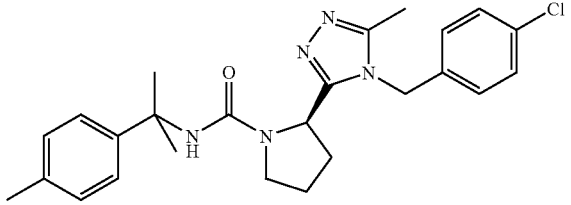 | *** |

TABLE 1-continued
| Compound # | Structure | Relative potency (IC$_{50}$)<br>* = 0.5-5.0 µM<br>** = 0.05-0.5 µM<br>*** < 0.05 µM |
|---|---|---|
| 323 | 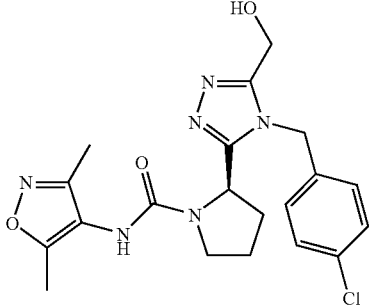 | ** |
| 324 | 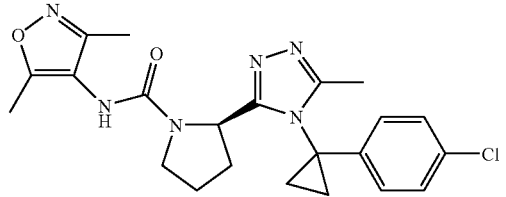 | ** |
| 325 | 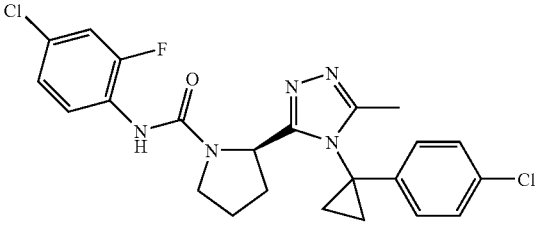 | ** |
| 326 | 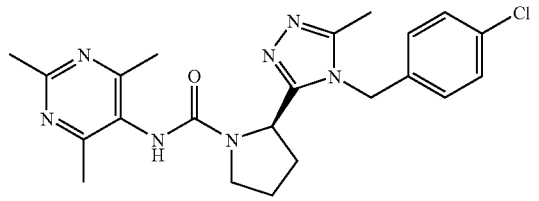 | *** |
| 327 | 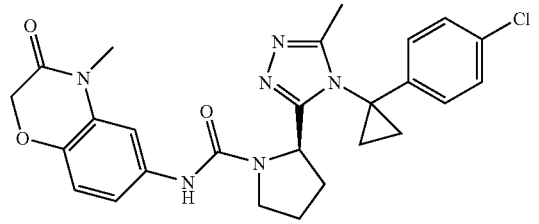 | ** |
| 328 | 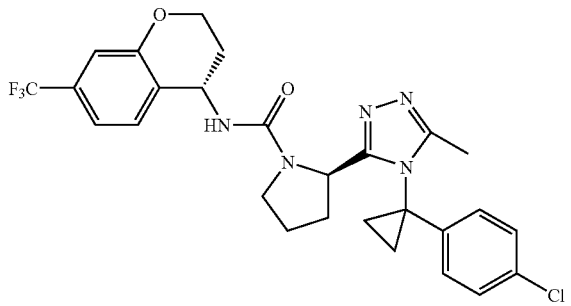 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 329 | 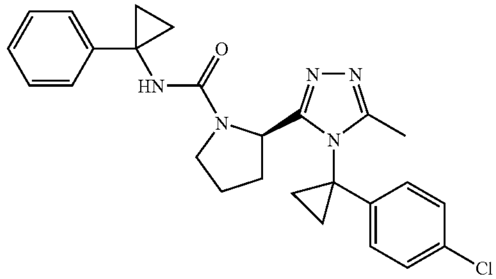 | ** |
| 330 | 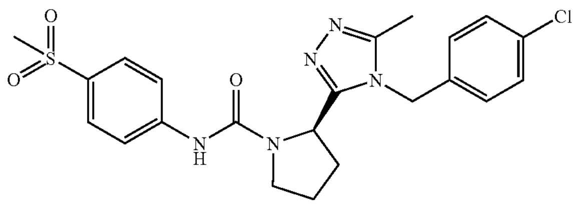 | ** |
| 331 | 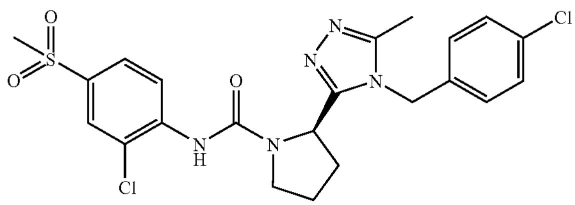 | ** |
| 332 | 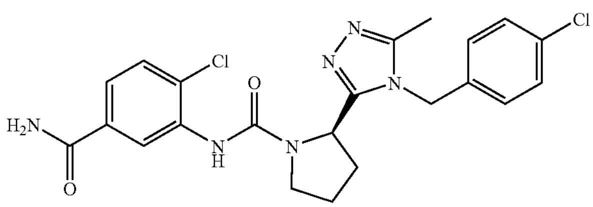 | ** |
| 333 | 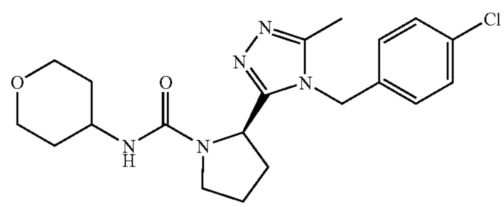 | * |
| 334 | 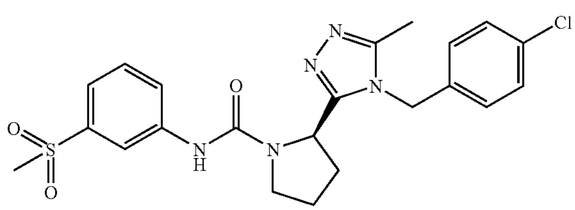 | * |
| 335 | 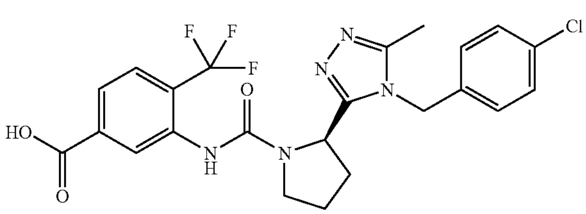 | * |

TABLE 1-continued

| Compound # | Structure | Relative potency (IC$_{50}$) * = 0.5-5.0 μM ** = 0.05-0.5 μM *** < 0.05 μM |
|---|---|---|
| 336 | 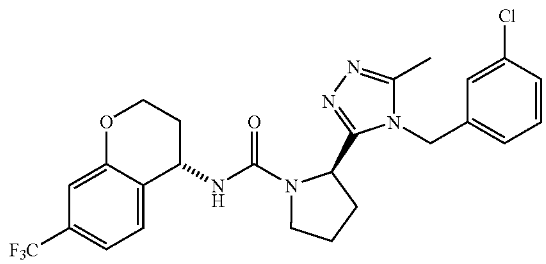 | * |
| 337 | 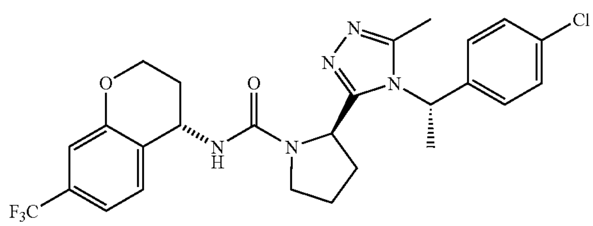 | ** |
| 338 | 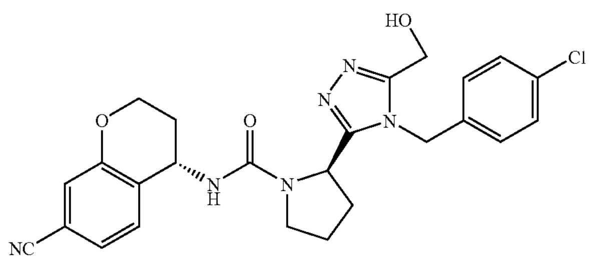 | *** |
| 339 | 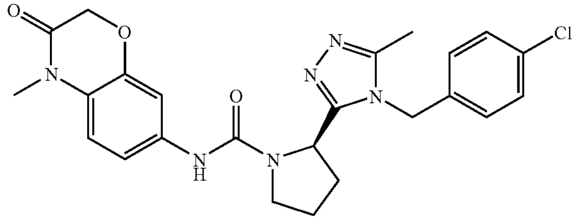 | * |
| 340 | 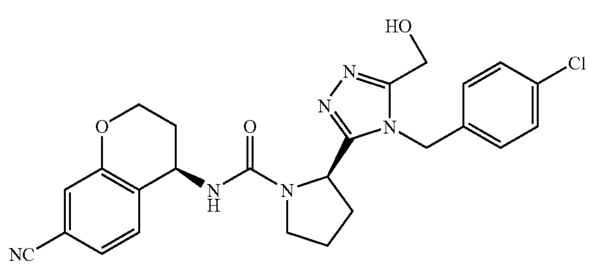 | *** |
| 341 | 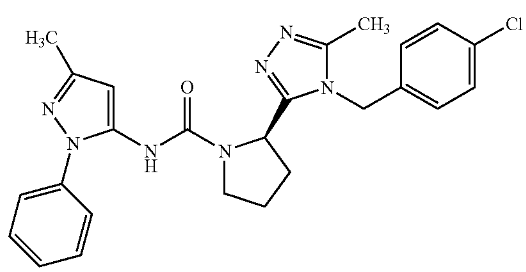 | *** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 342 | 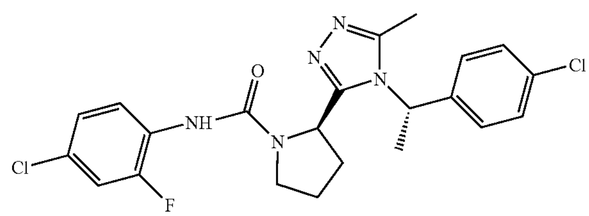 | * |
| 343 | 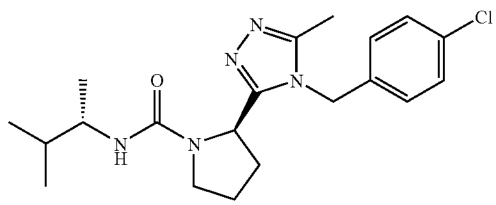 | ** |
| 344 | 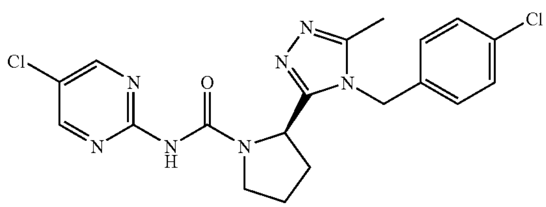 | * |
| 345 | 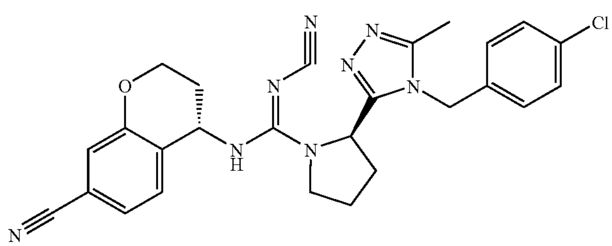 | ** |
| 346 | 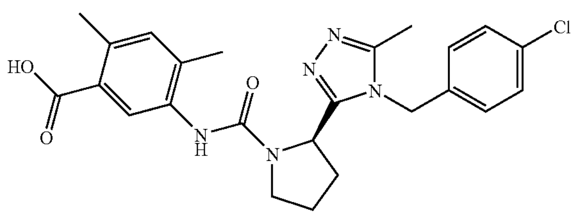 | ** |
| 347 | 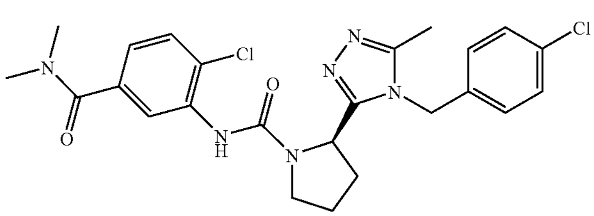 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 348 | 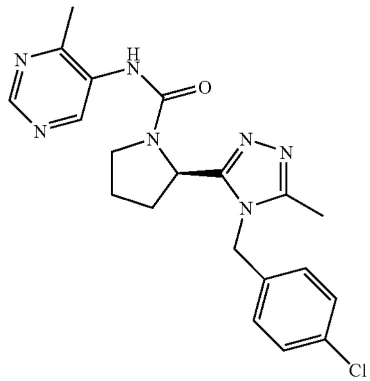 | *** |
| 349 | 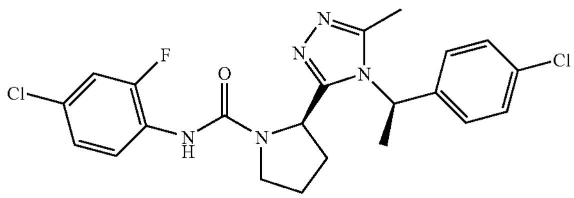 | ** |
| 350 | 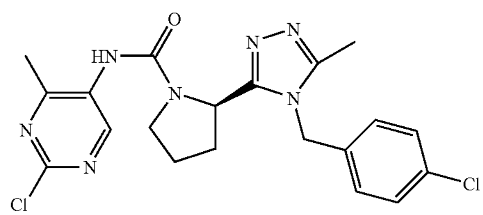 | *** |
| 351 | 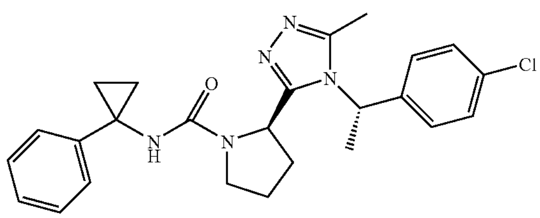 | ** |
| 352 | 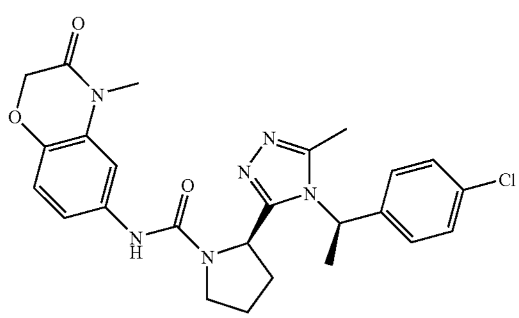 | ** |
| 353 | 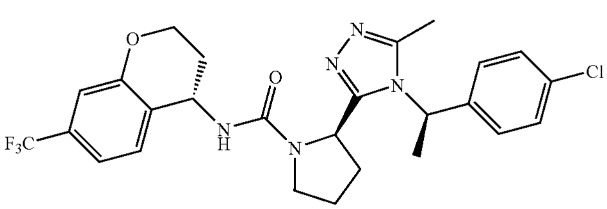 | ** |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 354 | 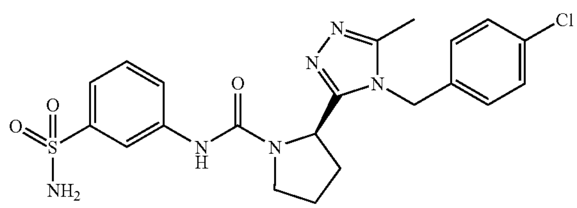 | \* |
| 355 | 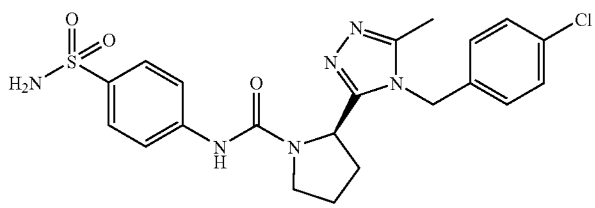 | \* |
| 356 | 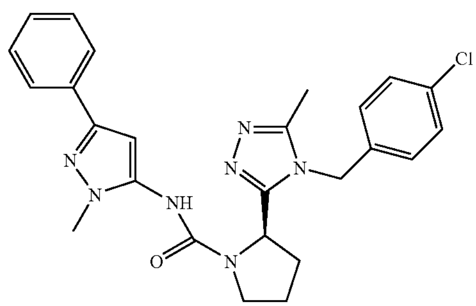 | \*\*\* |
| 357 | 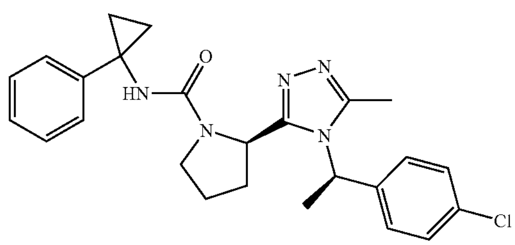 | \*\* |
| 358 | 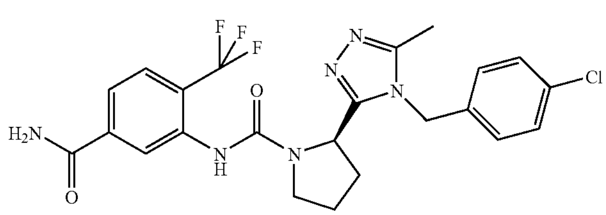 | \*\* |
| 359 | 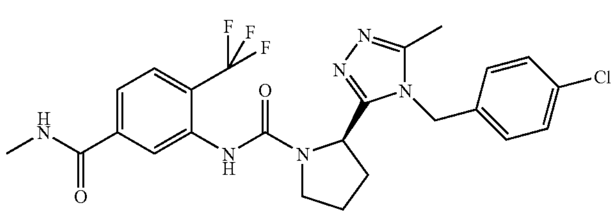 | \*\*\* |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 360 | 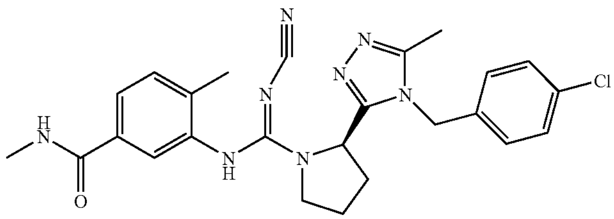 | ** |
| 361 | 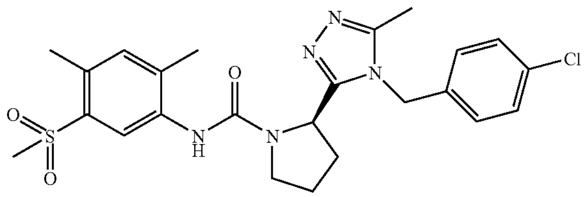 | *** |
| 362 | 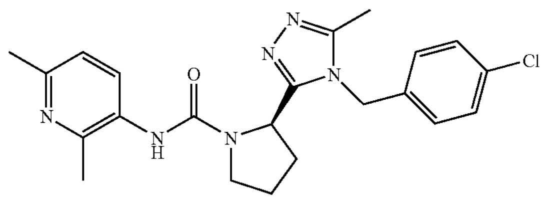 | *** |
| 363 | 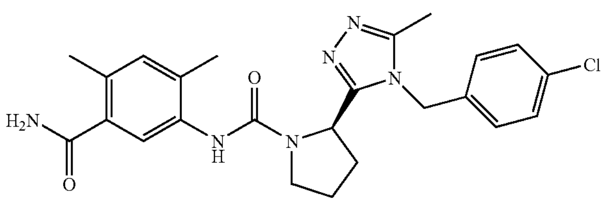 | ** |
| 364 | 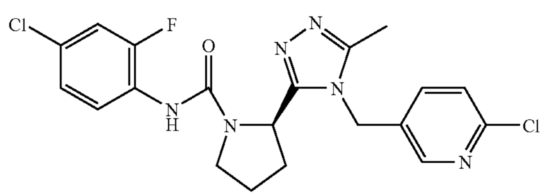 | * |
| 365 | 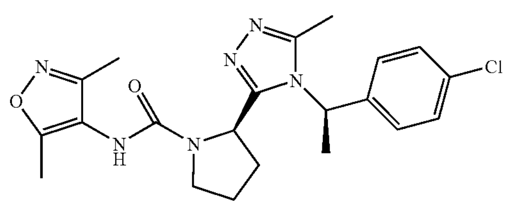 | ** |
| 366 | 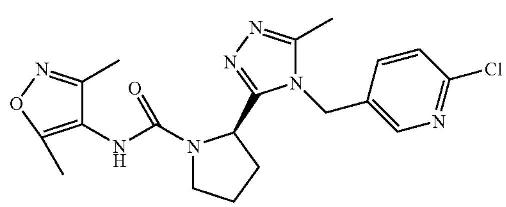 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 367 | 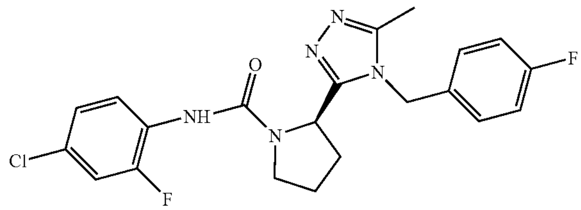 | ** |
| 368 | 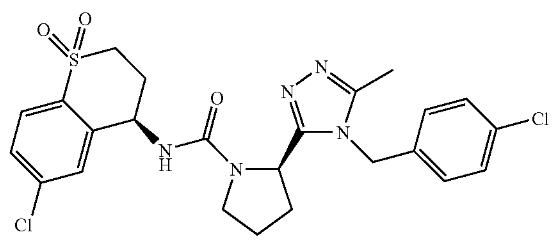 | *** |
| 369 | 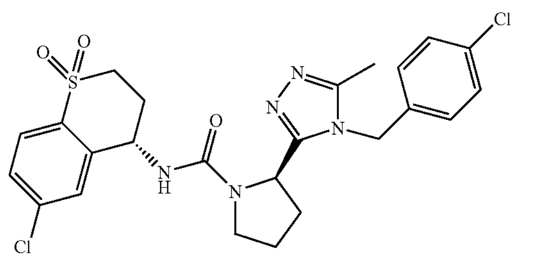 | *** |
| 370 | 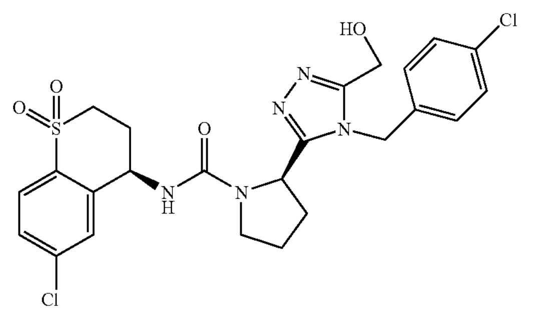 | *** |
| 371 | 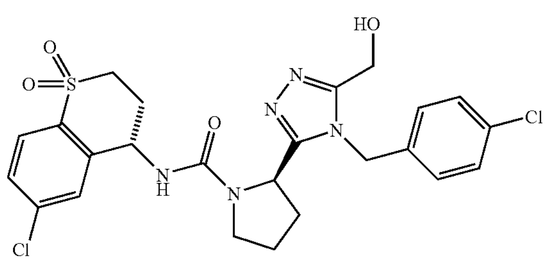 | ** |
| 372 | 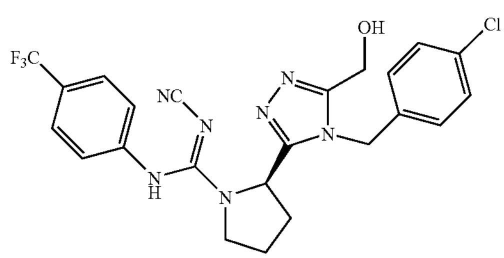 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 373 | 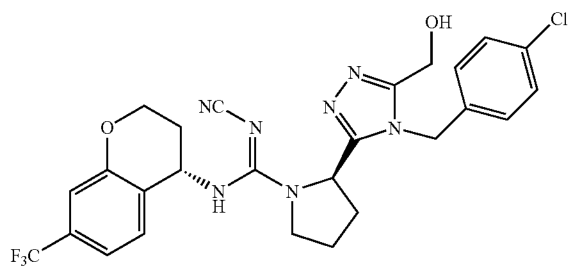 | ** |
| 374 | 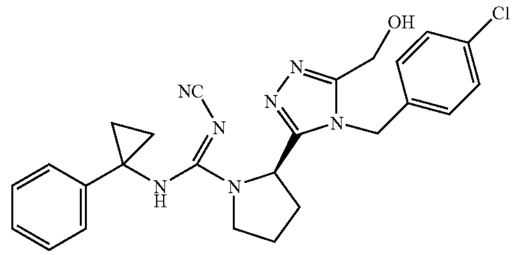 | * |
| 375 | 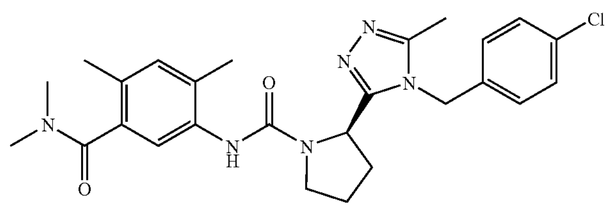 | ** |
| 376 | 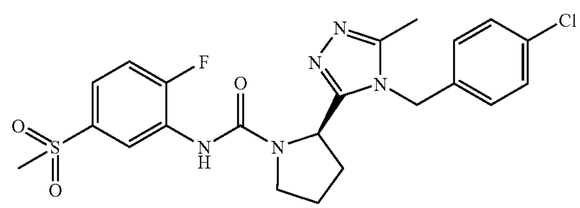 | ** |
| 377 | 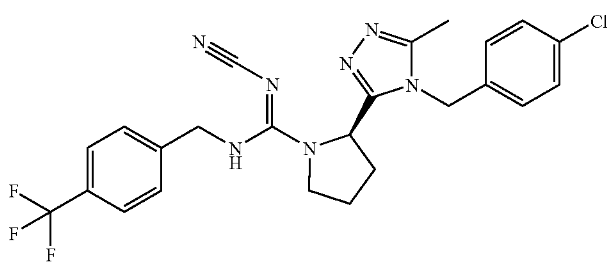 | ** |
| 378 | 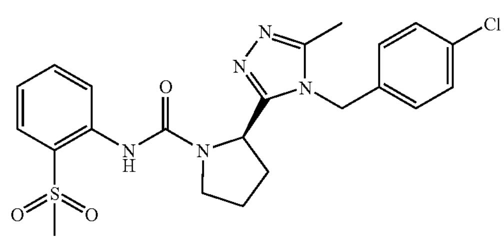 | ** |

TABLE 1-continued
| Compound # | Structure | Relative potency (IC$_{50}$)<br>* = 0.5–5.0 μM<br>** = 0.05–0.5 μM<br>*** < 0.05 μM |
|---|---|---|
| 379 | 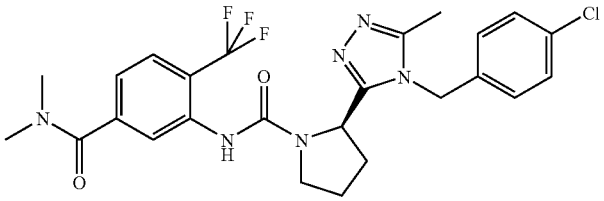 | ** |
| 380 | 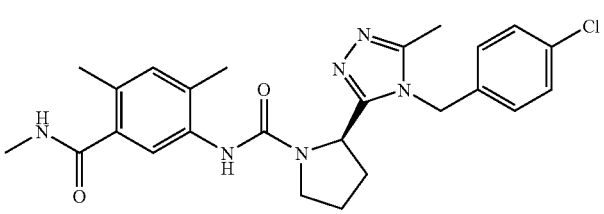 | *** |
| 381 | 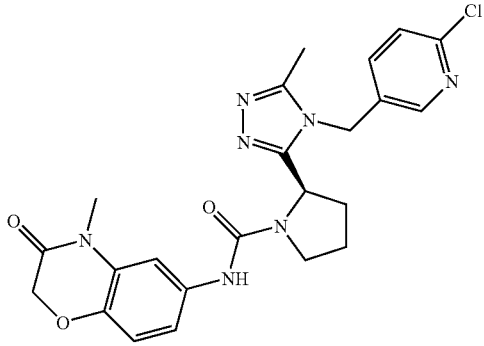 | * |
| 382 | 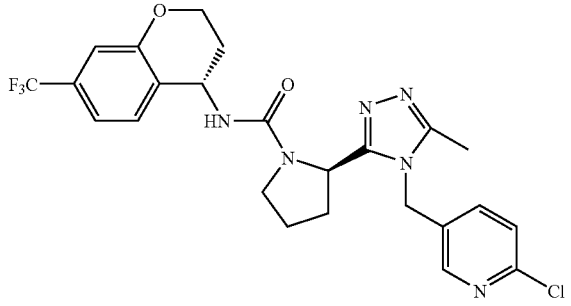 | ** |
| 383 | 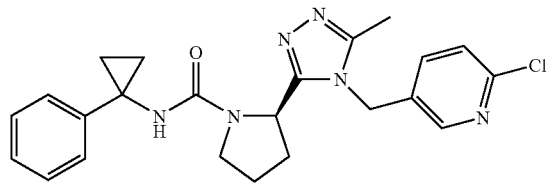 | ** |
| 384 | 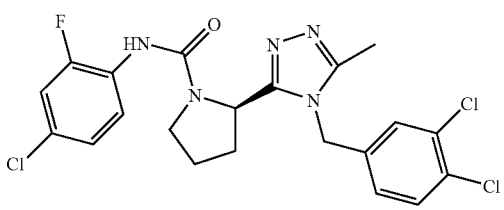 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 385 | 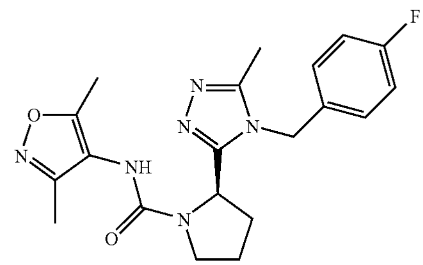 | ** |
| 386 | 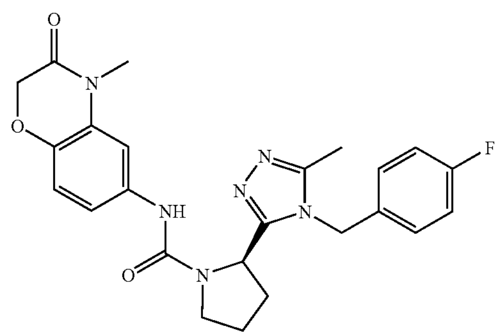 | ** |
| 387 | 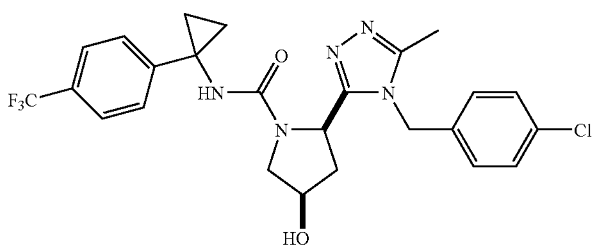 | *** |
| 388 | 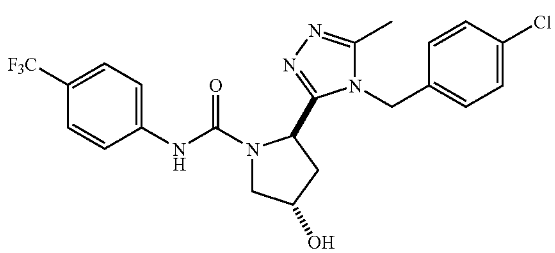 | ** |
| 389 | 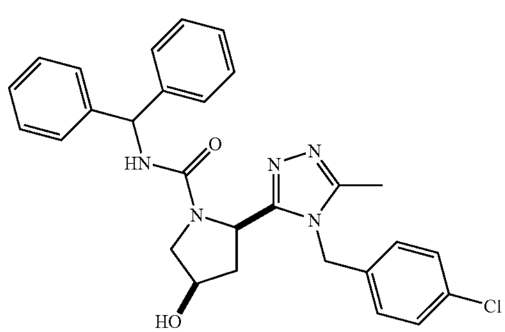 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 390 | 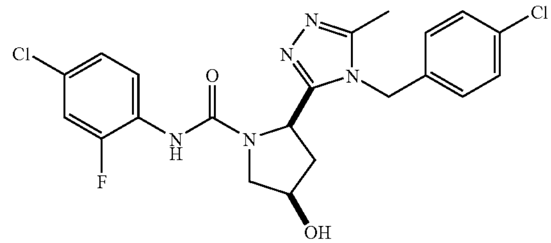 | * |
| 391 | 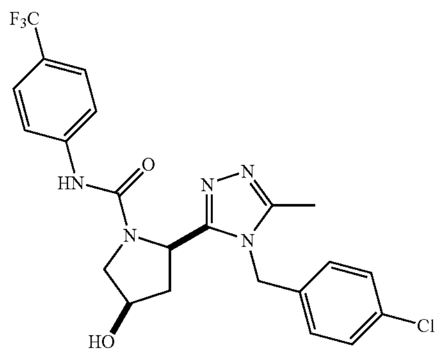 | * |
| 392 | 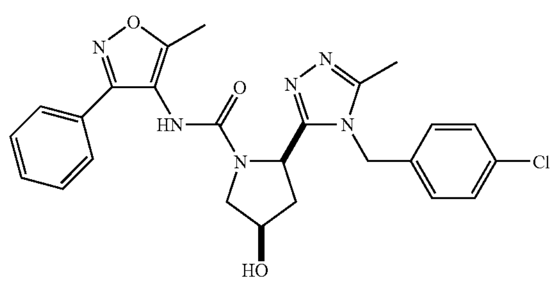 | ** |
| 393 | 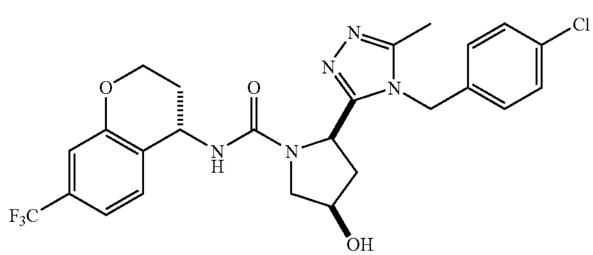 | *** |
| 394 | 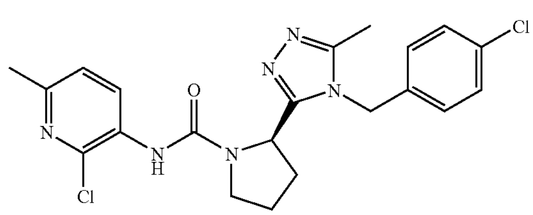 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 395 | 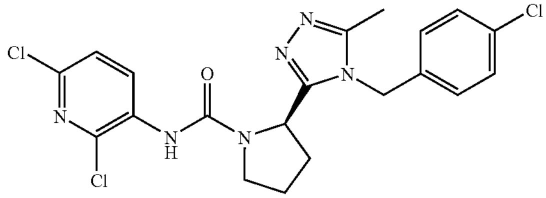 | *** |
| 396 | 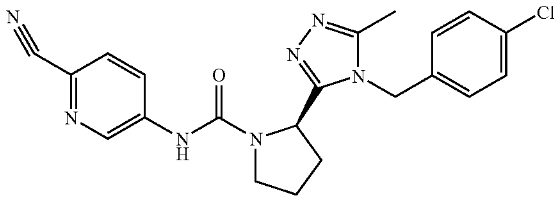 | ** |
| 397 | 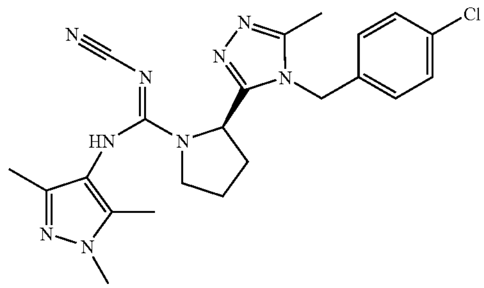 | ** |
| 398 | 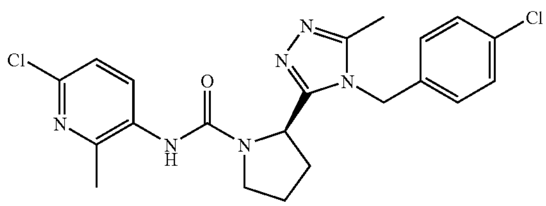 | *** |
| 399 | 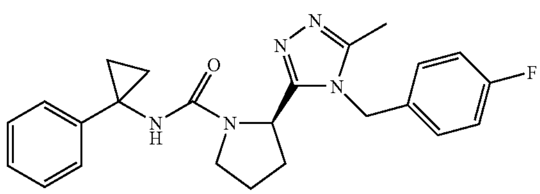 | ** |
| 400 | 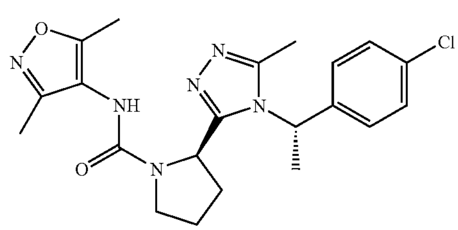 | * |

TABLE 1-continued

| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 401 | 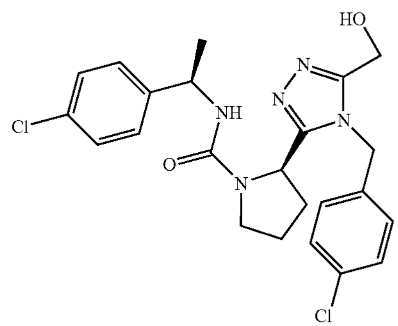 | \*\* |
| 402 | 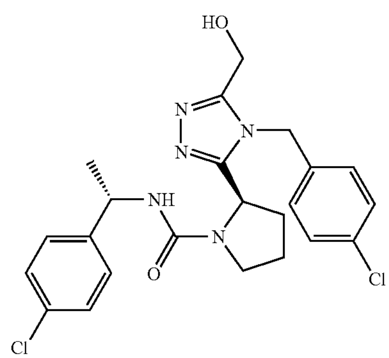 | \*\*\* |
| 403 | 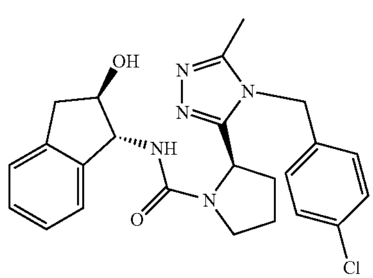 | \*\* |
| 404 | 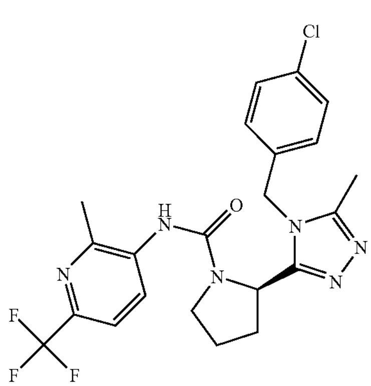 | \*\*\* |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 405 | 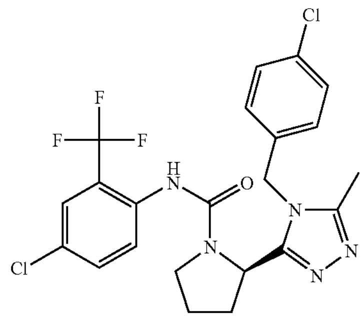 | *** |
| 406 | 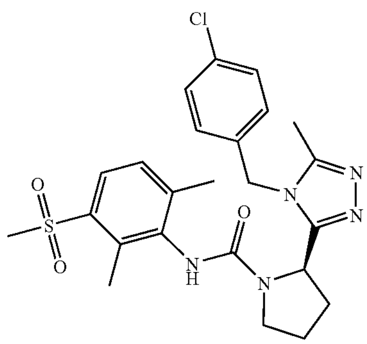 | *** |
| 407 | 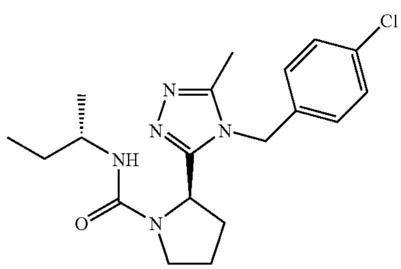 | ** |
| 408 | 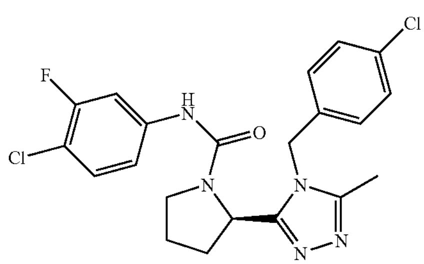 | ** |
| 409 | 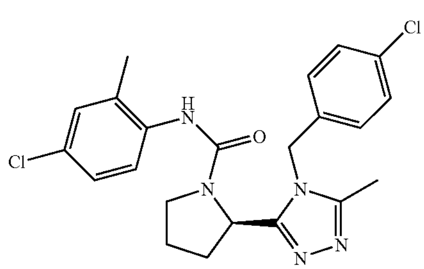 | *** |

TABLE 1-continued

| Compound # | Structure | Relative potency (IC$_{50}$) * = 0.5-5.0 μM ** = 0.05-0.5 μM *** < 0.05 μM |
|---|---|---|
| 410 | 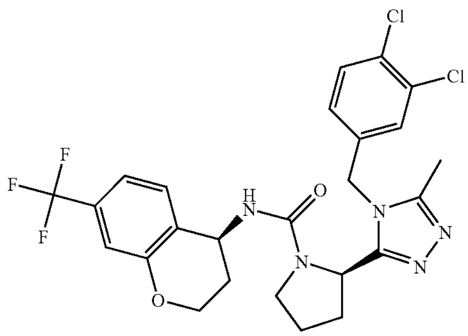 | ** |
| 411 | 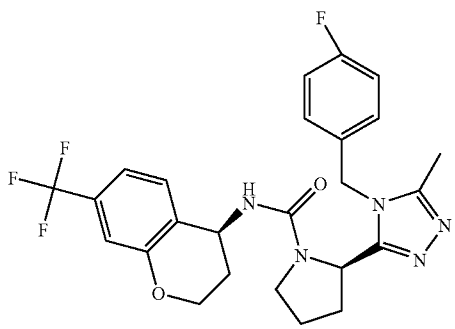 | *** |
| 412 | 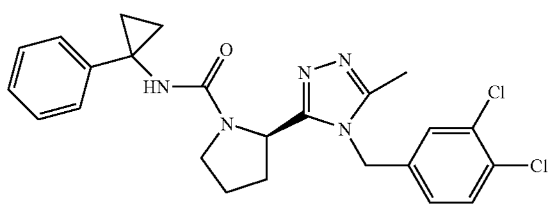 | *** |
| 413 | 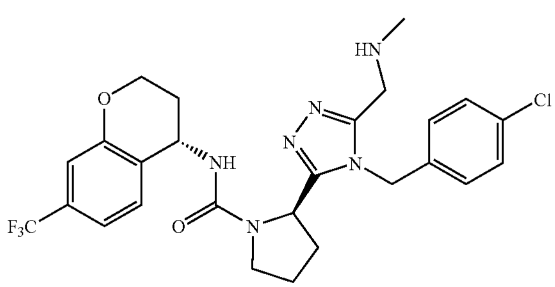 | ** |
| 414 | 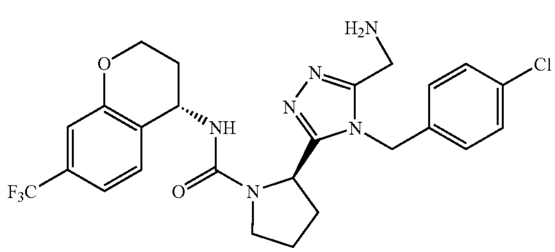 | ** |

TABLE 1-continued

| Compound # | Structure | Relative potency (IC$_{50}$)<br>* = 0.5-5.0 µM<br>** = 0.05-0.5 µM<br>*** < 0.05 µM |
|---|---|---|
| 415 | 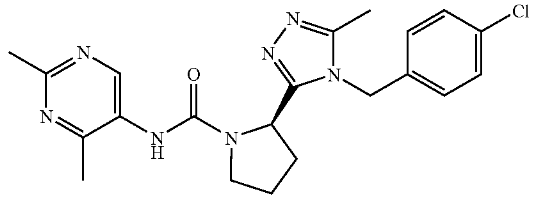 | *** |
| 416 | 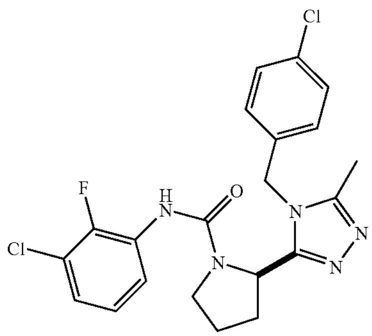 | *** |
| 417 | 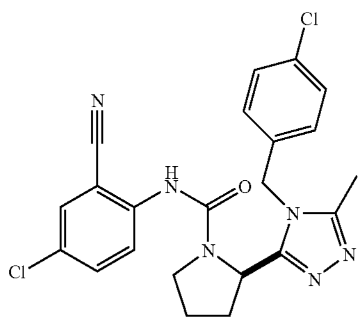 | *** |
| 418 | 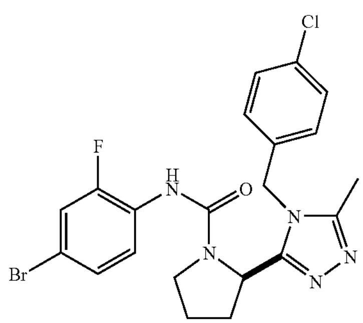 | *** |
| 419 | 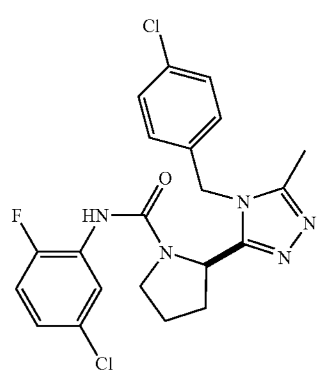 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 420 | 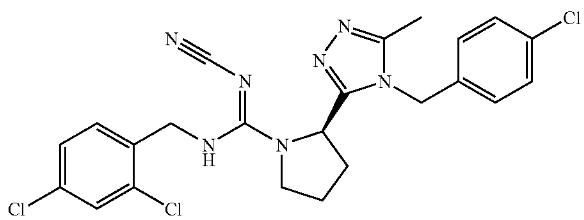 | ** |
| 421 | 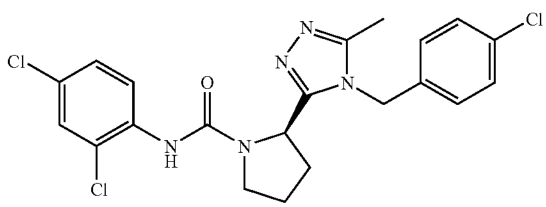 | ** |
| 422 | 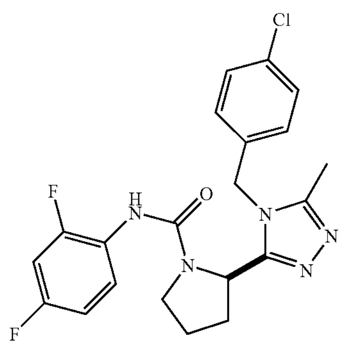 | ** |
| 423 | 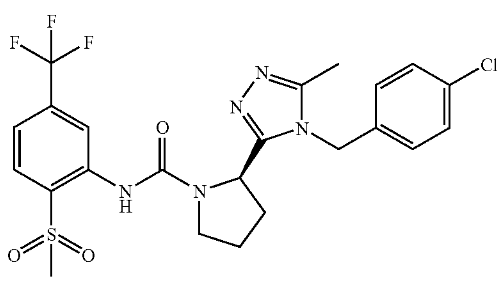 | ** |
| 424 | 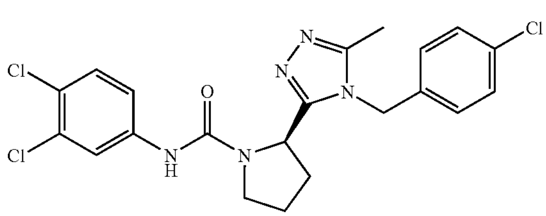 | ** |
| 425 | 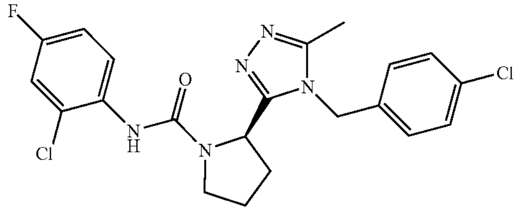 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 426 | 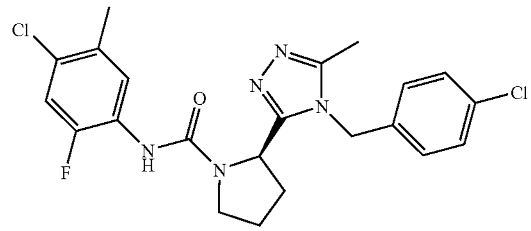 | *** |
| 427 | 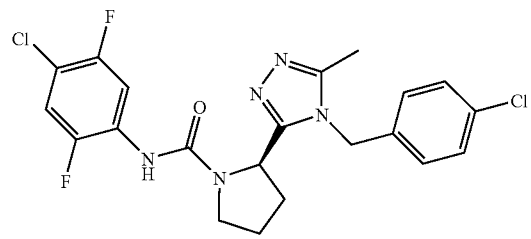 | *** |
| 428 | 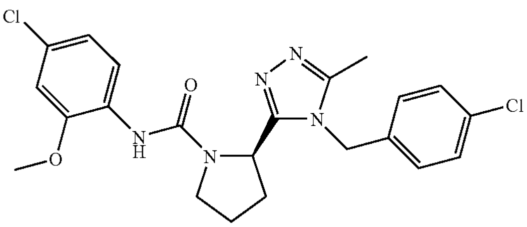 | *** |
| 429 | 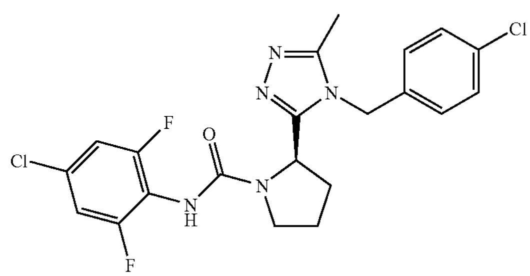 | *** |
| 430 | 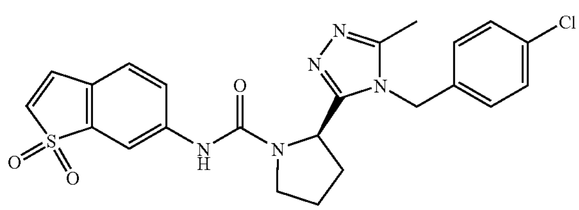 | ** |
| 431 | 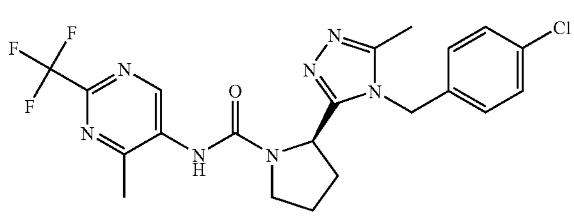 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 432 | 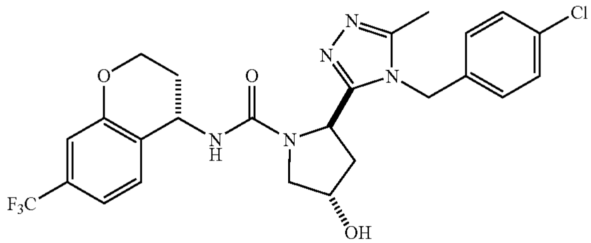 | *** |
| 433 | 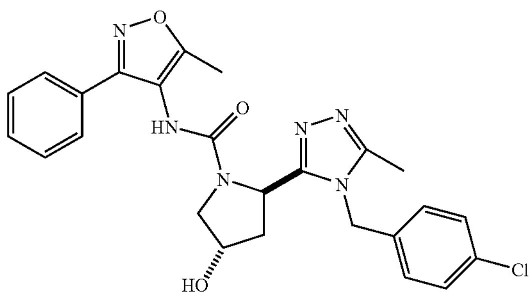 | *** |
| 434 | 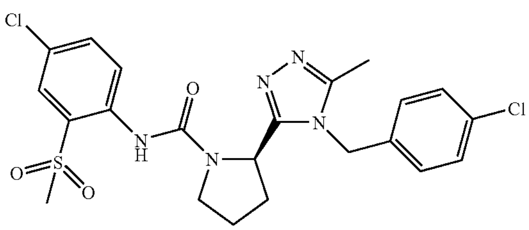 | *** |
| 435 | 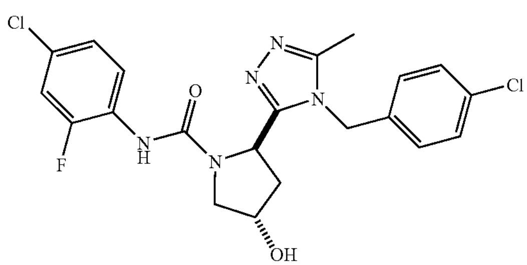 | *** |
| 436 | 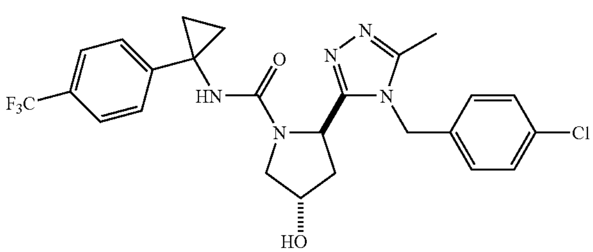 | *** |
| 437 | 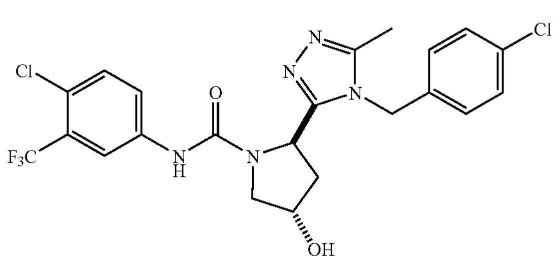 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 438 | 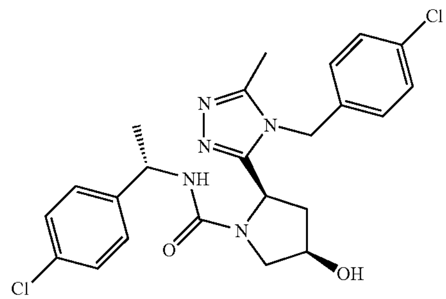 | *** |
| 439 | 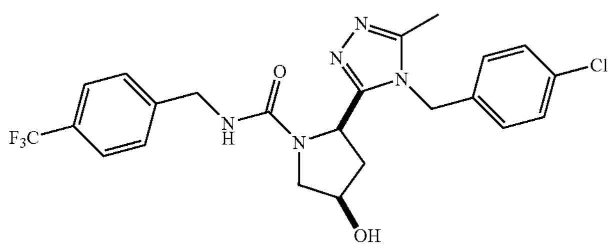 | ** |
| 440 | 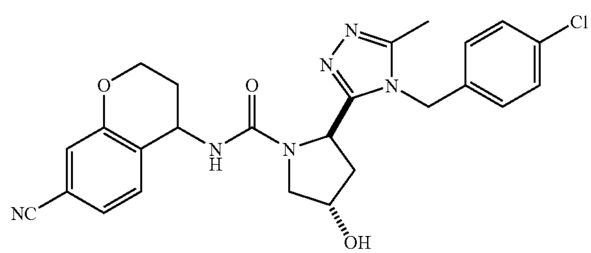 | *** |
| 441 | 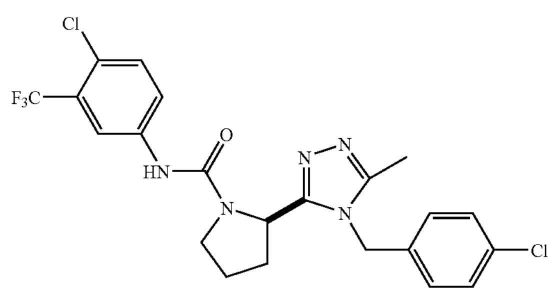 | ** |
| 442 | 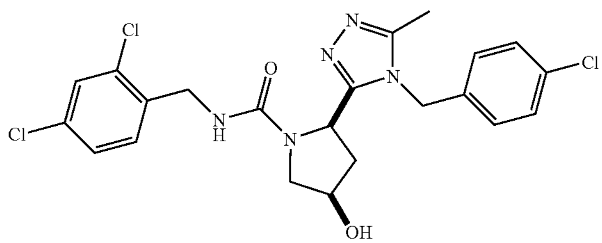 | *** |

TABLE 1-continued
| Compound # | Structure | Relative potency (IC$_{50}$) * = 0.5-5.0 μM ** = 0.05-0.5 μM *** < 0.05 μM |
|---|---|---|
| 443 | 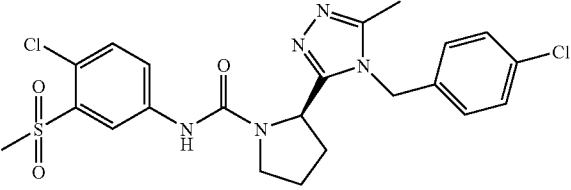 | ** |
| 444 | 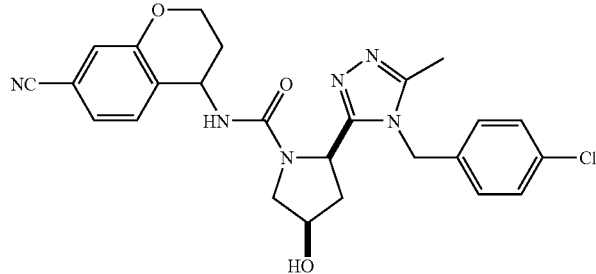 | ** |
| 445 | 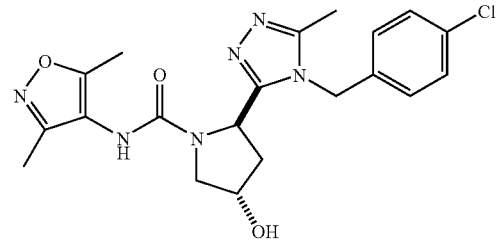 | ** |
| 446 | 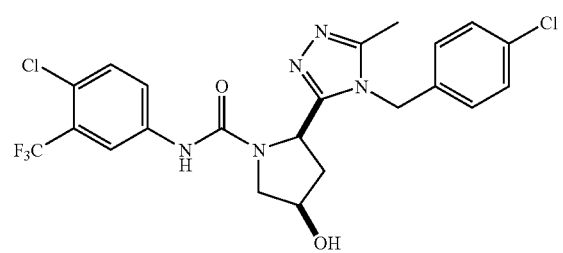 | ** |
| 447 | 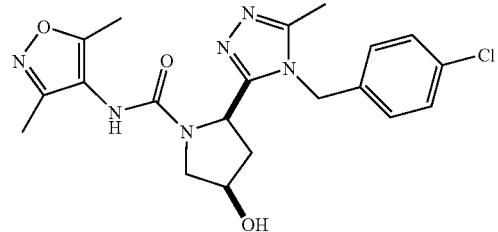 | ** |
| 448 | 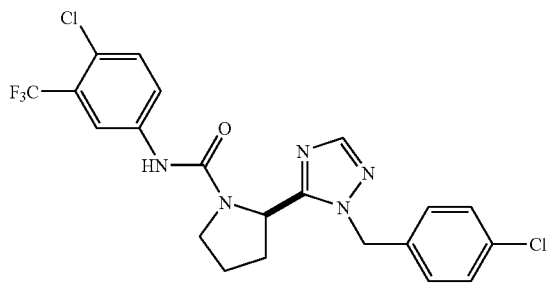 | ** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 449 | 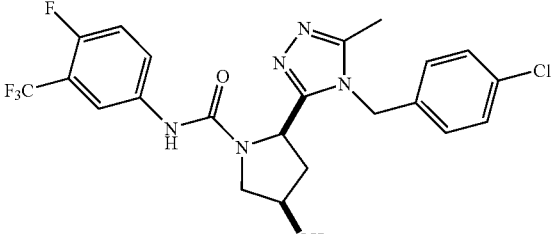 | * |
| 450 | 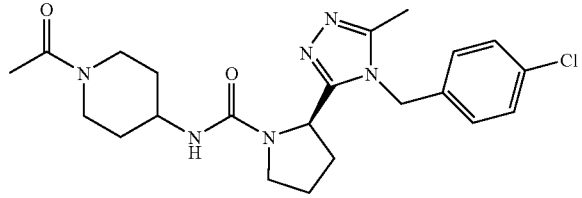 | * |
| 451 | 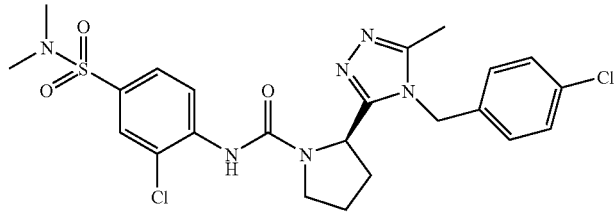 | *** |
| 452 | 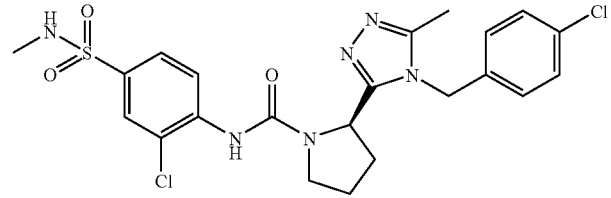 | *** |
| 453 | 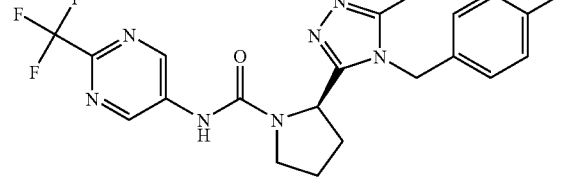 | ** |
| 454 | 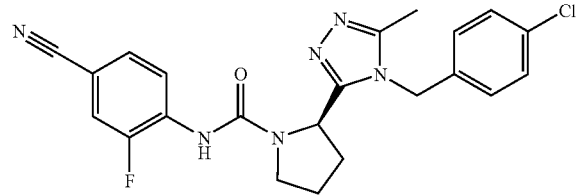 | ** |
| 455 | 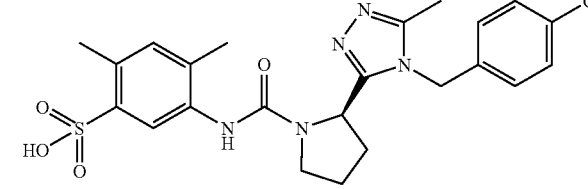 | ** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 456 | 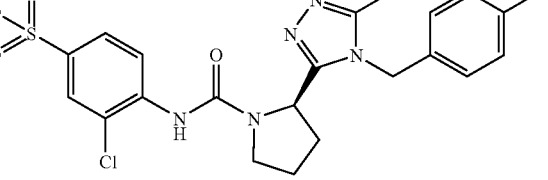 | ** |
| 457 | 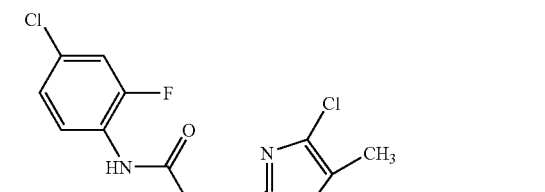 | ** |
| 458 | 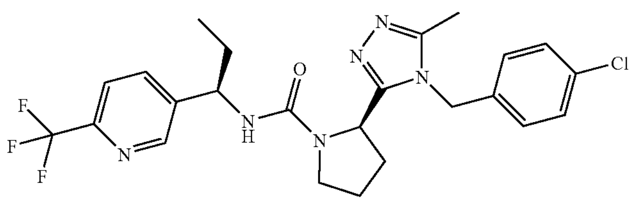 | *** |
| 459 | 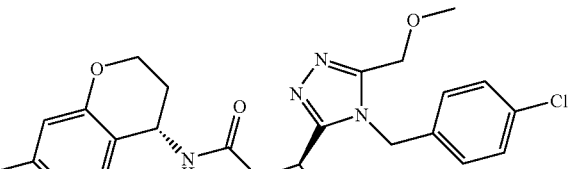 | *** |
| 460 | 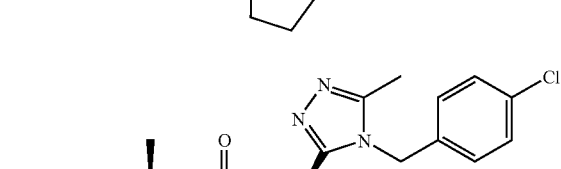 | *** |
| 461 | 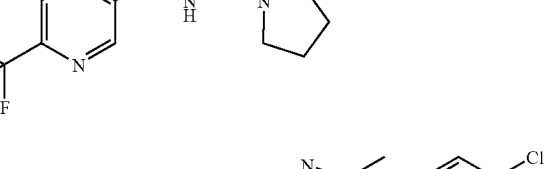 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 462 | 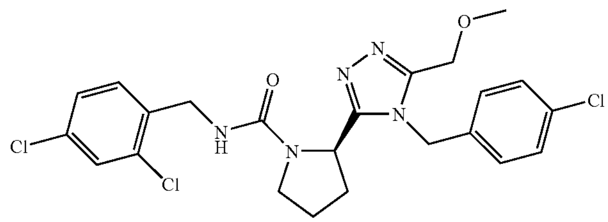 | ** |
| 463 | 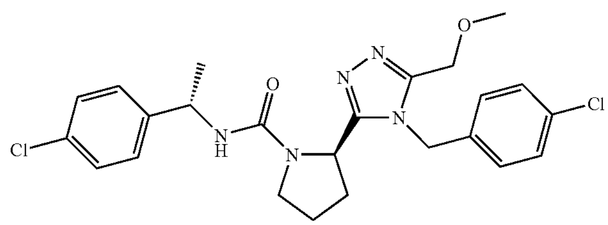 | ** |
| 464 | 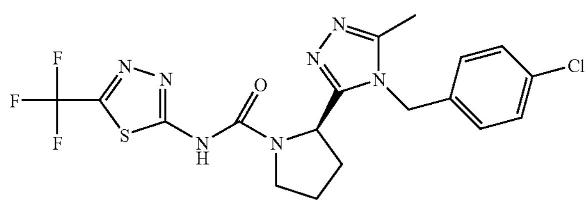 | * |
| 465 | 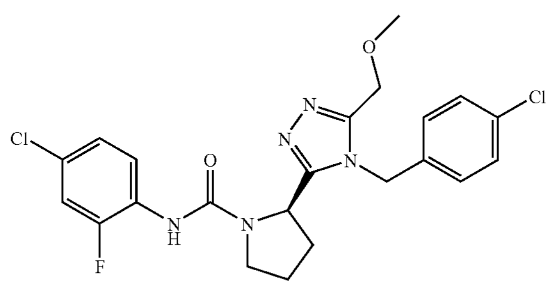 | * |
| 466 | 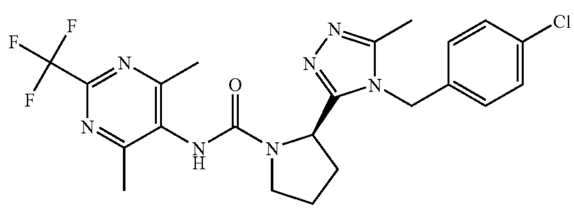 | *** |
| 467 | 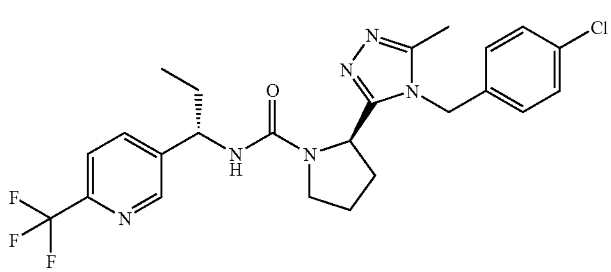 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 468 | 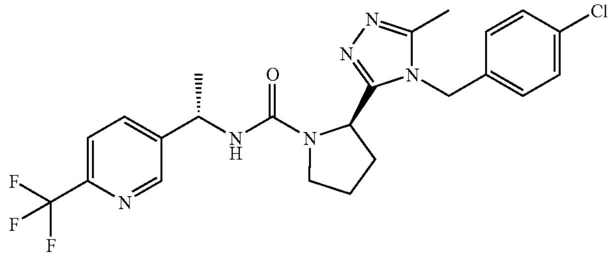 | *** |
| 469 | 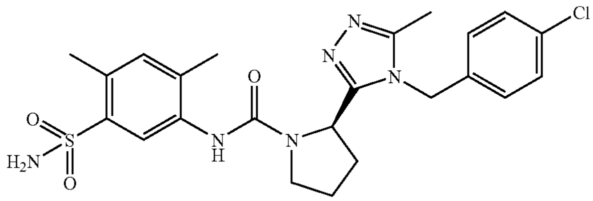 | *** |
| 470 | 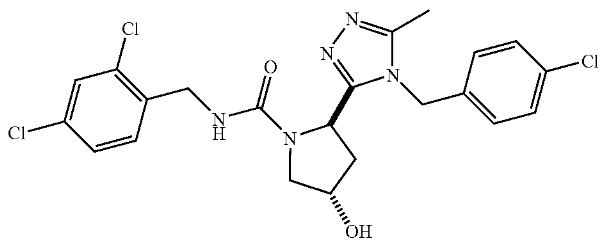 | *** |
| 471 | 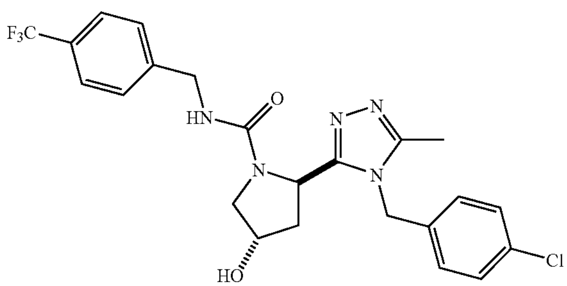 | *** |
| 472 | 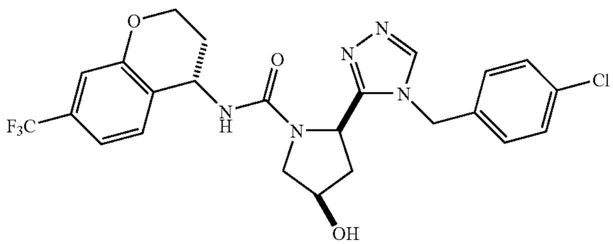 | *** |
| 473 | 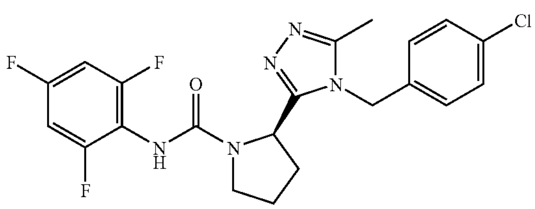 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 474 | 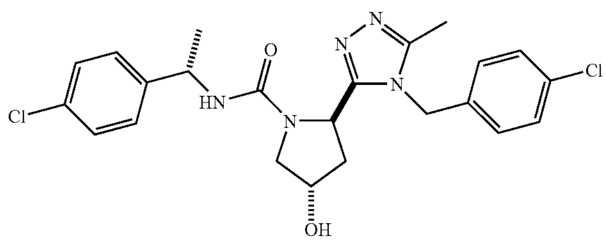 | *** |
| 475 | 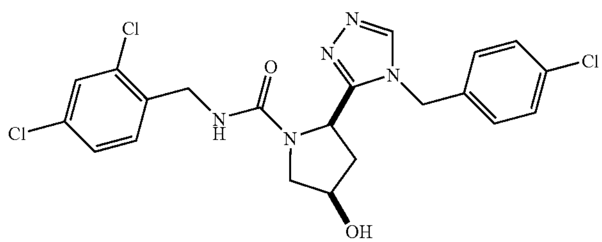 | ** |
| 476 | 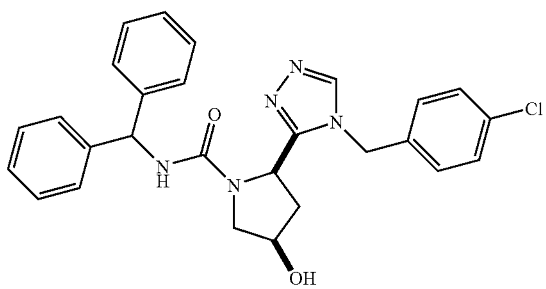 | ** |
| 477 | 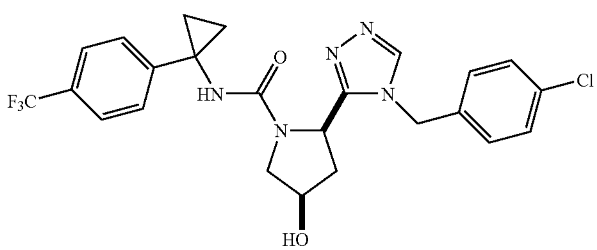 | ** |
| 478 | 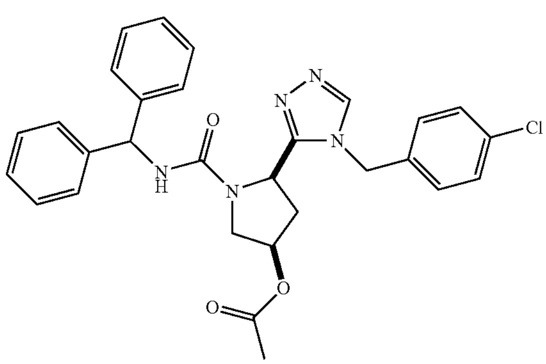 | ** |

… TABLE 1-continued

| Compound # | Structure | Relative potency (IC$_{50}$) * = 0.5–5.0 µM ** = 0.05–0.5 µM *** < 0.05 µM |
|---|---|---|
| 479 | 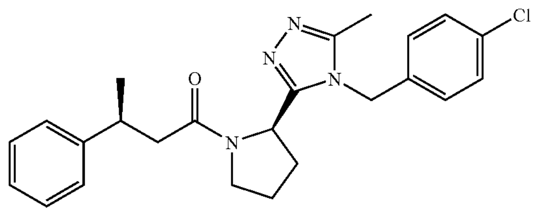 | ** |
| 480 | 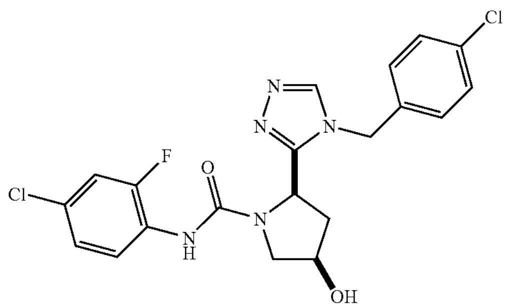 | ** |
| 481 | 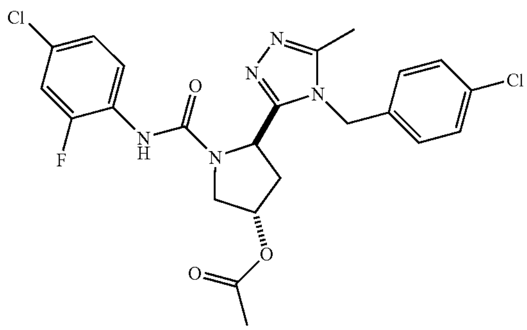 | * |
| 482 | 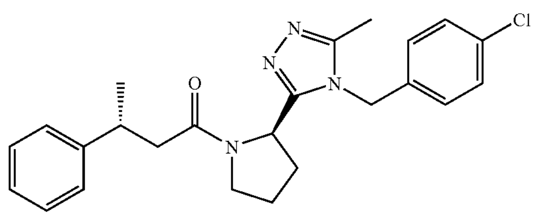 | * |
| 483 | 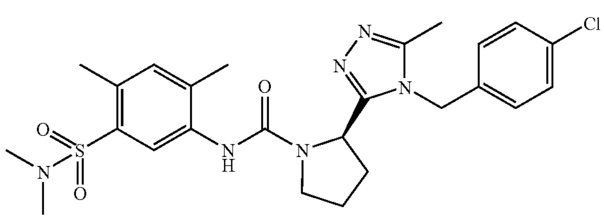 | *** |
| 484 | 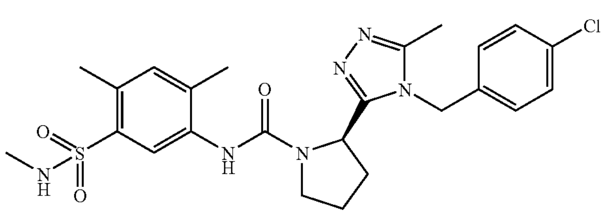 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 485 | 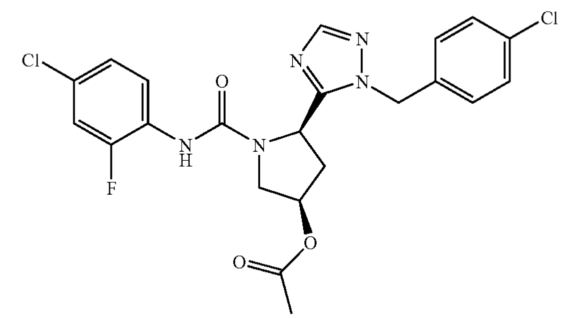 | * |
| 486 | 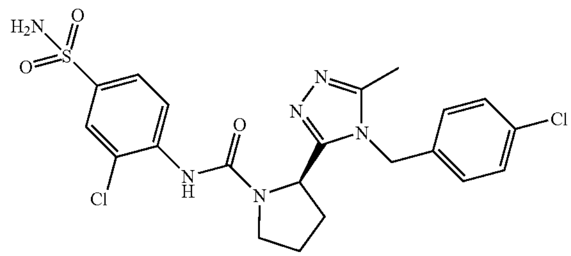 | *** |
| 487 | 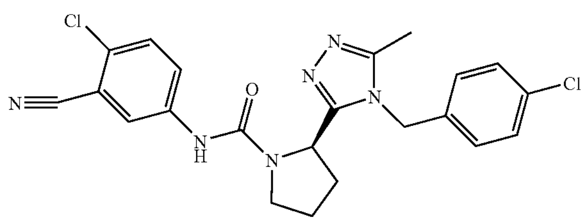 | *** |
| 488 | 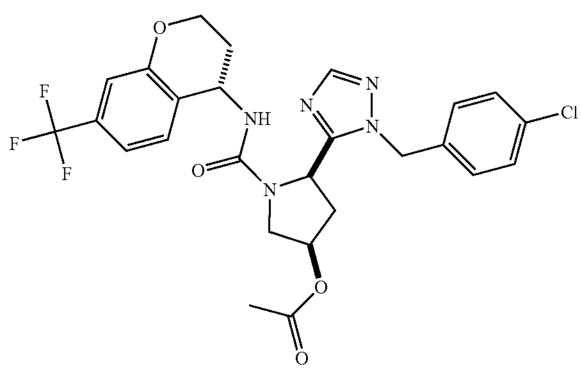 | *** |
| 489 | 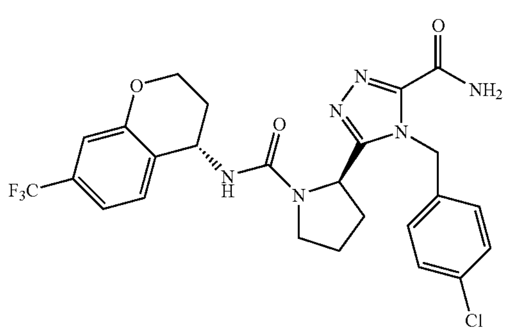 | * |

TABLE 1-continued

| Compound # | Structure | Relative potency (IC$_{50}$)<br>* = 0.5-5.0 μM<br>** = 0.05-0.5 μM<br>*** < 0.05 μM |
| --- | --- | --- |
| 490 | 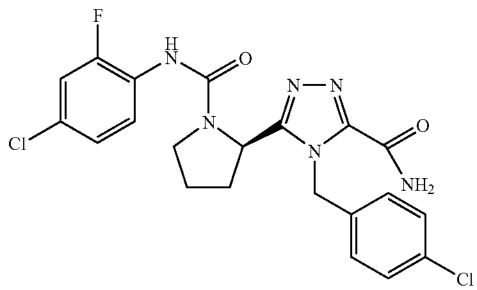 | * |
| 491 | 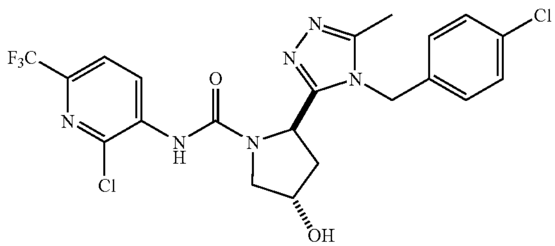 | *** |
| 492 | 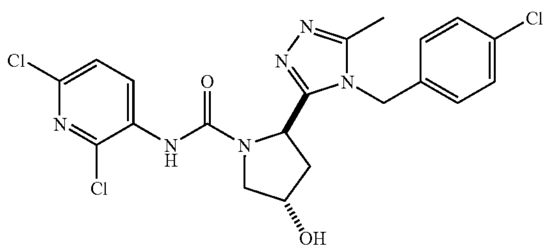 | ** |
| 493 | 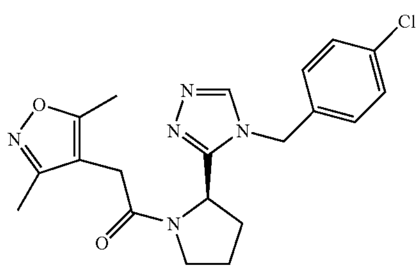 | ** |
| 494 | 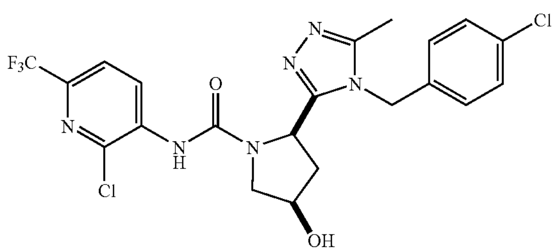 | ** |

TABLE 1-continued

| Compound # | Structure | Relative potency (IC$_{50}$)<br>* = 0.5–5.0 μM<br>** = 0.05–0.5 μM<br>*** < 0.05 μM |
|---|---|---|
| 495 | 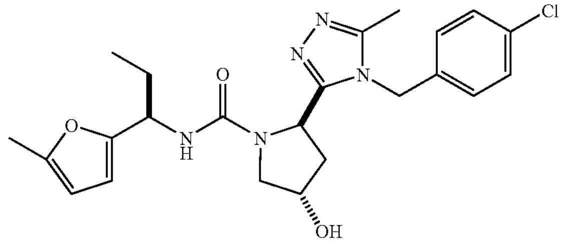 | ** |
| 496 | 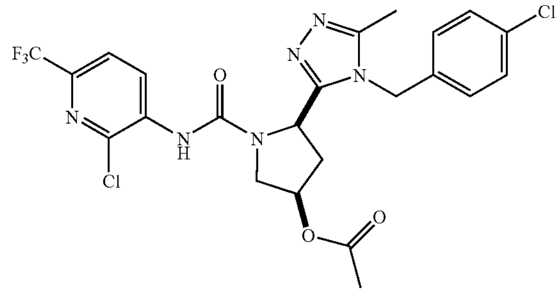 | ** |
| 497 | 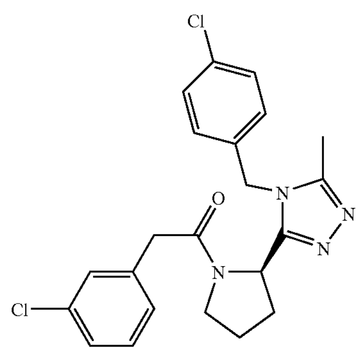 | ** |
| 498 | 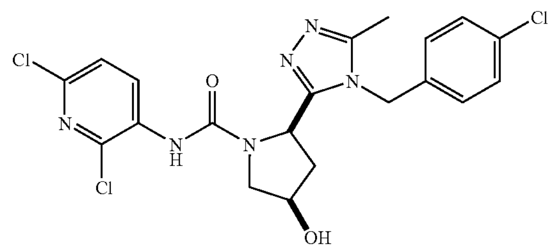 | ** |
| 499 | 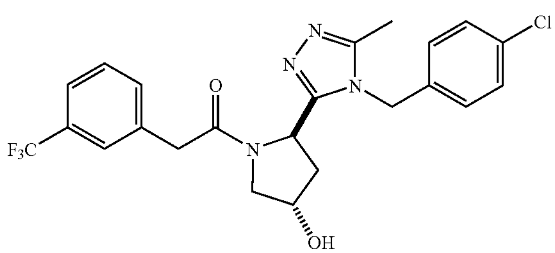 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 500 | 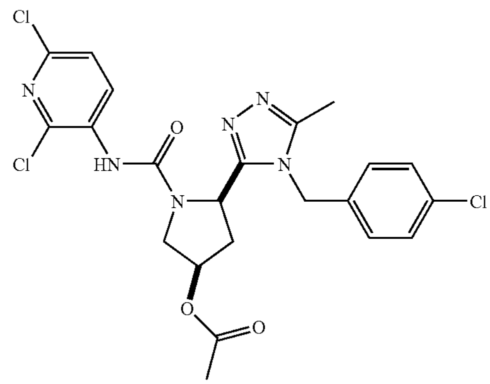 | ** |
| 501 | 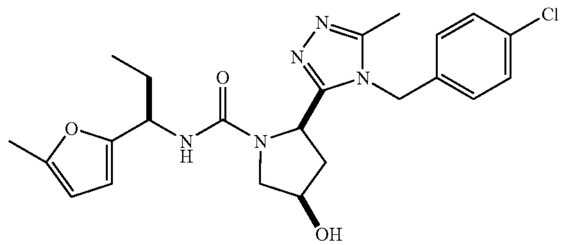 | ** |
| 502 | 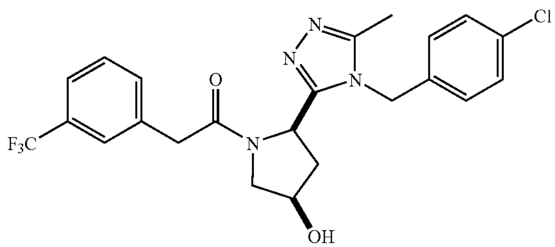 | ** |
| 503 | 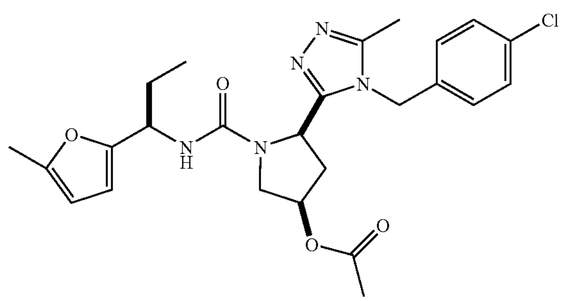 | * |
| 504 | 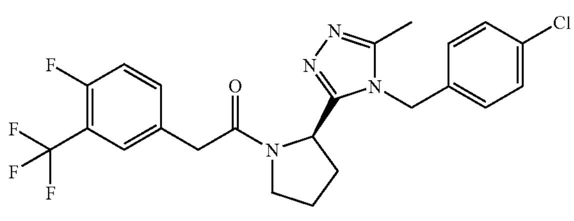 | ** |

TABLE 1-continued
| Compound # | Structure | Relative potency (IC$_{50}$)<br>\* = 0.5-5.0 μM<br>\*\* = 0.05-0.5 μM<br>\*\*\* < 0.05 μM |
|---|---|---|
| 505 | 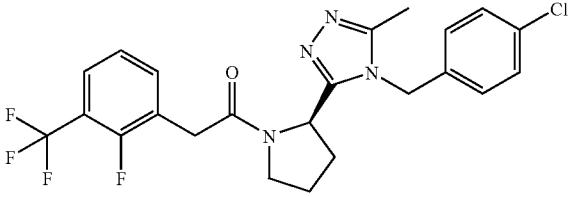 | \*\* |
| 506 | 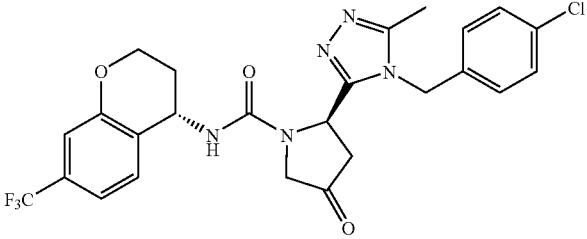 | \*\*\* |
| 507 | 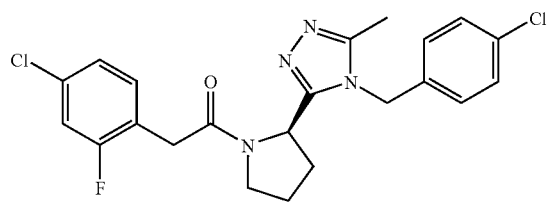 | \*\* |
| 508 | 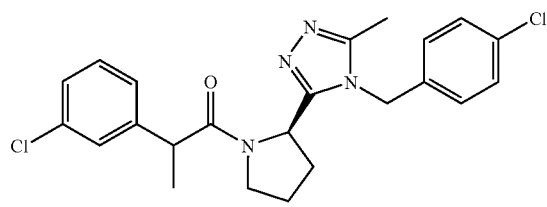 | \*\* |
| 509 | 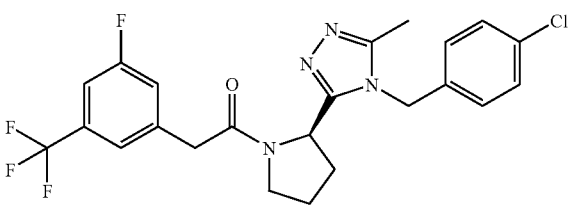 | \*\* |
| 510 | 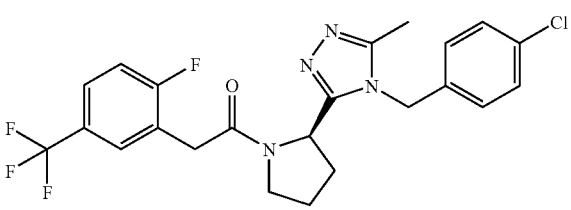 | \*\*\* |
| 511 | 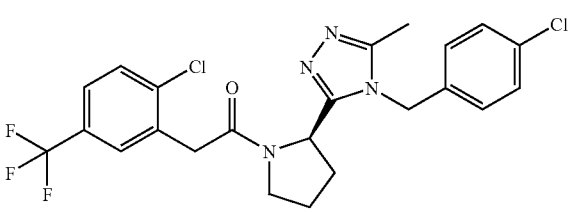 | \*\*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 512 | 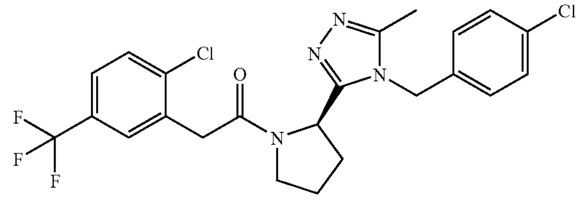 | *** |
| 513 | 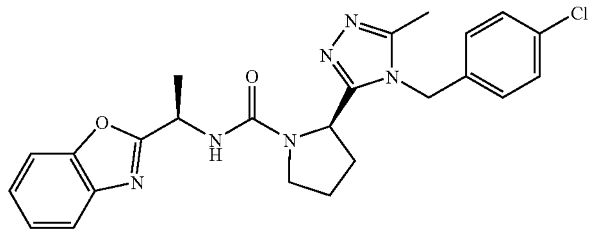 | *** |
| 514 | 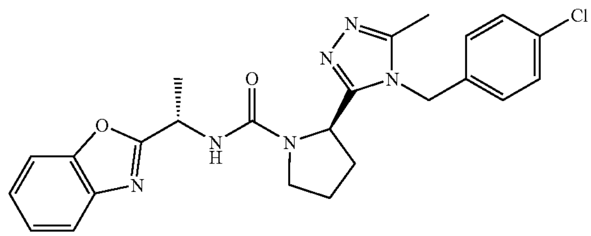 | ** |
| 515 | 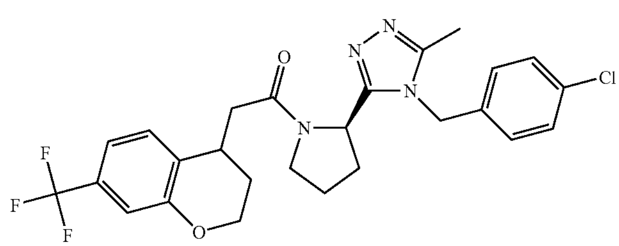 | *** |
| 516 | 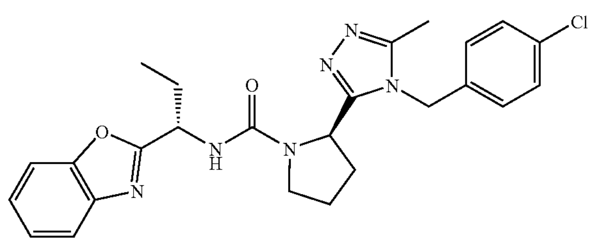 | * |
| 517 | 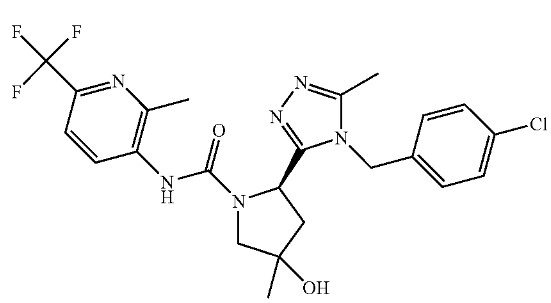 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 518 | 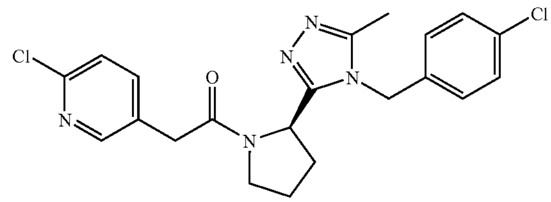 | *** |
| 519 | 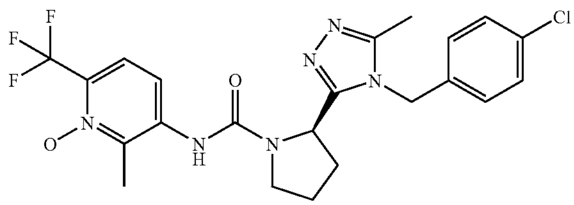 | *** |
| 520 | 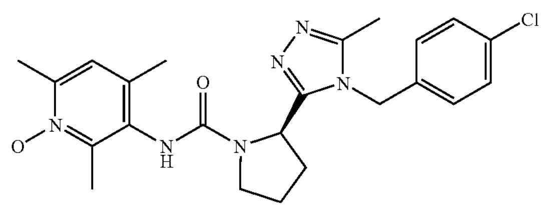 | *** |
| 521 | 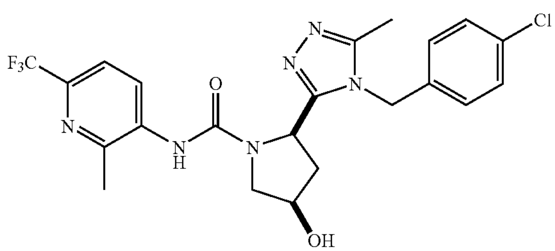 | *** |
| 522 | 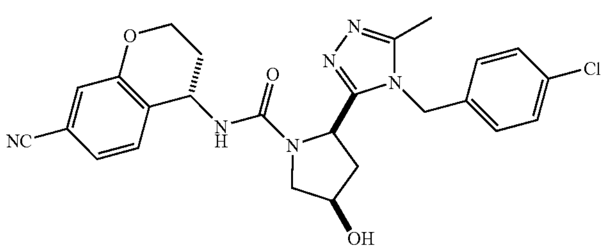 | *** |
| 523 | 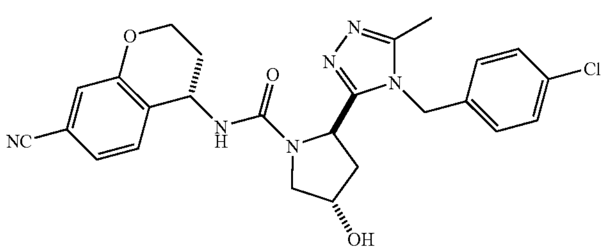 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 524 | 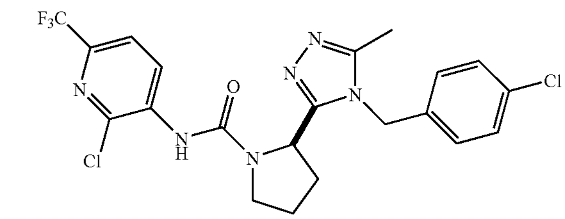 | *** |
| 525 | 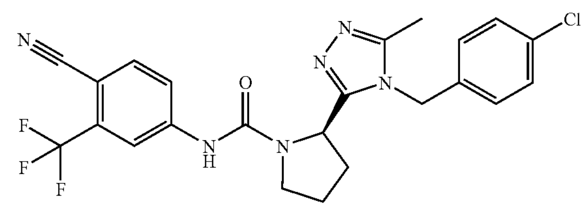 | ** |
| 526 | 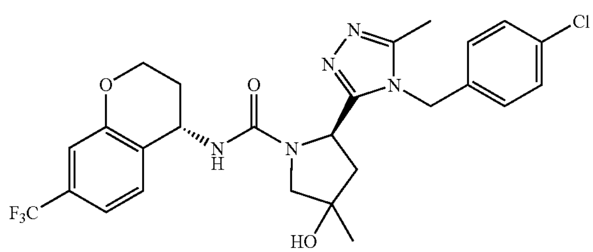 | ** |
| 527 | 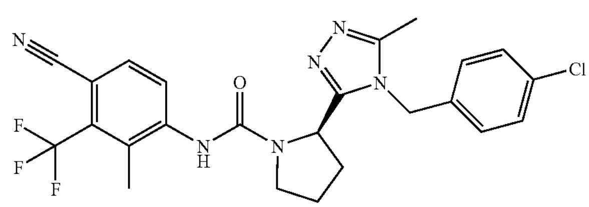 | *** |
| 528 | 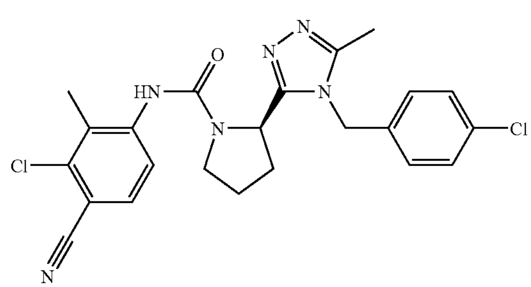 | *** |
| 529 | 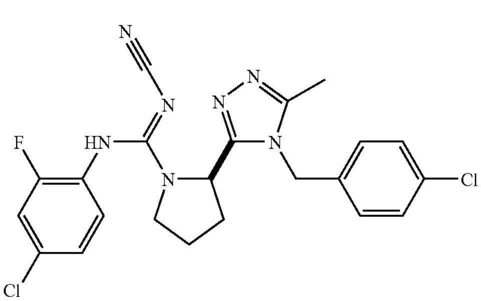 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 530 | 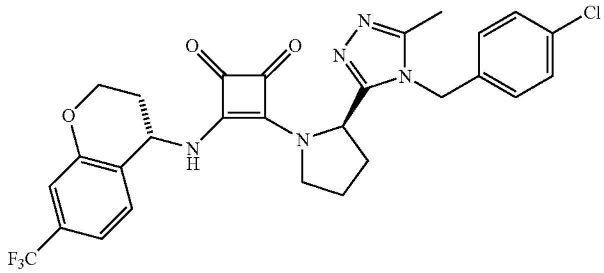 | ** |
| 531 | 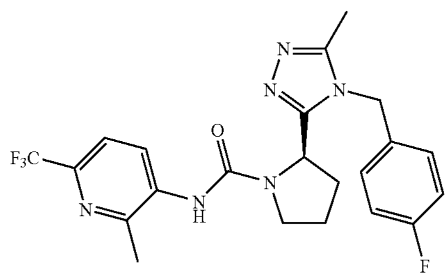 | ** |
| 532 | 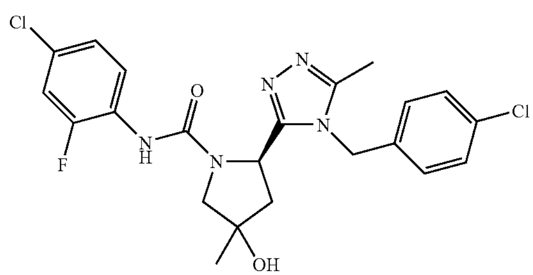 | ** |
| 533 | 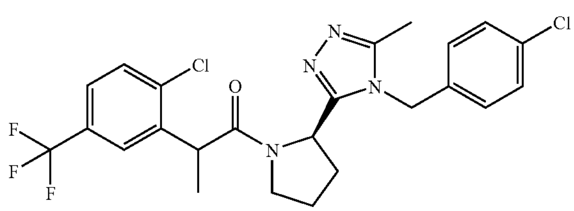 | ** |
| 534 | 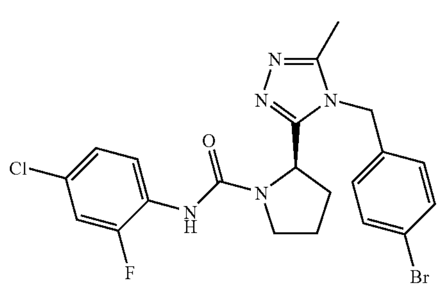 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 535 | 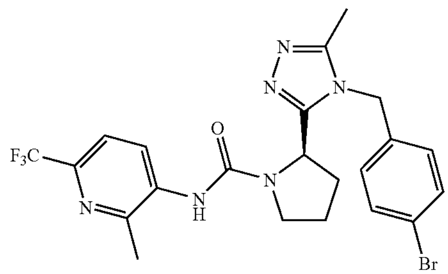 | *** |
| 536 | 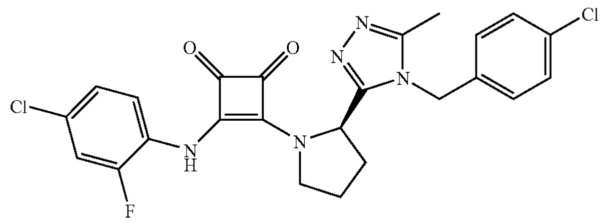 | * |
| 537 | 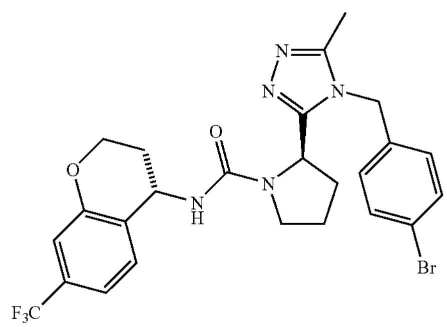 | *** |
| 538 | 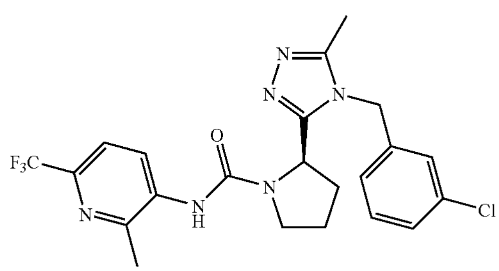 | * |
| 539 | 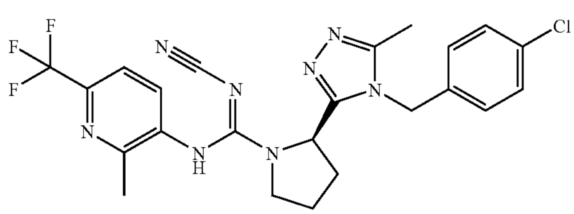 | ** |

TABLE 1-continued
| Compound # | Structure | Relative potency (IC$_{50}$)<br>\* = 0.5-5.0 µM<br>\*\* = 0.05-0.5 µM<br>\*\*\* < 0.05 µM |
|---|---|---|
| 540 | 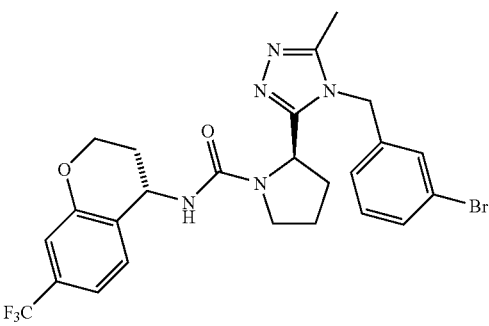 | \* |
| 541 | 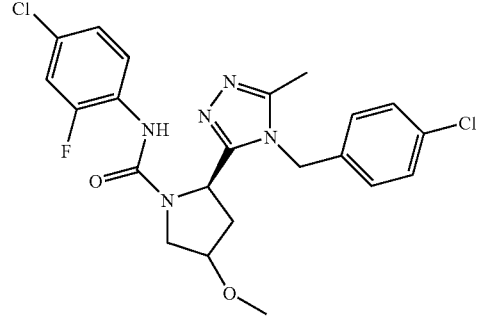 | \*\* |
| 542 | 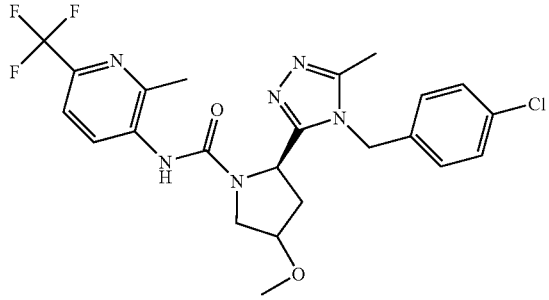 | \*\* |
| 543 | 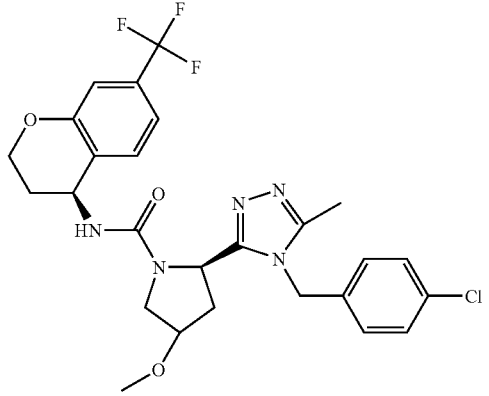 | \*\* |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 544 | 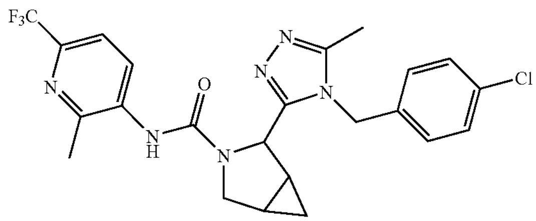 | ** |
| 545 | 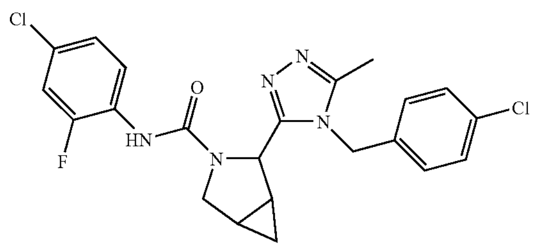 | ** |
| 546 | 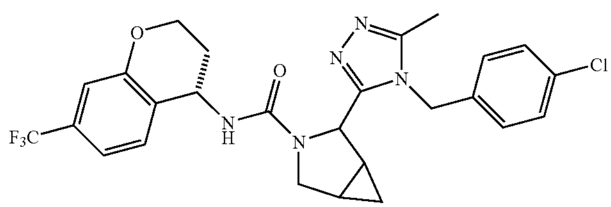 | ** |
| 547 | 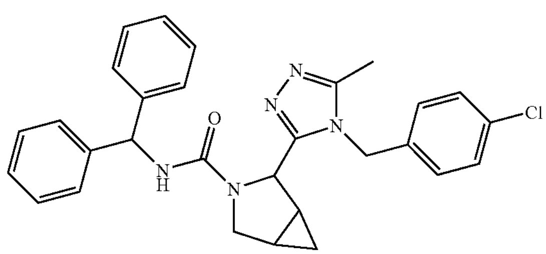 | ** |
| 548 | 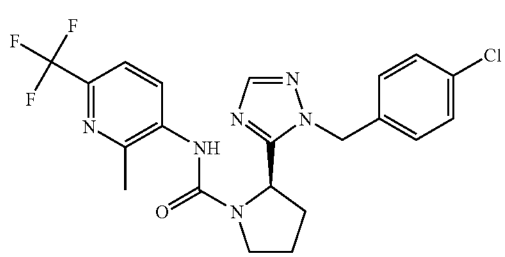 | ** |
| 549 | 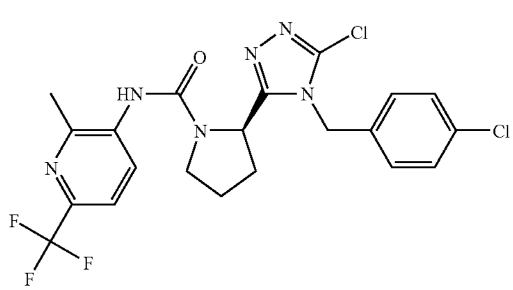 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 550 | 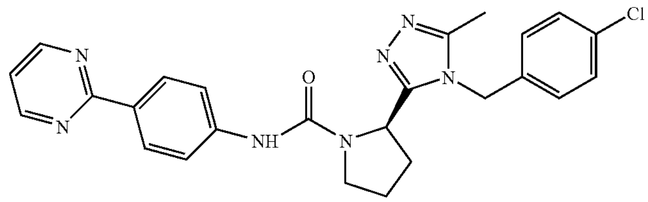 | * |
| 551 | 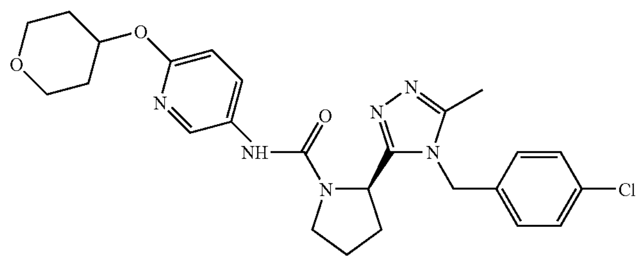 | * |
| 552 | 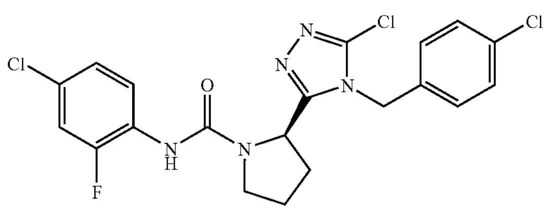 | *** |
| 553 | 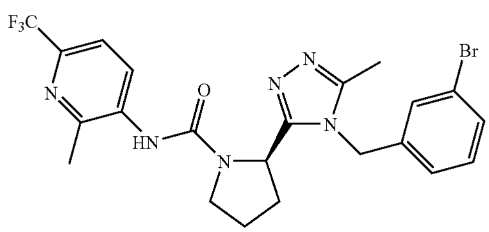 | * |
| 554 | 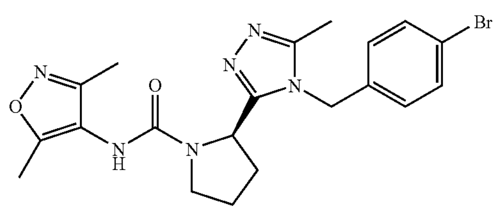 | ** |
| 555 | 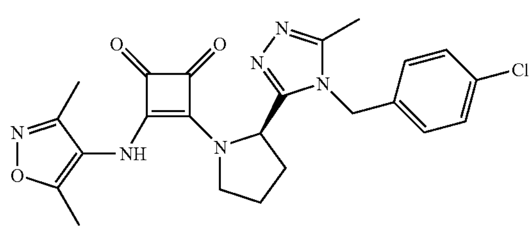 | * |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 556 | 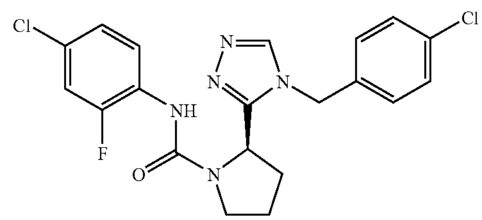 | *** |
| 557 | 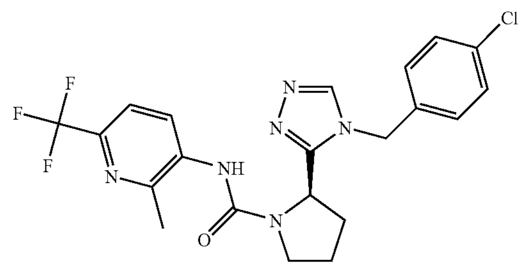 | *** |
| 558 | 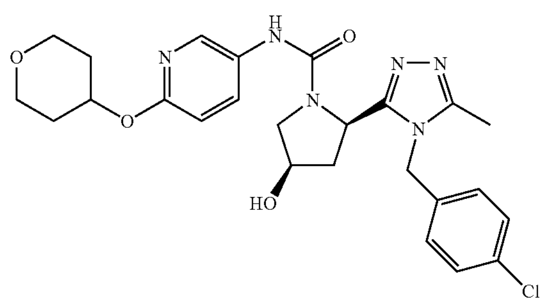 | * |
| 559 | 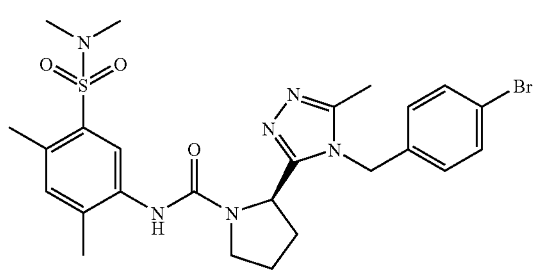 | *** |
| 560 | 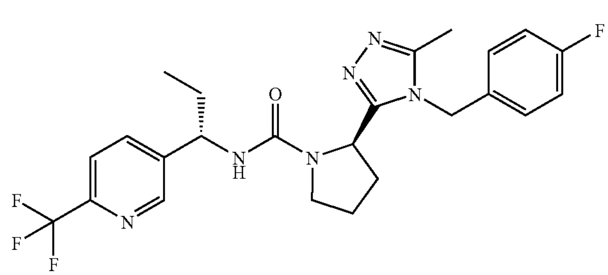 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 561 | 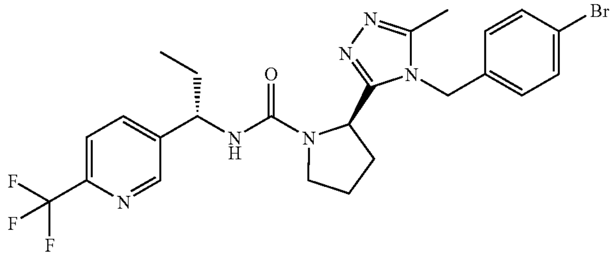 | *** |
| 562 | 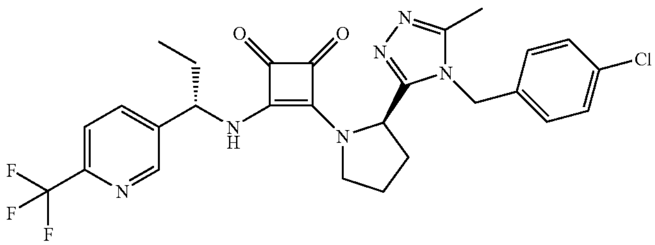 | ** |
| 563 | 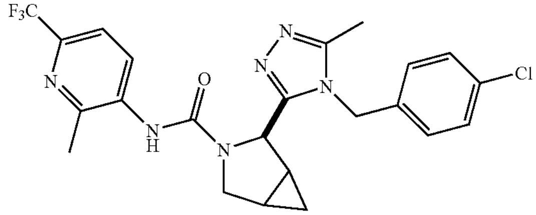 | *** |
| 564 | 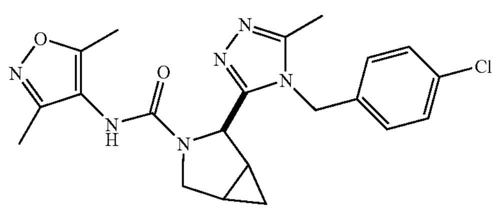 | ** |
| 565 | 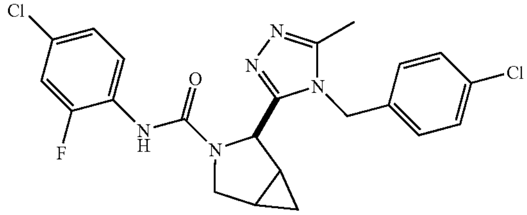 | ** |
| 566 | 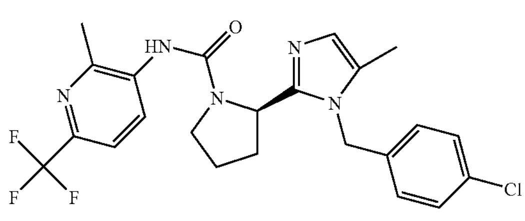 | ** |

TABLE 1-continued

| Compound # | Structure | Relative potency (IC$_{50}$) * = 0.5-5.0 µM ** = 0.05-0.5 µM *** < 0.05 µM |
|---|---|---|
| 567 | 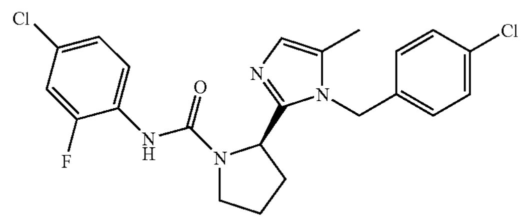 | ** |
| 568 | 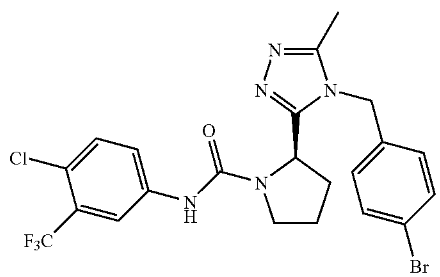 | ** |
| 569 | 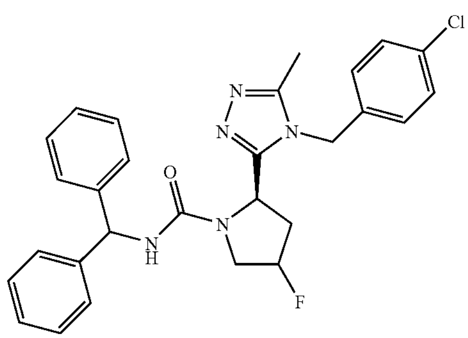 | ** |
| 570 | 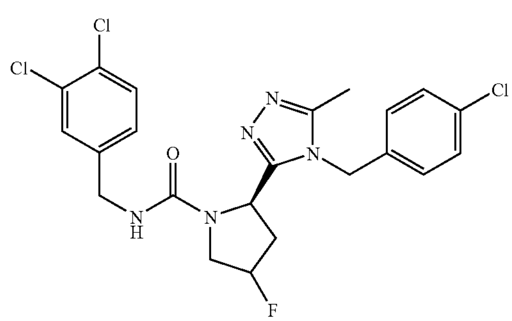 | *** |
| 571 | 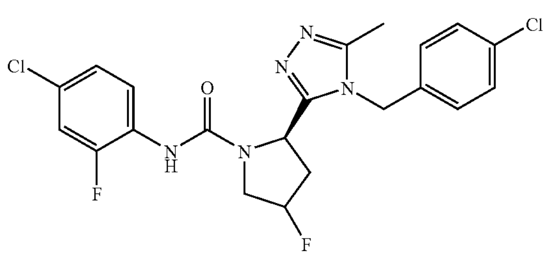 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 572 | 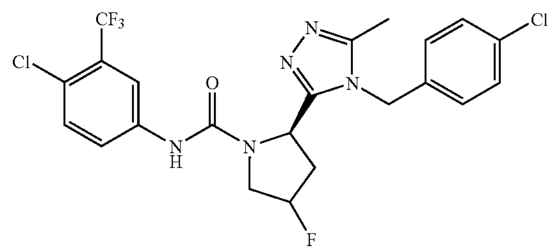 | ** |
| 573 | 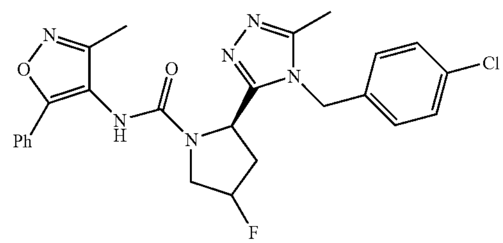 | *** |
| 574 | 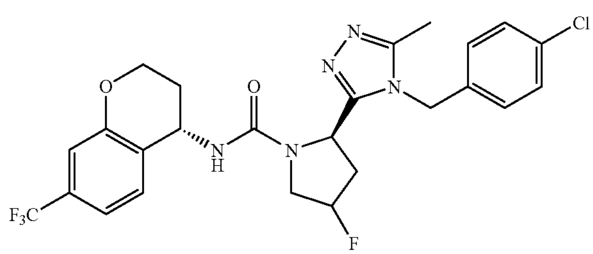 | *** |
| 575 | 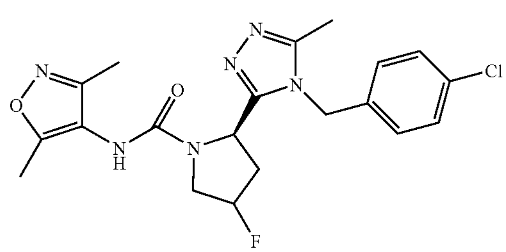 | *** |
| 576 | 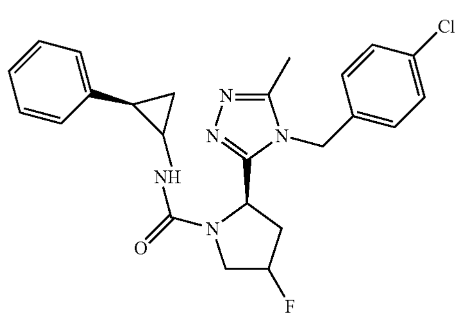 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 577 | 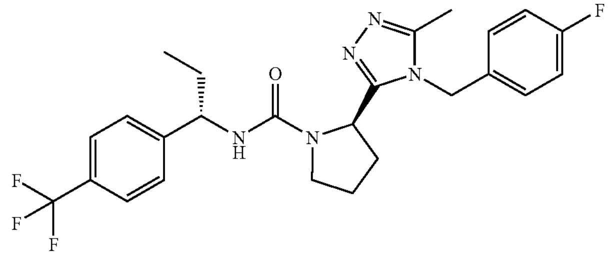 | *** |
| 578 | 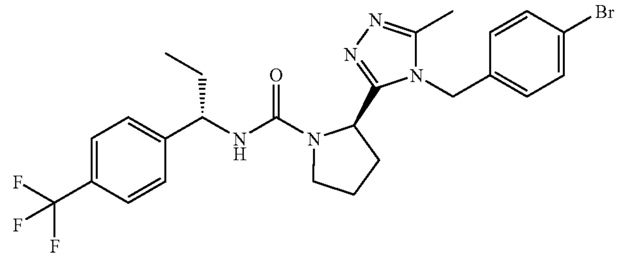 | *** |
| 579 | 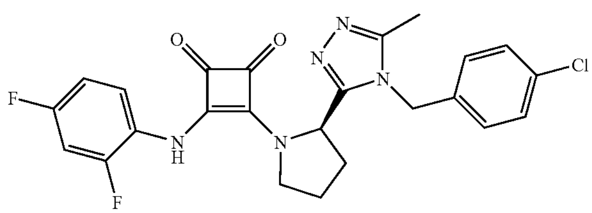 | * |
| 580 | 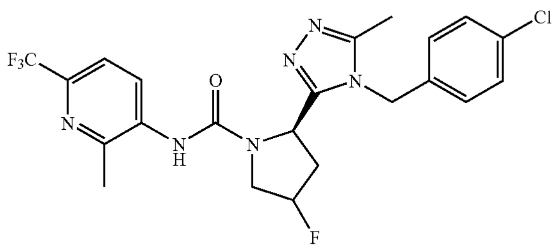 | *** |
| 581 | 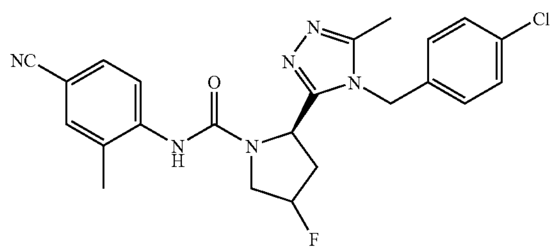 | ** |
| 582 | 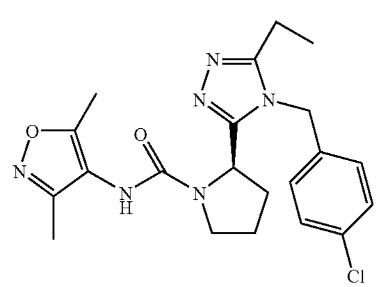 | ** |

TABLE 1-continued

| Compound # | Structure | Relative potency (IC$_{50}$) * = 0.5-5.0 μM ** = 0.05-0.5 μM *** < 0.05 μM |
|---|---|---|
| 583 | 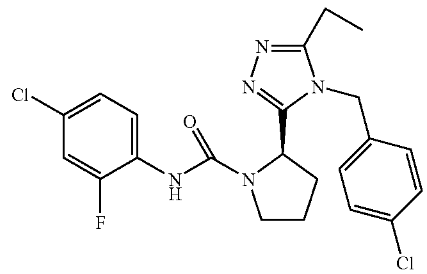 | *** |
| 584 | 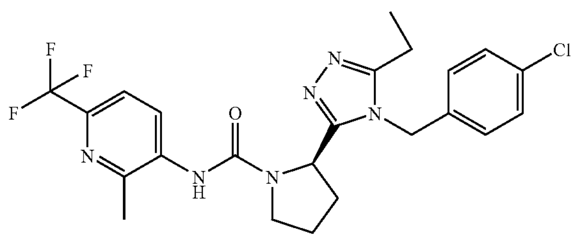 | *** |
| 585 | 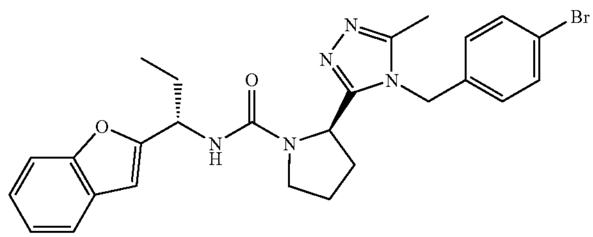 | *** |
| 586 | 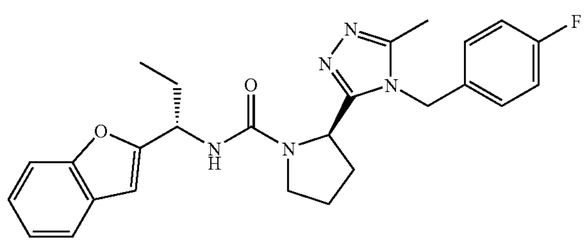 | *** |
| 587 | 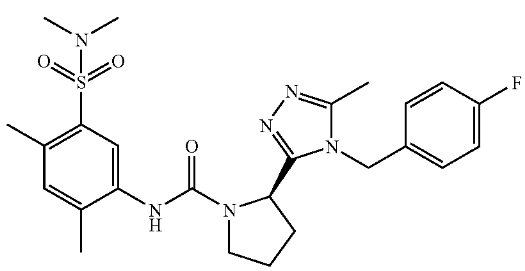 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 588 | 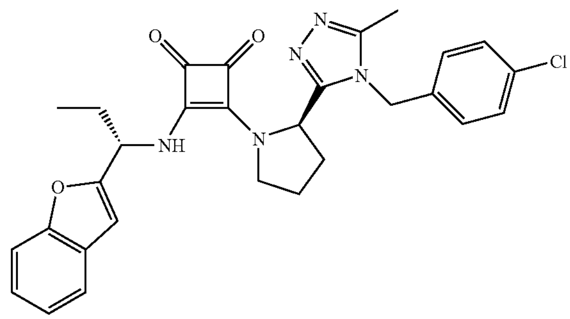 | ** |
| 589 | 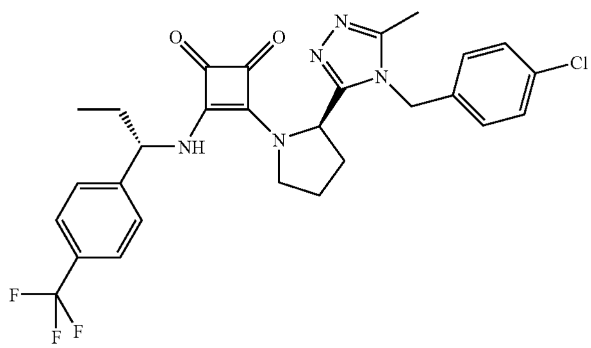 | ** |
| 590 | 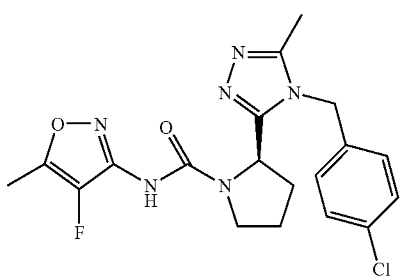 | ** |
| 591 | 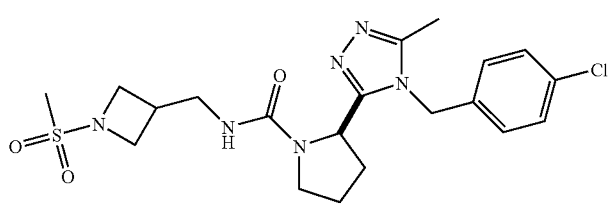 | * |
| 592 | 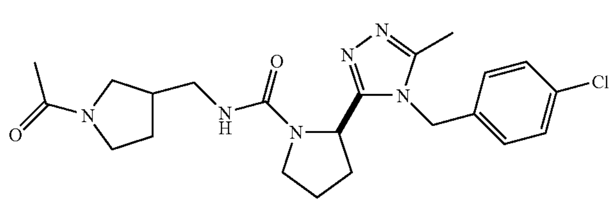 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 593 | 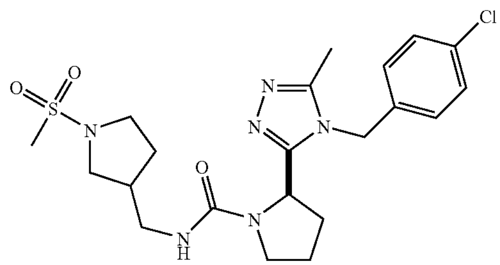 | ** |
| 594 | 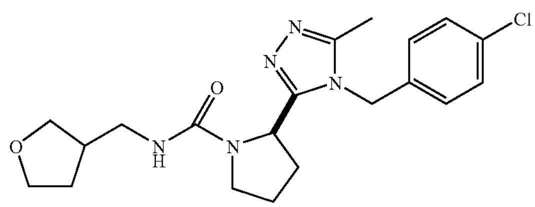 | * |
| 595 | 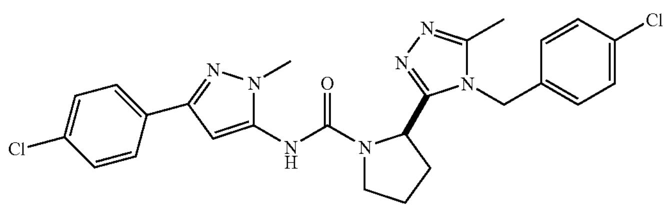 | ** |
| 596 | 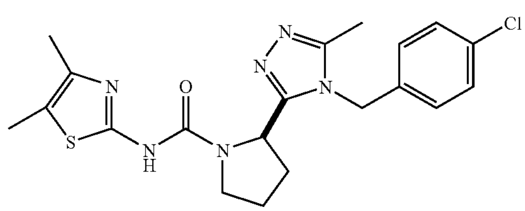 | * |
| 597 | 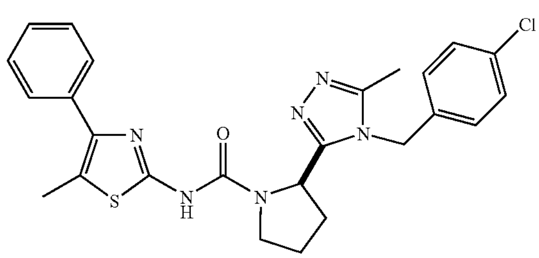 | * |
| 598 | 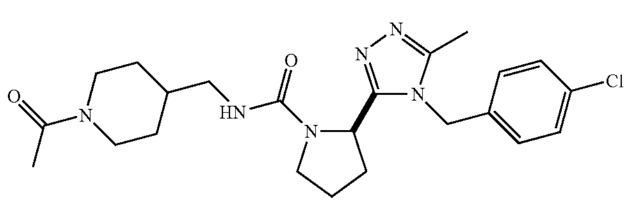 | ** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 599 | 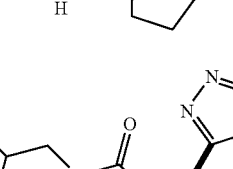 | ** |
| 600 | 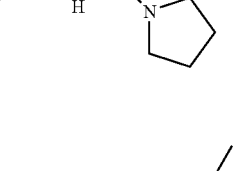 | ** |
| 601 | 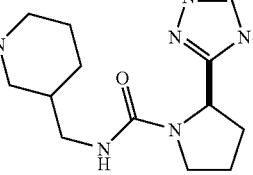 | ** |
| 602 | 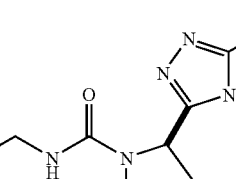 | ** |
| 603 | 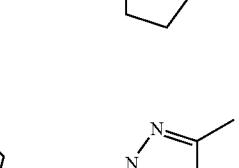 | * |
| 604 | 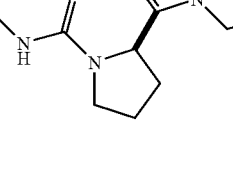 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 605 | 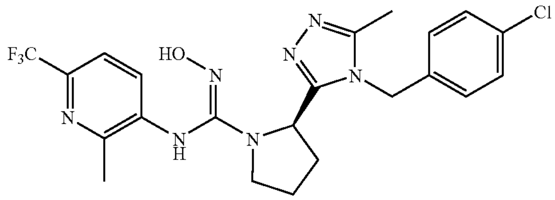 | ** |
| 606 | 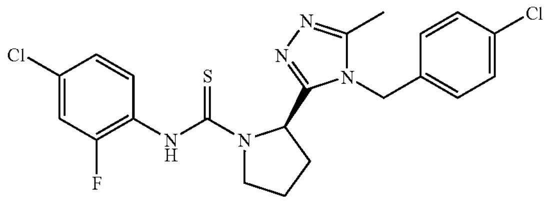 | *** |
| 607 | 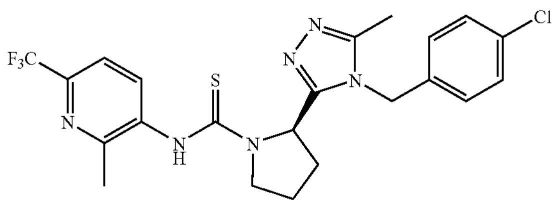 | *** |
| 608 | 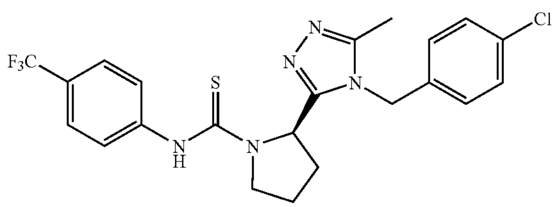 | *** |
| 609 | 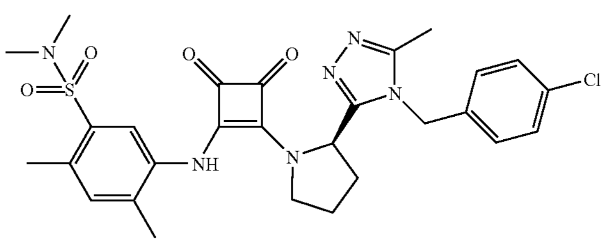 | ** |
| 610 | 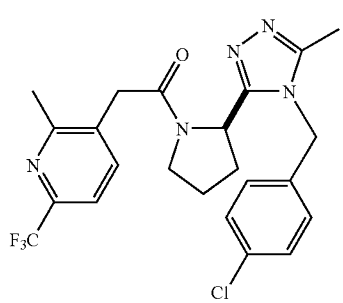 | *** |

TABLE 1-continued
| Compound # | Structure | Relative potency (IC$_{50}$)<br>* = 0.5-5.0 μM<br>** = 0.05-0.5 μM<br>*** < 0.05 μM |
|---|---|---|
| 611 | 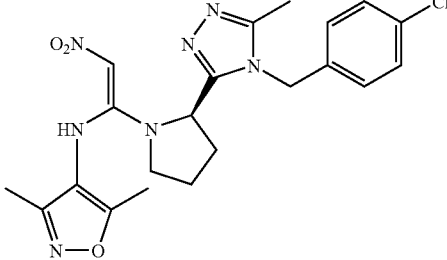 | *** |
| 612 | 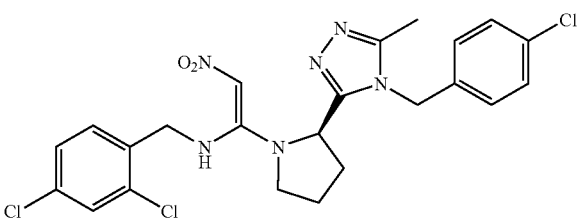 | ** |
| 613 | 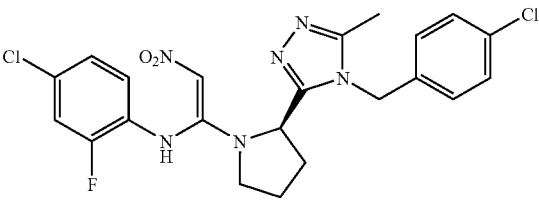 | ** |
| 614 | 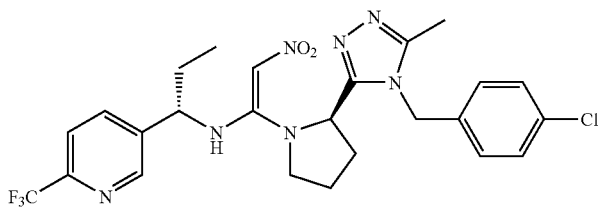 | *** |
| 615 | 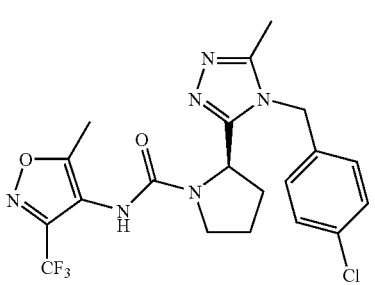 | *** |
| 616 | 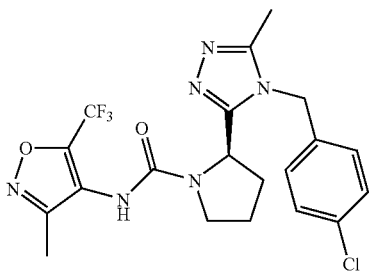 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 617 | 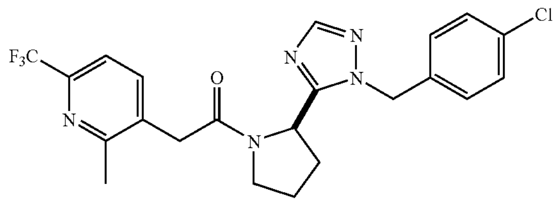 | ** |
| 618 | 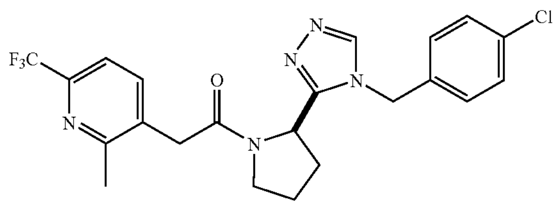 | *** |
| 619 | 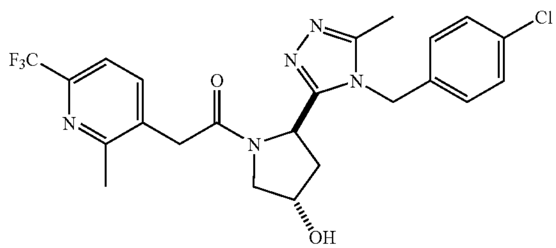 | *** |
| 620 | 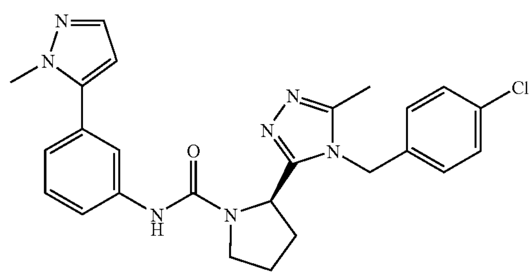 | * |
| 621 | 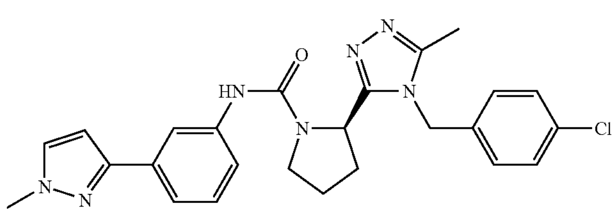 | ** |
| 622 | 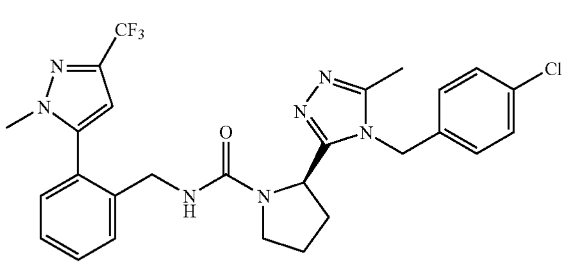 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 623 | 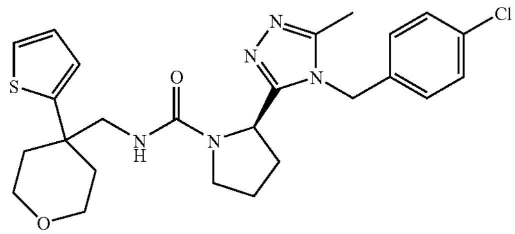 | * |
| 624 | 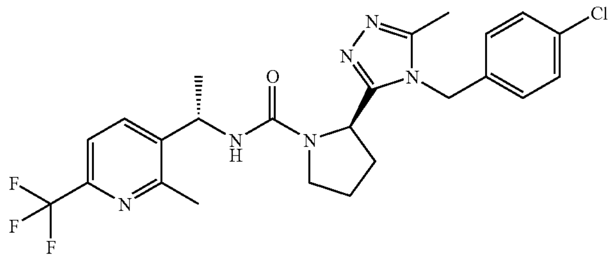 | *** |
| 625 | 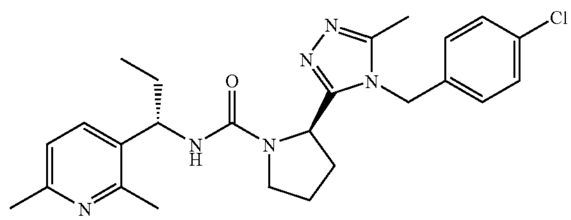 | *** |
| 626 | 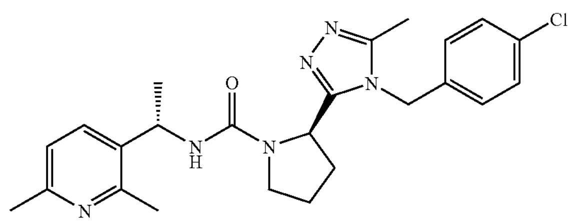 | ** |
| 627 | 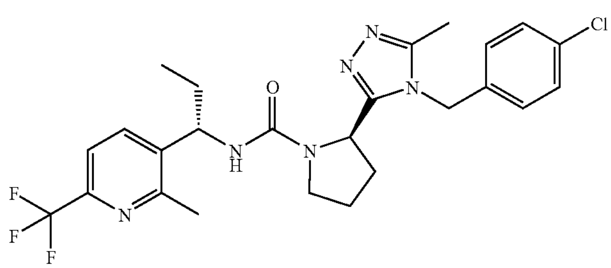 | *** |
| 628 | 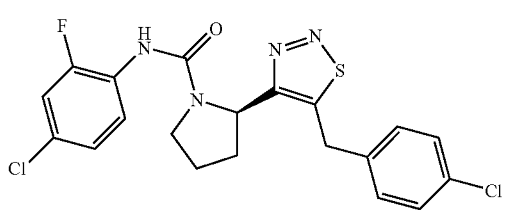 | ** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 629 | 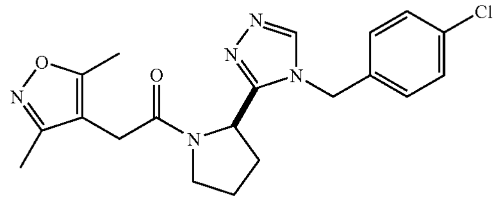 | ** |
| 630 | 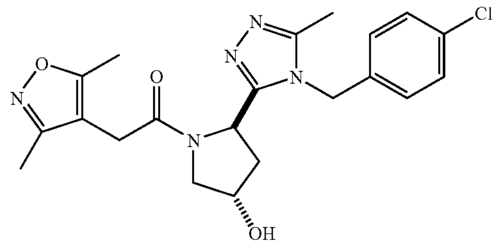 | ** |
| 631 | 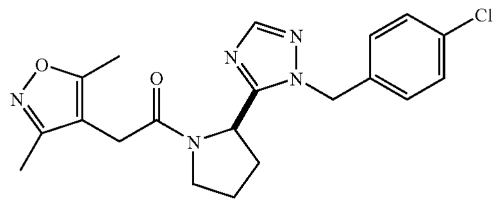 | * |
| 632 | 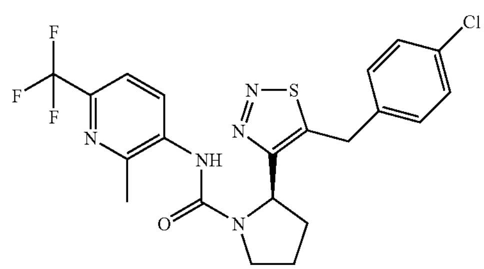 | *** |
| 633 | 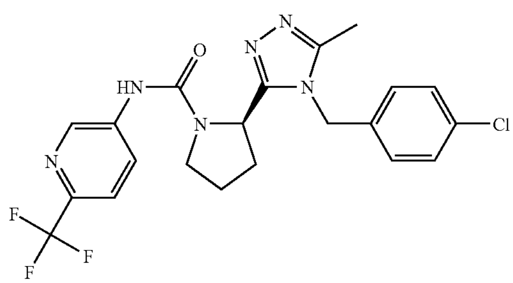 | ** |
| 634 | 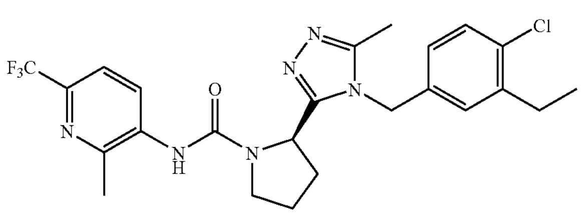 | *** |

TABLE 1-continued

| Compound # | Structure | Relative potency (IC$_{50}$)<br>* = 0.5-5.0 μM<br>** = 0.05-0.5 μM<br>*** < 0.05 μM |
|---|---|---|
| 635 | 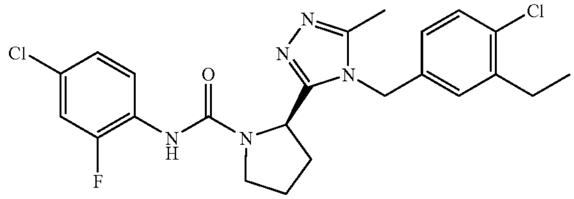 | ** |
| 636 | 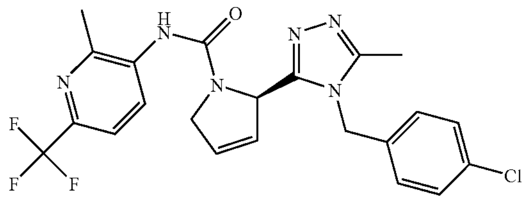 | *** |

We claim:

1. A compound of formula I:

I wherein

X is an sp$^2$-hybridized carbon atom;

X$^7$ is selected from sp$^2$-hybridized C and N;

Q, including X and X$^7$, is a 5- or 6-membered unsaturated, optionally substituted ring and is selected from carbocycle and heterocycle;

R$^{1a}$ and R$^{1b}$ are independently selected from H and CH$_3$ or R$^{1a}$ and R$^{1b}$ taken together with the carbon atom to which they are attached may form a (C$_3$-C$_7$)cycloalkyl group, with the proviso that both R$^{1a}$ and R$^{1b}$ cannot be CH$_3$;

R$^2$ is selected from H, methyl, ethyl, methoxy, ethoxy, cyano and halo;

R$^4$ is selected from H, methyl, ethyl, methoxy, ethoxy, cyano and halo;

Y is selected from —C(=O)—, —O—, and —CR$^5$R$^6$—, wherein R$^5$ is selected from H, methyl, ethyl, methoxy, ethoxy, —OH, F, —OC(=O)CH$_3$ and —OC(=O)CH$_2$CH$_3$; and R$^6$ is selected from H, methyl and ethyl;

W is —CHR$^8$— or Y—W taken together represents —CR$^5$=CR$^8$—;

R$^8$ is chosen from H, methyl and ethyl, or R$^8$ taken together with R$^5$ forms a carbocycle;

X$^8$ is selected from CH and N;

Z is

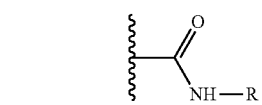

wherein R is selected from the group consisting of an optionally substituted alkyl group, an optionally substituted carbocycle and an optionally substituted heterocycle, wherein said alkyl group, carbocycle or heterocycle is attached to the remainder of Z through a carbon atom;

R$^{11}$ is selected from H, methyl and ethyl;

R$^{12}$ and R$^{13}$ are independently selected in each occurrence from H, methyl and ethyl or R$^{12}$ and R$^{13}$ taken together with the carbon atom to which they are attached may form a 3 to 7-membered cyclic group;

p is zero, one or two; and q is one or two.

2. A compound according to claim 1 of formula Ia:

Ia

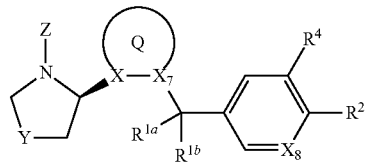

wherein

R$^2$ is selected from H, CH$_3$, Cl, F and Br;

R$^4$ is selected from H, CH$_3$, Cl, F and Br;

Y is selected from —C(=O)—, —O—, and —CHR$^5$—, wherein R$^5$ is selected from H, C$_{1-8}$alkyl, —OH, F, —OC$_{1-8}$alkyl, and —OC(=O)—C$_{1-8}$alkyl.

3. A compound according to claim 1 wherein Y is —CHR$^5$—.

4. A compound according to claim 1 wherein X$^7$ is N.

5. A compound according to claim 4 wherein Q contains at least one heteroatom in addition to X$^7$.

6. A compound according to claim 1 wherein X$^7$ is an sp$^2$-hybridized carbon.

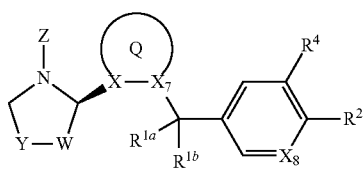

7. A compound according to claim 6 wherein Q contains at least one heteroatom.

8. A compound according to claim 6 wherein Q contains two heteroatoms.

9. A compound according to claim 7 wherein Q is Q is chosen from pyrimidine, pyrazole, oxazole, pyrrole, thiazole, 1H-1,2,3-triazole, 1,2,3-oxadiazole, 1,2,3-thiadiazole, 1,2,5-thiadiazole, 1,2,5-thiadiazole oxide, 1,2,5-thiadiazole dioxide, 1,2,5-oxadiazole, pyridine, pyrazine, pyridazine and isoxazole wherein each of said pyrimidine, pyrazole, oxazole, pyrrole, thiazole, 1H-1,2,3-triazole, 1,2,3-oxadiazole, 1,2,3-thiadiazole, 1,2,5-thiadiazole, 1,2,5-thiadiazole oxide, 1,2,5-thiadiazole dioxide, 1,2,5-oxadiazole, pyridine, pyrazine, pyridazine and isoxazole moieties is optionally substituted.

10. A compound according to claim 9 of formula

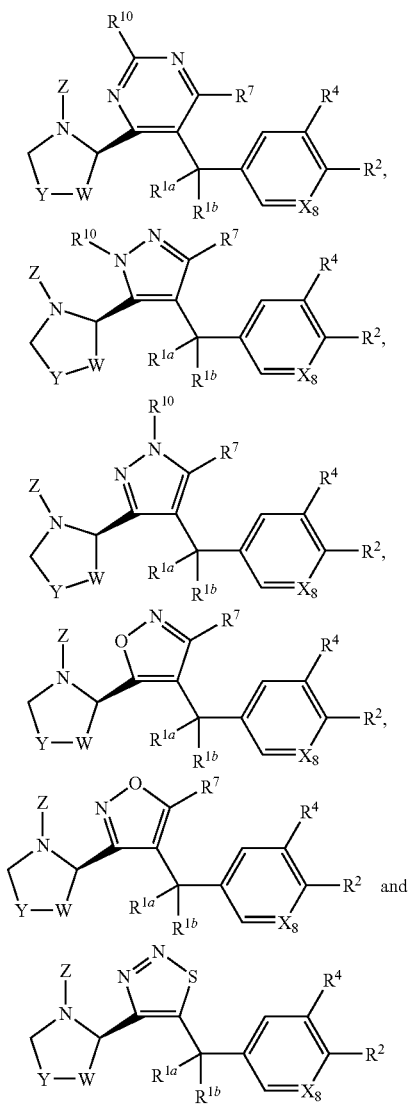

wherein $R^7$ is chosen from H, $(C_1-C_4)$alkyl, halo$(C_1-C_4)$alkyl, hydroxy$(C_1-C_4)$alkyl, $(C_1-C_4)$alkoxy$(C_1-C_4)$alkyl, hydroxyl, halo, amino $(C_1-C_4)$alkyl, $(C_1-C_4)$alkylamino $(C_1-C_4)$alkyl, di[$(C_1-C_4)$alkyl]amino$(C_1-C_4)$alkyl, and —C(=O)NH$_2$; and
$R^{10}$ is chosen from H and $(C_1-C_4)$alkyl.

11. A compound according to claim 10, wherein $R^7$ is selected from the group consisting of H, CH$_3$, Cl, F, Br, CF$_3$, ethyl, isopropyl, CH$_2$OH, CH$_2$OCH$_3$, CH$_2$NH$_2$, C(=O)NH$_2$ and CH$_2$NHCH$_3$ and $R^{10}$ is hydrogen or methyl.

12. A compound according to claim 1 wherein W is CH$_2$, Y is —CHR$^5$— and R$^5$ is selected from H, CH$_3$, —OH, —OCH$_3$, and —OCOCH$_3$.

13. A compound according to claim 4 wherein Q is selected from the group consisting of triazole, imidazole, and tetrazole, wherein each of said triazole and imidazole moieties is optionally substituted.

14. A compound having a formula chosen from among the following:

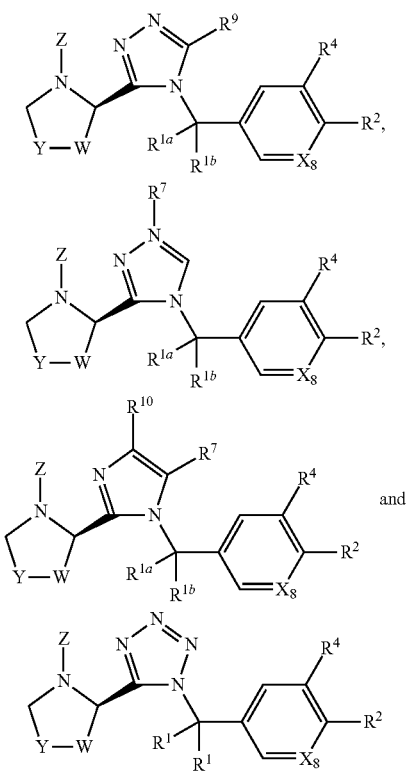

wherein $R^{1a}$ and $R^{1b}$ are independently selected from H and CH$_3$ or $R^{1a}$ and $R^{1b}$ taken together with the carbon atom to which they are attached may form a $(C_3-C_7)$cycloalkyl group, with the proviso that both $R^{1a}$ and $R^{1b}$ cannot be CH$_3$, $R^2$ is selected from H, methyl, ethyl, methoxy, ethoxy, cyano and halo;

$R^4$ is selected from H methyl, ethyl, methoxy, ethoxy, cyano and halo;

Y is selected from —C(=O)—, —O—, and —CR$^5$R$^6$—, wherein R$^5$ is selected from H, methyl, ethyl, methoxy, ethoxy, —OH, F, —OC(=O)CH$_3$ and —OC(=O)CH$_2$CH$_3$; and R$^6$ is selected from H, methyl and ethyl;

W is —CHR$^8$— or Y—W taken together represents —CR$^5$=CR$^8$—;

R$^8$ is chosen from H, methyl and ethyl or R$^8$ taken together with R$^5$ forms a carbocycle;

$X^8$ is selected from CH and N;

Z is selected from the group consisting of

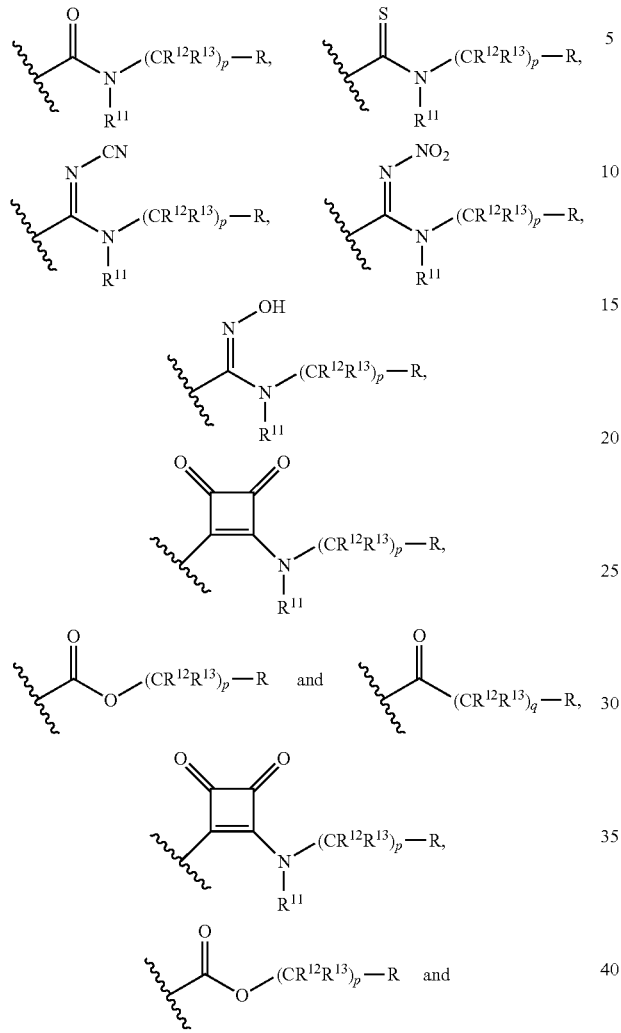

wherein R is selected from the group consisting of an optionally substituted alkyl group, an optionally substituted carbocycle and an optionally substituted heterocycle, wherein said alkyl group, carbocycle or heterocycle is attached to the remainder of Z through a carbon atom;

$R^{11}$ is selected from H, methyl and ethyl;

$R^{12}$ and $R^{13}$ are independently selected in each occurrence from H, methyl and ethyl or $R^{12}$ and $R^{13}$ taken to ether with the carbon atom to which the are attached ma form a 3 to 7-membered cyclic group;

p is zero, one or two q is one or two;

$R^7$ and $R^9$ are chosen from H, $(C_1-C_4)$alkyl, halo$(C_1-C_4)$alkyl, hydroxy$(C_1-C_4)$alkyl, $(C_1-C_4)$alkoxy$(C_1-C_4)$alkyl, hydroxyl, halo, amino $(C_1-C_4)$alkyl, $(C_1-C_4)$alkylamino $(C_1-C_4)$alkyl, di[$(C_1-C_4)$alkyl]amino$(C_1-C_4)$alkyl, and —C(=O)NH$_2$; and $R^{10}$ is chosen from H and $(C_1-C_4)$alkyl.

15. A compound according to claim 14 which has the structure selected from a group consisting of the following:

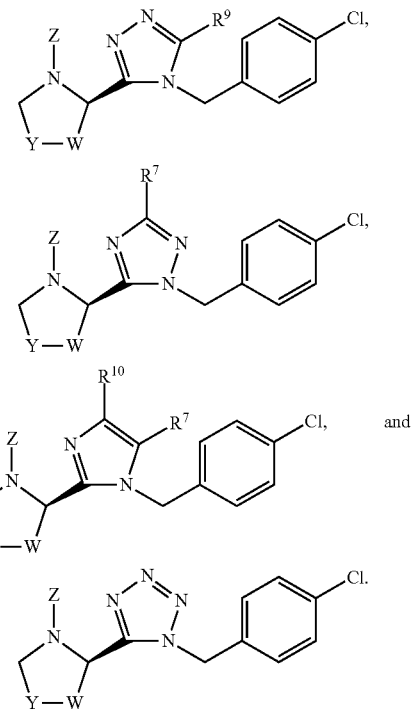

16. A compound according to claim 15 wherein:

$R^9$ is selected from the group consisting of H, Cl, F, Br, CF$_3$, methyl, ethyl, isopropyl, CH$_2$OH, CH$_2$OCH$_3$, CH$_2$NH$_2$, C(=O)NH$_2$ and CH$_2$NHCH$_3$; and Y is selected from CH$_2$, CHOH, C=O, CHF, C(CH$_3$)OH and CHOC(=O)CH$_3$ or Y—W is chosen from —CH=CH— and

17. A compound according to claim 16 wherein $R^9$ is selected from H, methyl, ethyl, isopropyl, —CH$_2$OH, —CH$_2$OCH$_3$, —CH$_2$NHCH$_3$, CF$_3$ and Cl.

18. A compound according to claim 14, wherein, in Z, $R^{12}$ and $R^{13}$ are independently selected in each occurrence from H, methyl, ethyl, propyl and butyl or, in one occurrence $R^{12}$ and $R^{13}$ taken together with the carbon atom to which they are attached form a cyclopropyl group.

19. A compound according to claim 18 wherein Z is selected from

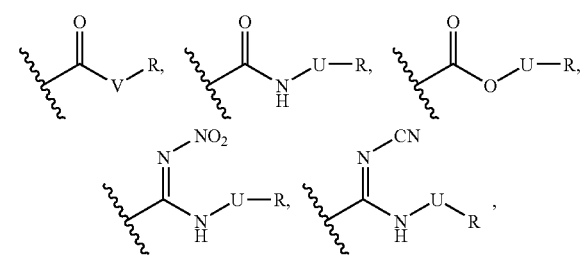

-continued

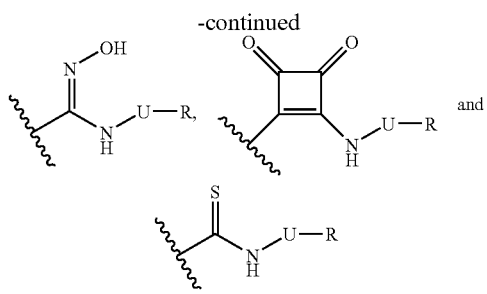

and

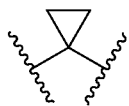

wherein U is chosen from direct bond, —CH$_2$—, —CH(CH$_3$)—, —C(CH$_3$)$_2$—, —CH(CH$_2$CH$_3$)—,

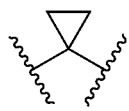

—CH$_2$CH$_2$—, —CH$_2$CH(CH$_3$)—, and —C(CH$_3$)CH$_2$—; and

V is chosen from —CH$_2$—, —CH(CH$_3$)—, —C(CH$_3$)$_2$—, —CH(CH$_2$CH$_3$)—,

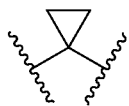

—CH$_2$CH$_2$—, —CH$_2$CH(CH$_3$)—, and —C(CH$_3$)CH$_2$—.

20. A compound according to claim 14, wherein R is selected from the group consisting of optionally substituted (C$_1$-C$_8$) linear or branched alkyl, (C$_3$-C$_8$)cycloalkyl, phenyl, isoxazolyl, benzoxazinyl, chromanyl, tetrahydronaphthalenyl, furanyl, benzoxepinyl, thiazolyl, pyrazolyl, benzoxadiazolyl, thiochromanyl, benzofuranyl, indanyl, pyridinyl, benzhydryl, naphthalenyl, isochromanyl, pyrimidinyl, piperidinyl, benzothiophenyl, thiadiazolyl, benzoxazolyl, azetidinyl, pyrrolidinyl, tetrahydrofuranyl, tetrahydropyranyl, indolyl and tetrahydroquinolyl.

21. A compound according to claim 20, wherein the optional substituents are selected from the group consisting of (C$_1$-C$_8$)alkyl, phenyl, substituted phenyl, oxo, hydroxy, (C$_1$-C$_8$)fluoroalkyl, halo, (C$_1$-C$_8$)alkoxy, (C$_1$-C$_8$)alkylthio, (C$_1$-C$_8$)fluoroalkylthio, (C$_1$-C$_8$)fluoroalkoxy, cyano, (C$_1$-C$_8$) alkylsulfonyl, di[(C$_1$-C$_8$)alkyl]amino, (C$_1$-C$_8$)alkylcarbonyl, amino, aminocarbonyl [H$_2$NC(=O)—], (C$_1$-C$_8$)alkylaminocarbonyl, di[(C$_1$-C$_8$)alkyl]aminocarbonyl, aminosulfonyl [H$_2$NSO$_2$—], (C$_1$-C$_8$)alkylaminosulfonyl [CH$_3$NHSO$_2$—], di[(C$_1$-C$_8$)alkyl]aminosulfonyl, hydroxysulfonyl [HOSO$_2$—], (C$_1$-C$_8$)alkylcarbonyl, carboxy [HOOC—], pyridinyl, pyrimidinyl, tetrahydropyranyloxy, pyrazolyl, substituted pyrazolyl, thienyl, and, in the case of nitrogen and sulfur-containing rings, oxide and dioxide.

22. A compound according to claim 21, wherein the optional substituents are selected from the group consisting of methyl, ethyl, propyl, butyl, phenyl, axe, hydroxy, trifluoromethyl, chloro, fluoro, bromo, methoxy, ethoxy, methylthio, trifluoromethylthio, trifluoromethoxy, cyano, methanesulfonyl, dimethylamino, methoxycarbonyl [CH$_3$C(=O)—], amino, aminocarbonyl [H$_2$NC(=O)—], methylaminocarbonyl [CH$_3$NHC(=O)—], dimethylaminocarbonyl [(CH$_3$)$_2$NC(=O)—], aminosulfonyl [H$_2$NSO$_2$—], methylaminosulfonyl [CH$_3$NHSO$_2$—], dimethylaminosulfonyl [(CH$_3$)$_2$NSO$_2$—], hydroxysulfonyl [HOSO$_2$—], acetyl, carboxy [HOOC—], halophenyl, methoxyphenyl, pyridinyl, pyrimidinyl, tetrahydropyranyloxy, pyrazolyl, methylpyrazolyl, methyltrifluoromethylpyrazolyl, thienyl, oxide and dioxide.

23. A compound of formula

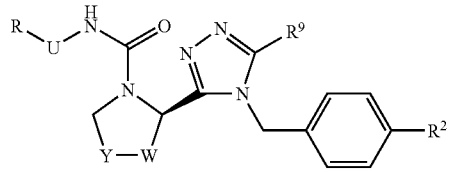

wherein R is substituted phenyl or pyridinyl;
U is chosen from direct bond, —CH$_2$—, —CH(CH$_3$)—, —C(CH$_3$)$_2$—, —CH(CH$_2$CH$_3$)—,

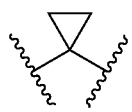

—CH$_2$CH$_2$—, —CH$_2$CH(CH$_3$)—, and —C(CH$_3$)CH$_2$—;
Y is selected from —C(=O)— and
W is —CHR$^8$— or Y—W taken together represents —CR$^5$=CR$^8$—;
R$^2$ is selected from H, methyl, ethyl, Cl, F and Br;
R$^5$ is selected from H, methyl, ethyl, —OH, F, methoxy, ethoxy, —OC(=O)CH$_3$ and —OC(=O)CH$_2$CH$_3$;
R$^8$ is chosen from H and methyl, ethyl, or R$^8$ taken together with R$^5$ forms cyclopropyl; and
R$^9$ is selected from H, methyl, ethyl, CF$_3$ and Cl.

24. A compound according to claim 23, wherein
R is chosen from 2-fluoro-4-chlorophenyl, 2-methyl-6-trifluoromethylpyridin-3-yl and 2,2-dimethyl-4-trifluoromethylphenyl;
U is a direct bond or —CH(CH$_2$CH$_3$)—;
Y is —CH$_2$—,
W is —CH—;
R$^2$ is Cl; and
R$^9$ is H or methyl.

25. A pharmaceutical formulation comprising a compound according to claim 1 and a pharmaceutically acceptable carrier.

26. A compound according to claim 14 wherein
R$^2$ is selected from H, CH$_3$, Cl, F and Br;
R$^4$ is selected from H, CH$_3$, Cl, F and Br;
Y is selected from —C(=O)—, —O—, and —CHR$^5$—, wherein R$^5$ is selected from H, C$_{1-6}$alkyl, —OH, F, —OC$_{1-8}$alkyl, and —OC(=O)—C$_{1-8}$alkyl.

27. A compound according to claim 14 wherein Y is —CHR$^5$—.

28. A pharmaceutical formulation comprising a compound according to claim 14 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,288,371 B2 | |
| APPLICATION NO. | : 12/245305 | |
| DATED | : October 16, 2012 | |
| INVENTOR(S) | : Vidyadhar Paradkar et al. | |

It is certified that error appears in the above-identified patent and that said Letters Patent is hereby corrected as shown below:

On the Title Page

At Page 1 (Item 56) Line 13, Under Other Publications, change "(Ipr)" to --(lpr)--.

At Page 1 (Item 56) Line 17, Under Other Publications, change "Subsituent,"" to --Substituent,"--.

At Column 3, Line 16, Change "synctial" to --syncytial--.

At Column 3, Line 17, Change "glumerulosclerosis" to --glomerulosclerosis--.

At Column 3, Line 20, Change "cardio" to --cardiac--.

At Column 3, Line 20, Change "vascalopathy" to --vasculopathy--.

At Column 5, Line 56, Change "napthalene." to --naphthalene.--.

At Column 7, Line 65, Change "n"solvate"" to --"solvate"--.

At Column 8, Line 29, Change "napthalenesulfonic" to --naphthalenesulfonic--.

At Column 8, Line 54, Change "dimethylformainide" to --dimethylformamide--.

At Column 10, Line 46, Change "Takayasu arthritis," to --Takayasu arteritis,--.

At Column 10, Line 66, Change "hyperuremia," to --hyperuricemia,--.

At Column 11, Line 1, Change "polyosis," to --polyposis,--.

At Column 11, Line 2, Change "Guillian-" to --Guillain- --.

At Column 13, Line 40, Change "structure" to --structure.--.

At Column 21, Line 36-37, Change "propiono-hydrazide" to --propionyl-hydrazide--.

Signed and Sealed this
Second Day of April, 2013

Teresa Stanek Rea
*Acting Director of the United States Patent and Trademark Office*

CERTIFICATE OF CORRECTION (continued)
U.S. Pat. No. 8,288,371 B2

At Column 22, Line 62, Change "100%+)" to --100%+).--.

At Column 29, Line 37 (Approx.), Change "1H)," to --1H).--.

At Column 38, Line 66, Change "diisopropylethylamine-" to --diisopropylethylamine--.

At Column 40, Line 28, Change "0.8 mmol)" to --0.18 mmol)--.

At Column 41, Line 3, Change "chlorofornate" to --chloroformate--.

At Column 43, Line 21, Change "mmmol)" to --mmol).--.

At Column 43, Line 66, Change "product" to --product.--.

At Column 43, Line 67, Change "435.3.." to --435.3.--.

At Column 44, Line 3, Change "pyrrolin" to --pyrrolidin--.

At Column 45, Line 58-59, Change "diisopropylethylamnine" to --diisopropylethylamine--.

At Column 47, Line 61, Change "methybenzylamine" to --methylbenzylamine--.

At Column 48, Line 13 (Approx.), Change "71%)" to --71%).--.

At Column 48, Line 18, Change "(M+-100)" to --(M+-100).--.

At Column 48, Line 23, Change "acetonitile" to --acetonitrile--.

At Column 48, Line 31, Change "(300" to --$^1$H NMR (300--.

At Column 48, Line 35, Change "291.2" to --291.2.--.

At Column 48, Line 42, Change "291.3" to --291.3.--.

At Column 48, Line 46, Change "carboxamide" to --carboxamide.--.

At Column 48, Line 55, Change "chlropheny)ethyl)" to --chlorophenyl)ethyl)--.

At Column 48, Line 67, Change "2H)," to --1H),--.

At Column 54, Line 19 (Approx.), Change "15%)" to --15%).--.

At Column 54, Line 24, Change "520.0" to --520.0.--.

At Column 56, Line 66, Change "δ□" to --δ--.

At Column 58, Line 56, Change "rotomers:" to --rotamers:--.

At Column 63, Line 37, Change "dimethylamino)" to --(dimethylamino)--.

At Column 64, Line 11, Change "chromen" to --chromene--.

At Column 65, Line 7, Change "caboxylate." to --carboxylate.--.

At Column 65, Line 8, Change "caboxylate" to --carboxylate--.

At Column 65, Line 40, Change "chlorobebzyl)" to --chlorobenzyl)--.

At Column 65, Line 40, Change "-methyl-" to -- -methyl-6-)--.

At Column 65, Line 44, Change "Iodotrimethylsilane" to --Iodotrimethylsilane--.

At Column 66, Line 62, Change "dicloromethane" to --dichloromethane--.

At Column 67, Line 50, Change "307" to --307.--.

At Column 67, Line 57, Change "dicloromethane" to --dichloromethane--.

At Column 71, Line 40, Change "Dimethoxycyclobutenedione" to --Dimethoxycyclobutanedione--. At Column 73, Line 12, Change "(trifluorometbyl)" to --(trifluoromethyl)--.

At Column 73, Line 20, Change "HgCl2" to --$HgCl_2$--.

At Column 74, Line 18, Change "N-Bromosuccinamide" to --N-Bromosuccinimide--.

At Column 74, Line 55, Change "Was" to --was--.

At Column 76, Line 64, Change "$CH_2C_2$" to --$CH_2Cl_2$--.

At Column 77, Line 10, Change "was," to --was--.

At Column 77, Line 19, Change "mmmol)" to --mmol)--.

At Column 77, Line 30, Change "(m, 2.06" to --(m, 1H), 2.58-2.06--.

At Column 78, Line 15, Change "methly" to --methyl--.

At Column 78, Line 62, Change "respectively" to --respectively.--.

At Column 169-170, Line 3 (Approx.), Change " 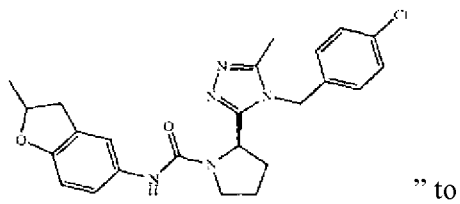 " to 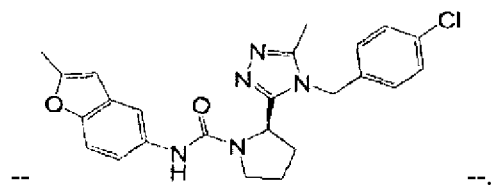 --.

CERTIFICATE OF CORRECTION (continued)

At Column 299, Line 5, In Claim 9, change "Q is Q is" to --Q is--.

At Column 300, Line 52, In Claim 14, change "CH$_3$," to --CH$_3$;--.

At Column 300, Line 55, In Claim 14, change "H" to --H,--.

At Column 300, Line 64, In Claim 14, change "ethyl" to --ethyl,--.

At Column 301, Line 31-41, In Claim 14, below " 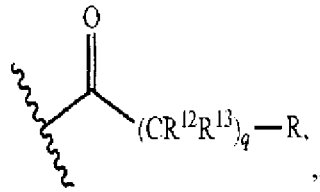 " delete

" 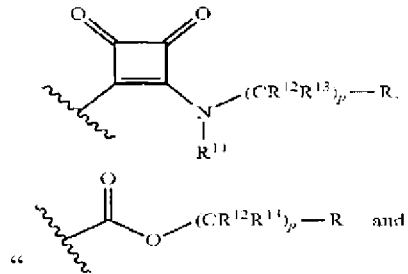 ".

At Column 301, Line 53, In Claim 14, change "to ether" to --together--.

At Column 301, Line 54, In Claim 14, change "ma" to --may--.

At Column 303, Line 65-66, In Claim 22, change "[CH$_3$C(=O)-]," to --[CH$_3$OC(=O)-],--.

At Column 304, Line 31, In Claim 23, change "and" to --and -CHR$^5$-.--.

At Column 304, Line 56, In Claim 26, change "C$_{1-6}$ alkyl," to --C$_{1-8}$alkyl,--.